United States Patent
Noureldin et al.

(10) Patent No.: US 9,851,153 B2
(45) Date of Patent: Dec. 26, 2017

(54) RECOVERY AND RE-USE OF WASTE ENERGY IN INDUSTRIAL FACILITIES

(71) Applicant: Saudi Arabian Oil Company, Dhahran (SA)

(72) Inventors: Mahmoud Bahy Mahmoud Noureldin, Dhahran (SA); Hani Mohammed Al Saed, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 15/241,998

(22) Filed: Aug. 19, 2016

(65) Prior Publication Data

US 2017/0082373 A1    Mar. 23, 2017

Related U.S. Application Data

(60) Provisional application No. 62/209,217, filed on Aug. 24, 2015, provisional application No. 62/209,147,
(Continued)

(51) Int. Cl.
*F28D 7/00* (2006.01)
*C10G 35/04* (2006.01)
(Continued)

(52) U.S. Cl.
CPC .......... *F28D 7/0083* (2013.01); *B01D 3/007* (2013.01); *B01D 3/32* (2013.01); *B01D 51/10* (2013.01);
(Continued)

(58) Field of Classification Search
CPC .......... C01B 3/24; C10G 45/00; C10G 45/02; C10G 45/44; C10G 65/00; C10G 69/00;
(Continued)

(56) References Cited

U.S. PATENT DOCUMENTS 3,995,428 A    12/1976 Roberts
4,109,469 A    8/1978 Carson
(Continued)

FOREIGN PATENT DOCUMENTS

CN        1844325 A      10/2006
CN       101424453        5/2009
(Continued)

OTHER PUBLICATIONS

Feng Xu, D. Yogi Goswami and Sunil S. Bhagwat, "A combined power/cooling cycle," Energy, 25 (2000), 233-246.
(Continued)

*Primary Examiner* — Brian McCaig
(74) *Attorney, Agent, or Firm* — Fish & Richardson P.C.

(57) ABSTRACT

Configurations and related processing schemes of direct or indirect inter-plants (or both) heating systems synthesized for grassroots medium grade crude oil semi-conversion refineries to increase energy efficiency from specific portions of low grade waste heat sources are described. Configurations and related processing schemes of direct or indirect inter-plants (or both) heating systems synthesized for integrated medium grade crude oil semi-conversion refineries and aromatics complex for increasing energy efficiency from specific portions of low grade waste sources are also described.

52 Claims, 117 Drawing Sheets

Related U.S. Application Data filed on Aug. 24, 2015, provisional application No. 62/209,188, filed on Aug. 24, 2015, provisional application No. 62/209,223, filed on Aug. 24, 2015.

(51) Int. Cl.

| | | |
|---|---|---|
| C10G 45/02 | (2006.01) | |
| C10G 45/44 | (2006.01) | |
| F28F 9/26 | (2006.01) | |
| B01D 3/32 | (2006.01) | |
| B01D 53/047 | (2006.01) | |
| B01D 53/48 | (2006.01) | |
| C10L 3/10 | (2006.01) | |
| C07C 7/08 | (2006.01) | |
| C10G 65/12 | (2006.01) | |
| C10G 33/06 | (2006.01) | |
| B01D 3/00 | (2006.01) | |
| B01D 51/10 | (2006.01) | |
| B01D 53/14 | (2006.01) | |
| B01D 53/18 | (2006.01) | |
| B01D 53/34 | (2006.01) | |
| B01D 53/86 | (2006.01) | |
| B01D 53/96 | (2006.01) | |
| C02F 1/58 | (2006.01) | |
| C10G 47/00 | (2006.01) | |
| C10G 65/00 | (2006.01) | |
| F01D 17/14 | (2006.01) | |
| F01K 3/18 | (2006.01) | |
| F01K 13/02 | (2006.01) | |
| H02K 7/18 | (2006.01) | |
| C10G 69/00 | (2006.01) | |
| F01K 25/06 | (2006.01) | |
| F01K 25/08 | (2006.01) | |
| F01K 27/02 | (2006.01) | |
| F01K 13/00 | (2006.01) | |
| F01K 23/06 | (2006.01) | |
| C01B 3/24 | (2006.01) | |
| C10G 45/00 | (2006.01) | |
| C10K 3/04 | (2006.01) | |
| F01K 27/00 | (2006.01) | |
| C02F 101/10 | (2006.01) | |
| C02F 101/16 | (2006.01) | |
| C02F 103/18 | (2006.01) | |
| C02F 103/36 | (2006.01) | |

(52) U.S. Cl.
CPC ....... *B01D 53/047* (2013.01); *B01D 53/1462* (2013.01); *B01D 53/185* (2013.01); *B01D 53/343* (2013.01); *B01D 53/48* (2013.01); *B01D 53/8603* (2013.01); *B01D 53/96* (2013.01); *C01B 3/24* (2013.01); *C02F 1/586* (2013.01); *C07C 7/08* (2013.01); *C10G 33/06* (2013.01); *C10G 35/04* (2013.01); *C10G 45/00* (2013.01); *C10G 45/02* (2013.01); *C10G 45/44* (2013.01); *C10G 47/00* (2013.01); *C10G 65/00* (2013.01); *C10G 65/12* (2013.01); *C10G 69/00* (2013.01); *C10K 3/04* (2013.01); *C10L 3/101* (2013.01); *C10L 3/103* (2013.01); *C10L 3/104* (2013.01); *F01D 17/145* (2013.01); *F01K 3/185* (2013.01); *F01K 13/00* (2013.01); *F01K 13/02* (2013.01); *F01K 23/06* (2013.01); *F01K 23/064* (2013.01); *F01K 25/06* (2013.01); *F01K 25/08* (2013.01); *F01K 27/00* (2013.01); *F01K 27/02* (2013.01); *F28F 9/26* (2013.01); *H02K 7/1823* (2013.01); *B01D 2252/204* (2013.01); *C01B 2203/0233* (2013.01); *C02F 2101/10* (2013.01); *C02F 2101/101* (2013.01); *C02F 2101/16* (2013.01); *C02F 2103/18* (2013.01); *C02F 2103/36* (2013.01); *C10G 2300/202* (2013.01); *C10G 2300/207* (2013.01); *C10G 2300/4006* (2013.01); *C10G 2300/4056* (2013.01); *C10G 2400/04* (2013.01); *C10G 2400/30* (2013.01); *C10L 2290/06* (2013.01); *C10L 2290/541* (2013.01); *Y02P 20/129* (2015.11)

(58) Field of Classification Search
CPC ......... C02F 1/586; B01D 3/32; B01D 53/047; B01D 53/185; B01D 53/343; B01D 53/96; F01D 17/145; F01K 23/06
See application file for complete search history.

(56) References Cited

U.S. PATENT DOCUMENTS

| | | |
|---|---|---|
| 4,291,232 A | 9/1981 | Cardone |
| 4,471,619 A | 9/1984 | Nolley, Jr. |
| 4,512,155 A | 4/1985 | Sheinbaum |
| 4,792,390 A | 12/1988 | Staggs |
| 4,962,238 A | 10/1990 | Wolfe |
| 5,007,240 A | 4/1991 | Ishida |
| 5,164,070 A | 11/1992 | Munro |
| 5,240,476 A | 8/1993 | Hegarty |
| 5,497,624 A | 3/1996 | Amir |
| 6,733,636 B1 | 5/2004 | Heins |
| 8,046,999 B2 | 11/2011 | Doty |
| 9,328,634 B2 | 5/2016 | Ikegami |
| 9,562,201 B2 | 2/2017 | Noureldin |
| 2002/0023538 A1* | 2/2002 | Agarwal ............... B01D 53/12 95/108 |
| 2003/0092952 A1 | 5/2003 | Netzer |
| 2003/0132138 A1* | 7/2003 | Mehra ................. C10G 49/007 208/107 |
| 2004/0186332 A1 | 9/2004 | Kong |
| 2006/0010872 A1 | 1/2006 | Singh |
| 2008/0128134 A1 | 6/2008 | Mudunuri |
| 2008/0174115 A1 | 7/2008 | Lambirth |
| 2008/0257413 A1 | 10/2008 | Noureldin et al. |
| 2008/0289588 A1 | 11/2008 | Wees et al. |
| 2008/0314726 A1 | 12/2008 | Choros |
| 2009/0000299 A1 | 1/2009 | Ast |
| 2009/0000906 A1 | 1/2009 | Petri |
| 2009/0071652 A1 | 3/2009 | Vinegar |
| 2009/0225929 A1 | 9/2009 | Genta et al. |
| 2009/0287029 A1 | 11/2009 | Anumakonda et al. |
| 2009/0301087 A1 | 12/2009 | Borissov et al. |
| 2010/0146974 A1 | 6/2010 | Ast |
| 2010/0242476 A1 | 9/2010 | Ast |
| 2010/0263380 A1 | 10/2010 | Biederman |
| 2010/0319346 A1 | 12/2010 | Ast |
| 2010/0326076 A1 | 12/2010 | Ast |
| 2011/0016863 A1 | 1/2011 | Ernst |
| 2011/0072819 A1 | 3/2011 | Silva |
| 2011/0072820 A1 | 3/2011 | Finkenrath |
| 2011/0083437 A1 | 4/2011 | Ast |
| 2011/0158858 A1 | 6/2011 | Alves |
| 2012/0031096 A1 | 2/2012 | Acikgoz et al. |
| 2012/0047889 A1 | 3/2012 | Acikgoz et al. |
| 2012/0048718 A1 | 3/2012 | Werba |
| 2012/0085096 A1 | 4/2012 | Penton et al. |
| 2012/0131921 A1 | 5/2012 | Held |
| 2012/0279728 A1 | 11/2012 | Northrop |
| 2012/0279900 A1 | 11/2012 | Noureldin et al. |
| 2012/0285169 A1 | 11/2012 | Freund |
| 2012/0298552 A1 | 11/2012 | Koseoglu |
| 2013/0104546 A1 | 5/2013 | Goswami |
| 2013/0145763 A1 | 6/2013 | Mirmobin et al. |
| 2013/0165534 A1 | 6/2013 | McComish |
| 2013/0213040 A1 | 8/2013 | Goswami |
| 2013/0231909 A1 | 9/2013 | Noureldin |

(56) References Cited

U.S. PATENT DOCUMENTS

| | | | |
|---|---|---|---|
| 2013/0238154 | A1 | 9/2013 | Noureldin |
| 2013/0334060 | A1 | 12/2013 | Koseoglu et al. |
| 2014/0090405 | A1 | 4/2014 | Held et al. |
| 2014/0142364 | A1 | 5/2014 | Io |
| 2014/0260311 | A1 | 9/2014 | Berlowitz |
| 2015/0377079 | A1 | 12/2015 | Noureldin |
| 2016/0045841 | A1 | 2/2016 | Kaplan |

FOREIGN PATENT DOCUMENTS

| | | |
|---|---|---|
| CN | 104560082 | 4/2015 |
| DE | 3731978 A1 | 3/1988 |
| EP | 0292391 A1 | 11/1988 |
| EP | 0949318 A2 | 10/1999 |
| EP | 2516326 | 10/2012 |
| FR | 2990990 | 11/2013 |
| SU | 295317 A1 | 10/1977 |
| WO | 97/21786 | 6/1997 |
| WO | 2004102082 | 11/2004 |
| WO | 2011090553 | 7/2011 |
| WO | 2012048132 | 4/2012 |
| WO | 2013055864 | 4/2013 |
| WO | 2014205163 | 12/2014 |

OTHER PUBLICATIONS

D. Zheng, B. Chen, Y. Qi and H. Jin, "Thermodynamic analysis of a novel absorption power/cooling combined cycle," Applied Energy, 83 (2006), 311-323.

PCT International Search Report and Written Opinion of the International Searching Authority, PCT/US2016/027794, dated Oct. 19, 2016, 12 pages.

PCT International Search Report and Written Opinion of the International Searching Authority, PCT/US2016/027797, dated Oct. 19, 2016, 13 pages.

PCT International Search Report and Written Opinion of the International Searching Authority, PCT/US2016/030063, dated Oct. 19, 2016, 13 pages.

PCT International Search Report and Written Opinion of the International Searching Authority, PCT/US2016/030156, dated Oct. 19, 2016, 12 pages.

PCT International Search Report and Written Opinion of the International Searching Authority, PCT/US2016/048074, dated Nov. 9, 2016, 12 pages.

PCT International Search Report and Written Opinion of the International Searching Authority, PCT/US2016/048042, dated Nov. 9, 2016, 12 pages.

PCT International Search Report and Written Opinion of the International Searching Authority, PCT/US2016/048067, dated Nov. 15, 2016, 11 pages.

PCT International Search Report and Written Opinion of the International Searching Authority, PCT/US2016/048066, dated Nov. 15, 2016, 11 pages.

PCT International Search Report and Written Opinion of the International Searching Authority, PCT/US2016/048076, dated Nov. 15, 2016, 12 pages.

PCT International Search Report and Written Opinion of the International Searching Authority, PCT/US2016/048207, dated Nov. 21, 2016, 12 pages.

PCT International Search Report and Written Opinion of the International Searching Authority, PCT/US2016/048219, dated Nov. 21, 2016, 13 pages.

PCT International Search Report and Written Opinion of the International Searching Authority, PCT/US2016/048229, dated Nov. 21, 2016, 13 pages.

PCT International Search Report and Written Opinion of the International Searching Authority, PCT/US2016/048236, dated Nov. 21, 2016, 13 pages.

PCT International Search Report and Written Opinion of the International Searching Authority, PCT/US2016/027413, dated Nov. 22, 2016, 11 pages.

PCT International Search Report and Written Opinion of the International Searching Authority, PCT/US2016/048063, dated Nov. 23, 2016, 11 pages.

PCT International Search Report and Written Opinion of the International Searching Authority, PCT/US2016/048071, dated Nov. 23, 2016, 11 pages.

PCT International Search Report and Written Opinion of the International Searching Authority, PCT/US2016/048078, Nov. 15, 2016, 12 pages.

PCT International Search Report and Written Opinion of the International Searching Authority, PCT/US2016/048210, dated Dec. 22, 2016, 11 pages.

PCT International Search Report and Written Opinion of the International Searching Authority, PCT/US2016/048224, dated Dec. 22, 2016, 11 pages.

PCT International Search Report and Written Opinion of the International Searching Authority, PCT/US2016/048209, dated Dec. 22, 2016, 11 pages.

PCT International Search Report and Written Opinion of the International Searching Authority, PCT/US2016/048237, dated Dec. 22, 2016, 11 pages.

PCT International Search Report and Written Opinion of the International Searching Authority, PCT/US2016/048223, dated Dec. 22, 2016, 11 pages.

PCT International Search Report and Written Opinion of the International Searching Authority, PCT/US2016/048212, dated Dec. 22, 2016, 11 pages.

Schaschke, "A Dictionary of Chemical Engineering: Tatoray Process," Oxford, 2014, p. 371.

Marcilly, "Acido-Basic Catalysis: Applications to refining and Petrochemistry," IFP Publications, 2005, pp. 512-513.

Gary, "Petroleum Refining Technology and Economics: Figure 1.1 Refinery Flow Diagram," CRC Press, 5th ed., 2007, p. 3.

Meng Lui, and Na Zhang, "Proposal and analysis of a novel ammonia-water cycle for power and refrigeration cogeneration," Energy, 32 (2007), 961-970.

J.Wang, Y. Dai and L. Gao, "Parametric analysis and optimization for a combined power and refrigeration cycle," Applied Energy, 85 (2008), 1071-1085.

R.V. Padilla, G. Demirkaya, D. Yogi Goswami, E. Stefanakos, and M. A. Rahman, "Analysis of power and cooling cogeneration using ammonia-water mixture," Energy, 35 (2010), 4649-4657.

D. Ayou, J. C. Bruno, R. Saravanan and A. Coronas, "An Overview of Combined Absorption Power and Cooling Cycles," Renewable sustainable energy reviews, 21 (2013), 728-748.

J. Hua, Y. Chen, Y. Wang and A.P. Roskiliy, "Thermodynamic analysis of ammonia-water power/chilling cogeneration cycle with low grade waste heat," Applied thermal engineering , 64 (2014), 483-490.

Hasan et al., "First and Second Law Analysis of a New Power and Refrigeration Thermodynamic Cycle using a Solar Heat Source," Pergamon, Solar Energy, vol. 73, No. 5, Nov. 1, 2002, pp. 385-393.

Stecco, "Kalina Cycles: Some Possible Applications and Comments," Proceedings of the American Power Conference, XP 000609703, Jan. 1, 1993, vol. 1, pp. 196-201.

Tamm et al., "Theoretical and Experimental Investigation of an Ammonia-Water Power and Refrigeration Thermodynamic Cycle," Science Direct, Solar Energy, vol. 76, No. 1-3, Jan. 1, 2004, pp. 217-228.

Sadrameli et al., "Optimum Operating Conditions for a Combined Power and Cooling Thermodynamic Cycle," Science Direct, Applied Energy, vol. 84, No. 3, Nov. 10, 2006, pp. 254-265.

Vidal, "Analysis of a Combined Power and Refrigeration Cycle by the Exergy Method," Science Direct, Energy 31, Dec. 1, 2006, pp. 3401-3414.

PCT International Search Report and Written Opinion of the International Searching Authority, PCT/US2016/027417, dated Jul. 6, 2016, 11 pages.

\* cited by examiner

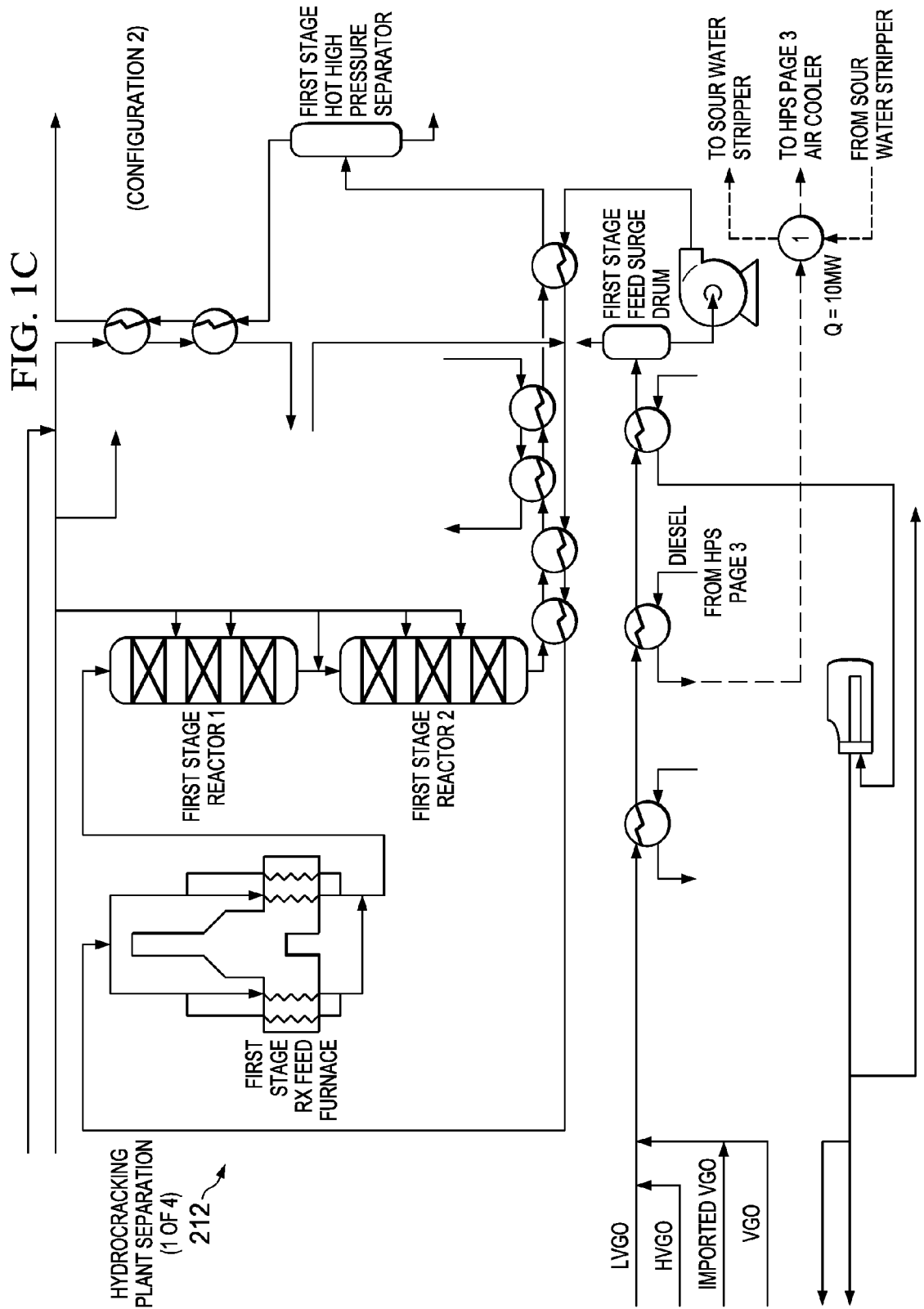

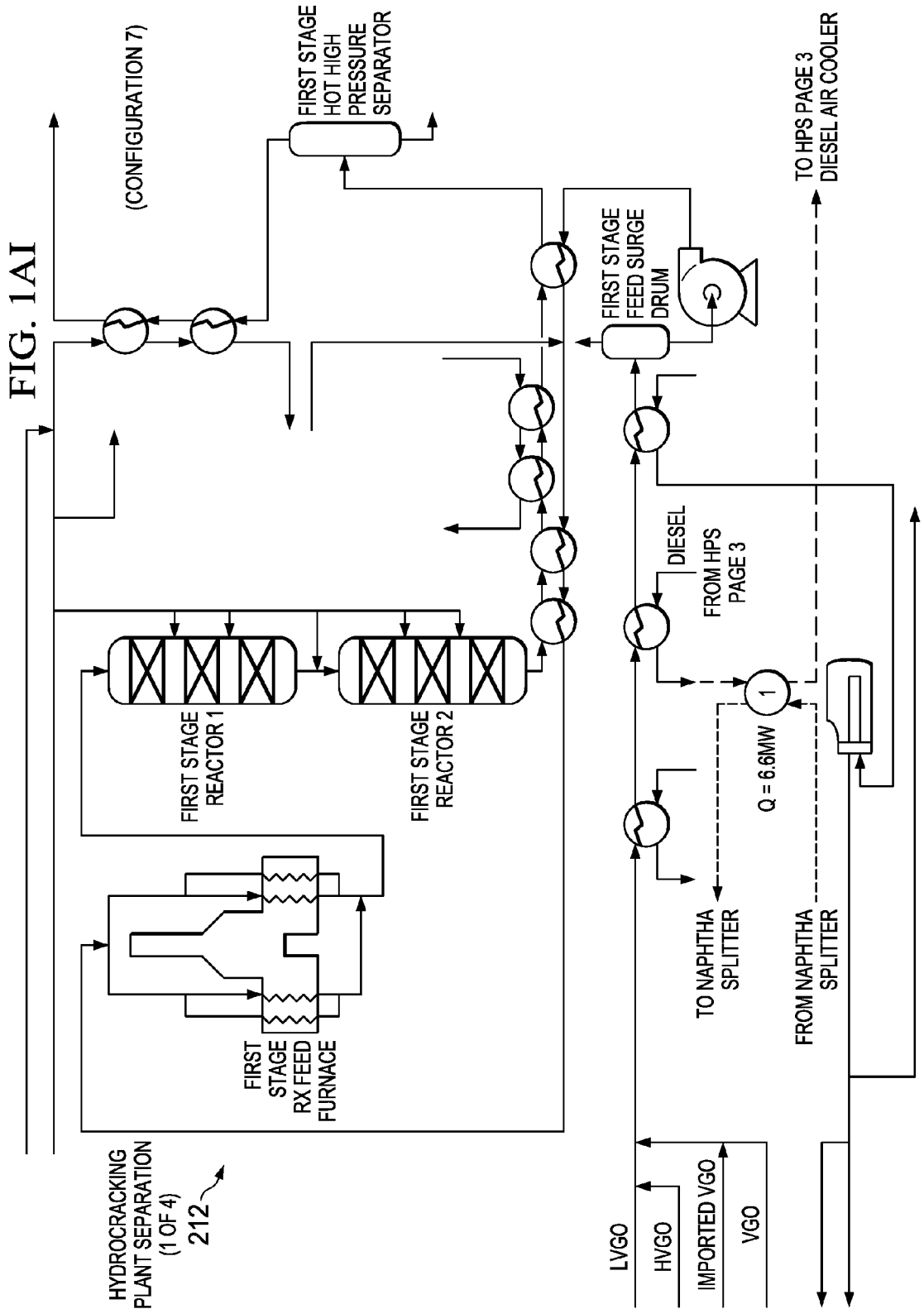

RECOVERY AND RE-USE OF WASTE ENERGY IN INDUSTRIAL FACILITIES

CROSS-REFERENCE TO RELATED APPLICATIONS

This application claims priority under 35 U.S.C. §119 to U.S. Provisional Patent Application Ser. No. 62/209,217, filed on Aug. 24, 2015; U.S. Provisional Patent Application Ser. No. 62/209,147, filed on Aug. 24, 2015; U.S. Provisional Patent Application Ser. No. 62/209,188, filed on Aug. 24, 2015; and U.S. Provisional Patent Application Ser. No. 62/209,223, filed on Aug. 24, 2015. The entire contents of each of the preceding applications are incorporated herein by reference in their respective entireties.

TECHNICAL FIELD

This specification relates to operating industrial facilities, for example, crude oil refining facilities or other industrial facilities that include operating plants that generate heat.

BACKGROUND

Petroleum refining processes are chemical engineering processes and other facilities used in petroleum refineries to transform crude oil into products, for example, liquefied petroleum gas (LPG), gasoline, kerosene, jet fuel, diesel oils, fuel oils, and other products. Petroleum refineries are large industrial complexes that involve many different processing units and auxiliary facilities, for example, utility units, storage tanks, and other auxiliary facilities. Each refinery can have its own unique arrangement and combination of refining processes determined, for example, by the refinery location, desired products, economic considerations, or other factors. The petroleum refining processes that are implemented to transform the crude oil into the products such as those listed earlier can generate heat, which may not be reused, and byproducts, for example, greenhouse gases (GHG), which may pollute the atmosphere. It is believed that the world's environment has been negatively affected by global warming caused, in part, due to the release of GHG into the atmosphere.

SUMMARY

This specification describes technologies relating to specific direct or indirect inter-plants and hybrid, intra- and inter-plants integration for energy consumption reduction from waste energy in industrial facilities.

Details of one or more implementations of the subject matter described in this specification are set forth in the accompanying drawings and the description later. Other features, aspects, and advantages of the subject matter will become apparent from the description, the drawings, and the claims.

BRIEF DESCRIPTION OF THE DRAWINGS

FIG. 1A is a schematic diagram of a hydrocracking plant.
FIG. 1B is a schematic diagram of a sulfur recovery plant.
FIGS. 1C-1G illustrate configurations and related scheme details for heating a sour water stripper plant stream.
FIG. 1C is a schematic diagram of a hydrocracking plant.
FIG. 1D is a schematic diagram of a hydrocracking plant.
FIG. 1E-1 is a schematic diagram of a hydrocracking plant.
FIG. 1E-2 is a schematic diagram of a hydrocracking plant.
FIG. 1F is a schematic diagram of a hydrocracking plant.
FIG. 1G is a schematic diagram of a sour water stripper plant.
FIGS. 1H-1M illustrate configurations and related scheme details for heating streams in a gas separation plant and a sulfur recovery plant.
FIG. 1H is a schematic diagram of a hydrocracking plant.
FIG. 1I is a schematic diagram of a hydrocracking plant.
FIG. 1J-1 is a schematic diagram of a hydrocracking plant.
FIG. 1J-2 is a schematic diagram of a hydrocracking plant.
FIG. 1K is a schematic diagram of a hydrocracking plant.
FIG. 1L is a schematic diagram of a gas separation plant.
FIG. 1M is a schematic diagram of a sulfur recovery plant.
FIGS. 1N-1S illustrate configurations and related scheme details for heating streams in a naphtha hydro-treating plant and a sulfur recovery plant.
FIG. 1N is a schematic diagram of a hydrocracking plant.
FIG. 1O is a schematic diagram of a hydrocracking plant.
FIG. 1P-1 is a schematic diagram of a hydrocracking plant.
FIG. 1P-2 is a schematic diagram of a hydrocracking plant.
FIG. 1Q is a schematic diagram of a hydrocracking plant.
FIG. 1R is a schematic diagram of a naphtha hydro-treating plant product splitting section.
FIG. 1S is a schematic diagram of a sulfur recovery plant.
FIGS. 1T-1Y illustrate configurations and related scheme details for heating streams in a naphtha hydro-treating plant and a sulfur recovery plant.
FIG. 1T is a schematic diagram of a hydrocracking plant.
FIG. 1U is a schematic diagram of a hydrocracking plant.
FIG. 1V-1 is a schematic diagram of a hydrocracking plant.
FIG. 1V-2 is a schematic diagram of a hydrocracking plant.
FIG. 1W is a schematic diagram of a hydrocracking plant.
FIG. 1X is a schematic diagram of a sour water stripper plant.
FIG. 1Y is a schematic diagram of a gas separation plant.
FIGS. 1Z-1AH illustrate configurations and related scheme details for heating a stream in an amine regeneration plant.
FIG. 1Z is a schematic diagram of a hydrocracking plant.
FIG. 1AA is a schematic diagram of a hydrocracking plant.
FIG. 1AB-1 is a schematic diagram of a hydrocracking plant.
FIG. 1AB-2 is a schematic diagram of a hydrocracking plant.
FIG. 1AC is a schematic diagram of a hydrocracking plant.
FIG. 1AD is a schematic diagram of an amine regeneration plant separation section.
FIG. 1AE is a schematic diagram of a hydrocracking plant.
FIG. 1AF-1 is a schematic diagram of a hydrocracking plant.
FIG. 1AF-2 is a schematic diagram of a hydrocracking plant.

FIG. 1AG is a schematic diagram of a hydrocracking plant.

FIG. 1AH is a schematic diagram of an amine regeneration plant separation section.

FIGS. 1AI-1AN illustrate configurations and related scheme details for heating a stream in a naphtha hydro-treating plant and a sour water stripper plant.

FIG. 1AI is a schematic diagram of a hydrocracking plant.

FIG. 1AJ is a schematic diagram of a hydrocracking plant.

FIG. 1AK-1 is a schematic diagram of a hydrocracking plant.

FIG. 1AK-2 is a schematic diagram of a hydrocracking plant.

FIG. 1AL is a schematic diagram of a hydrocracking plant.

FIG. 1AM is a schematic diagram of a naphtha hydro-treating plant product splitting section.

FIG. 1AN is a schematic diagram of a sour water stripper plant.

FIGS. 1AO-1AT illustrate configurations and related schemes for heating streams in a sulfur recovery plant and a sour water stripper plant.

FIG. 1AO is a schematic diagram of a hydrocracking plant.

FIG. 1AP is a schematic diagram of a hydrocracking plant.

FIG. 1AQ-1 is a schematic diagram of a hydrocracking plant.

FIG. 1AQ-2 is a schematic diagram of a hydrocracking plant.

FIG. 1AR is a schematic diagram of a hydrocracking plant.

FIG. 1AS is a schematic diagram of a sour water stripper plant.

FIG. 1AT is a schematic diagram of a sulfur recovery plant.

FIGS. 1AU-1BA illustrate configurations and the related schemes for heating streams in a naphtha hydro-treating plant, a sour water stripper plant and a gas separation plant.

FIG. 1AU is a schematic diagram of a hydrocracking plant.

FIG. 1AV is a schematic diagram of a hydrocracking plant.

FIG. 1AW-1 is a schematic diagram of a hydrocracking plant.

FIG. 1AW-2 is a schematic diagram of a hydrocracking plant.

FIG. 1AX is a schematic diagram of a hydrocracking plant.

FIG. 1AY is a schematic diagram of a naphtha hydro-treating plant product splitting section.

FIG. 1AZ is a schematic diagram of a sour water stripper plant.

FIG. 1BA is a schematic diagram of a gas separation plant.

FIGS. 1BB-1BG illustrate configurations and the related schemes for heating streams in an amine regeneration plant and a gas separation plant.

FIG. 1BB is a schematic diagram of a hydrocracking plant.

FIG. 1BC is a schematic diagram of a hydrocracking plant.

FIG. 1BD-1 is a schematic diagram of a hydrocracking plant.

FIG. 1BD-2 is a schematic diagram of a hydrocracking plant.

FIG. 1BE is a schematic diagram of a hydrocracking plant.

FIG. 1BF is a schematic diagram of an amine regeneration plant separation section.

FIG. 1BG is a schematic diagram of a gas separation plant.

FIGS. 1BH-1N illustrate configurations and the related schemes for heating streams in an amine regeneration plant and a sulfur recovery plant.

FIG. 1BH is a schematic diagram of a hydrocracking plant.

FIG. 1BI is a schematic diagram of a hydrocracking plant.

FIG. 1BJ is a schematic diagram of a hydrocracking plant.

FIG. 1BK-1 is a schematic diagram of a hydrocracking plant.

FIG. 1BK-2 is a schematic diagram of a hydrocracking plant.

FIG. 1BL is a schematic diagram of a hydrocracking plant.

FIG. 1BM is a schematic diagram of a sulfur recovery plant.

FIG. 1BN is a schematic diagram of an amine regeneration plant separation section.

FIGS. 1BO-1BT illustrate configurations and related schemes for heating streams in an amine regeneration plant and a naphtha hydro-treating plant.

FIG. 1BO is a schematic diagram of a hydrocracking plant.

FIG. 1BP is a schematic diagram of a hydrocracking plant.

FIG. 1BQ-1 is a schematic diagram of a hydrocracking plant.

FIG. 1BQ-2 is a schematic diagram of a hydrocracking plant.

FIG. 1BR is a schematic diagram of a hydrocracking plant.

FIG. 1BS is a schematic diagram of an amine regeneration plant separation section.

FIG. 1BT is a schematic diagram of a naphtha hydro-treating plant product splitting section.

FIGS. 1BU-1CB illustrate configurations and related schemes for streams in an amine regeneration plant, a sulfur recovery plant and a sour water stripper plant.

FIG. 1BU is a schematic diagram of a hydrocracking plant.

FIG. 1BV is a schematic diagram of a hydrocracking plant.

FIG. 1BW-1 is a schematic diagram of a hydrocracking plant.

FIG. 1BW-2 is a schematic diagram of a hydrocracking plant.

FIG. 1BX is a schematic diagram of a hydrocracking plant.

FIG. 1BY is a schematic diagram of a diesel hydro-treating plant stripping section.

FIG. 1BZ is a schematic diagram of a sulfur recovery plant.

FIG. 1CA is a schematic diagram of an amine regeneration plant separation section.

FIG. 1CB is a schematic diagram of a sour water stripper plant.

FIGS. 1CC-1CL illustrate configurations and related schemes for streams in an amine regeneration plant, a sulfur recovery plant, a gas separation plant and a sour water stripper plant.

FIG. 1CC is a schematic diagram of a hydrocracking plant.

FIG. 1CD is a schematic diagram of a hydrocracking plant.

FIG. 1CE-1 is a schematic diagram of a hydrocracking plant.

FIG. 1CE-2 is a schematic diagram of a hydrocracking plant.

FIG. 1CF is a schematic diagram of a hydrocracking plant.

FIG. 1CG is a schematic diagram of a diesel hydro-treating plant stripping section.

FIG. 1CH is a schematic diagram of a natural gas steam reforming hydrogen plant.

FIG. 1CI is a schematic diagram of a sulfur recovery plant.

FIG. 1CJ is a schematic diagram of an amine regeneration plant separation section.

FIG. 1CK is a schematic diagram of a sour water stripper plant.

FIG. 1CL is a schematic diagram of a gas separation plant.

FIGS. 1CM-1CX illustrate configurations and related schemes for streams in amine regeneration plant, a sulfur recovery plant, a gas separation plant, a naphtha hydro-treating plant and a sour water stripper plant.

FIG. 1CM is a schematic diagram of a hydrocracking plant.

FIG. 1CN is a schematic diagram of a hydrocracking plant.

FIG. 1CO is a schematic diagram of a hydrocracking plant.

FIG. 1CP-1 is a schematic diagram of a hydrocracking plant.

FIG. 1CP-2 is a schematic diagram of a hydrocracking plant.

FIG. 1CQ is a schematic diagram of a hydrocracking plant.

FIG. 1CR is a schematic diagram of a diesel hydro-treating plant stripping section.

FIG. 1CS is a schematic diagram of a natural gas steam reforming hydrogen plant.

FIG. 1CT is a schematic diagram of a naphtha hydro-treating plant product splitting section.

FIG. 1CU is a schematic diagram of a sulfur recovery plant.

FIG. 1CV is a schematic diagram of an amine regeneration plant separation section.

FIG. 1CW is a schematic diagram of a sour water stripper plant.

FIG. 1CX is a schematic diagram of a gas separation plant.

DETAILED DESCRIPTION

Figure 1A:
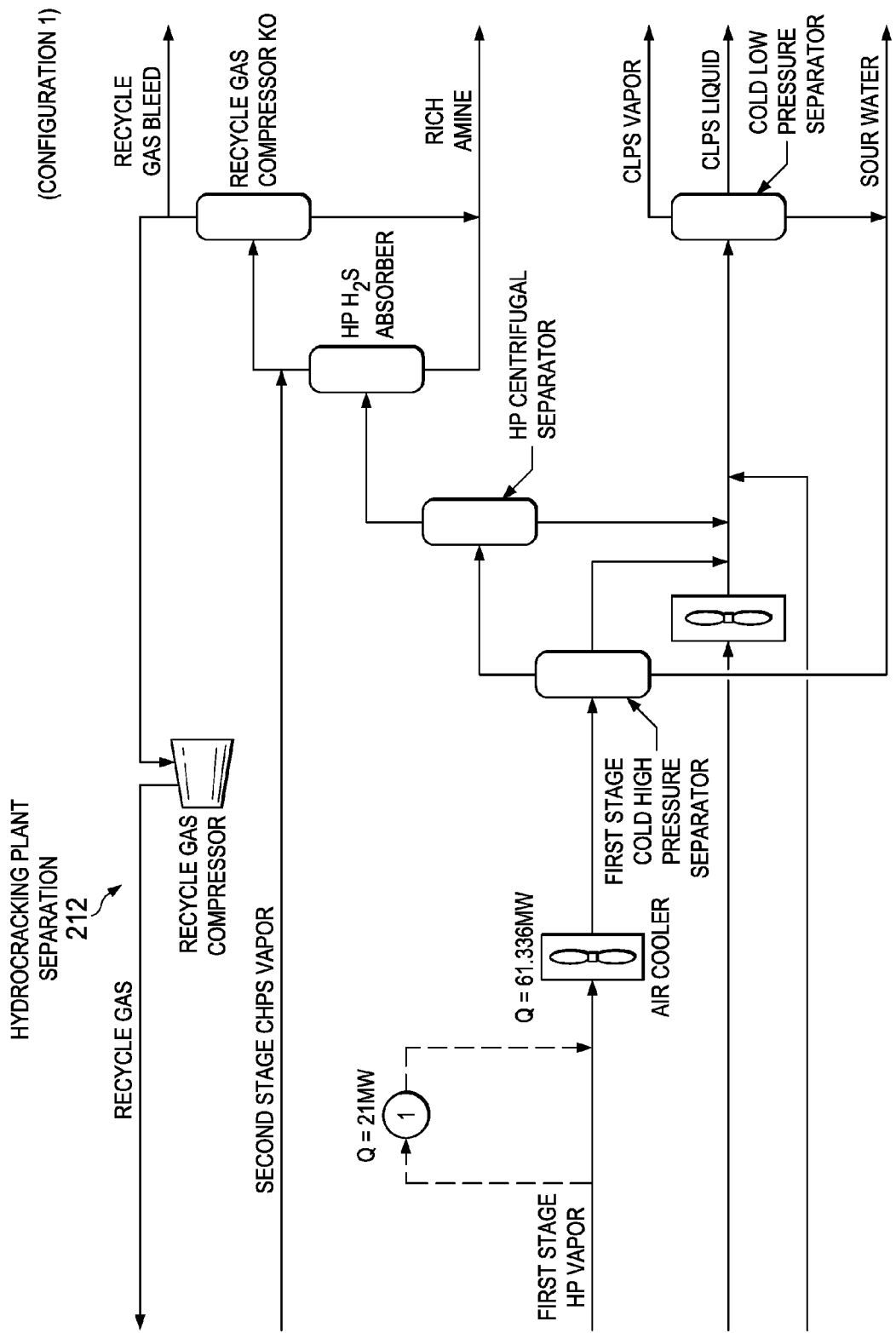
FIGS. 1A-1B illustrate configurations and related scheme details for heating a sulfur recovery plant stream in a sulfur recovery plant in the crude oil refining facility.

Industrial waste heat is a source for potential carbon-free power generation in many industrial facilities, for example, crude oil refineries, petrochemical and chemical complexes, and other industrial facilities. For example, a medium-size integrated crude oil refinery with aromatics up to 4,000 MM Btu/h (Million British Thermal Units per Hour) can be wasted to a network of air coolers extended along the crude oil and aromatics site. Some of the wasted heat can be reused to heat streams in refining sub-units of the crude oil refinery, thereby decreasing a quantity of heat that would otherwise need to be used to heat the streams. In this manner, a quantity of heat consumed by the crude oil refinery can decrease. In addition, a quantity of greenhouse gas (GHG) emission can also decrease. In some implementations, a reduction of about 34% in heating utility consumption and a reduction of about 20% in cooling utility consumption can be achieved without affecting an operational philosophy of the crude oil refinery.

The waste heat recovery and reuse techniques described here can be implemented in medium grade crude oil refining semi-conversion facilities and integrated medium grade crude oil refining semi-conversion oil refining and aromatics facilities. The implementations can result in energy efficient systems that can consume about 66% of the heating utility consumed by current state-of-the-art designs of existing and new crude oil refining facilities. The implementations can also result in decrease in pollution and in GHG emissions by about one-third relative to GHG emissions from current state-of-the-art designs of existing and new crude oil refining facilities.

In certain existing oil refining facilities, a stream in a plant (for example, a naphtha hydro-treating plant, a sour water stripper plant, or other plant) is heated using heat energy generated in a steam reboiler. In some implementations of the subject matter described here, the stream in the plant can be heated using waste heat carried by another stream in another plant (for example, a hydrocracking plant, a hydro-treating plant, a hydrogen plant, or other plant). By doing so, the heat energy generated in the steam reboiler can be decreased or eliminated. In other words, the steam reboiler need not be the only source of heat energy to heat the stream in the plant. The waste heat carried by the other stream in the other plant can either replace the heat energy generated in the steam reboiler or supplement the heat energy thereby decreasing a quantity of heat energy needed from the steam reboiler.

The subject matter described here can be implemented at different plants' specific operating modes and can be retrofitted without the need to change the network designs of existing heat exchanger designs in crude oil refineries. The minimum approach temperature used in the waste heat recovery and reuse processes can be as low as 3. In some implementations, higher minimum approach temperatures can be used in an initial phase at the expense of less waste heat/energy recovery, while relatively better energy saving is realized in a subsequent phase upon using the minimum approach temperature for the specific hot sources uses.

In sum, this disclosure describes several crude oil refinery-wide separation/distillation networks, configurations, and processing schemes for increasing energy efficiency of heating/cooling utilities. The increase in energy efficiency is realized by reusing all or part of waste heat, for example, low grade waste heat, carried by multiple, scattered low grade energy quality process streams.

Examples of Crude Oil Refinery Plants

1. Hydrogen Plant

Hydrogen is generally used in refineries for sulfur removal and quality improvement of hydrocarbon products. As sulfur restrictions on gasoline and diesel become stringent, the refining demand for hydrogen continues to grow. Two process schemes are employed in on-purpose hydrogen generation plants—conventional process and pressure swing adsorption (PSA) based process. Hydrogen production can include hydro-desulfurization, steam reforming, shift conversion and purification. The conventional process produces a medium-purity hydrogen, whereas the PSA-based process recovers and purifies the hydrogen to high purities, for example, purities greater than 99.9%.

2. Aromatics Complex

A typical aromatics complex includes a combination of process units for the production of basic petrochemical intermediates of benzene, toluene and xylenes (BTX) using the catalytic reforming of naphtha using continuous catalytic reformer (CCR) technology.

3. Gas Separation Plant

A gas separation plant includes a de-ethanizer and a de-propanizer, which are distillation columns used to isolate ethane and propane, respectively, in natural gas liquids (NGL) and light ends fractionation in gas plants and refineries. The de-ethanizer removes ethane from a mixture of propane, butane and other heavier components. An output of the de-ethanizer is fed to a de-propanizer to separate propane from the mixture.

4. Amine Regeneration Plant

Hydrogen sulfide and carbon dioxide are the most common contaminants present in natural gas and are present in relatively larger quantities than other contaminants which can adversely impact the natural gas processing facility if not removed. Amine is used in an acid gas absorber and regenerator to sweeten sour gases in a chemical process in which a weak base (for example, the amine) reacts with weak acids such as hydrogen sulfide and carbon dioxide to form a weak salt.

5. Hydrocracking Plant

Hydrocracking is a two-stage process combining catalytic cracking and hydrogenation. In this process heavy feedstocks are cracked in the presence of hydrogen to produce more desirable products. The process employs high pressure, high temperature, a catalyst, and hydrogen. Hydrocracking is used for feedstocks that are difficult to process by either catalytic cracking or reforming, since these feedstocks are characterized usually by high polycyclic aromaticscontent or high concentrations of the two principal catalyst poisons, sulfur and nitrogen compounds (or combinations of them).

The hydrocracking process depends on the nature of the feedstock and the relative rates of the two competing reactions, hydrogenation and cracking. Heavy aromaticsfeedstock is converted into lighter products under a wide range of high pressures and high temperatures in the presence of hydrogen and special catalysts. When the feedstock has a high paraffinic content, hydrogen prevents the formation of polycyclic aromaticscompounds. Hydrogen also reduces tar formation and prevents buildup of coke on the catalyst. Hydrogenation additionally converts sulfur and nitrogen compounds present in the feedstock to hydrogen sulfide and ammonia. Hydrocracking produces iso-butane for alkylation feedstock, and also performs isomerization for pour-point control and smoke-point control, both of which are important in high-quality jet fuel.

6. Diesel Hydro-Treating Plant

Hydro-treating is a refinery process for reducing sulfur, nitrogen and aromatics while enhancing cetane number, density and smoke point. Hydro-treating assists the refining industry's efforts to meet the global trend for stringent clean fuels specifications, the growing demand for transportation fuels and the shift toward diesel. In this process, fresh feed is heated and mixed with hydrogen. Reactor effluent exchanges heat with the combined feed and heats recycle gas and stripper charge. Sulphide (for example, ammonium bisulphide and hydrogen sulphide) is then removed from the feed.

7. Sour Water Stripper Utility Plant (SWSUP)

The SWSUP receives sour water streams from acid gas removal, sulfur recovery, and flare units, and the sour gas stripped and released from the soot water flash vessel. The SWSUP strips the sour components, primarily carbon dioxide ($CO_2$), hydrogen sulfide ($H_2S$) and ammonia ($NH_3$), from the sour water stream.

8. Sulfur Recovery Plant

Sulfur recovery facilities in refineries operate to regulate the discharge of sulfur compounds to the atmosphere to meet environmental regulations. In a sulfur recovery plant, combustion products that include sulfur can be processed, for example, by heating, cooling with condensers, using sulfur conversion catalyst, and by other processing techniques. One technique is to use amines to extract the sulfur and other acid gas compounds.

9. Naphtha Hydro-Treating Plant and Continuous Catalytic Reformer Plants

A Naphtha Hydrotreater (NHT) produces 101 Research Octane Number (RON) reformate, with a maximum 4.0 psi Reid Vapor Pressure (RVP), as a blending stock in the gasoline pool. It usually has the flexibility to process blends of Naphtha from the Crude Unit, Gas Condensate Splitter, Hydrocracker, Light Straight-Run Naphtha (LSRN) and Visbreaker Plants. The NHT processes naphtha to produce desulfurized feed for the CCR platformer and gasoline blending.

Heat Exchangers

In the configurations described in this disclosure, heat exchangers are used to transfer heat from one medium (for example, a stream flowing through a plant in a crude oil refining facility, a buffer fluid or other medium) to another medium (for example, a buffer fluid or different stream flowing through a plant in the crude oil facility). Heat exchangers are devices which transfer (exchange) heat typically from a hotter fluid stream to a relatively less hotter fluid stream. Heat exchangers can be used in heating and cooling applications, for example, in refrigerators, air conditions or other cooling applications. Heat exchangers can be distinguished from one another based on the direction in which liquids flow. For example, heat exchangers can be parallel-flow, cross-flow or counter-current. In parallel-flow heat exchangers, both fluid involved move in the same direction, entering and exiting the heat exchanger side-by-side. In cross-flow heat exchangers, the fluid path runs perpendicular to one another. In counter-current heat exchangers, the fluid paths flow in opposite directions, with one fluid exiting whether the other fluid enters. Counter-current heat exchangers are sometimes more effective than the other types of heat exchangers.

In addition to classifying heat exchangers based on fluid direction, heat exchangers can also be classified based on their construction. Some heat exchangers are constructed of multiple tubes. Some heat exchangers include plates with room for fluid to flow in between. Some heat exchangers enable heat exchange from liquid to liquid, while some heat exchangers enable heat exchange using other media.

Heat exchangers in crude oil refining and petrochemical facilities are often shell and tube type heat exchangers which include multiple tubes through which liquid flows. The tubes are divided into two sets—the first set contains the liquid to be heated or cooled; the second set contains the liquid responsible for triggering the heat exchange, i.e., the fluid that either removes heat from the first set of tubes by absorbing and transmitting the heat away or warms the first set by transmitting its own heat to the liquid inside. When designing this type of exchanger, care must be taken in determining the correct tube wall thickness as well as tube diameter, to allow optimum heat exchange. In terms of flow, shell and tube heat exchangers can assume any of three flow path patterns.

Heat exchangers in crude oil refining and petrochemical facilities can also be plate and frame type heat exchangers. Plate heat exchangers include thin plates joined together with a small amount of space in between, often maintained by a rubber gasket. The surface area is large, and the corners of each rectangular plate feature an opening through which fluid can flow between plates, extracting heat from the plates as it flows. The fluid channels themselves alternate hot and cold liquids, meaning that the heat exchangers can effectively cool as well as heat fluid. Because plate heat exchangers have large surface area, they can sometimes be more effective than shell and tube heat exchangers.

Other types of heat exchangers can include regenerative heat exchangers and adiabatic wheel heat exchangers. In a regenerative heat exchanger, the same fluid is passed along both sides of the exchanger, which can be either a plate heat exchanger or a shell and tube heat exchanger. Because the fluid can get very hot, the exiting fluid is used to warm the incoming fluid, maintaining a near constant temperature. Energy is saved in a regenerative heat exchanger because the process is cyclical, with almost all relative heat being transferred from the exiting fluid to the incoming fluid. To maintain a constant temperature, a small quantity of extra energy is needed to raise and lower the overall fluid temperature. In the adiabatic wheel heat exchanger, an intermediate liquid is used to store heat, which is then transferred to the opposite side of the heat exchanger. An adiabatic wheel consists of a large wheel with threats that rotate through the liquids—both hot and cold—to extract or transfer heat. The heat exchangers described in this disclosure can include any one of the heat exchangers described earlier, other heat exchangers, or combinations of them.

Each heat exchanger in each configuration can be associated with a respective thermal duty (or heat duty). The thermal duty of a heat exchanger can be defined as an amount of heat that can be transferred by the heat exchanger from the hot stream to the cold stream. The amount of heat can be calculated from the conditions and thermal properties of both the hot and cold streams. From the hot stream point of view, the thermal duty of the heat exchanger is the product of the hot stream flow rate, the hot stream specific heat, and a difference in temperature between the hot stream inlet temperature to the heat exchanger and the hot stream outlet temperature from the heat exchanger. From the cold stream point of view, the thermal duty of the heat exchanger is the product of the cold stream flow rate, the cold stream specific heat and a difference in temperature between the cold stream outlet from the heat exchanger and the cold stream inlet temperature from the heat exchanger. In several applications, the two quantities can be considered equal assuming no heat loss to the environment for these units, particularly, where the units are well insulated. The thermal duty of a heat exchanger can be measured in watts (W), megawatts (MW), millions of British Thermal Units per hour (Btu/hr), or millions of kilocalories per hour (Kcal/h). In the configurations described here, the thermal duties of the heat exchangers are provided as being "about X MW," where "X" represents a numerical thermal duty value. The numerical thermal duty value is not absolute. That is, the actual thermal duty of a heat exchanger can be approximately equal to X, greater than X or less than X.

Configurations in which heat exchangers are described as being in series can have multiple implementations. In some implementations, the heat exchangers can be arranged in series in one order (for example, a first heat exchanger, a second heat exchanger and a third heat exchanger in that order) while in other implementations, the heat exchangers can be arranged in series in a different order (for example, a third heat exchanger, a first heat exchanger and a second heat exchanger in that order). In other words, a first heat exchanger described as being in series with and downstream of a second heat exchanger in one implementation can be in series with and upstream of the second heat exchanger in a second, different implementation.

Flow Control System

In each of the configurations described later, process streams (also called "streams") are flowed within each plant in a crude oil refining facility and between plants in the crude oil refining facility. The process streams can be flowed using one or more flow control systems implemented throughout the crude oil refining facility. A flow control system can include one or more flow pumps to pump the process streams, one or more flow pipes through which the process streams are flowed and one or more valves to regulate the flow of streams through the pipes.

In some implementations, a flow control system can be operated manually. For example, an operator can set a flow rate for each pump and set valve open or close positions to regulate the flow of the process streams through the pipes in the flow control system. Once the operator has set the flow rates and the valve open or close positions for all flow control systems distributed across the crude oil refining facility, the flow control system can flow the streams within a plant or between plants under constant flow conditions, for example, constant volumetric rate or other flow conditions. To change the flow conditions, the operator can manually operate the flow control system, for example, by changing the pump flow rate or the valve open or close position.

In some implementations, a flow control system can be operated automatically. For example, the flow control system can be connected to a computer system to operate the flow control system. The computer system can include a computer-readable medium storing instructions (such as flow control instructions and other instructions) executable by one or more processors to perform operations (such as flow control operations). An operator can set the flow rates and the valve open or close positions for all flow control systems distributed across the crude oil refining facility using the computer system. In such implementations, the operator can manually change the flow conditions by providing inputs through the computer system. Also, in such implementations, the computer system can automatically (that is, without manual intervention) control one or more of the flow control systems, for example, using feedback systems implemented in one or more plants and connected to the computer system. For example, a sensor (such as a pressure sensor, temperature sensor or other sensor) can be connected to a pipe through which a process stream flows. The sensor can monitor and provide a flow condition (such as a pressure, temperature, or other flow condition) of the process stream to the computer system. In response to the flow condition exceeding a threshold (such as a threshold pressure value, a threshold temperature value, or other threshold value), the computer system can automatically perform operations. For example, if the pressure or temperature in the pipe exceeds the threshold pressure value or the threshold temperature value, respectively, the computer system can provide a signal to the pump to decrease a flow rate, a signal to open a valve to relieve the pressure, a signal to shut down process stream flow, or other signals.

This disclosure describes new energy efficient hydrocracking-based configurations and related processing schemes for medium grade semi-conversion crude oil refining facility.

A semi-conversion medium grade crude oil refining facility is one that does not include an aromatics complex. This disclosure describes a waste heat recovery and reuse network for such a refining facility. As described later, waste heat can be recovered from one or more of the units in the refining facility. Such a refinery typically consumes several hundred megawatts of energy (for example, about 400 MW) in heating utilities. Implementing the configurations described here can not only reduce energy consumption but also reduce energy-based greenhouse gas (GHG) emissions. In particular, this disclosure describes a method implemented in a crude oil refining facility to heat a stream in a plant of the crude oil refining facility using a hydrocracking plant stream in a hydrocracking plant of the crude oil refining facility. Several configurations of process schemes for doing so are described below with reference to the following figures.

Configuration 1

Figure 1B:
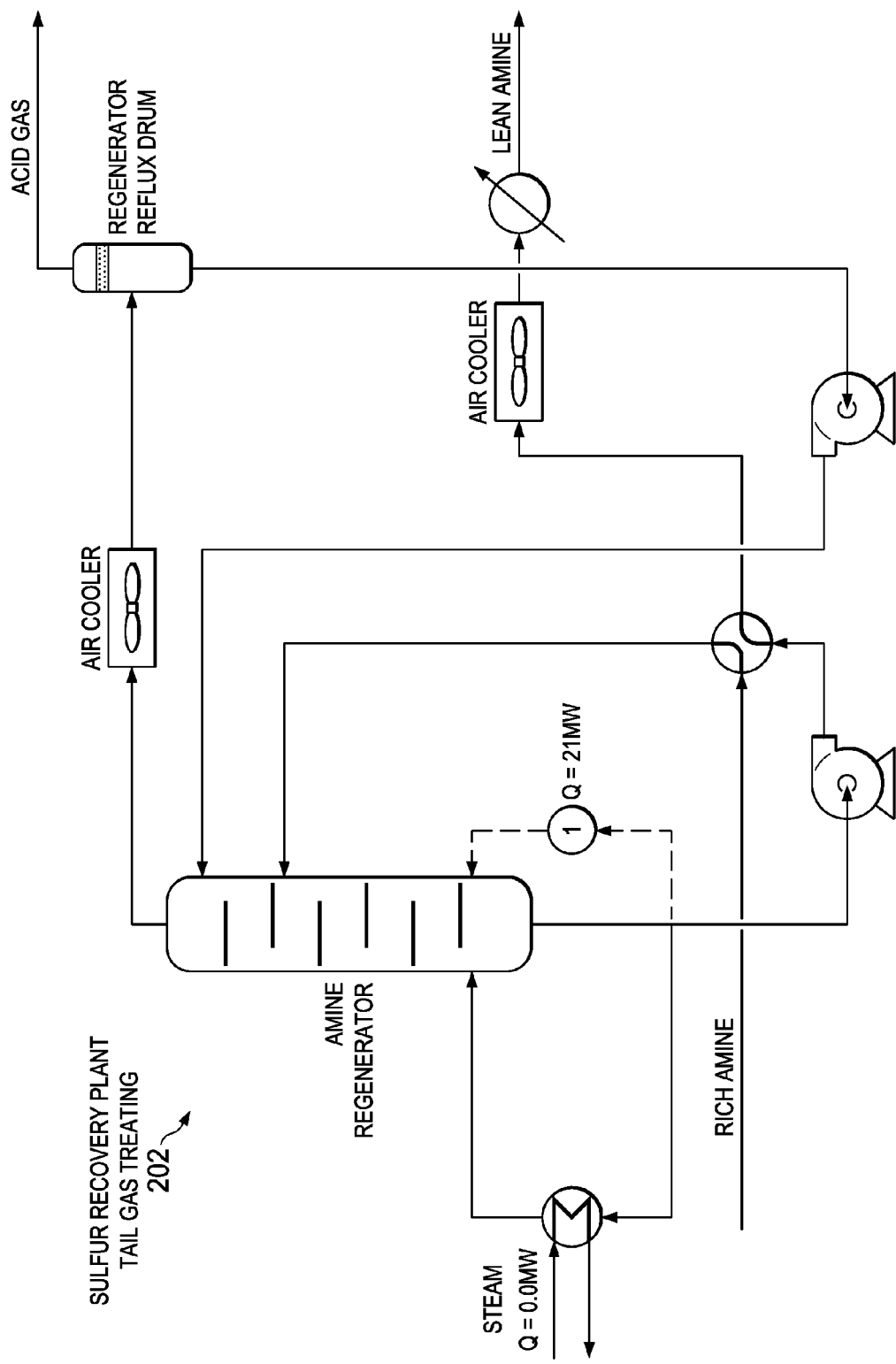

FIGS. 1A-1B illustrate configurations and related scheme details for heating a sulfur recovery plant stream in a sulfur recovery plant in the crude oil refining facility. In some implementations, a first stream in a first plant can be directly heated using a second stream in a second plant. In some implementations, the first plant is sulfur recovery plant; the first stream is the amine regenerator bottoms stream; the second plant is the hydrocracking plant; and the second stream is the first stage reaction section feed to a first stage cold high pressure separator stream.

The configurations illustrated in FIGS. 1A-1B thermally integrate the hydrocracking plant and the sulfur recovery plant to in the crude oil refining facility to reduce the crude oil refining facility's energy consumption (for example, heating and cooling utilities). For example, a reduction in energy consumption by about 21 MW can translate to about 6% of the energy consumption in the crude oil refining facility. As described later, in certain schemes, a process stream (for example, a sulfur recovery plant stream or other process streams) can be used to directly heat another process stream (for example, a hydrocracking plant stream or other process stream).

As shown in FIG. 1A, a first stage reaction section feed to a first stage cold high pressure separator stream in the hydrocracking plant 212 directly heats a sulfur recovery plant amine regenerator bottom stream in a first heat exchanger with a thermal duty that can range between about 15 MW and 25 MW (for example, 21 MW). The transfer of heat directly to another process stream captures heat that would have otherwise been discharged to the environment. The first stage reaction section feed to a first stage cold high pressure separator stream is returned to the hydrocracking plant 212 for further processing.

FIG. 1B shows a sulfur recovery plant 202 in the crude oil refining facility. The heated amine regenerator bottom stream is flowed to the sulfur recovery plant 202. As shown in FIG. 1B, the steam heat input for the amine regenerator can be 0 MW because the alternative flow path disclosed in this configuration may satisfy the entire heat load for the operation of the column. In an alternative embodiment, the steam heat input for the amine regenerator can be reduced because the alternative flow path disclosed in this configuration may partially satisfy the heat load for the operation of the column.

In this manner, the sulfur recovery plant is heated directly using the hydrocracking plant, thereby saving about 21 MW of heat energy.

Configuration 2

FIGS. 1C-1G illustrate configurations and related scheme details for heating a sour water stripper plant stream. In some implementations, a first stream in a first plant can be directly heated using multiple second streams in a second plant. In some implementations, the first plant is sulfur recovery plant; the first stream is the amine regenerator bottoms stream; the second plant is the hydrocracking plant; and the second multiple streams are the diesel product, the first stage reaction section feed to a first stage cold high pressure separator stream and the kerosene product streams.

The configurations illustrated in FIGS. 1C-1G thermally integrate the hydrocracking plant and the sour water stripper plant in the crude oil refining facility to reduce the crude oil refining facility's energy consumption (for example, heating and cooling utilities). For example, a reduction in energy consumption by about 32 MW can translate to about 8% of the energy consumption in the crude oil refining facility. As described later, in certain schemes, a process stream (for example, a sour water stripper stream or other process streams) can be used to directly heat another process stream (for example, a hydrocracking plant stream or other process stream).

Figure 1D:
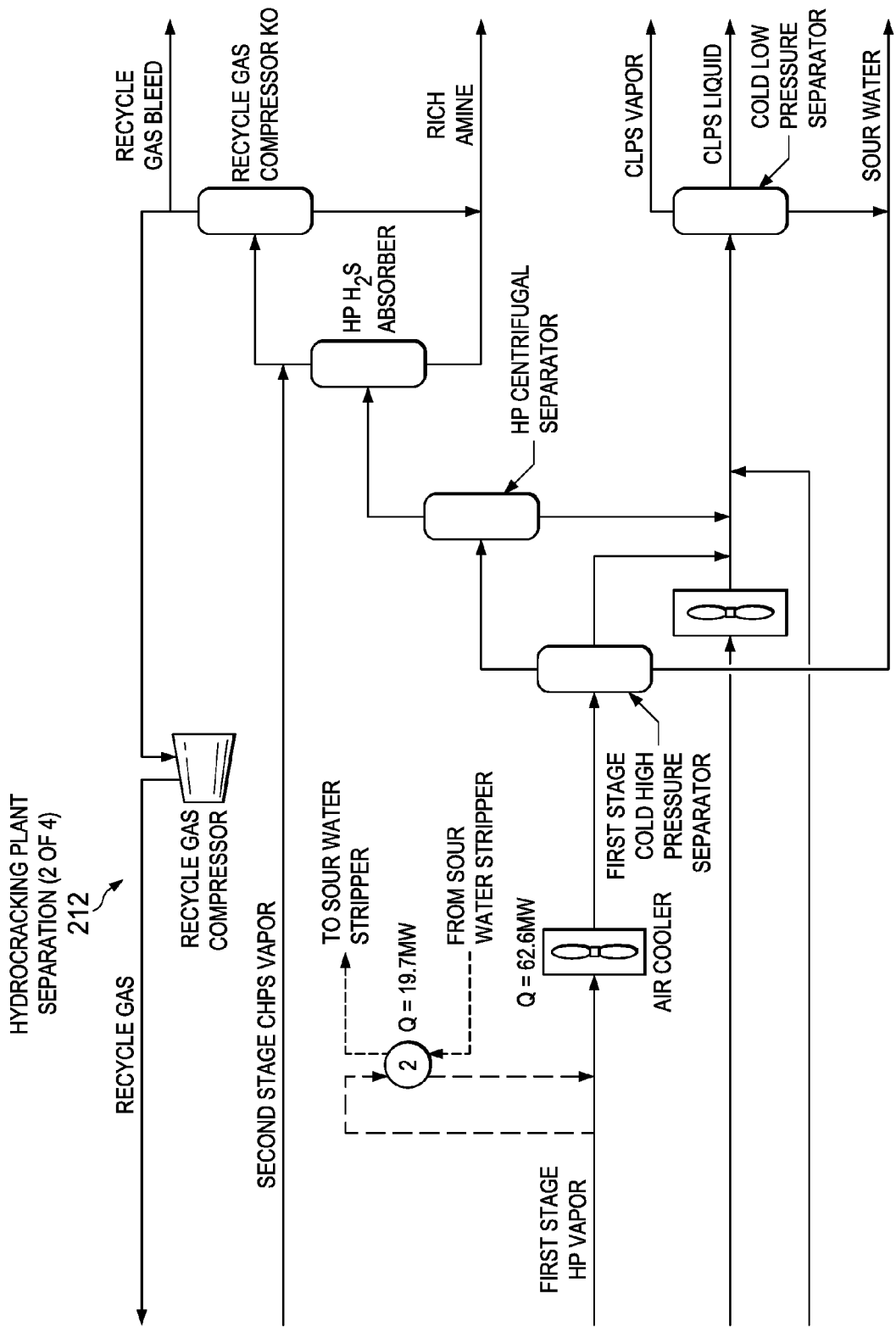
Figures 1, 1E:
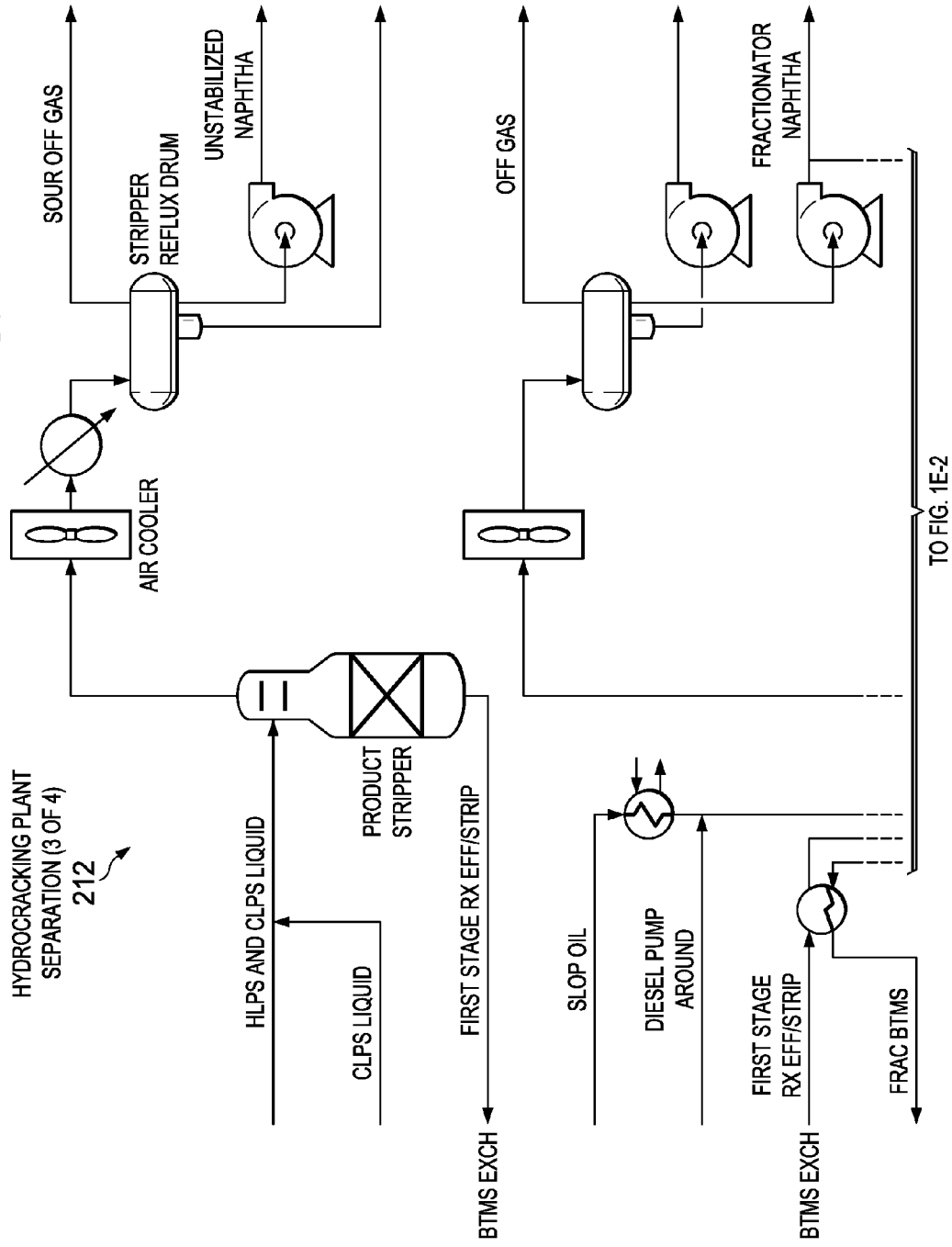
Figures 1, 1E, 2:
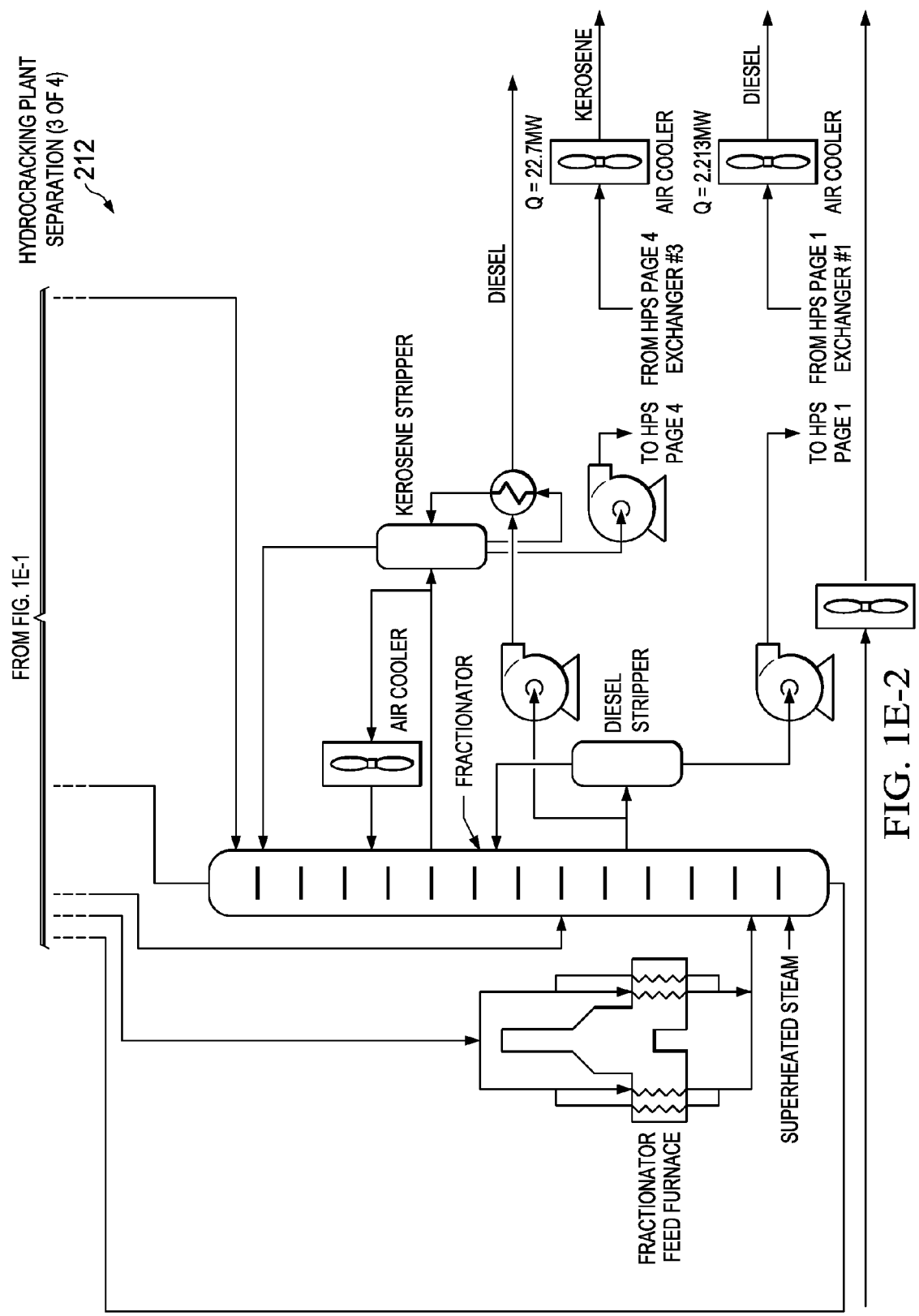
Figure 1F:
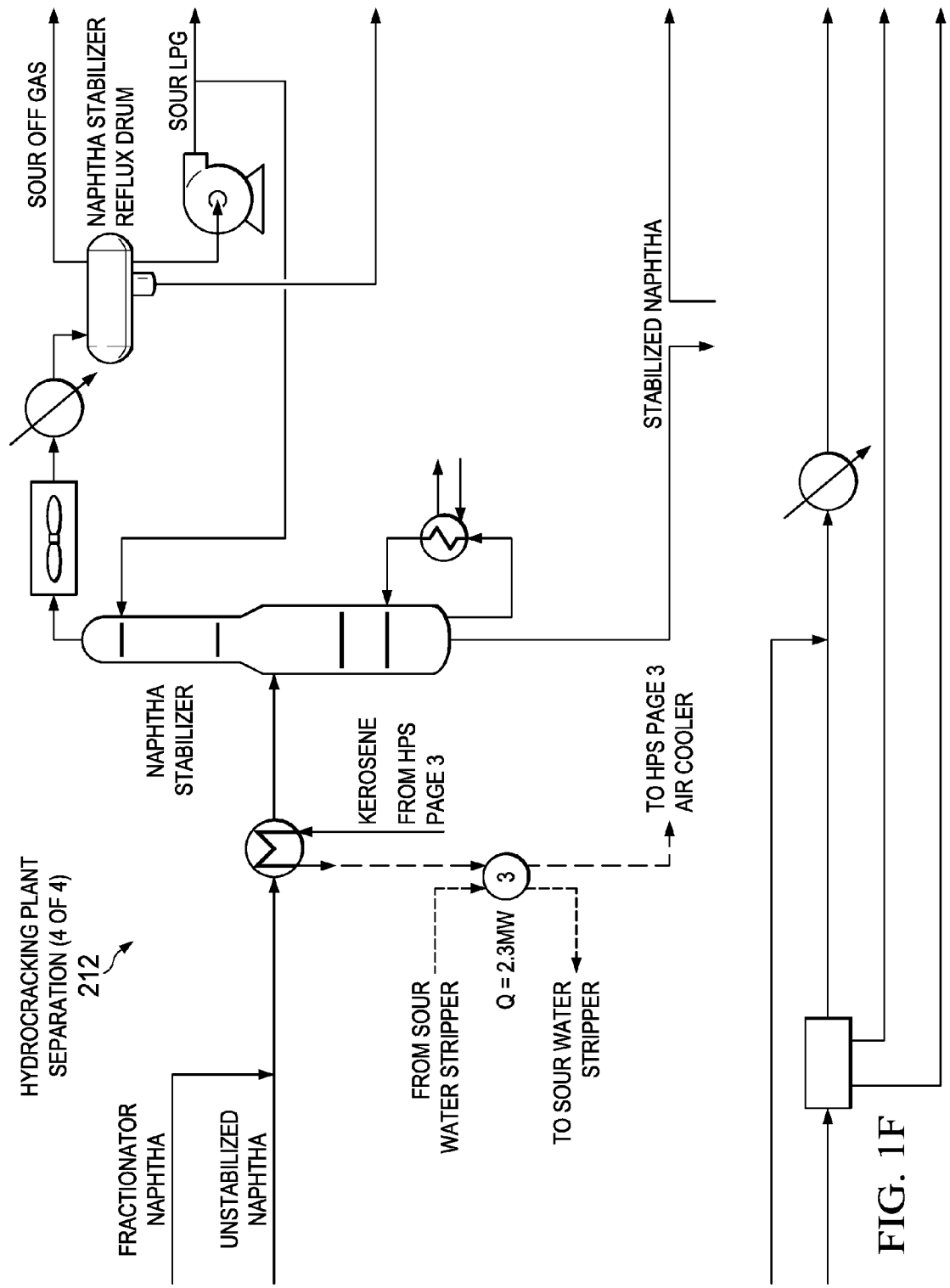
Figure 1G:
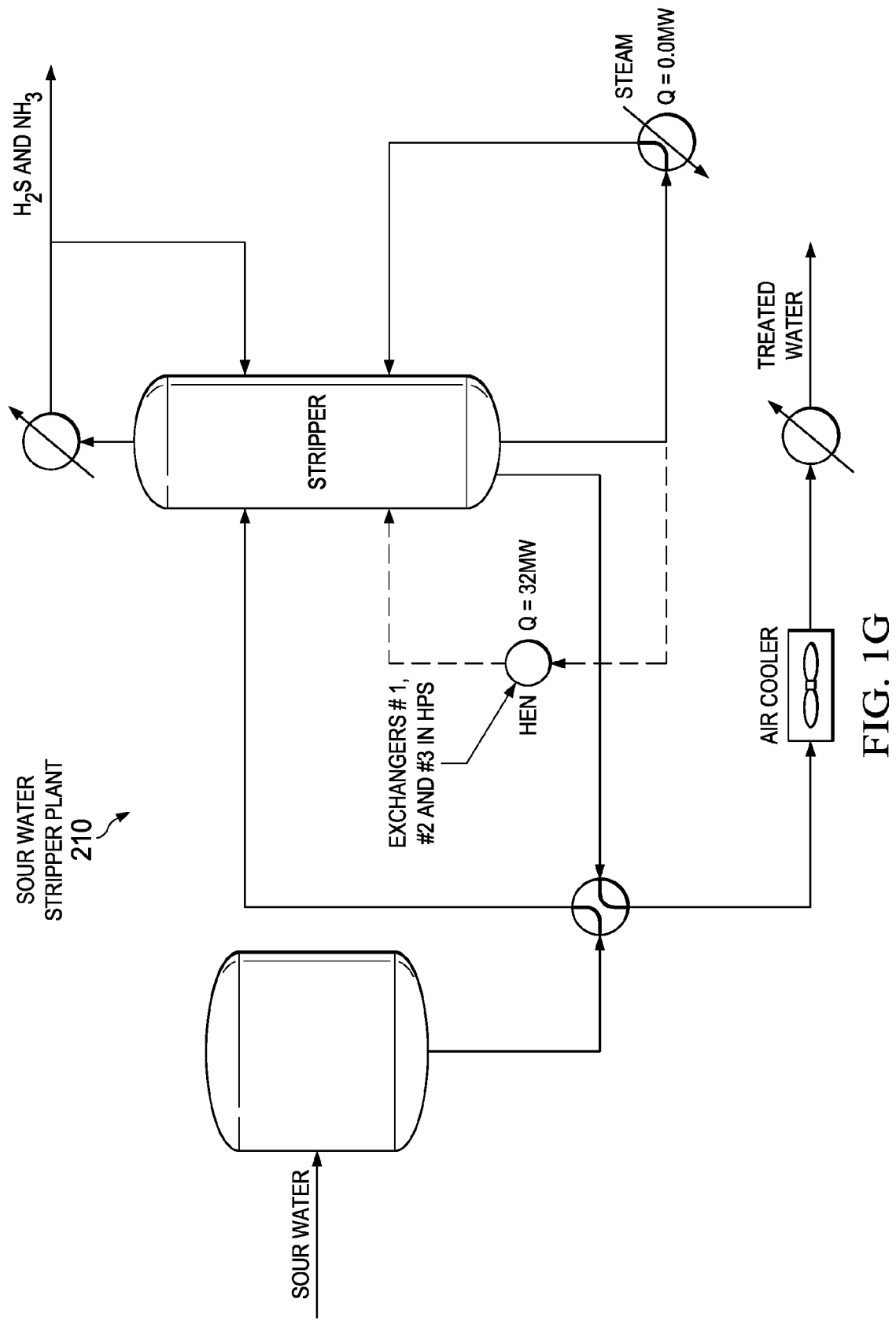
Figure 1H:
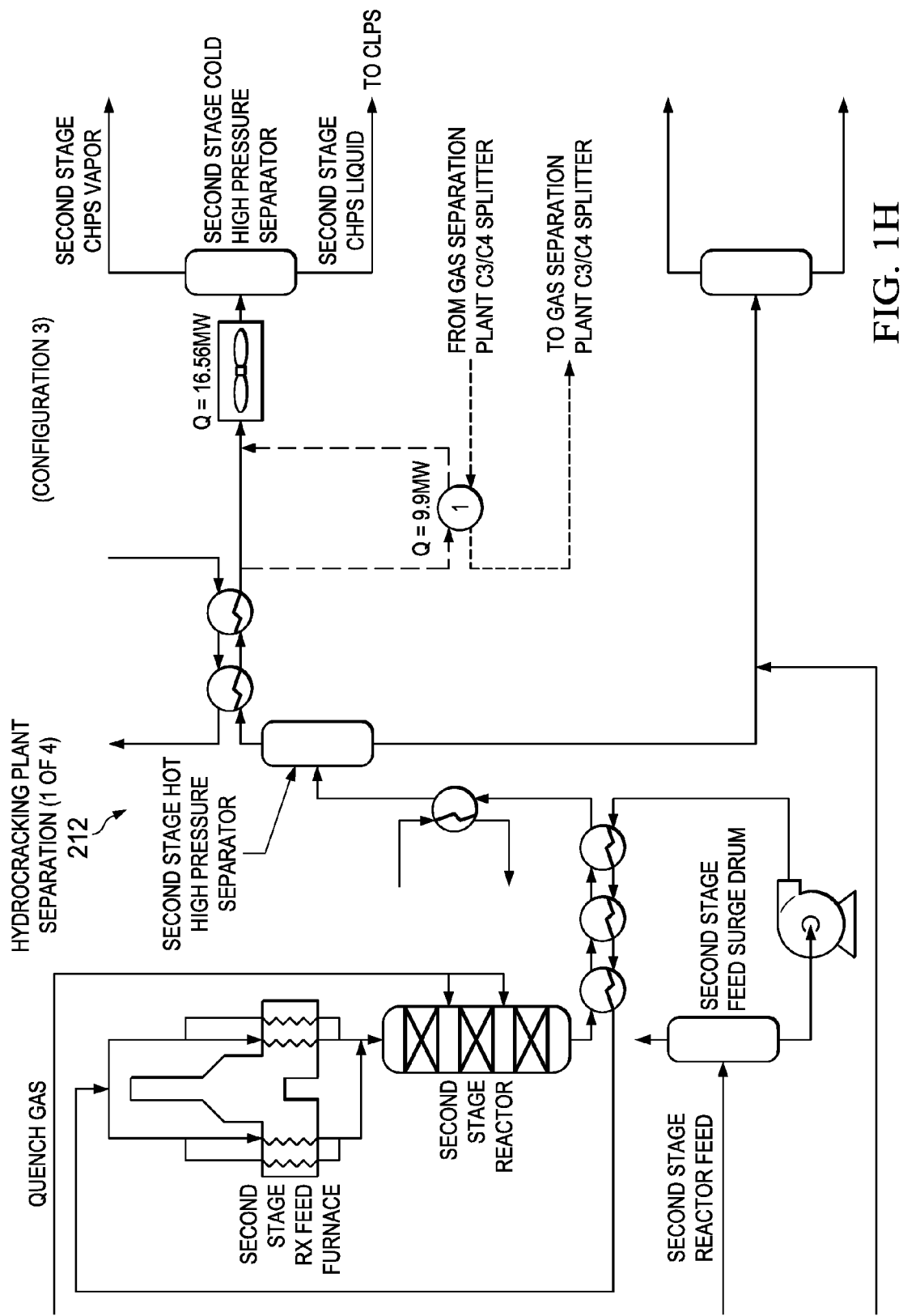
Figure 1I:
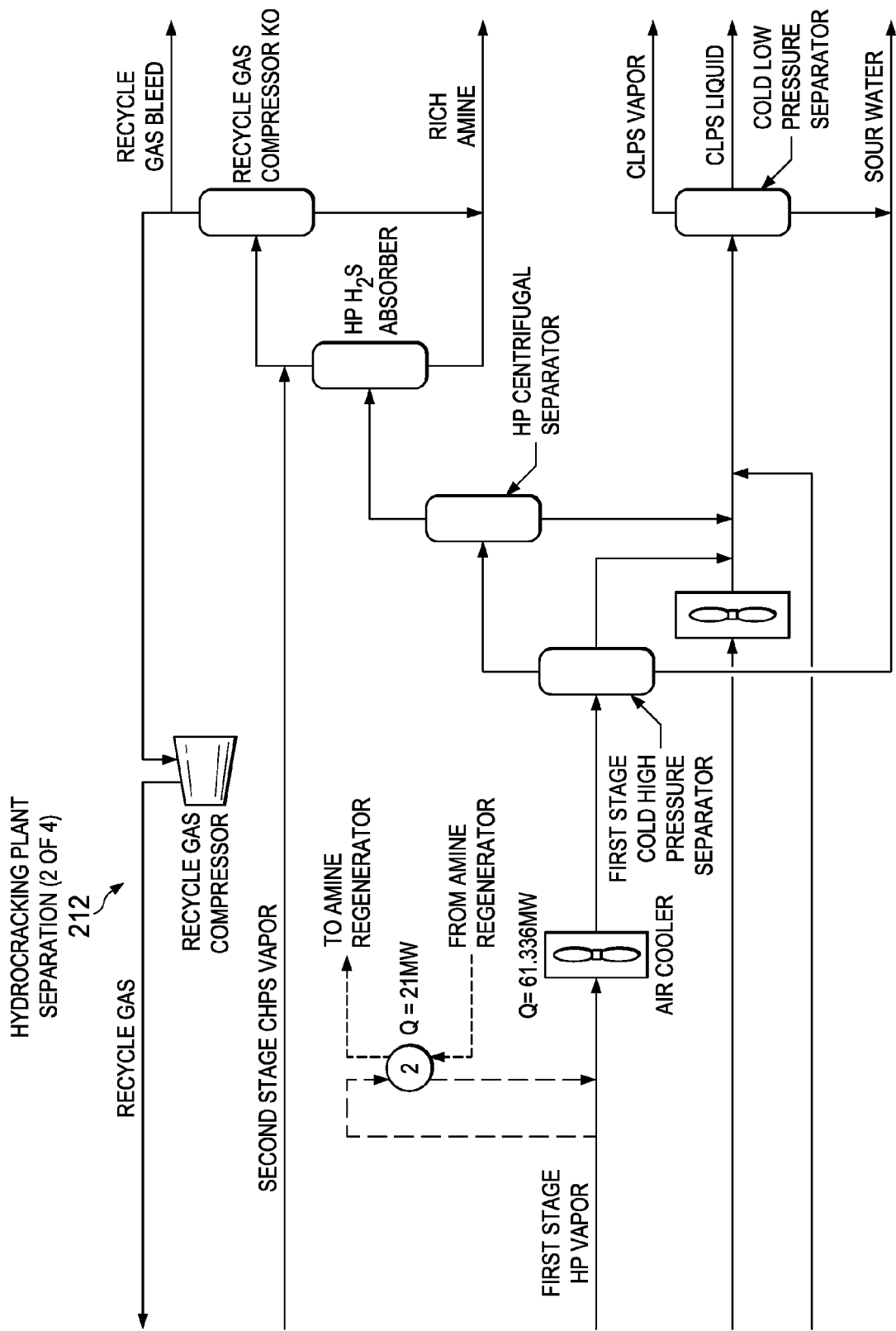
Figures 1, 1J:
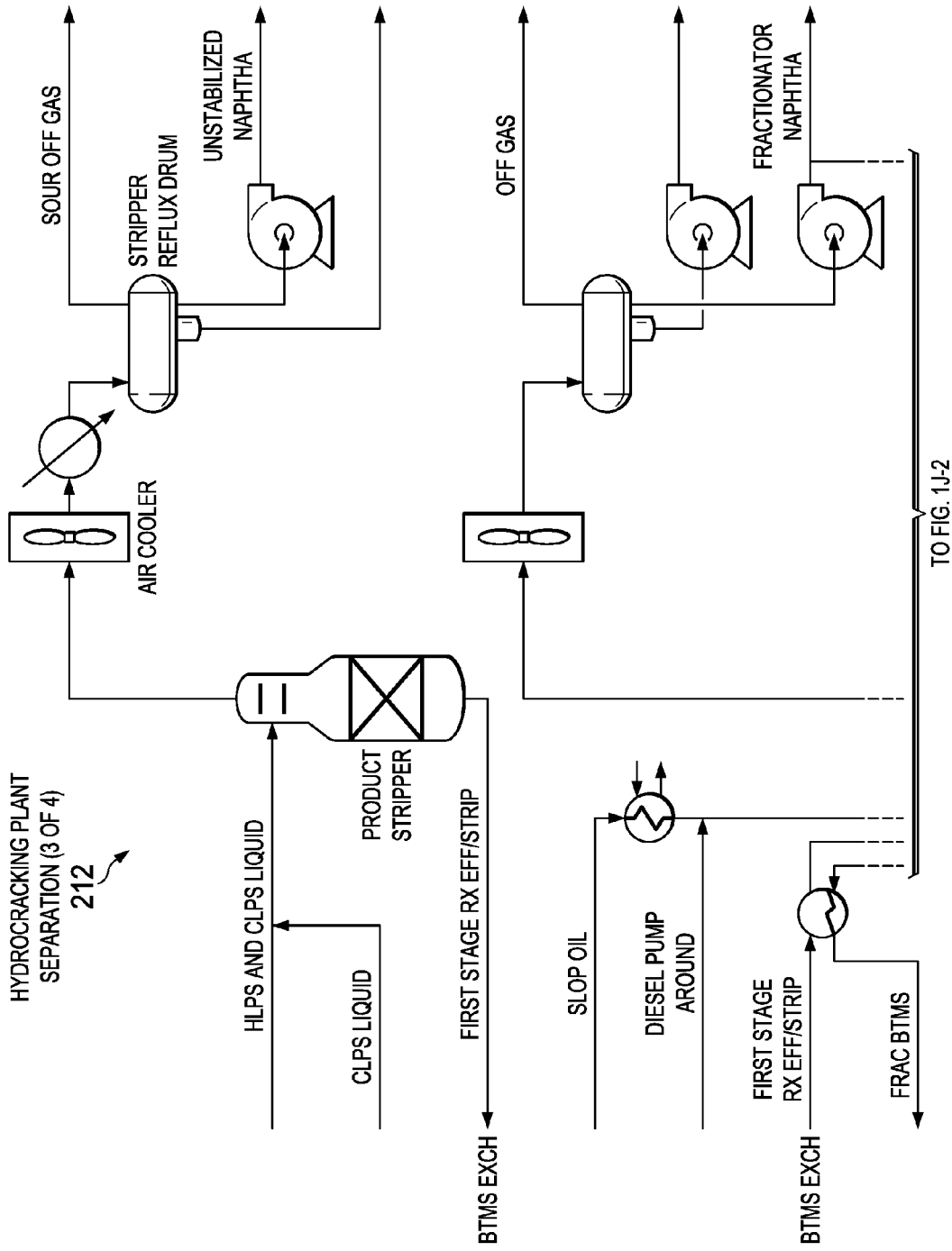
Figures 1, 1J, 2:
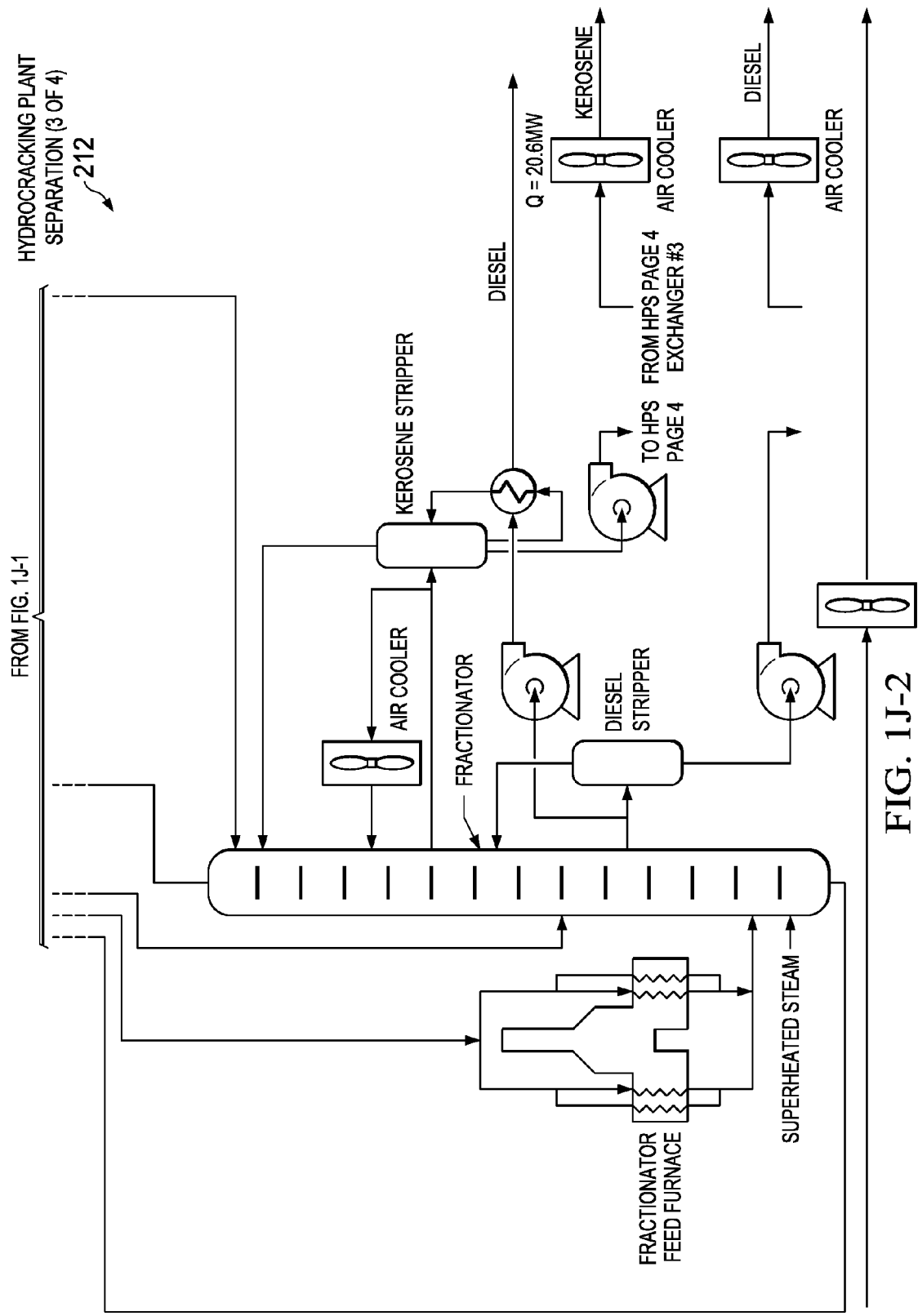
Figure 1K:
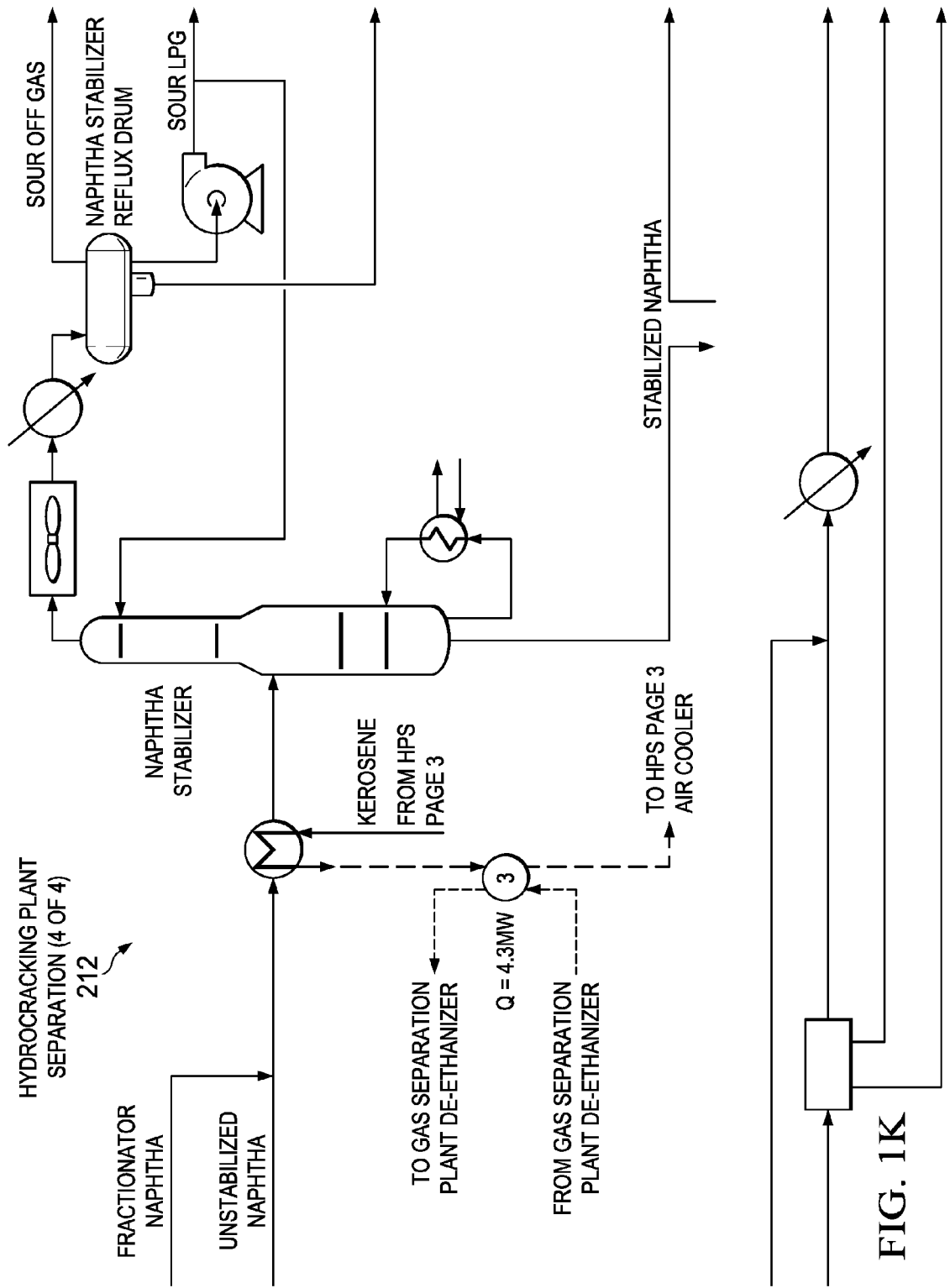
Figure 1L:
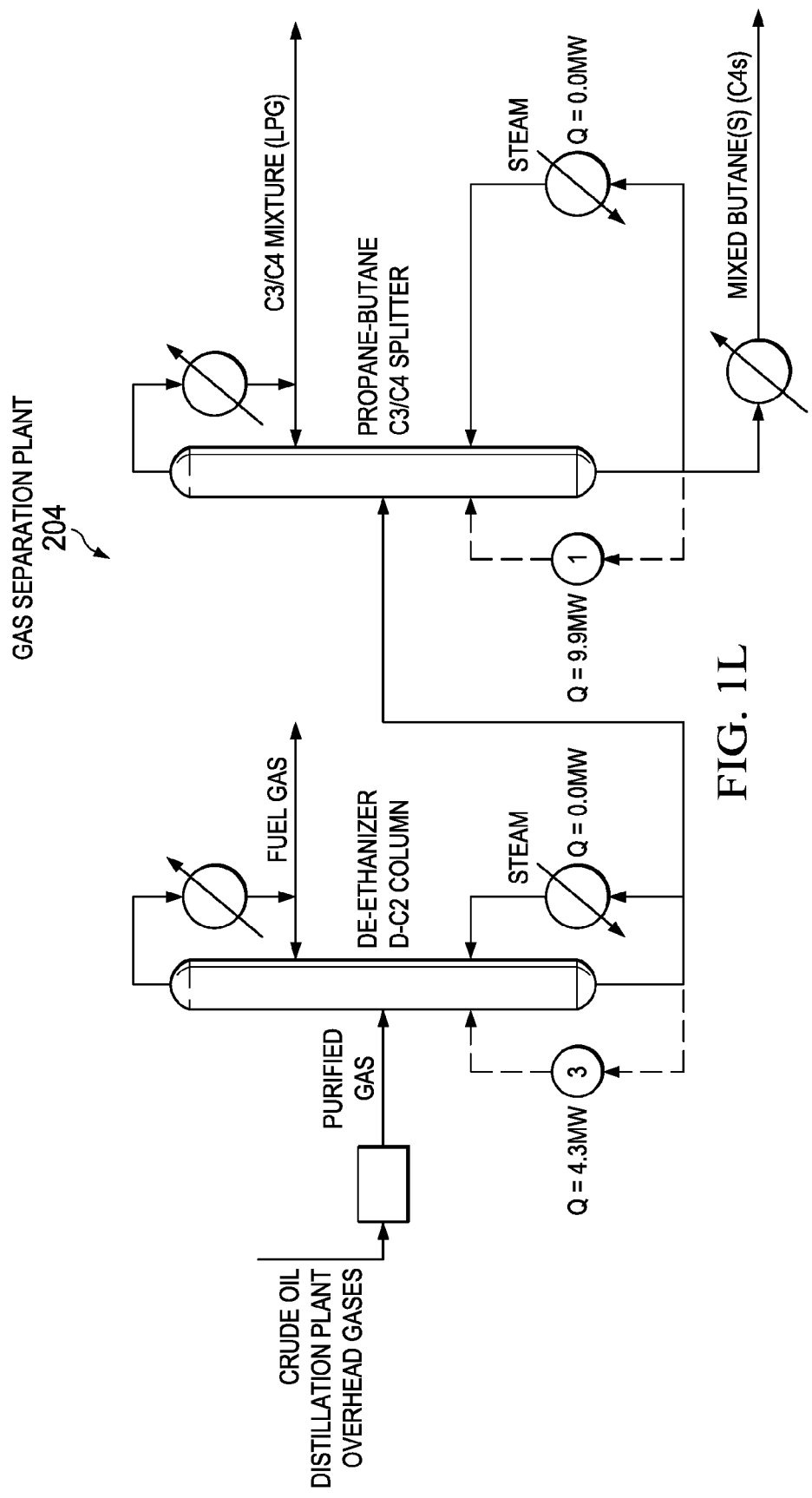
Figure 1M:
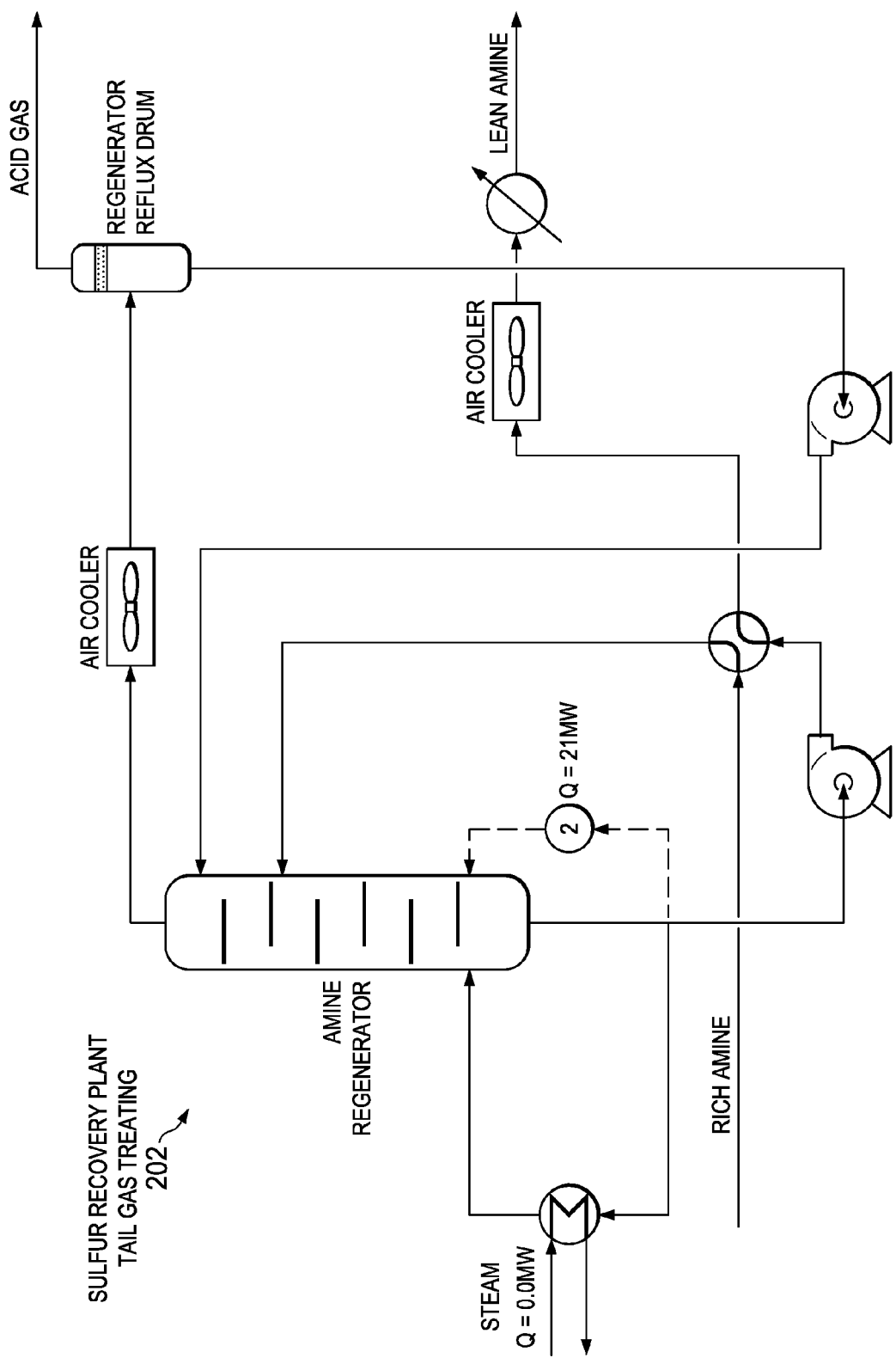
Figure 1N:
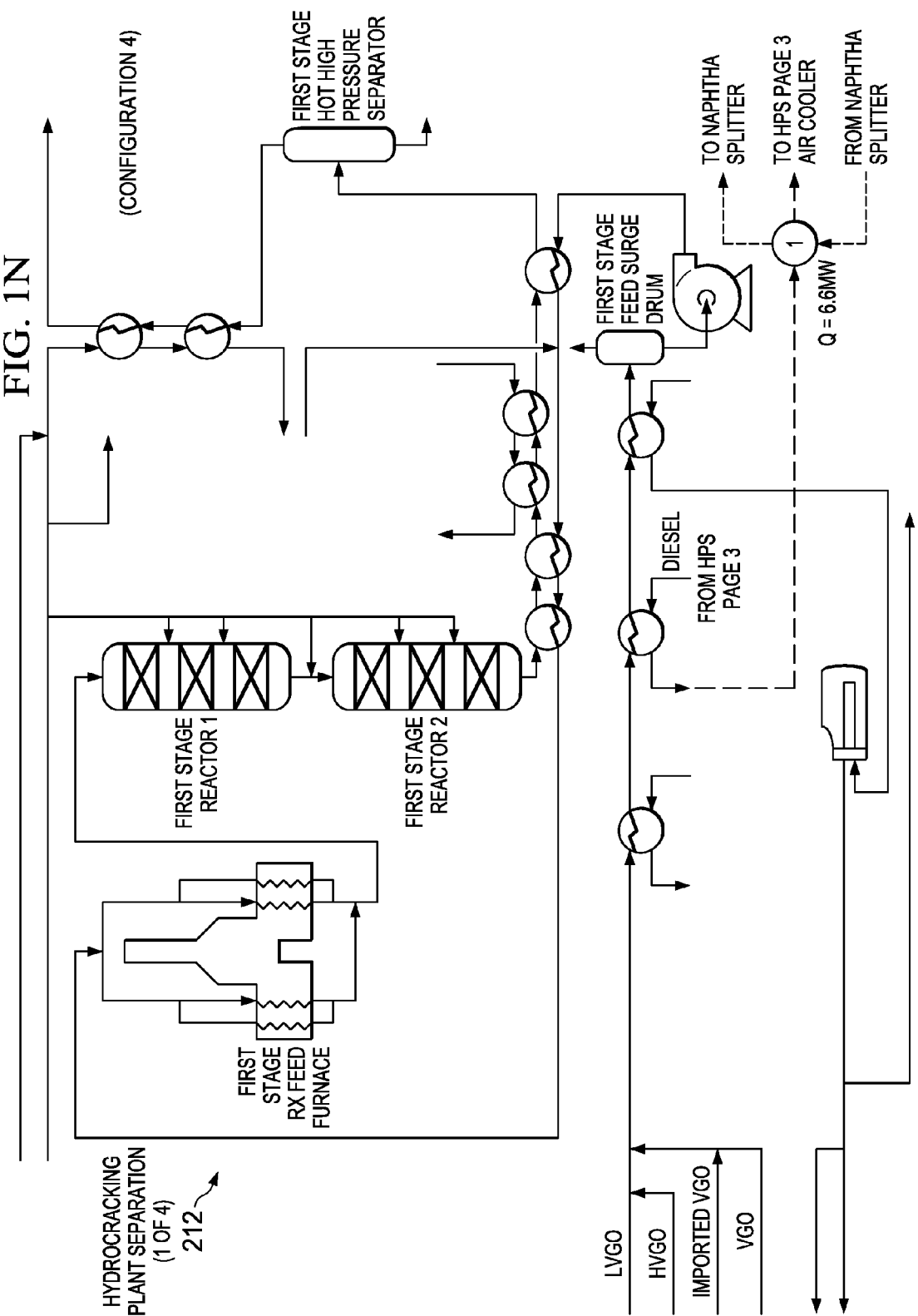
Figure 1O:
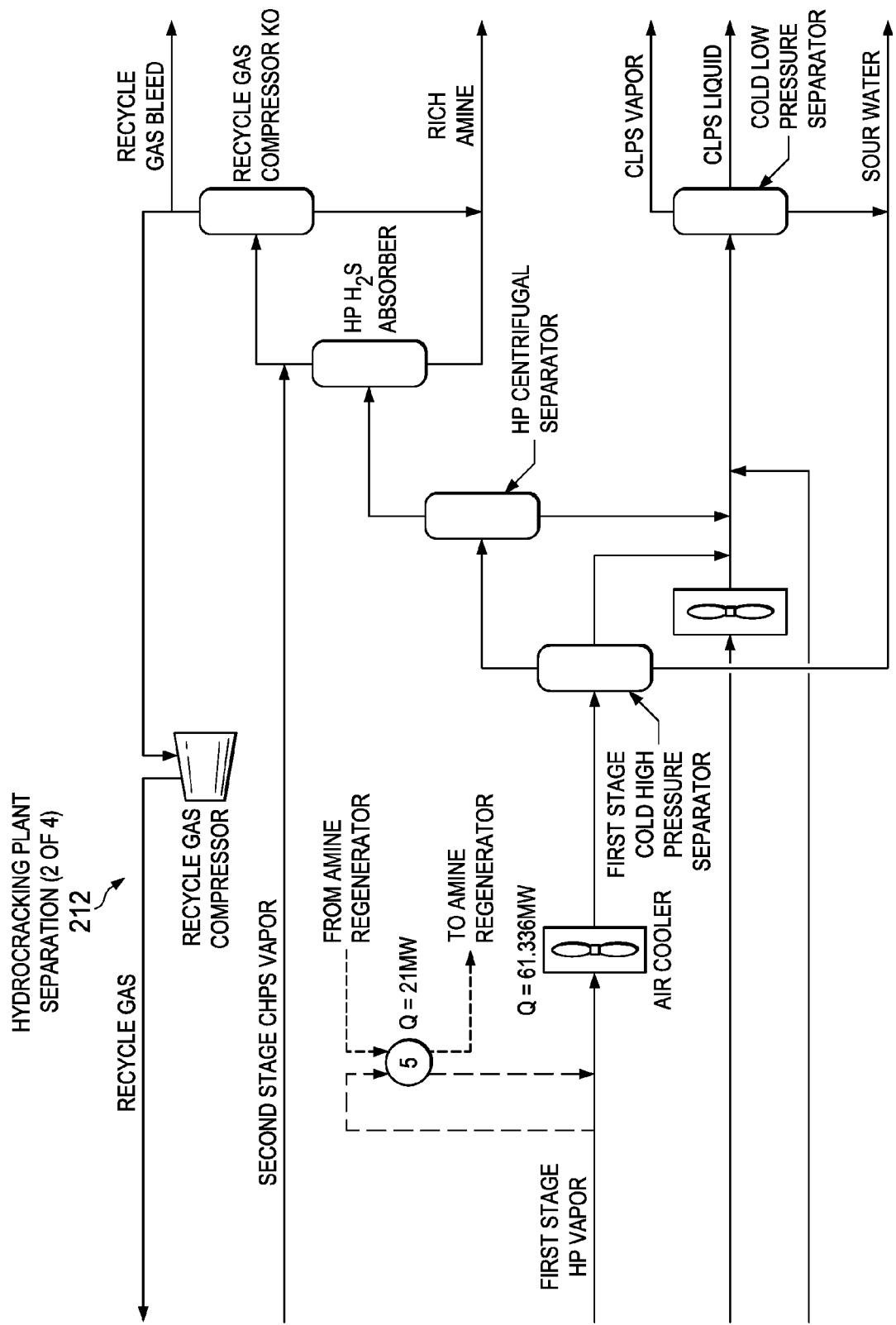
Figures 1, 1P:
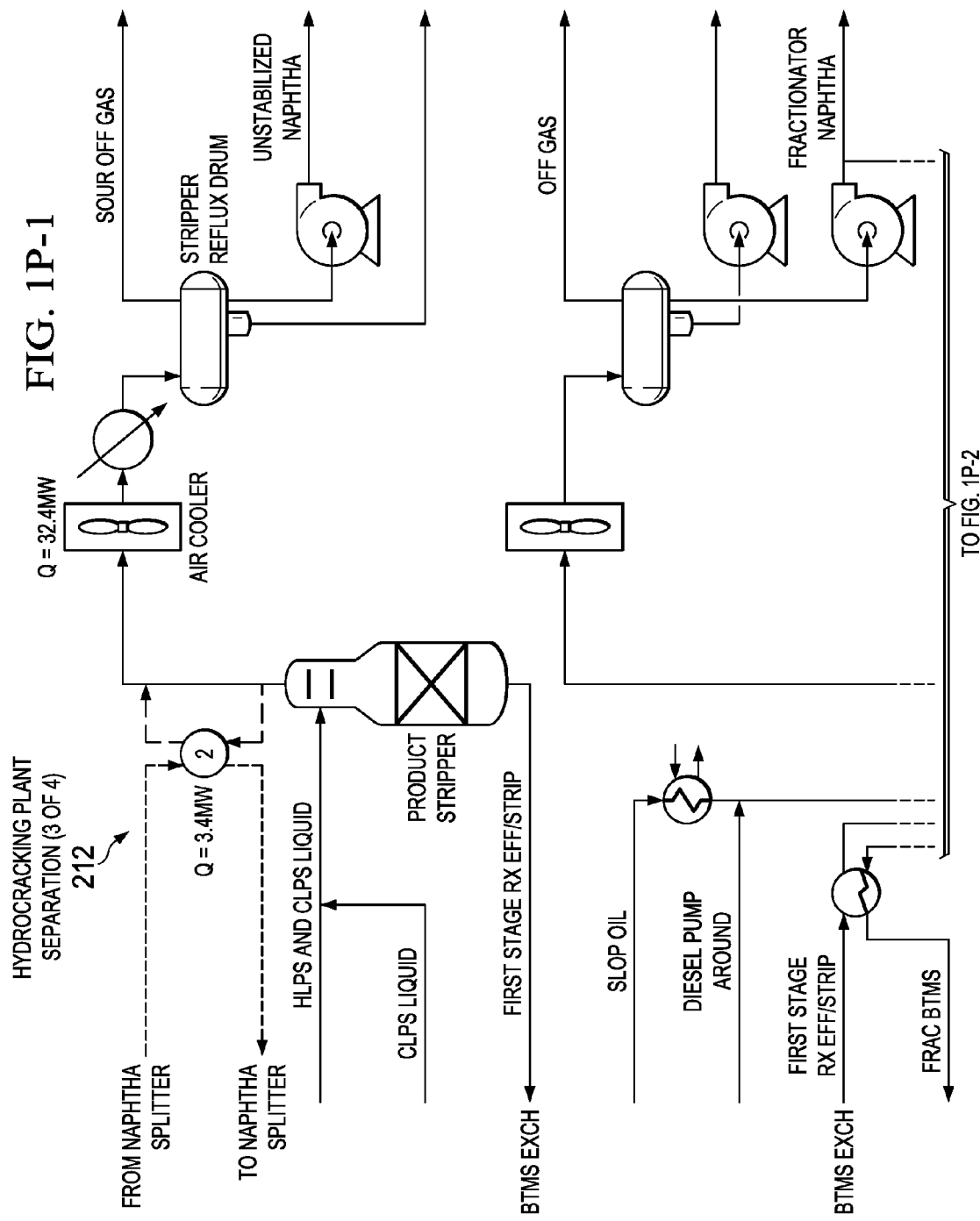
Figures 1, 1P, 2:
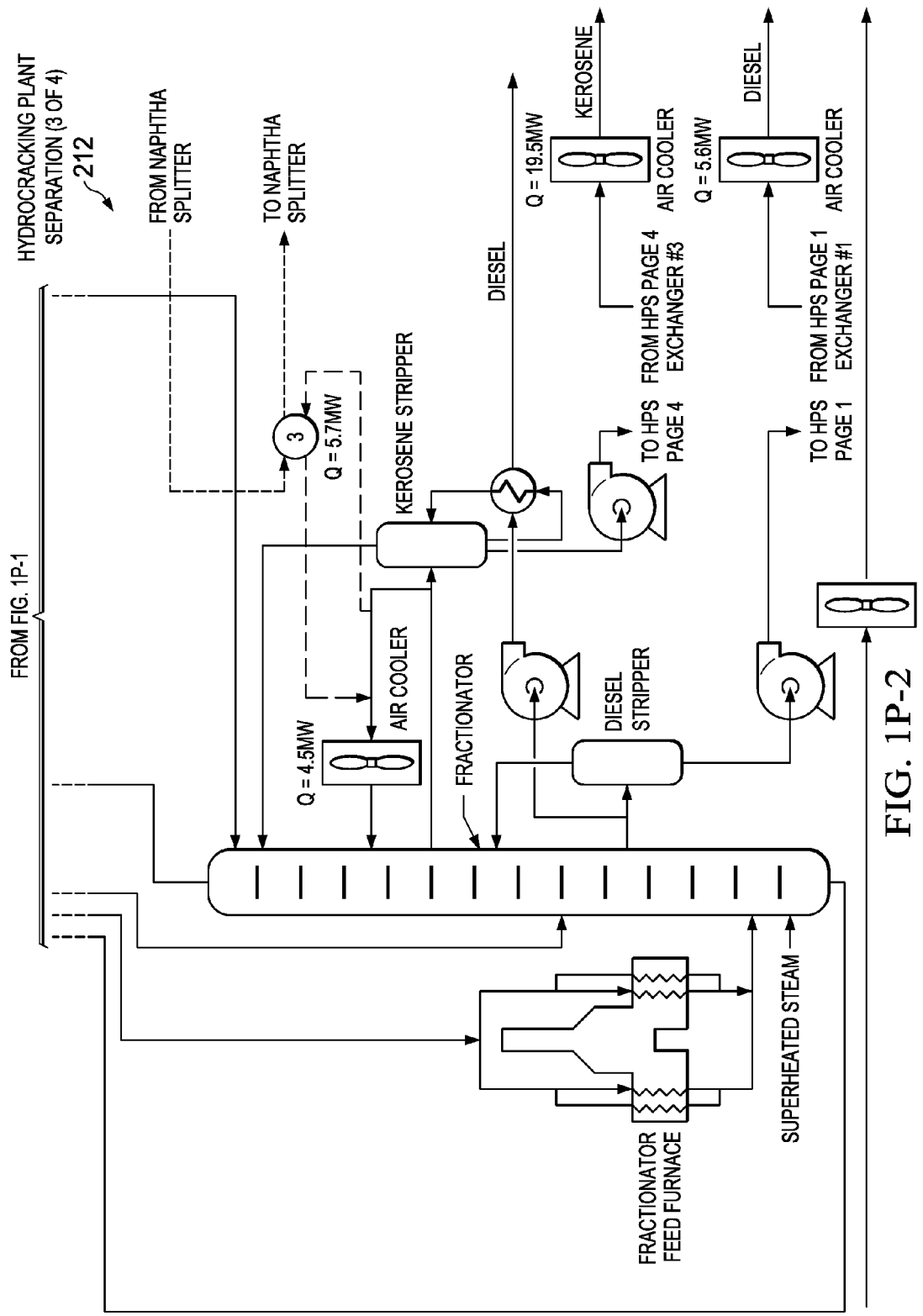
Figure 1Q:
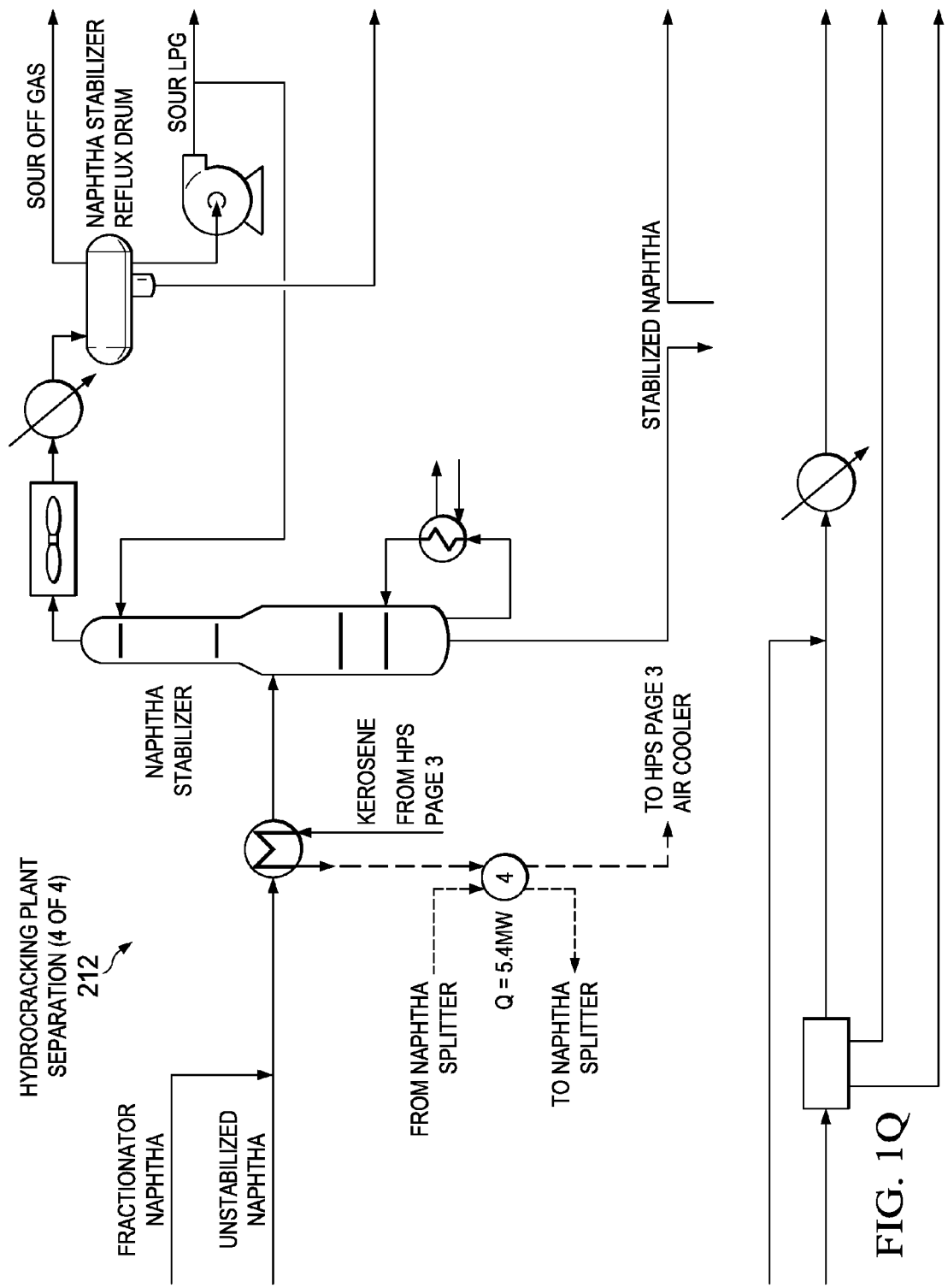
Figure 1R:
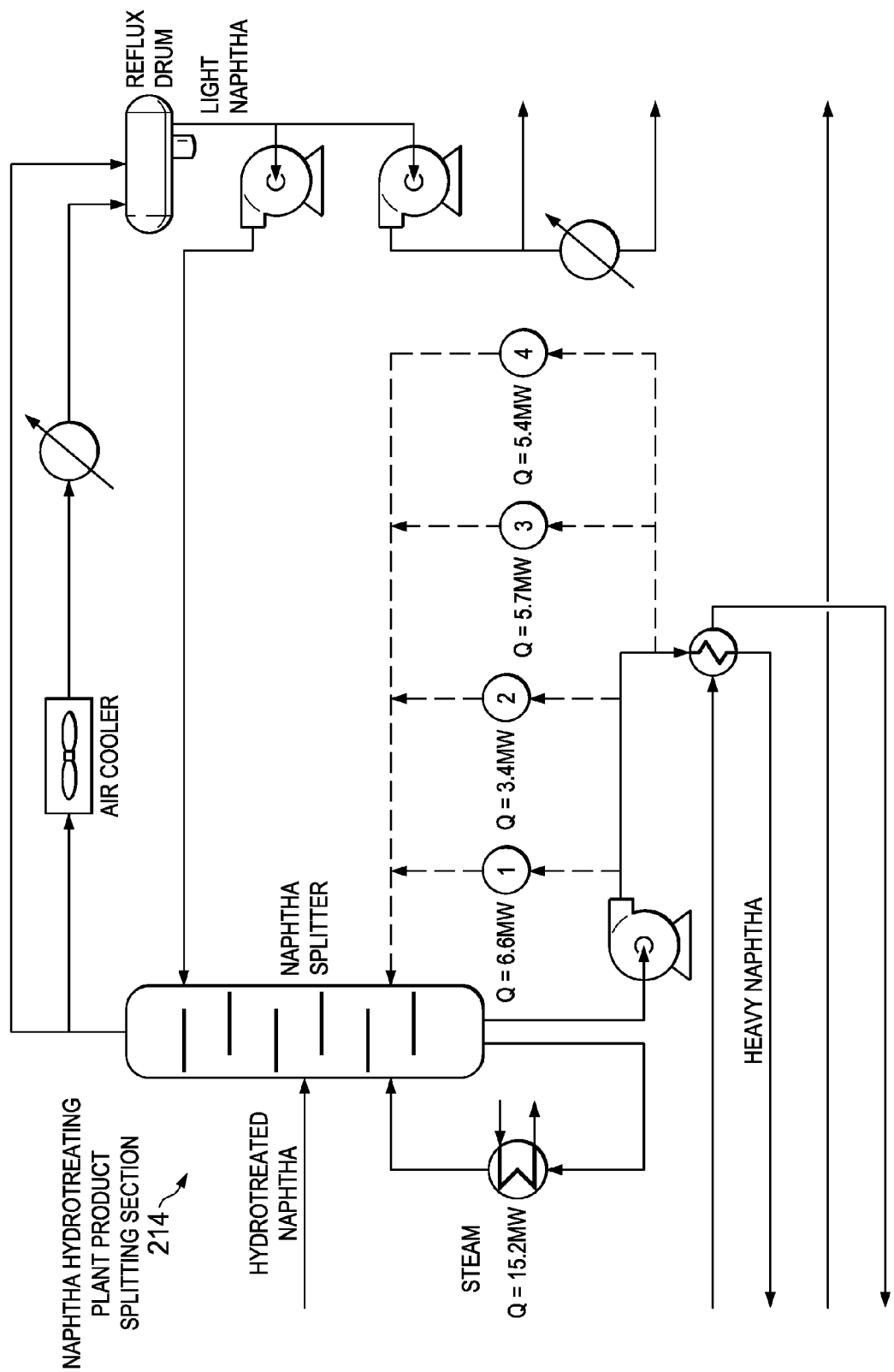
Figure 1S:
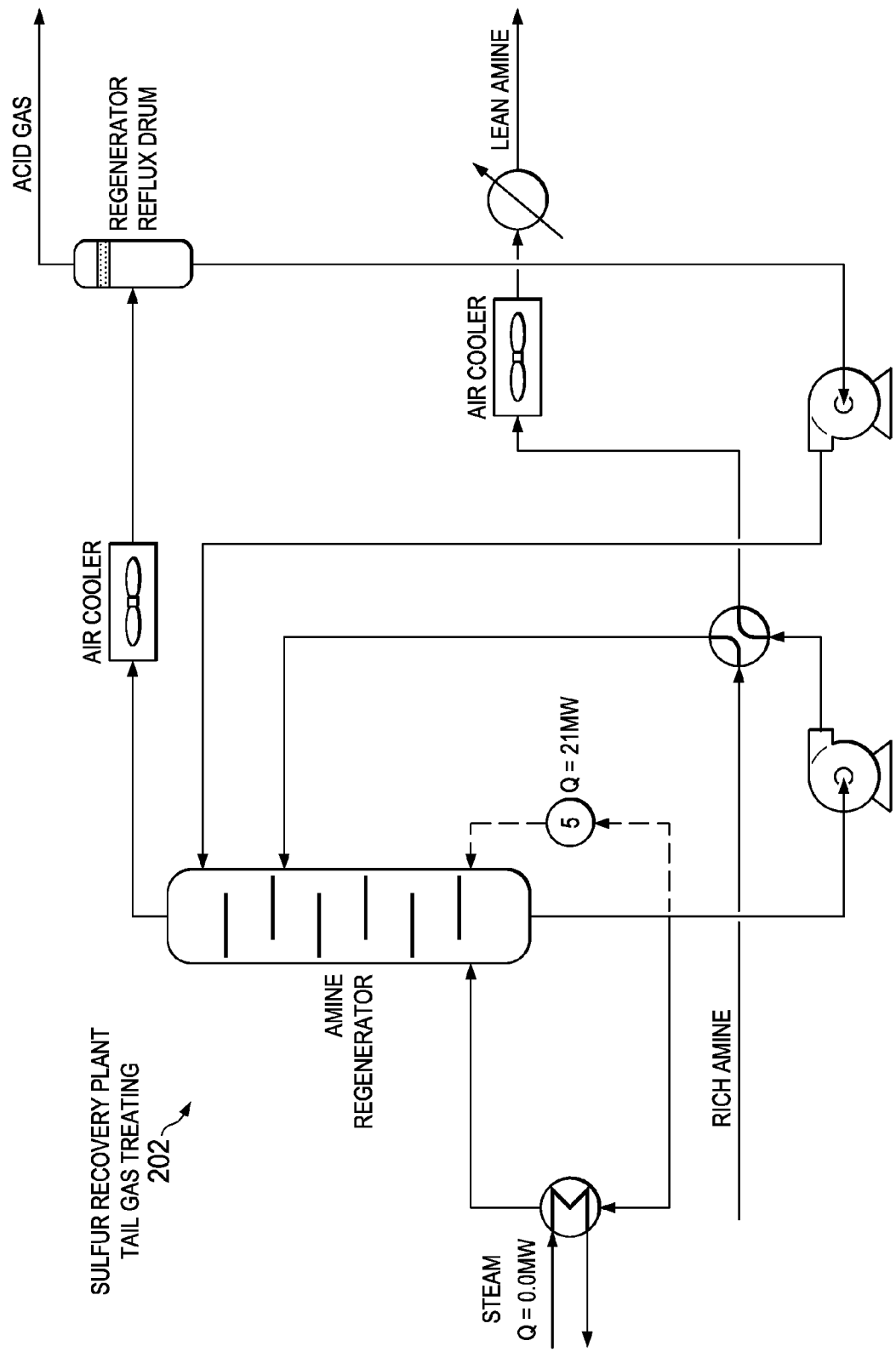
Figure 1T:
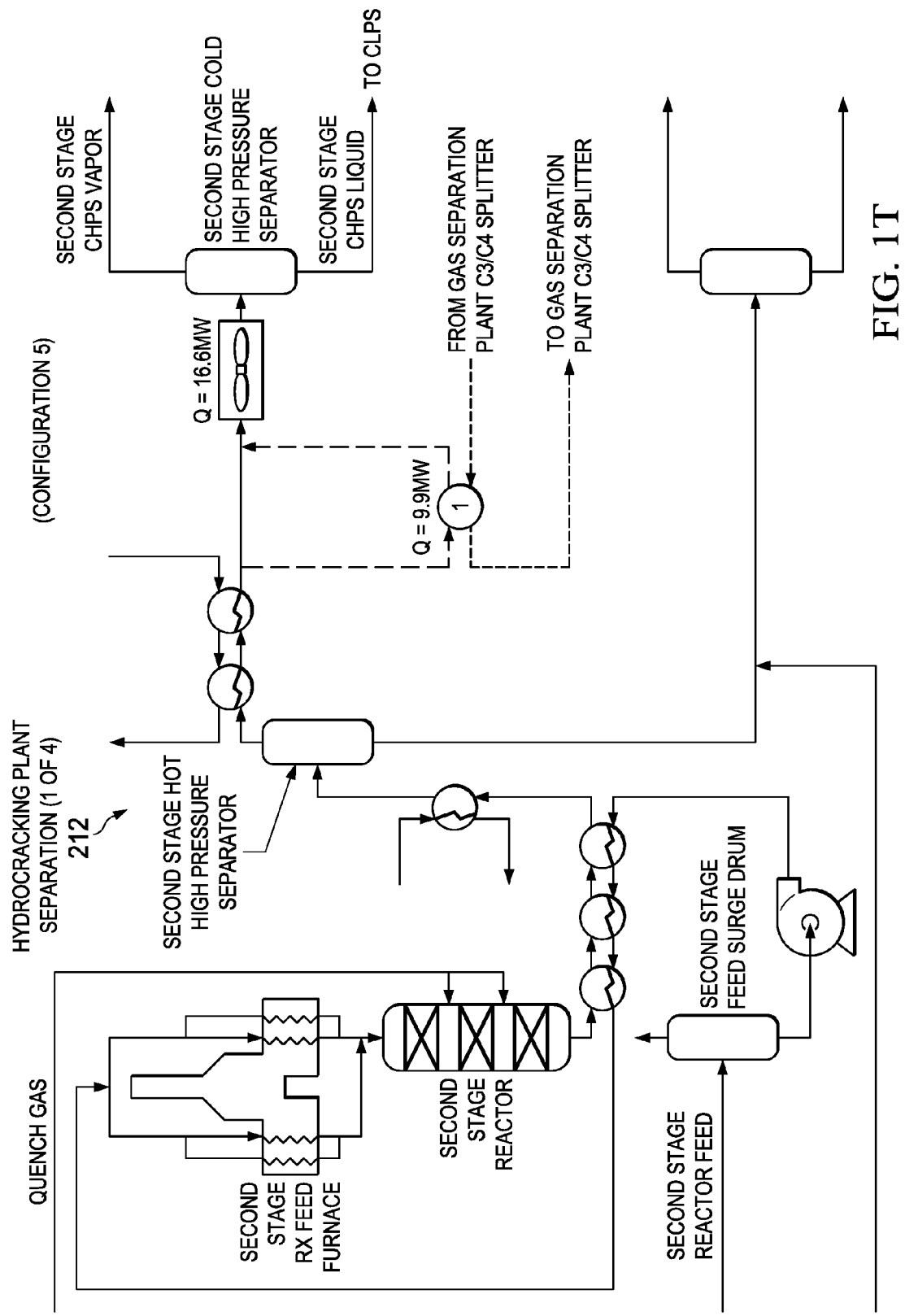
Figure 1U:
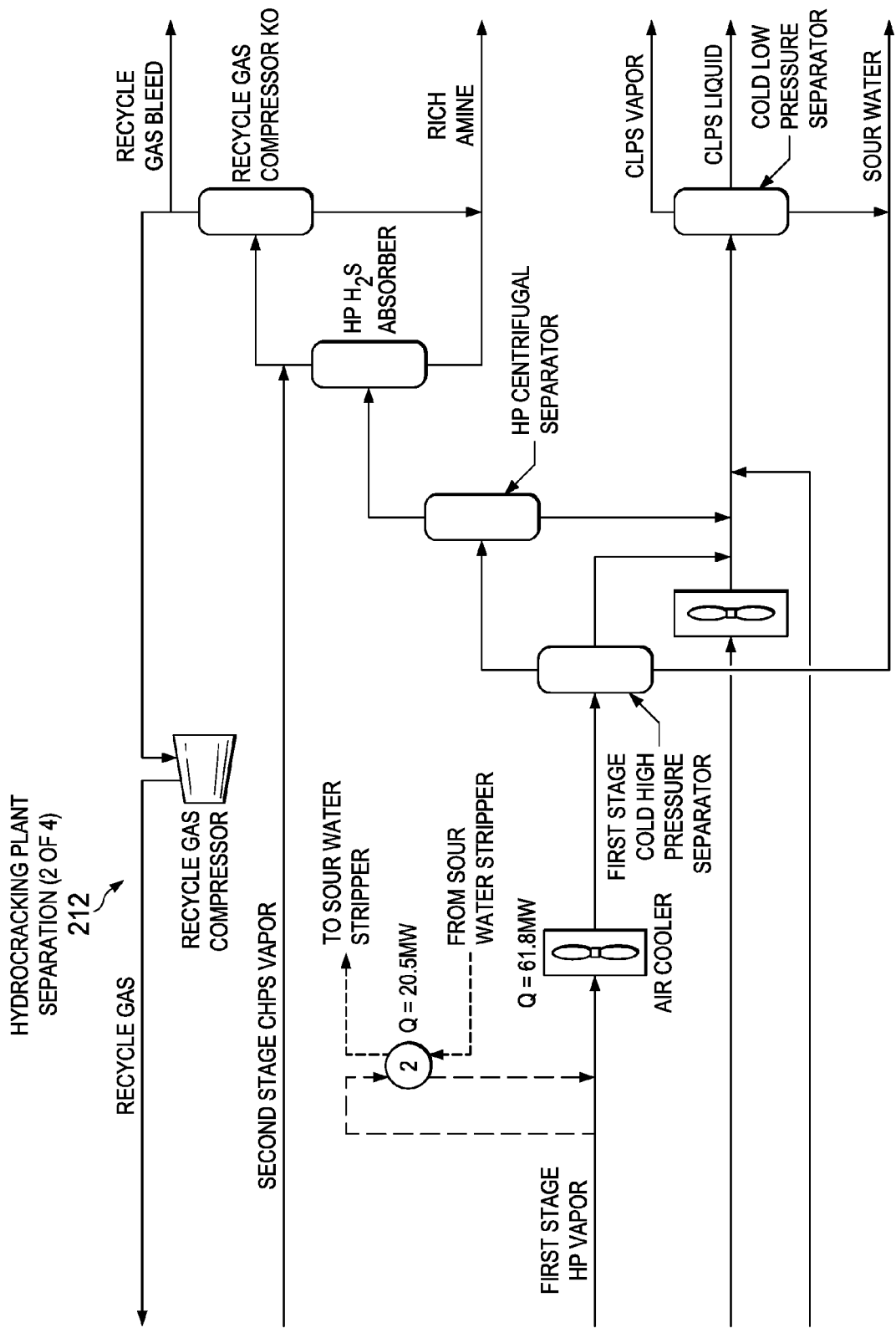
Figures 1, 1V:
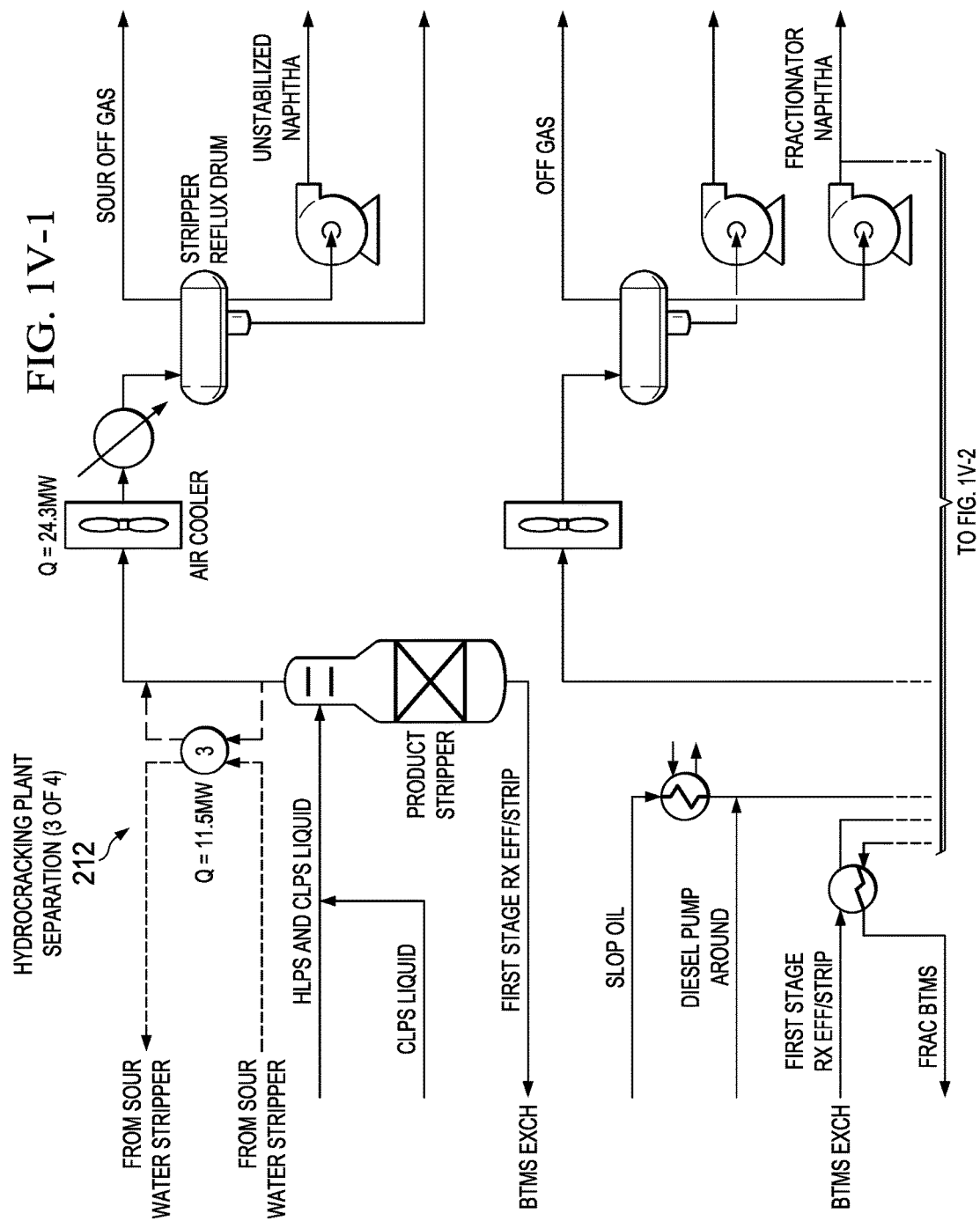
Figures 1, 1V, 2:
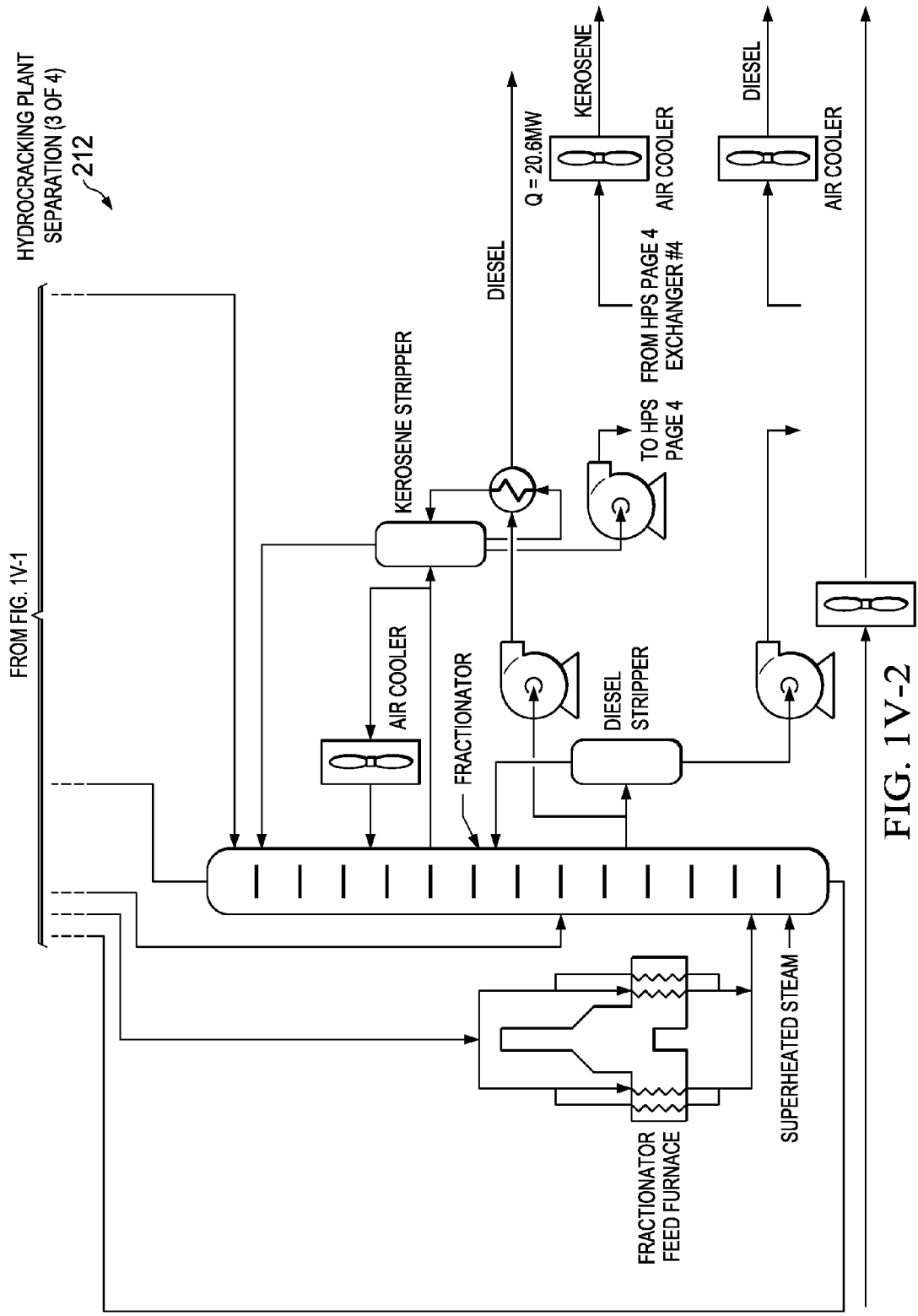
Figure 1W:
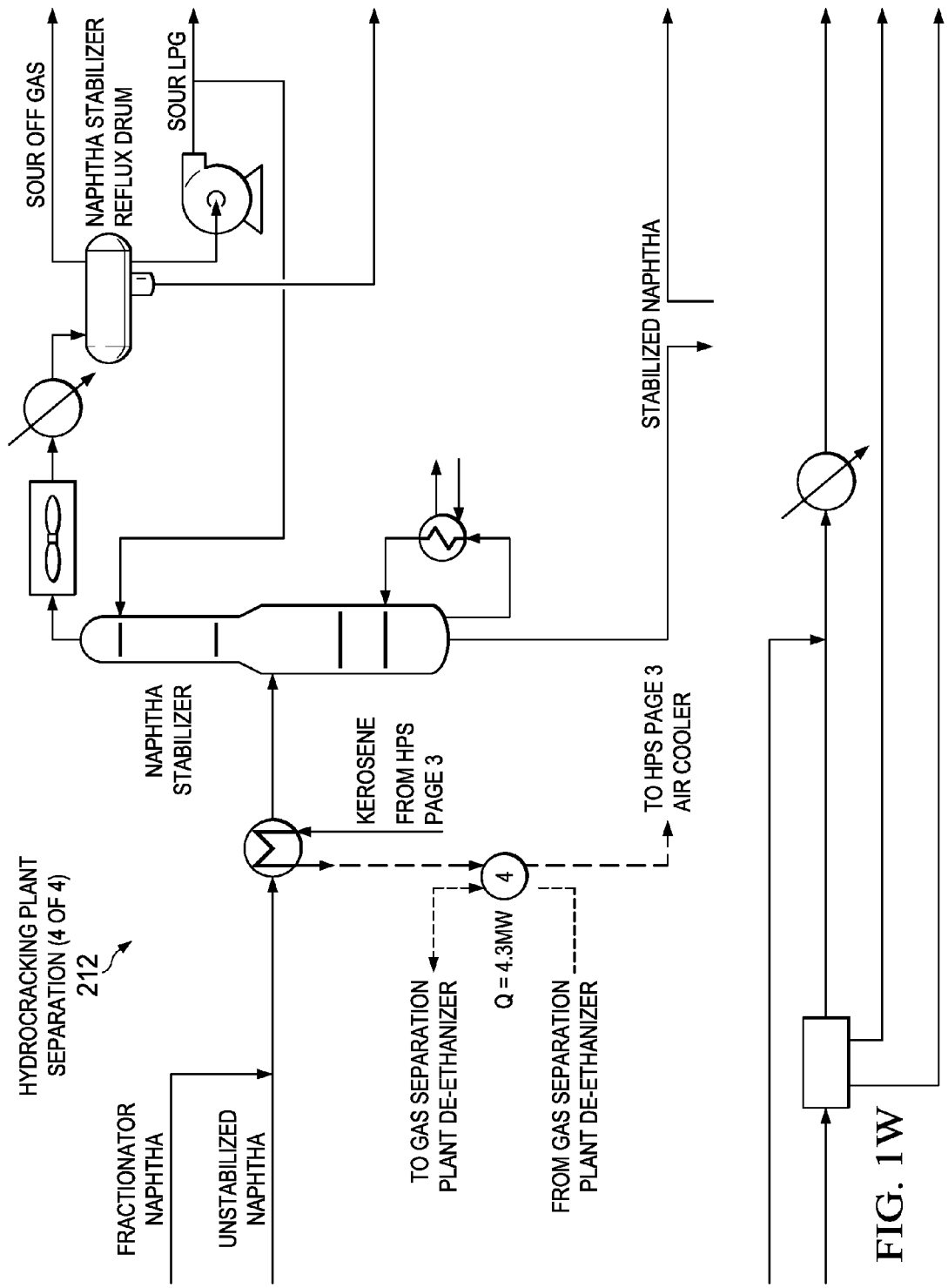
Figure 1X:
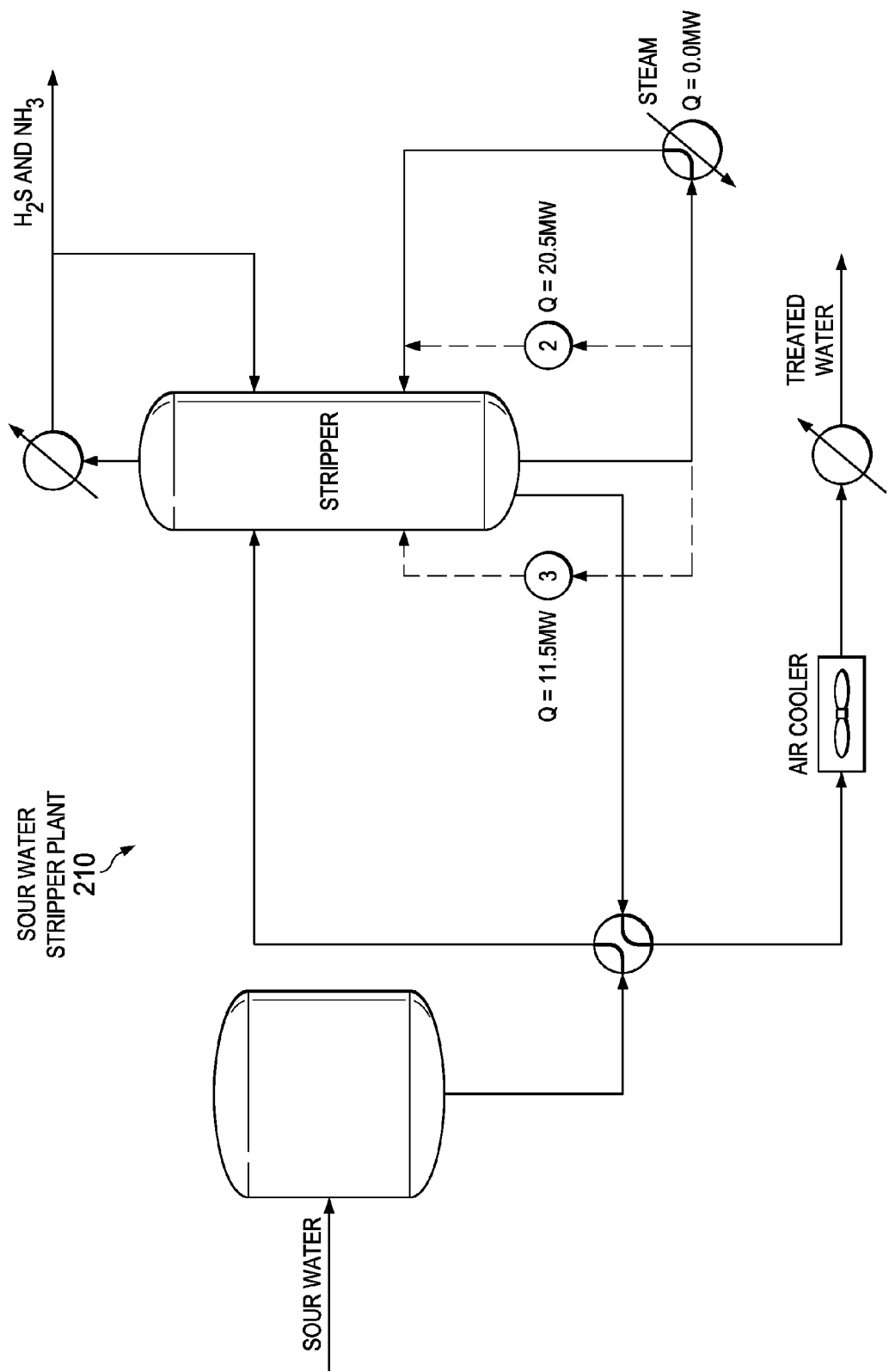
Figure 1Y:
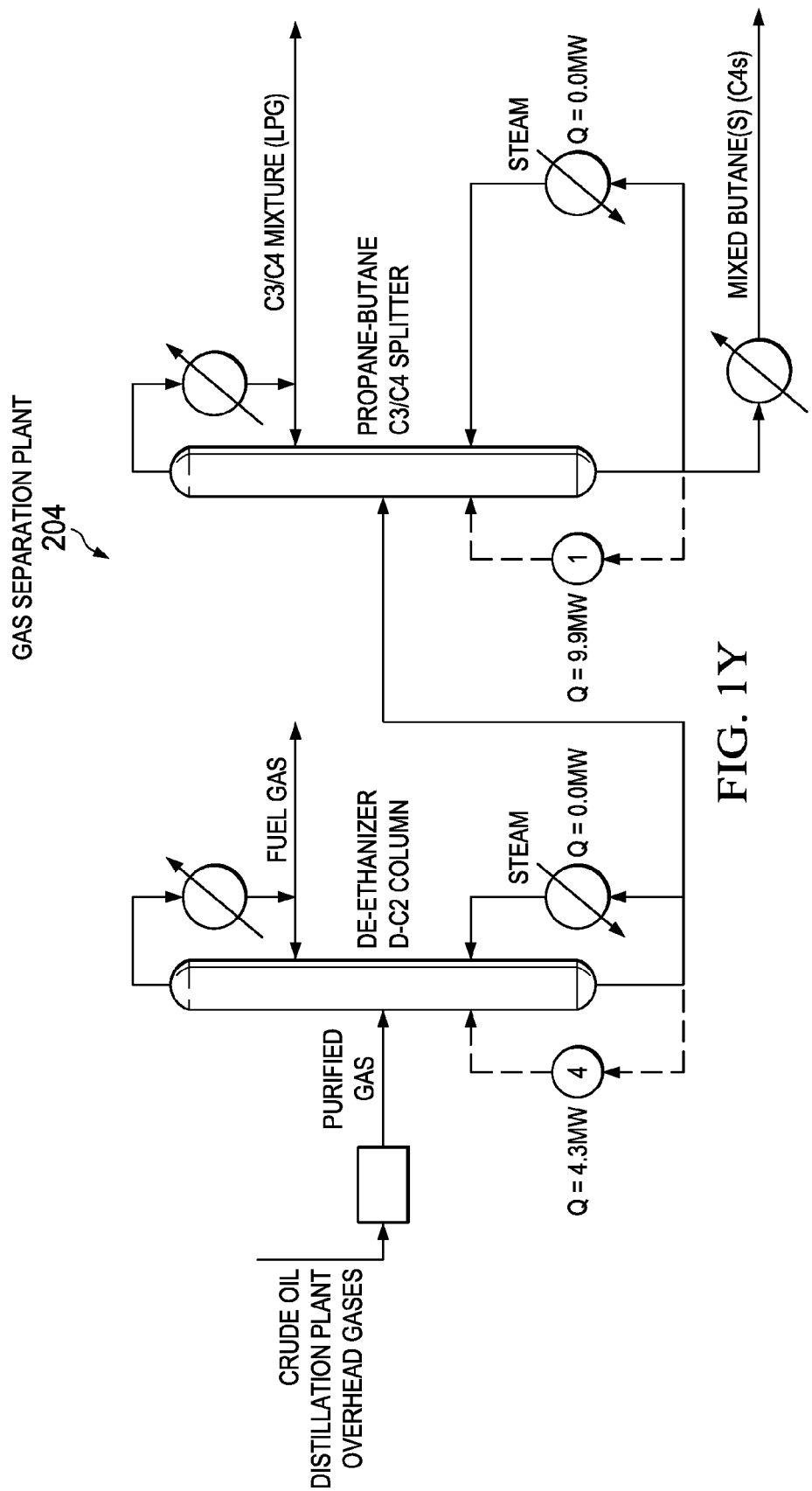
Figure 1Z:
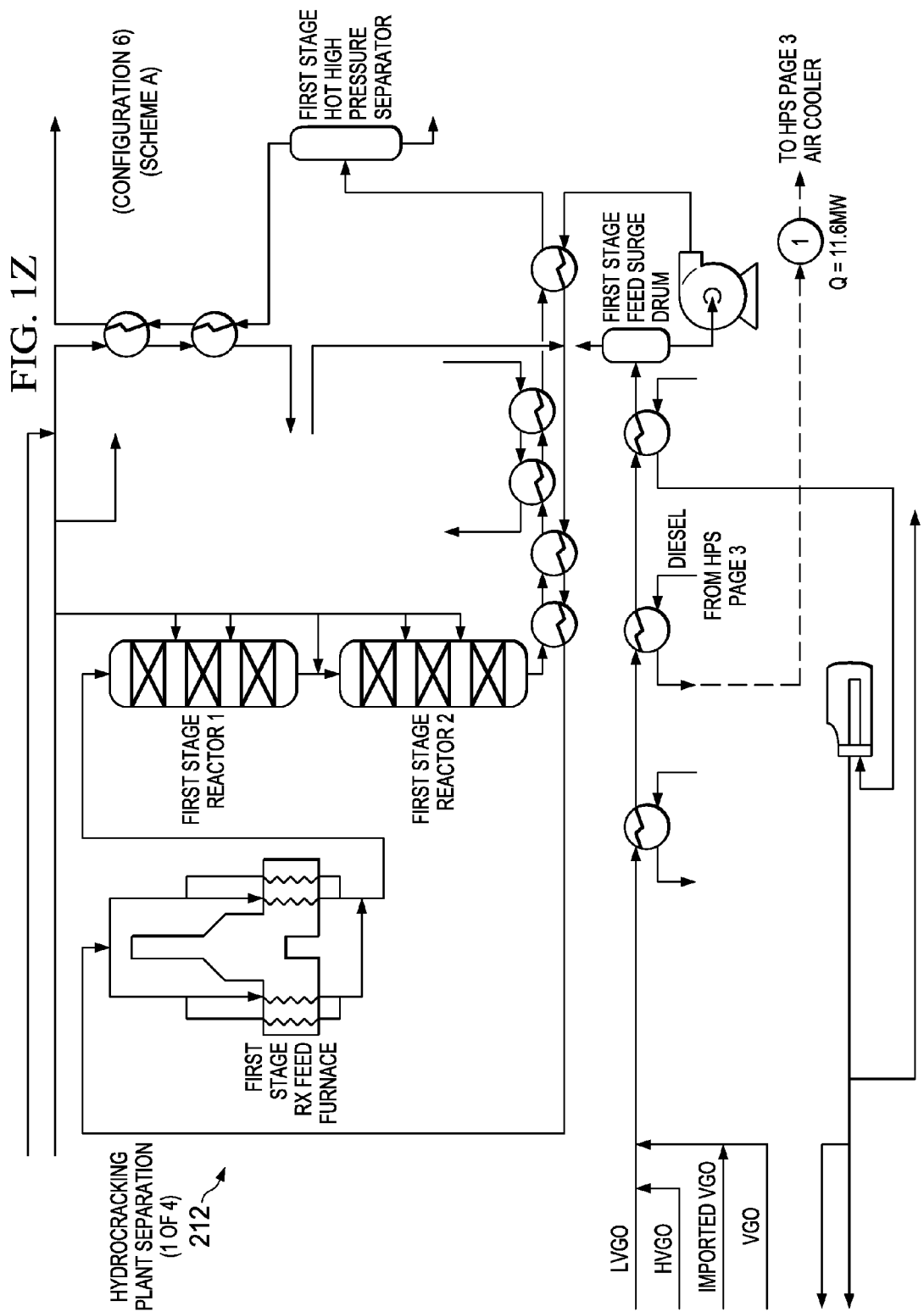
Figure 1A:
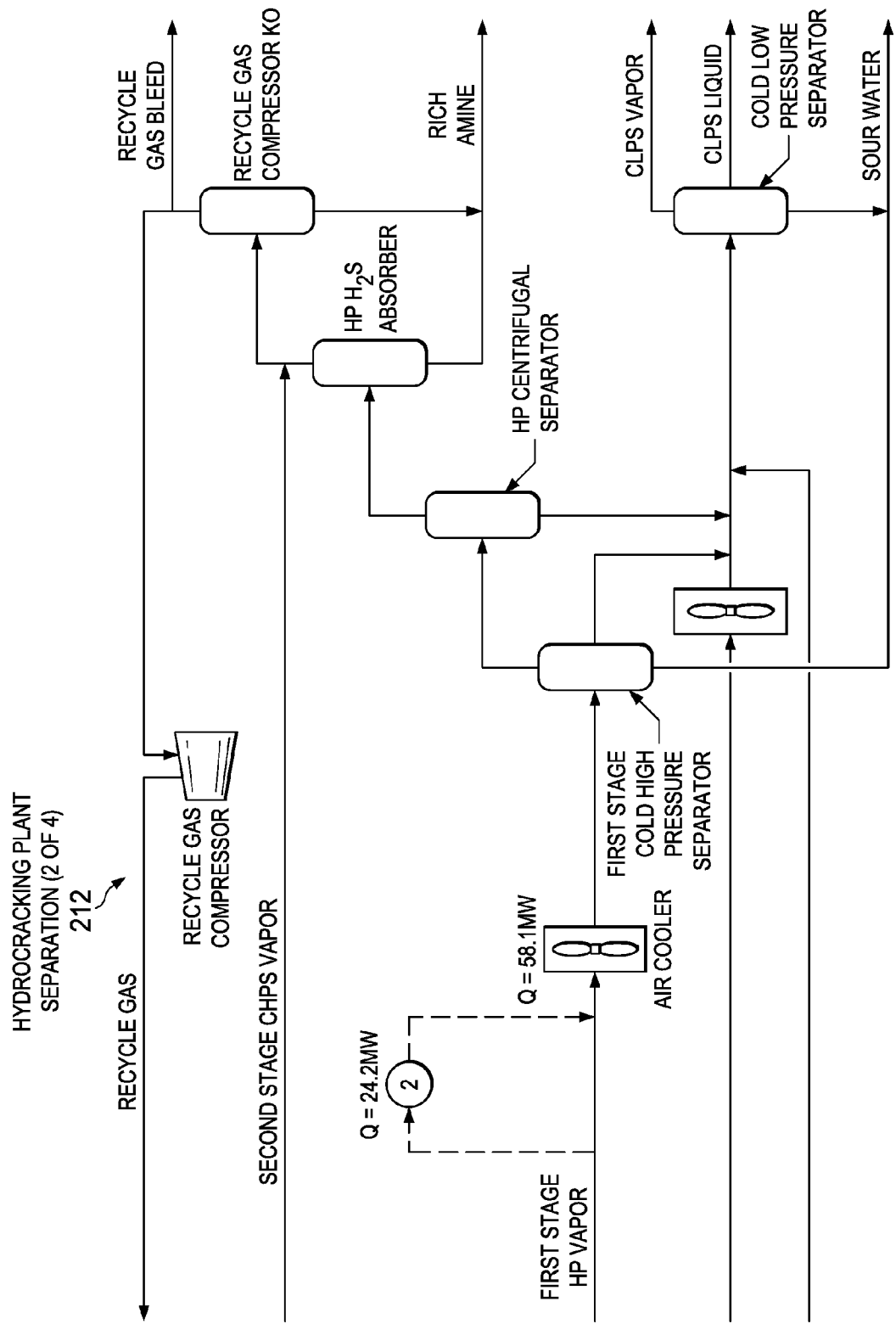
Figure 1A:
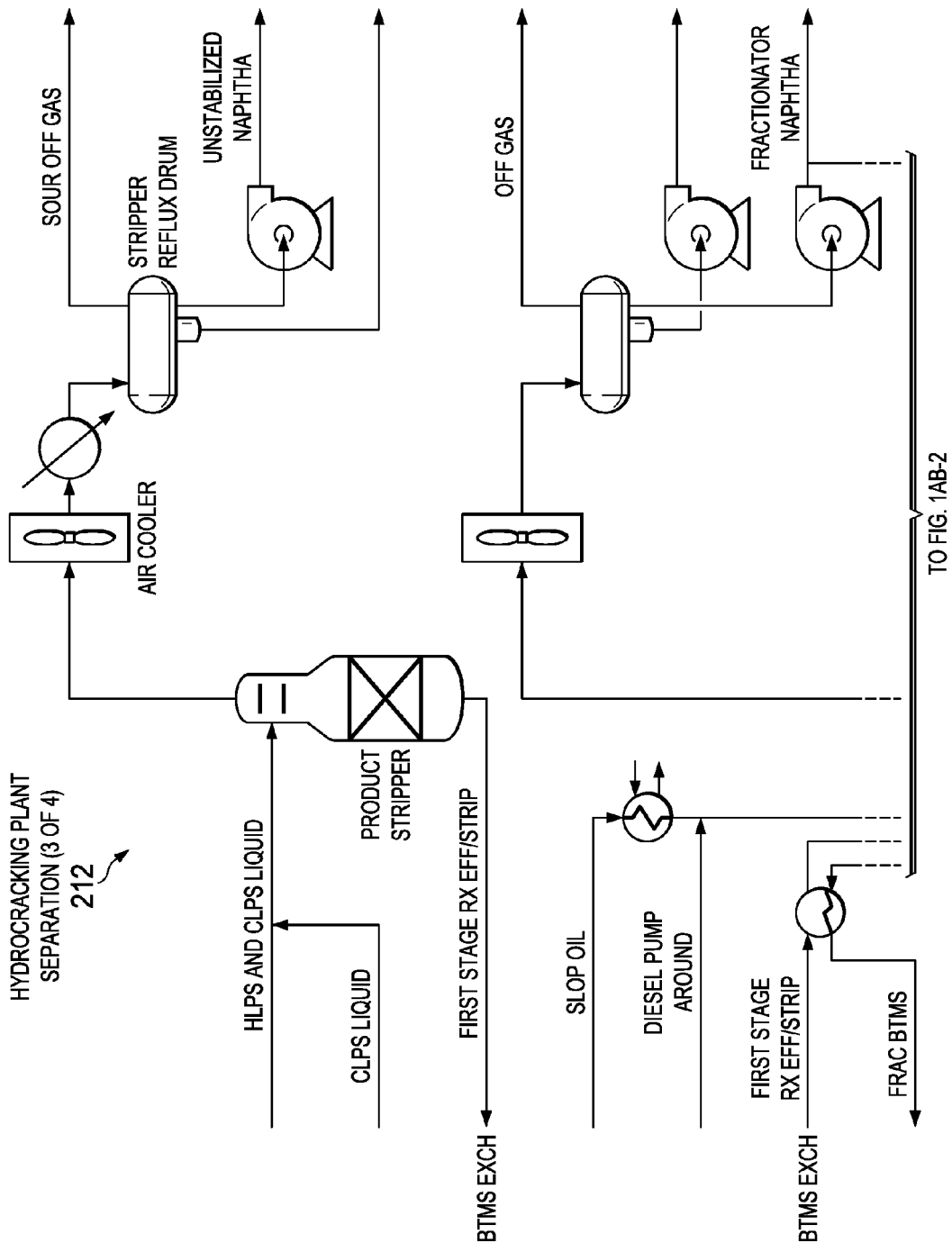
Figure 1A:
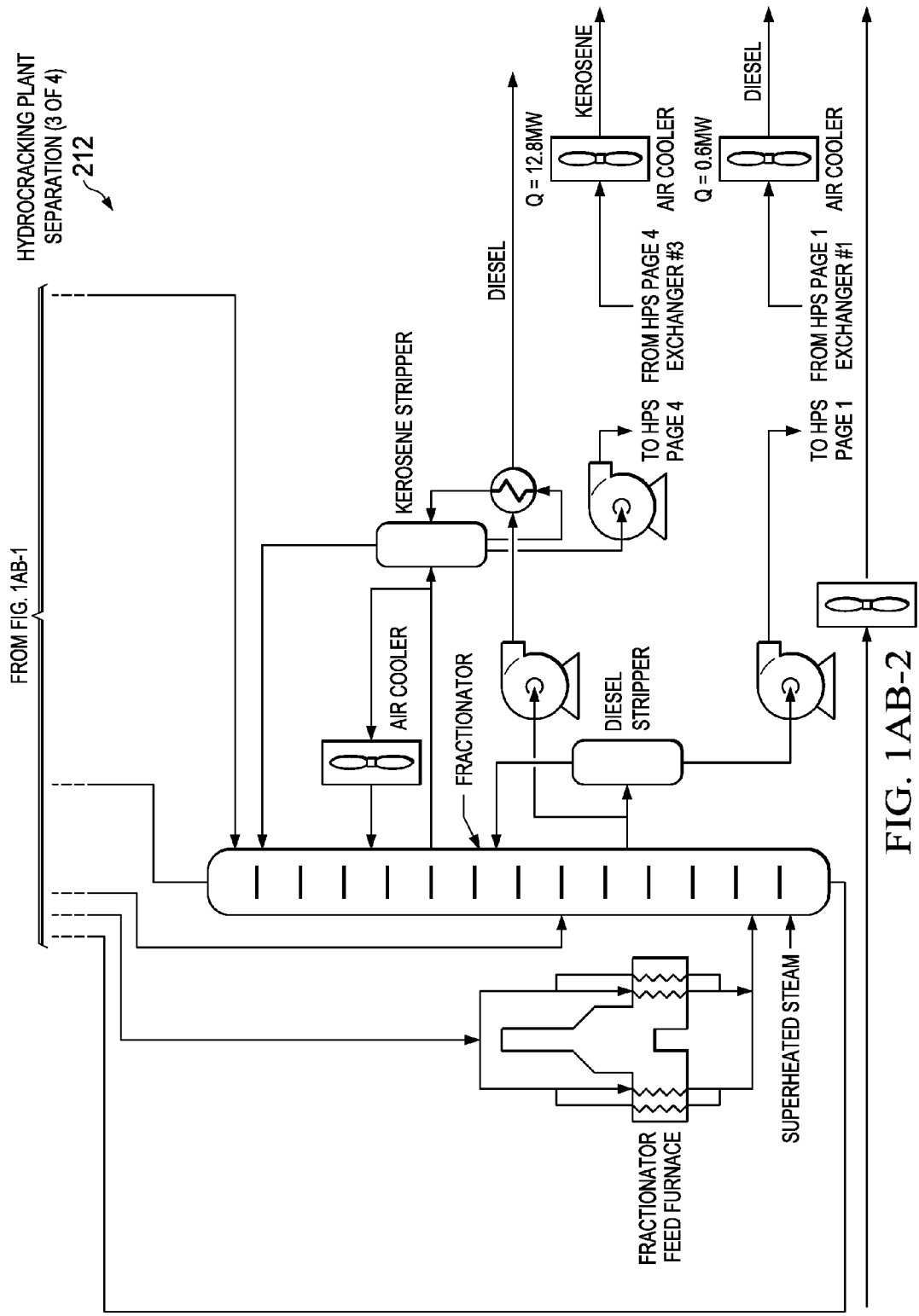
Figure 1A:
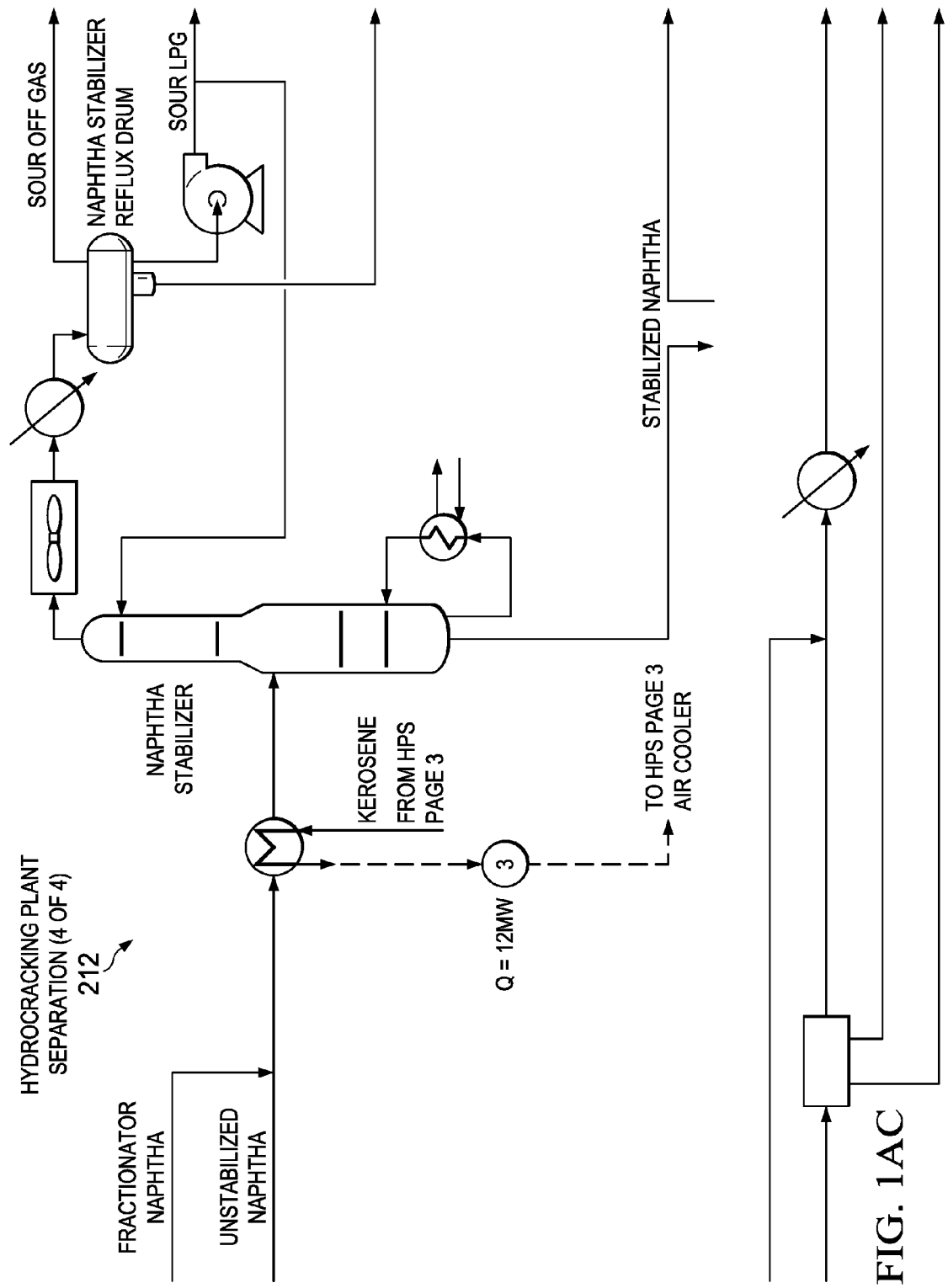
Figure 1A:
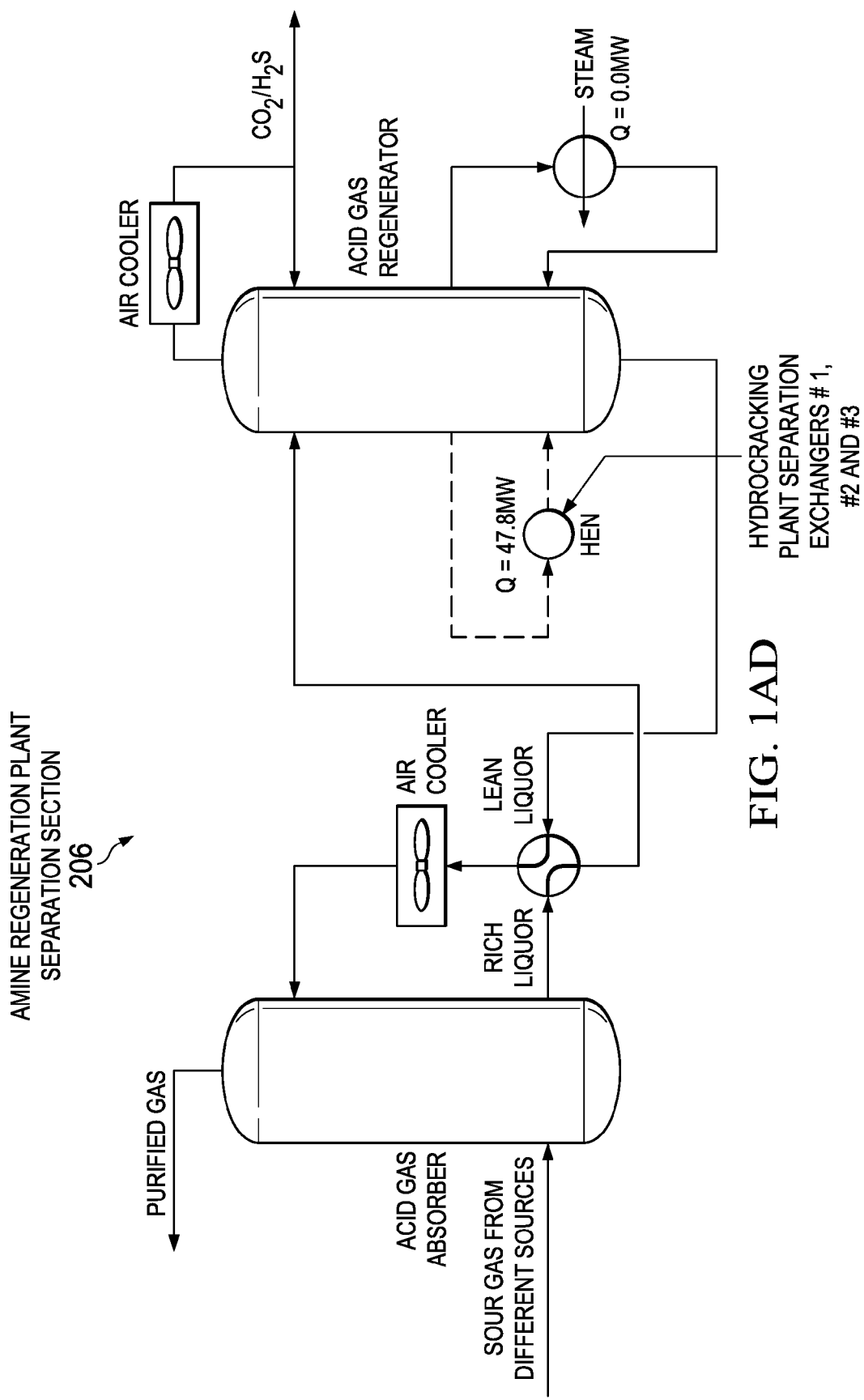
Figure 1A:
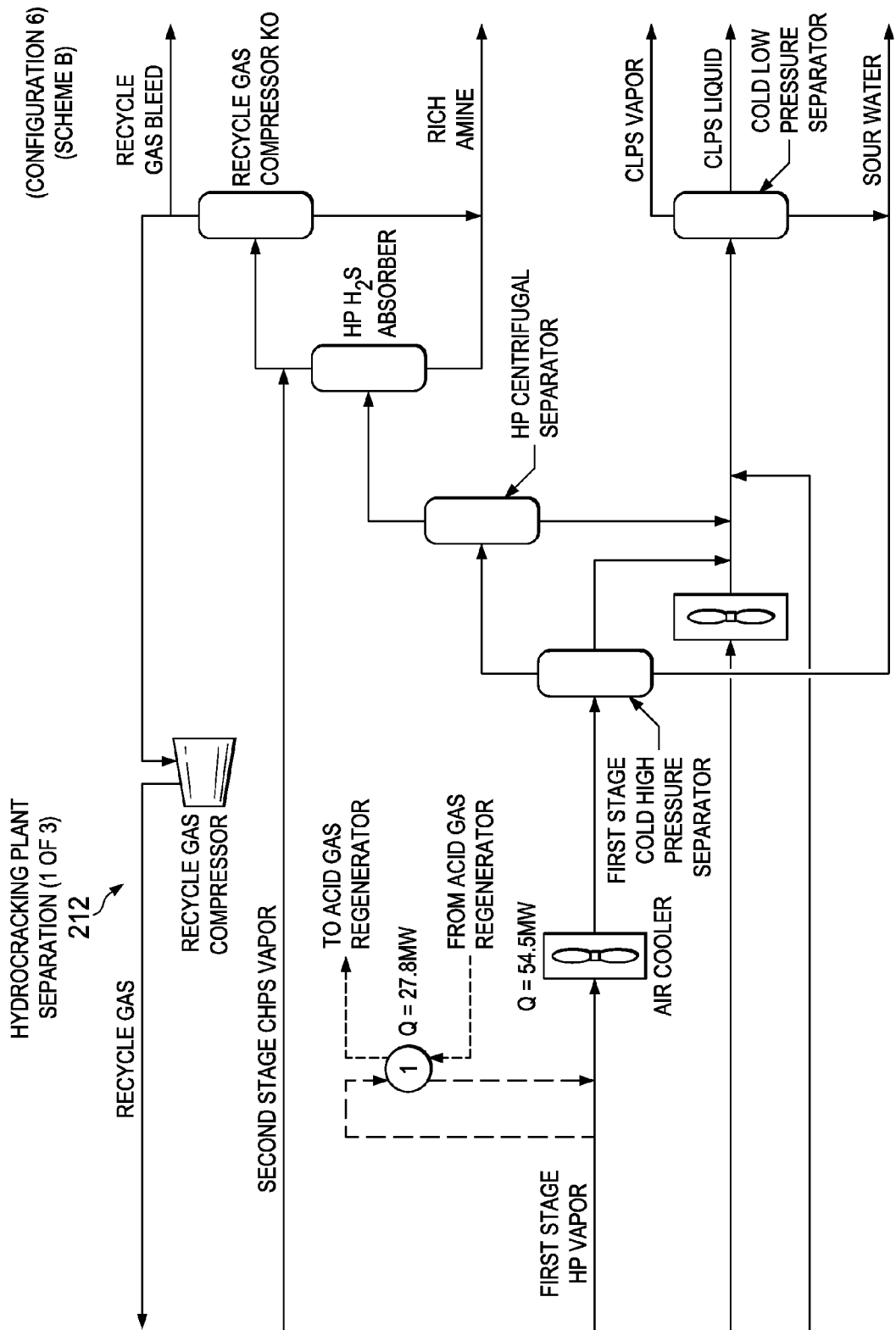
Figure 1A:
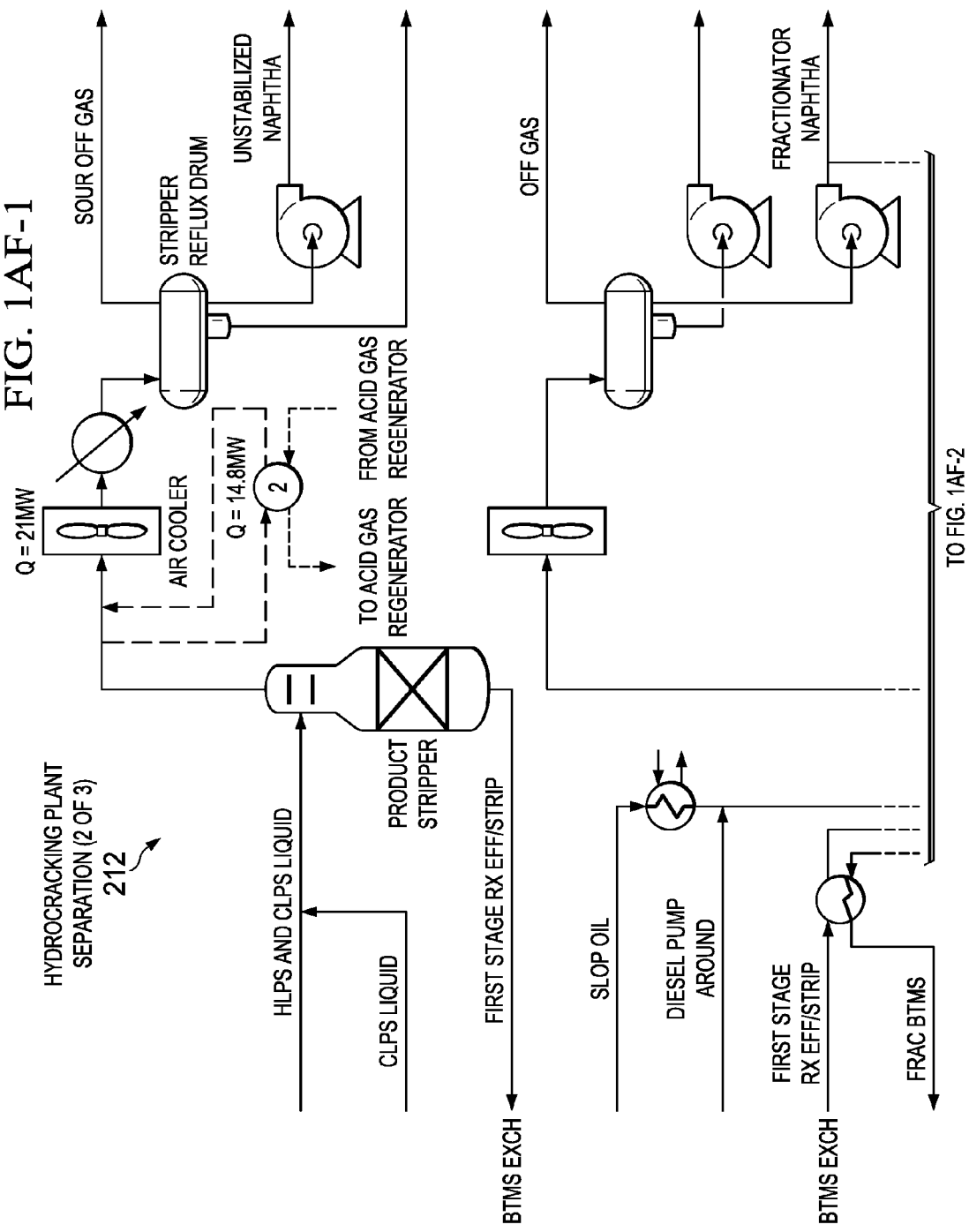
Figure 1A:
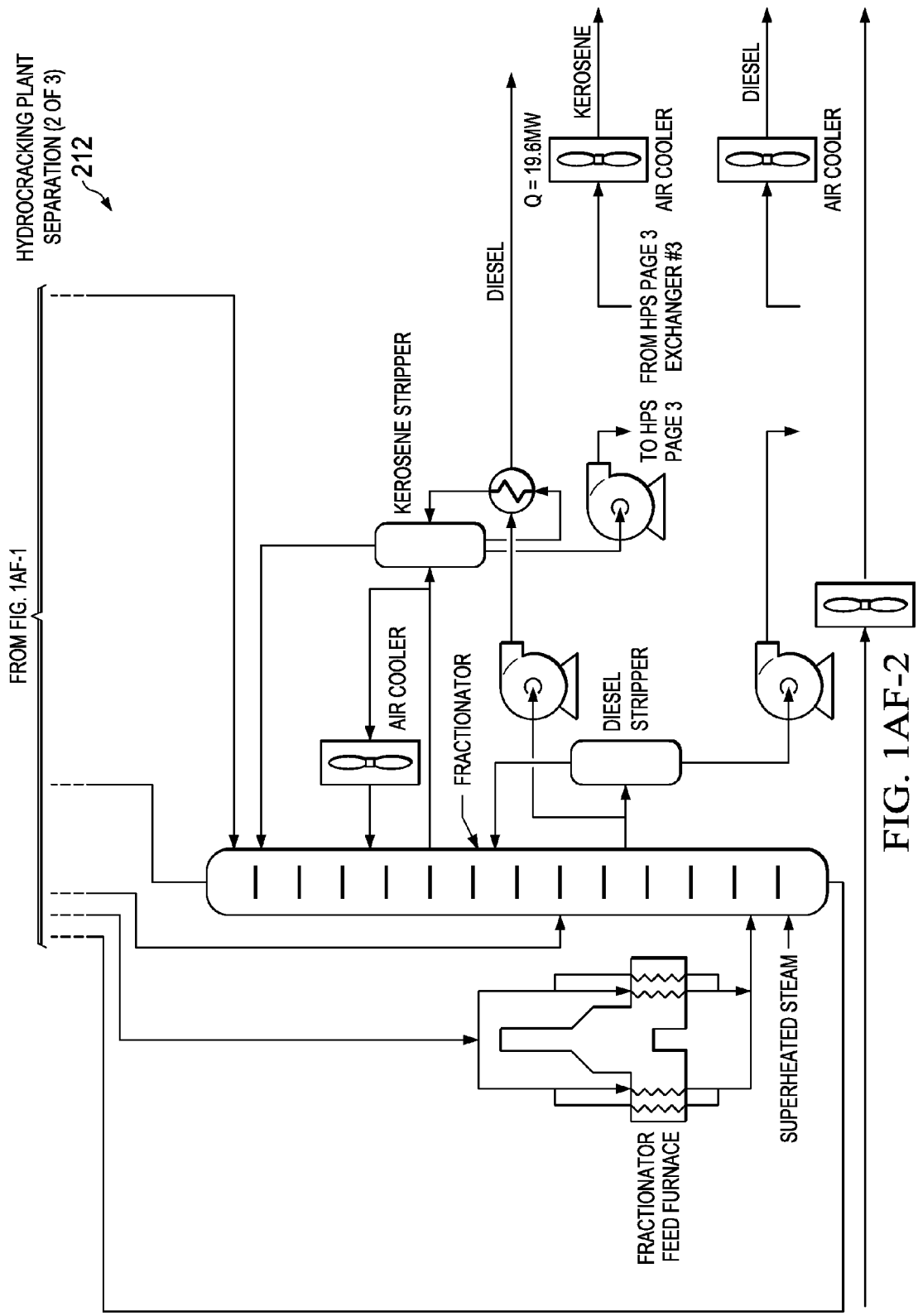
Figure 1A:
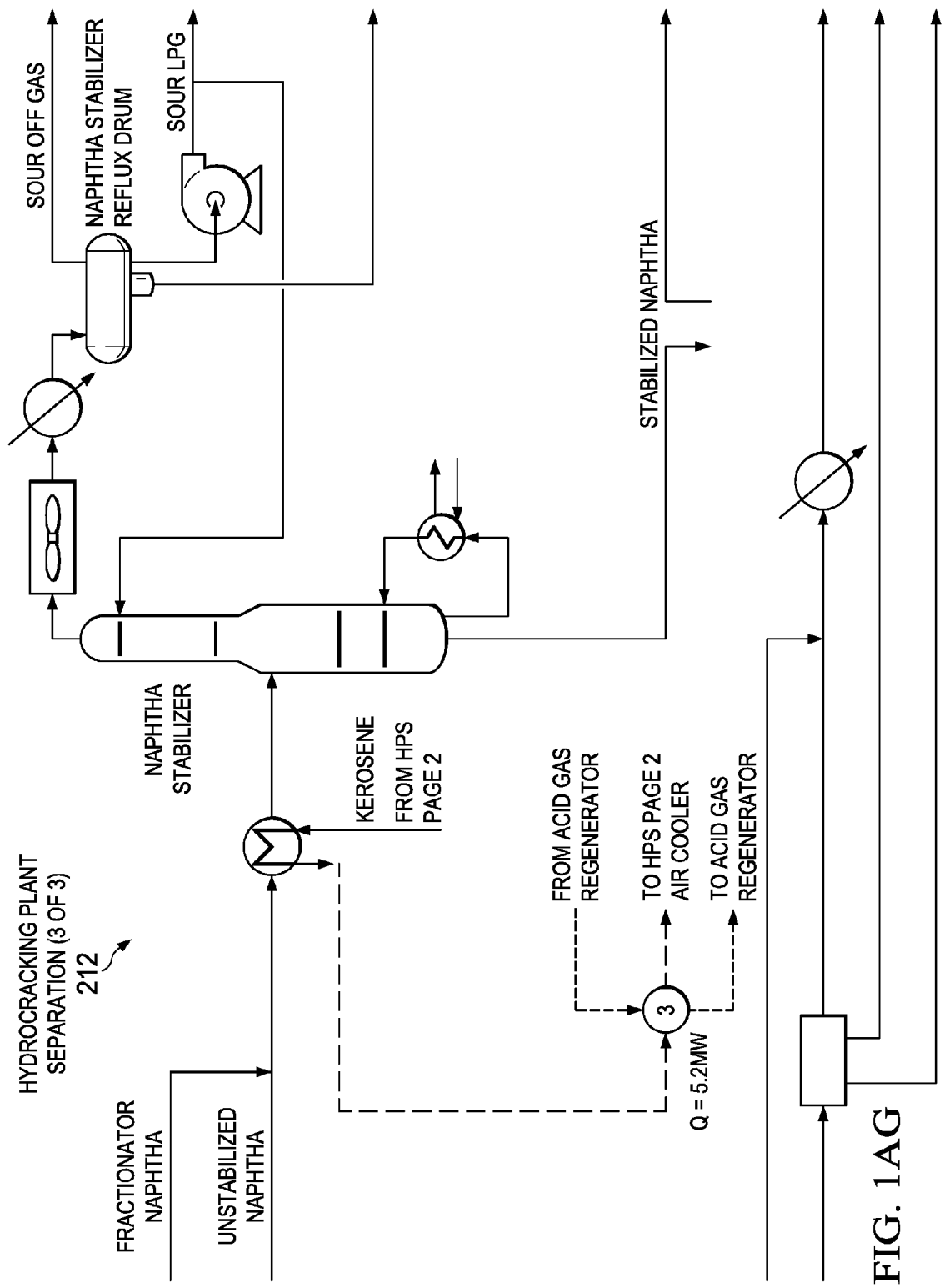
Figure 1A:
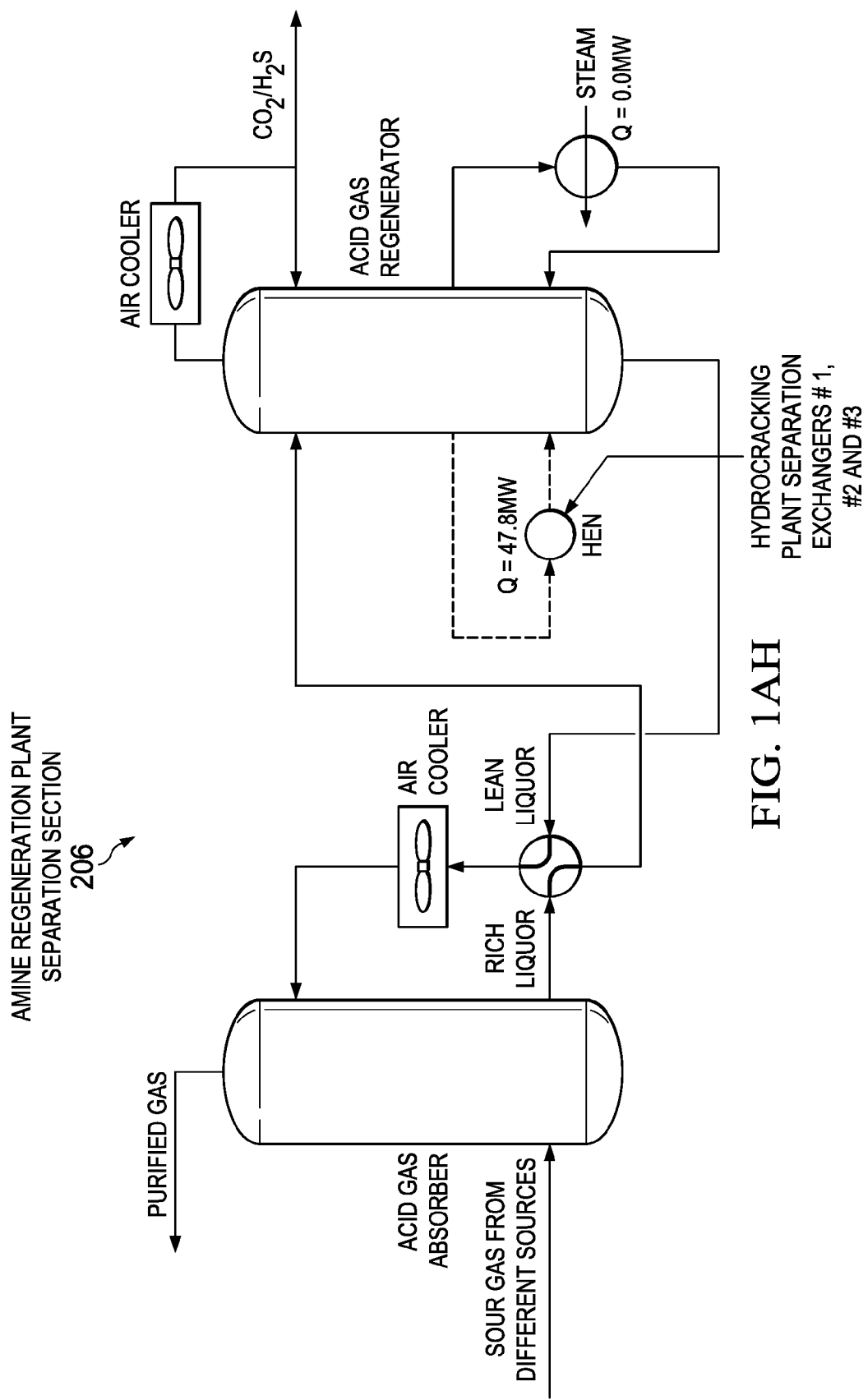
Figure 1A:
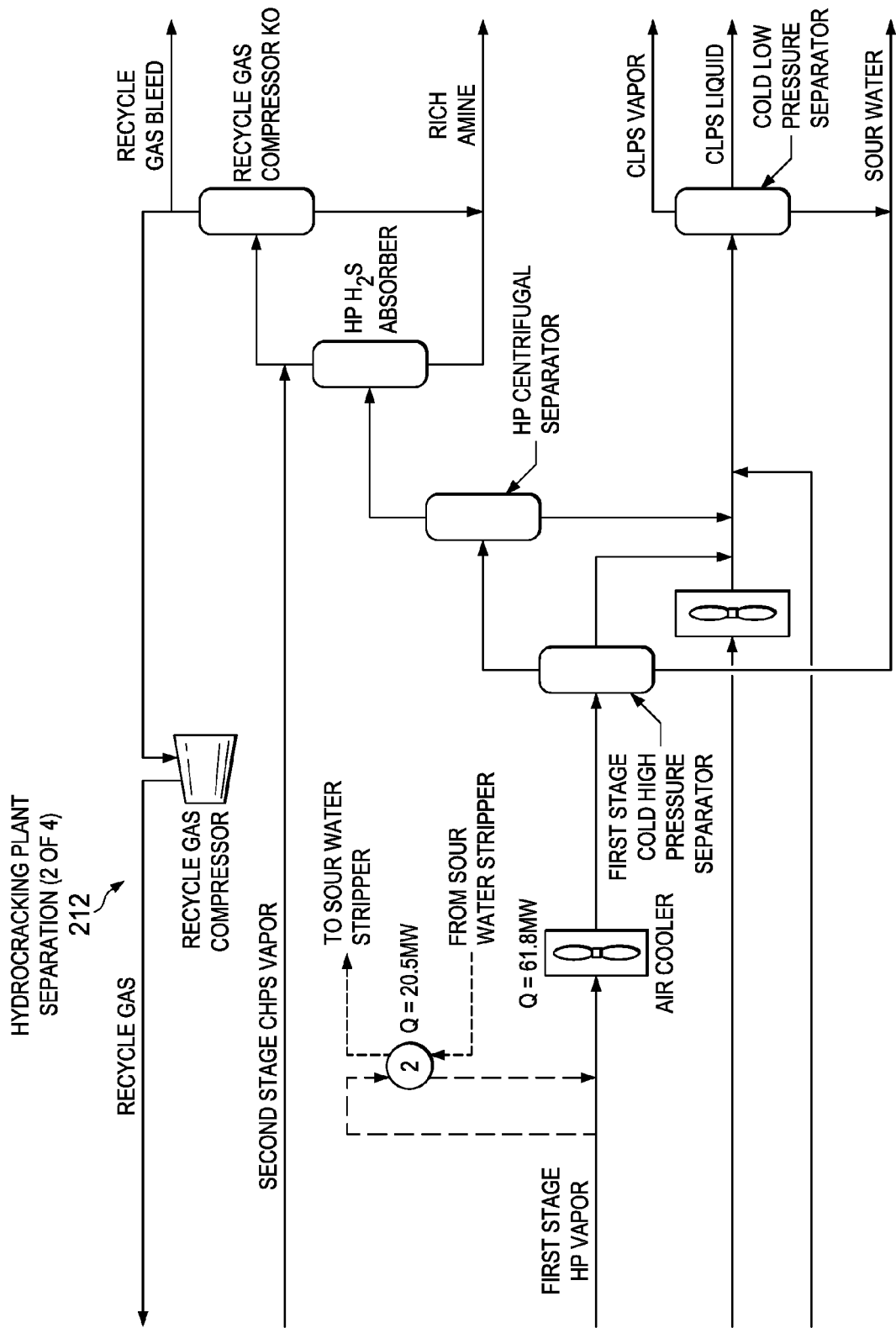
Figure 1A:
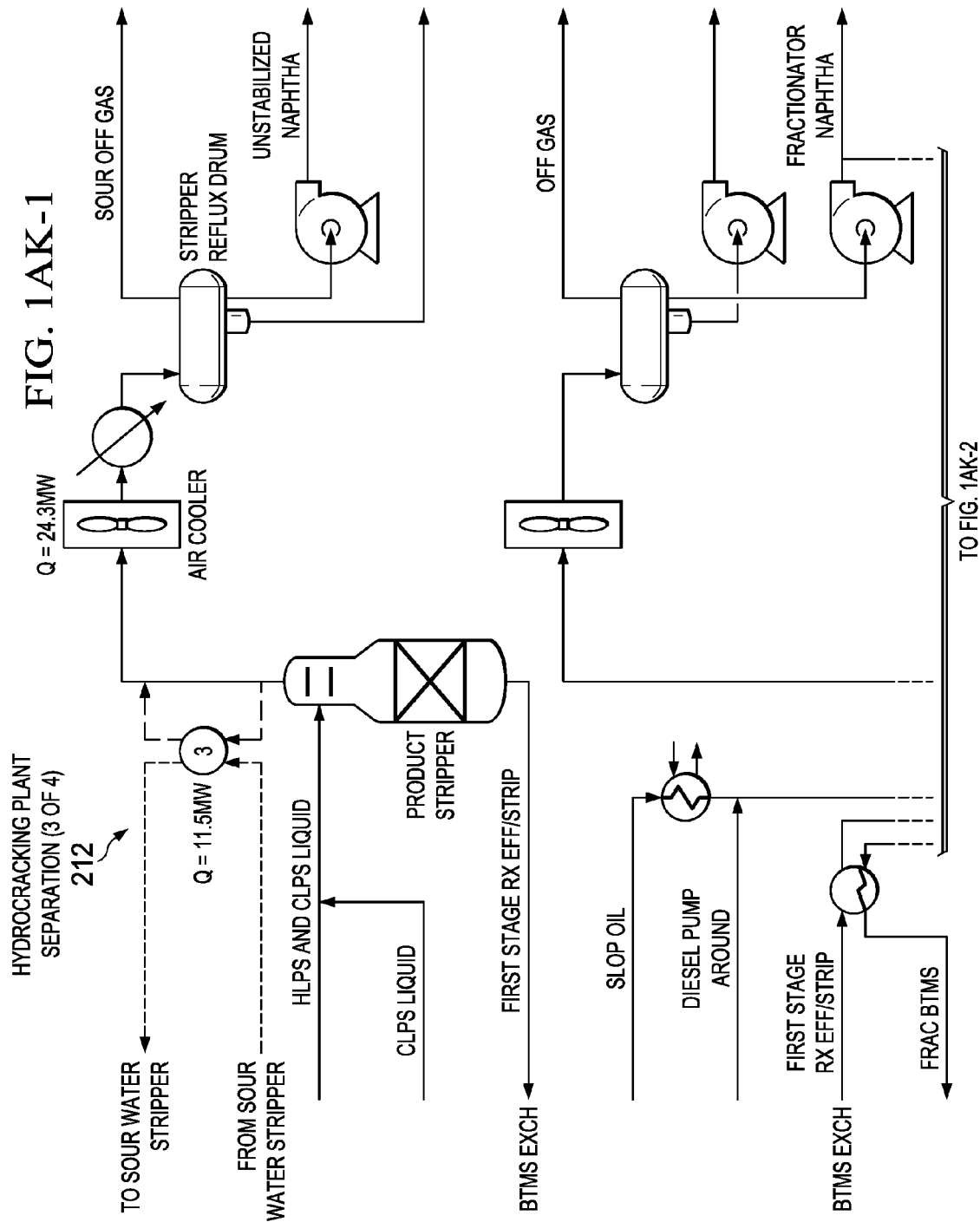
Figure 1A:
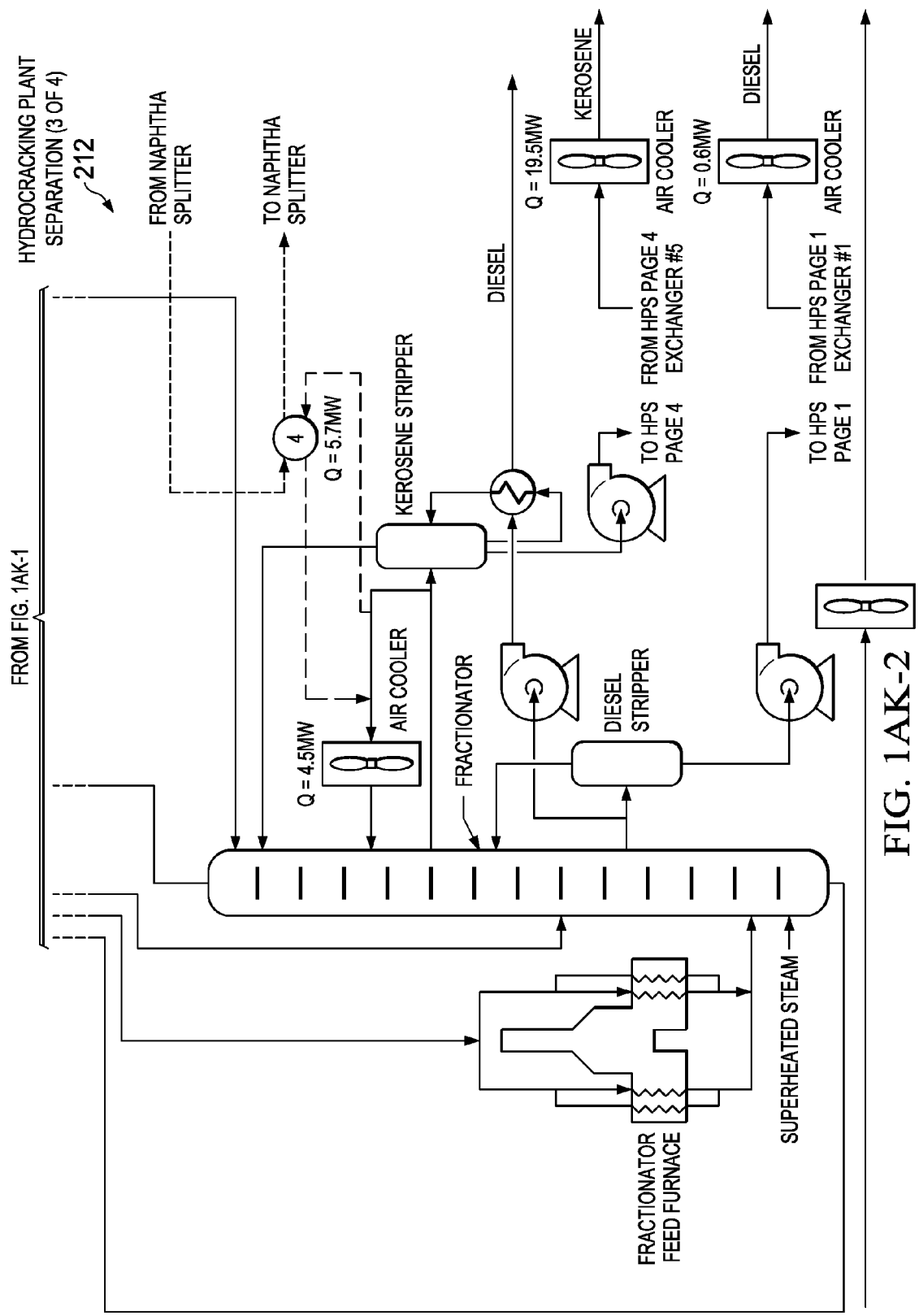
Figure 1A:
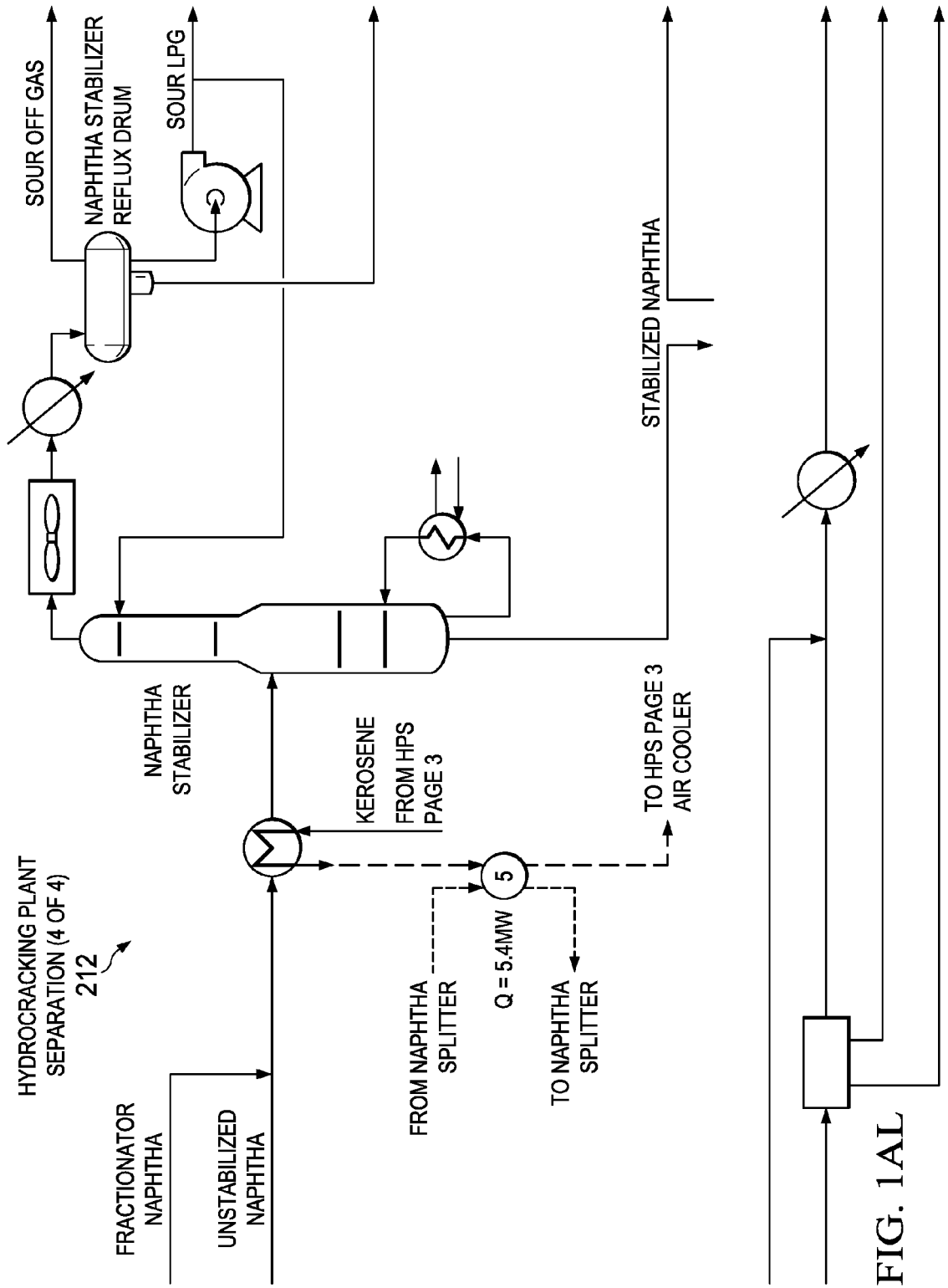
Figure 1A:
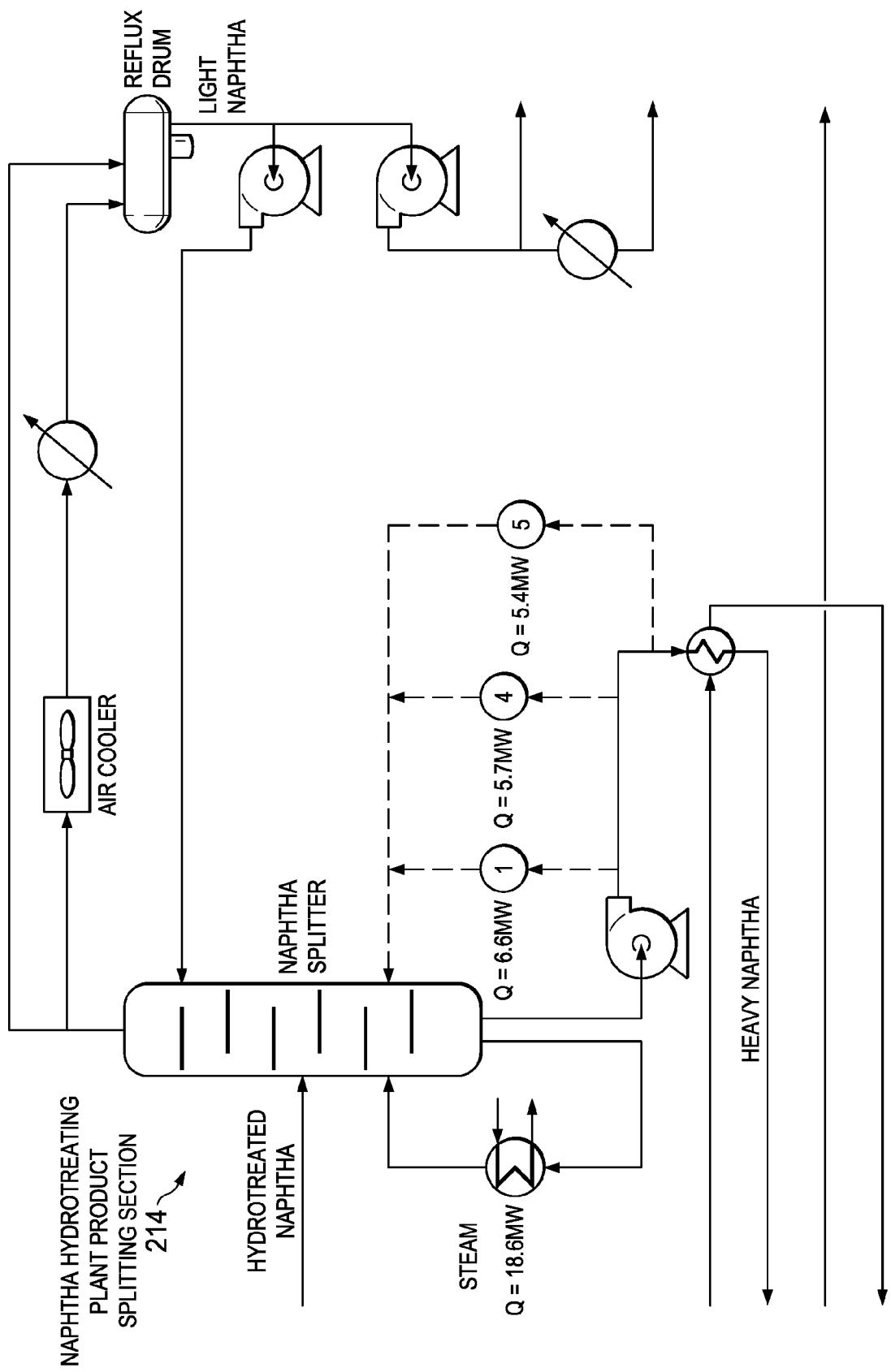
Figure 1A:
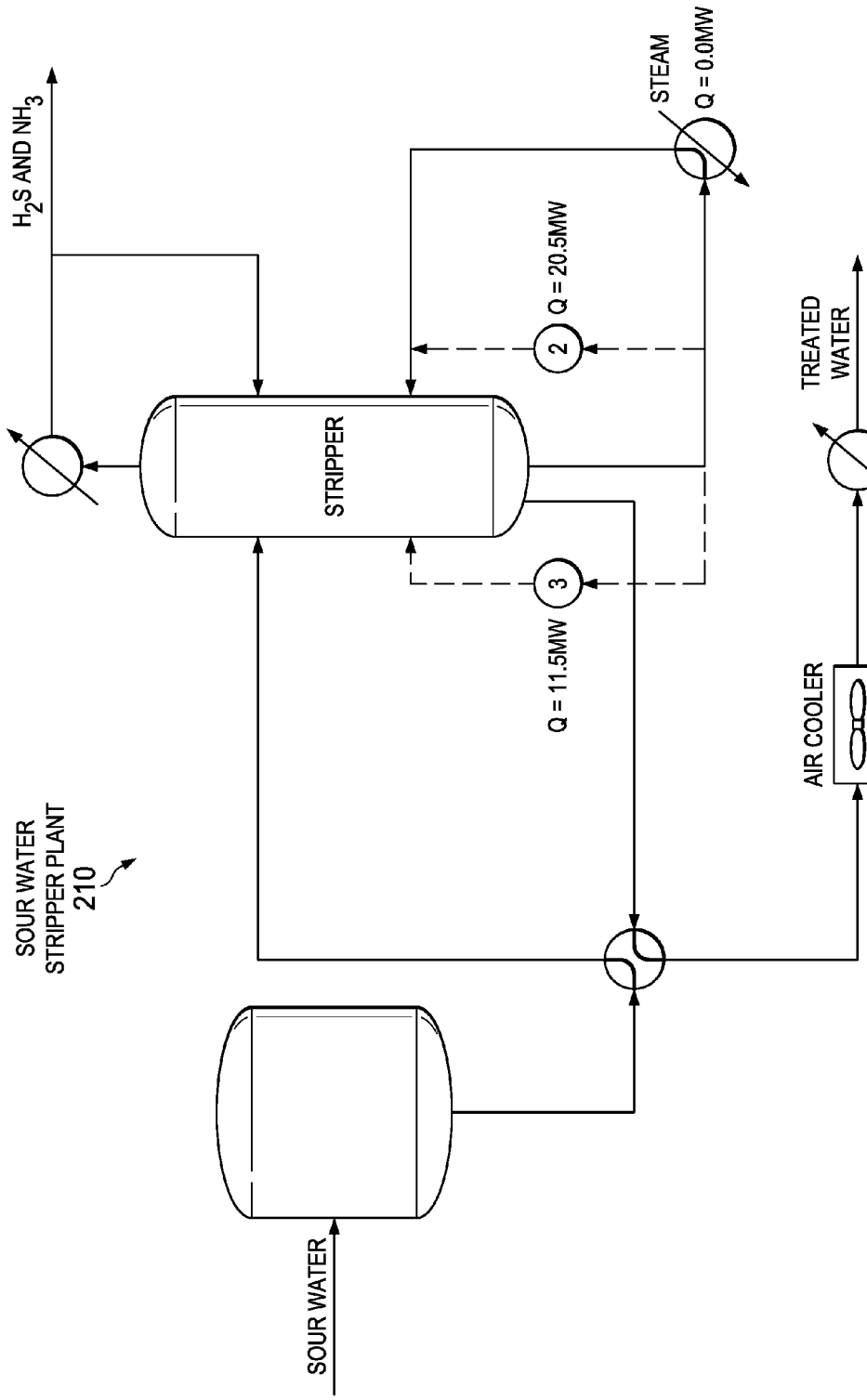
Figure 1A:
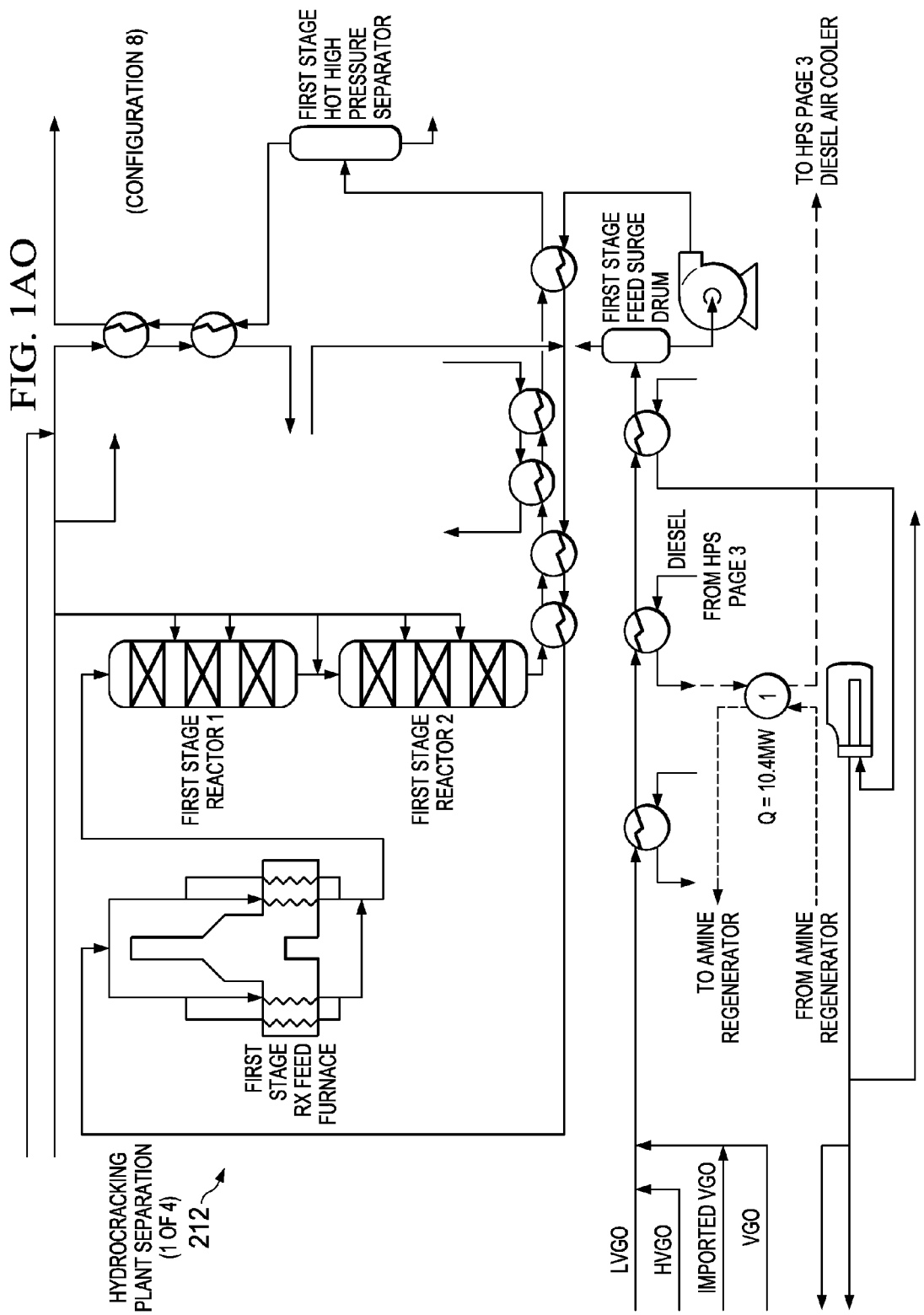
Figure 1A:
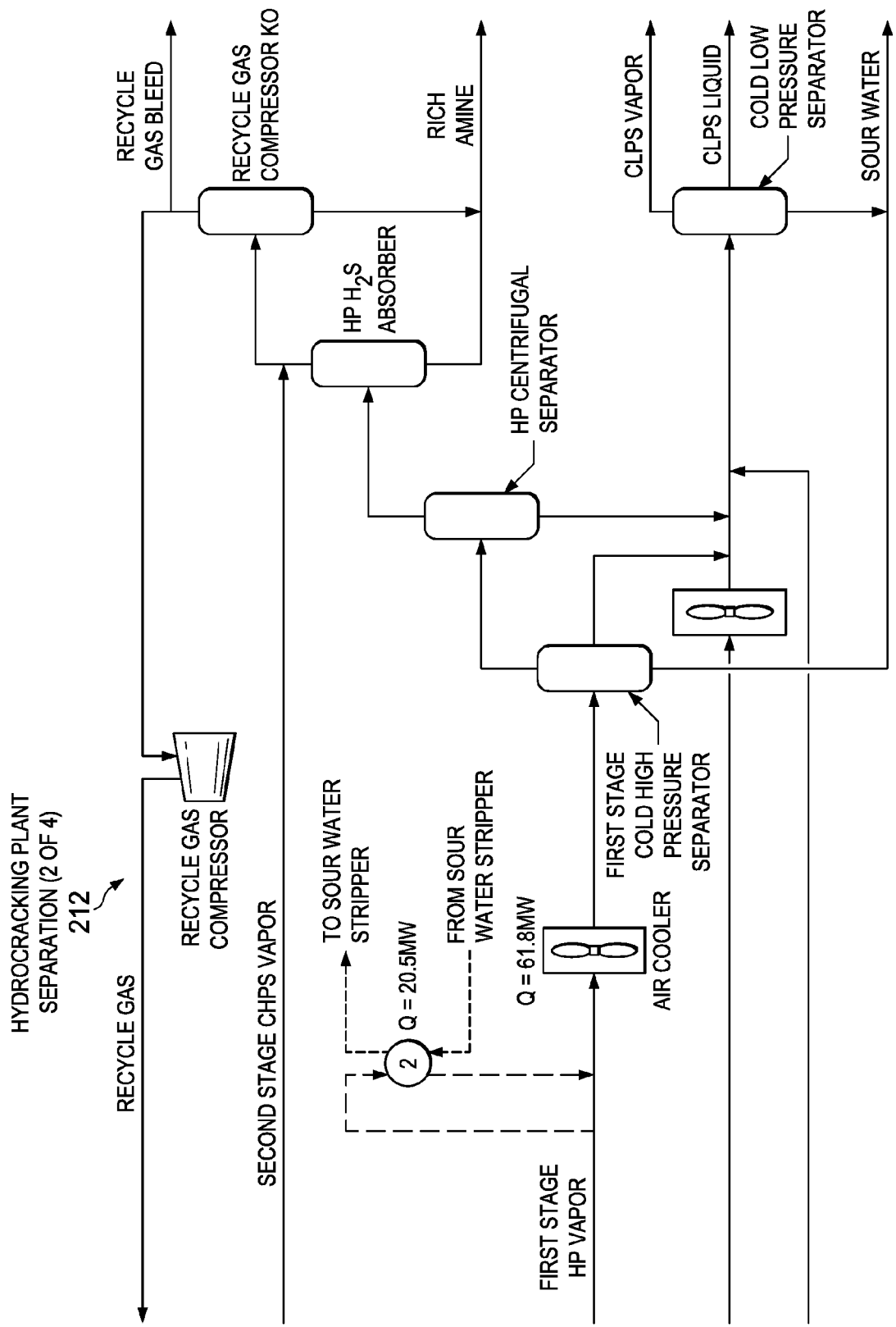
Figure 1A:
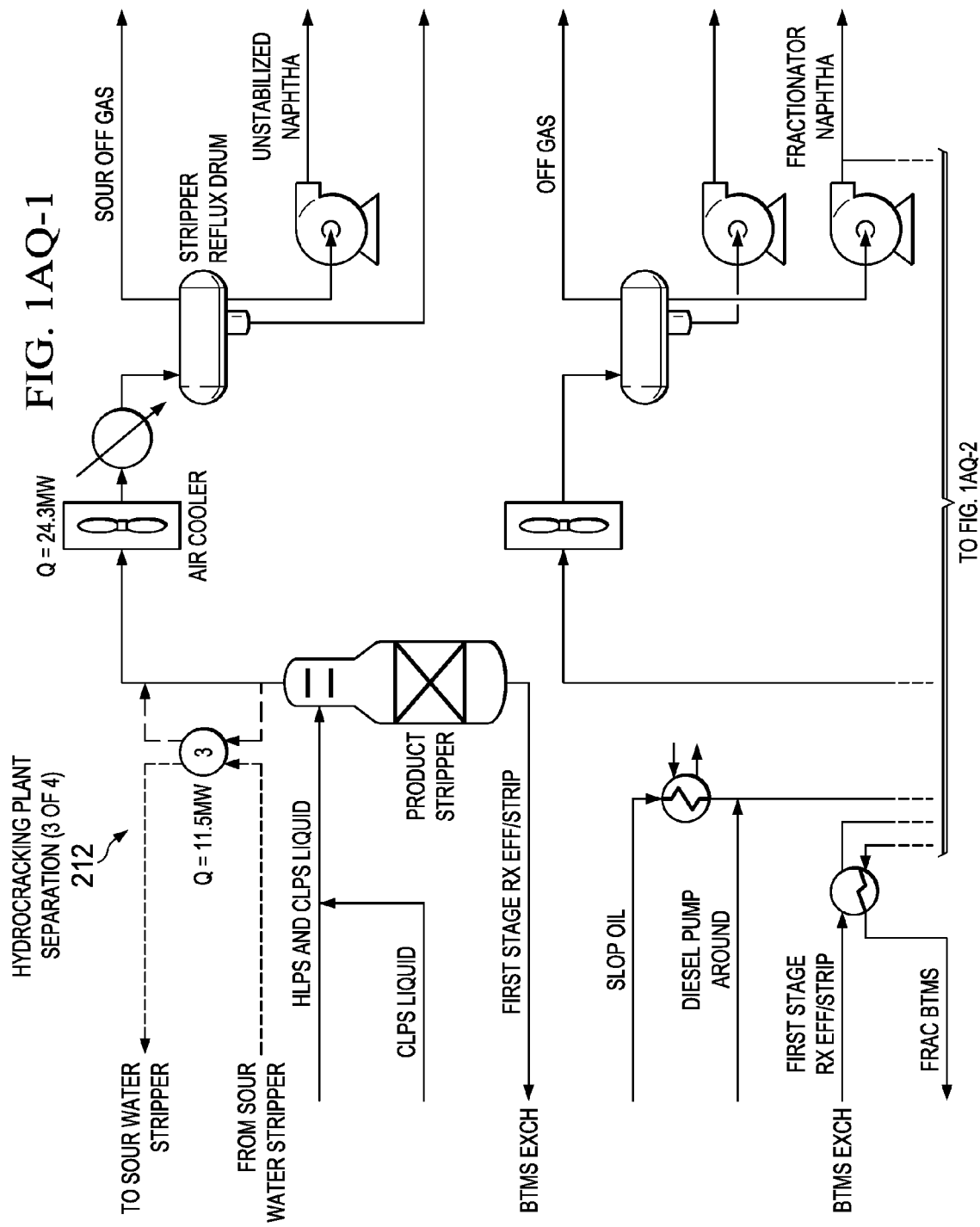
Figure 1A:
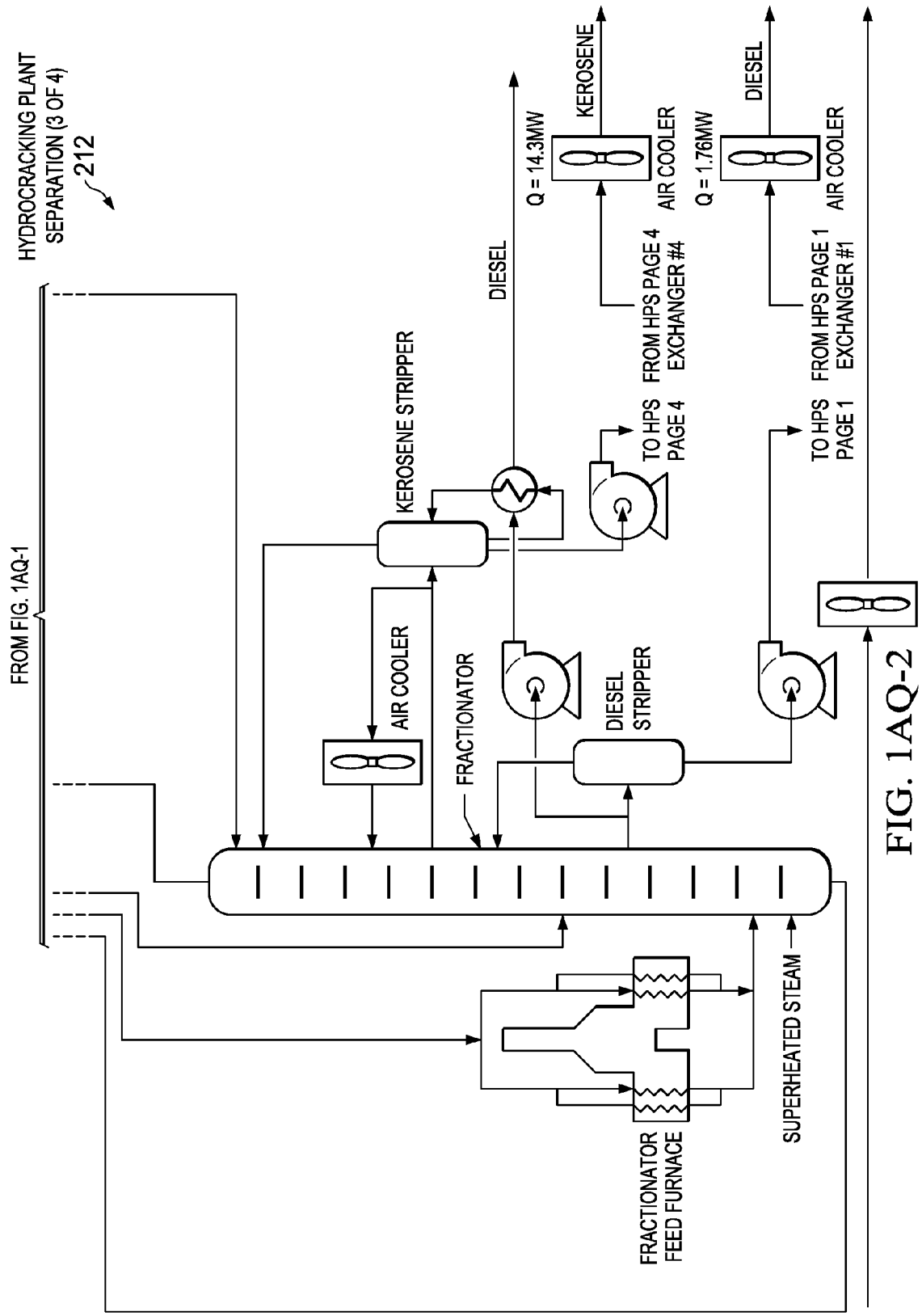
Figure 1A:
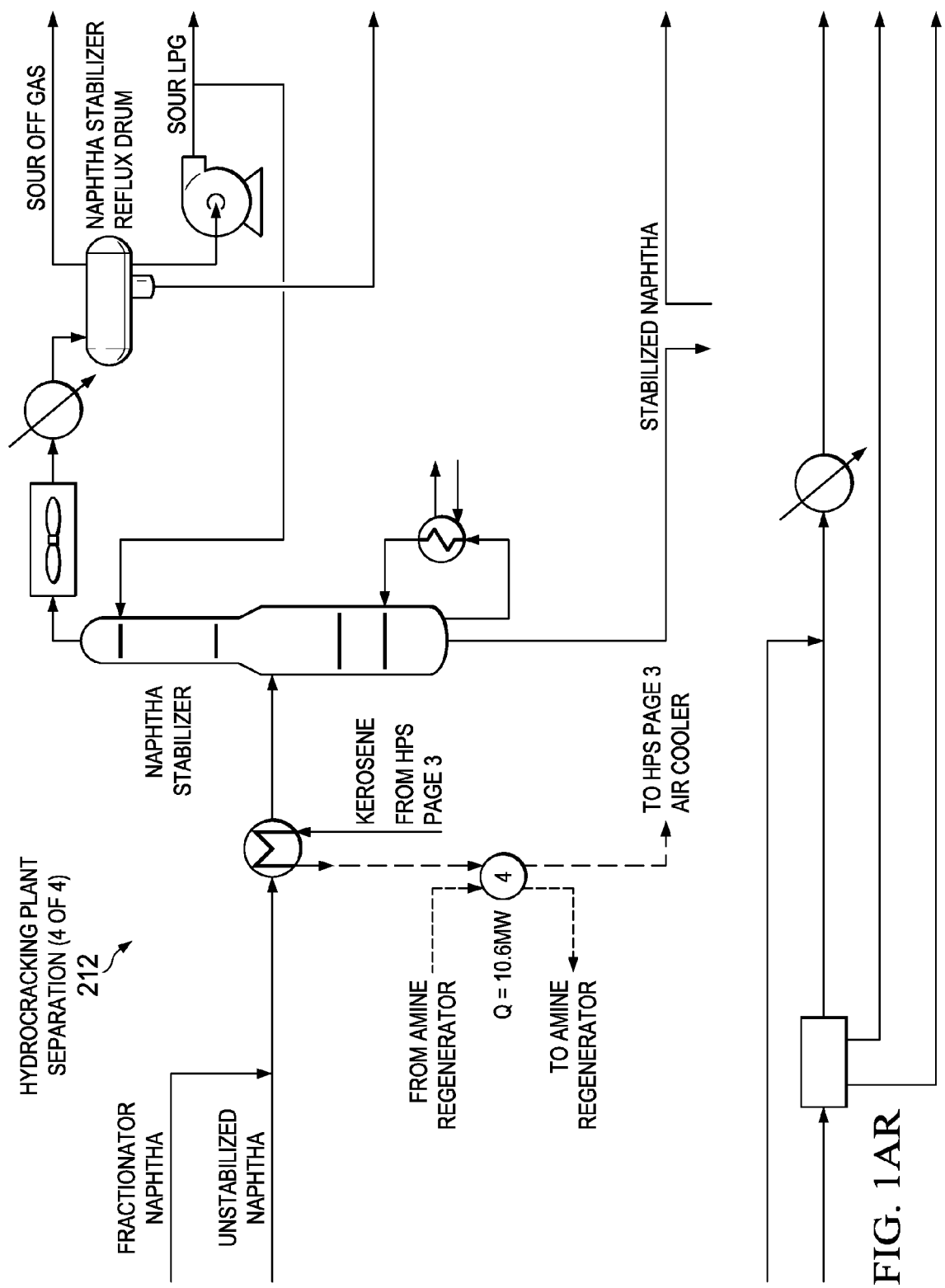
Figure 1A:
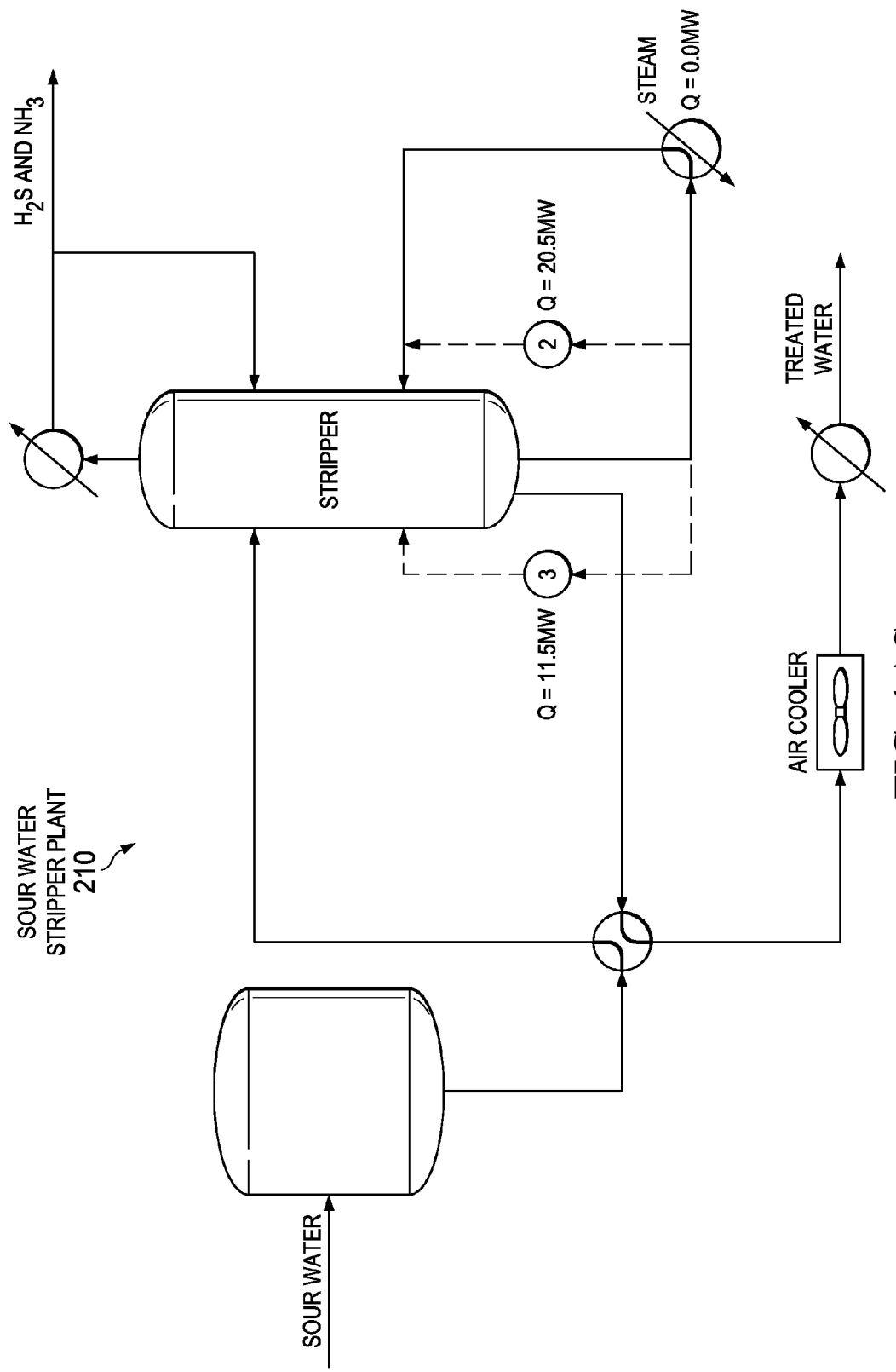
Figure 1A:
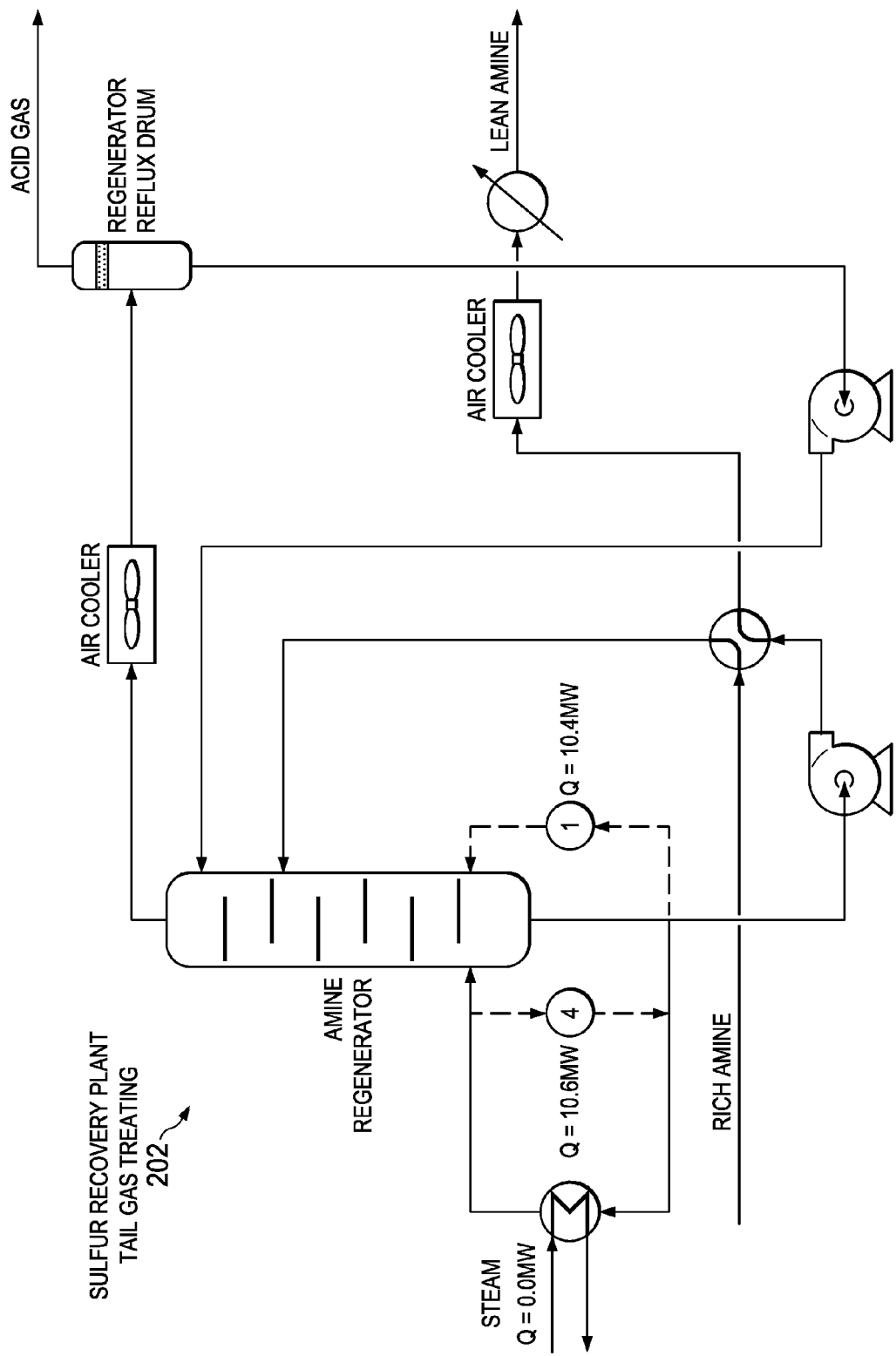
Figure 1A:
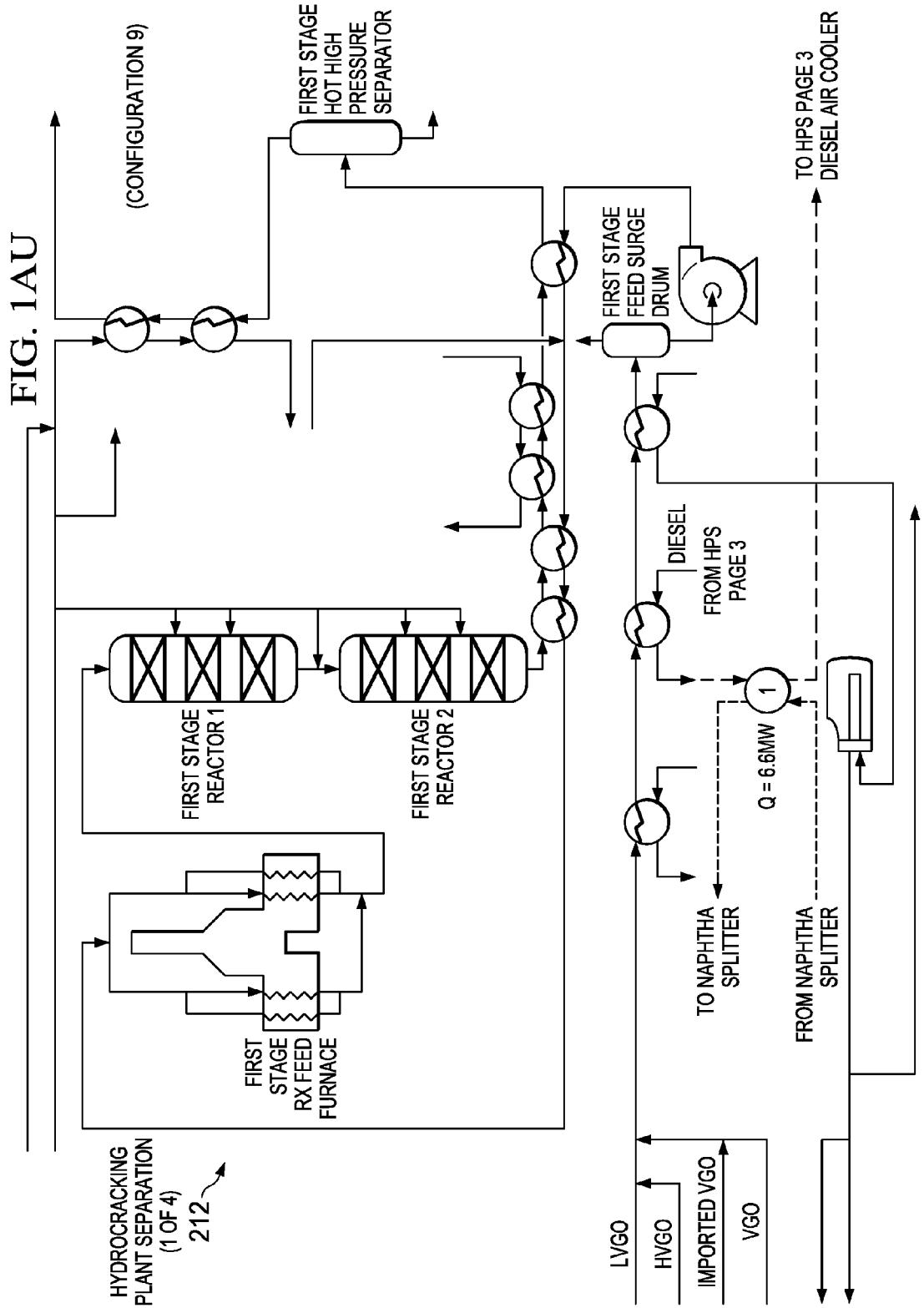
Figure 1A:
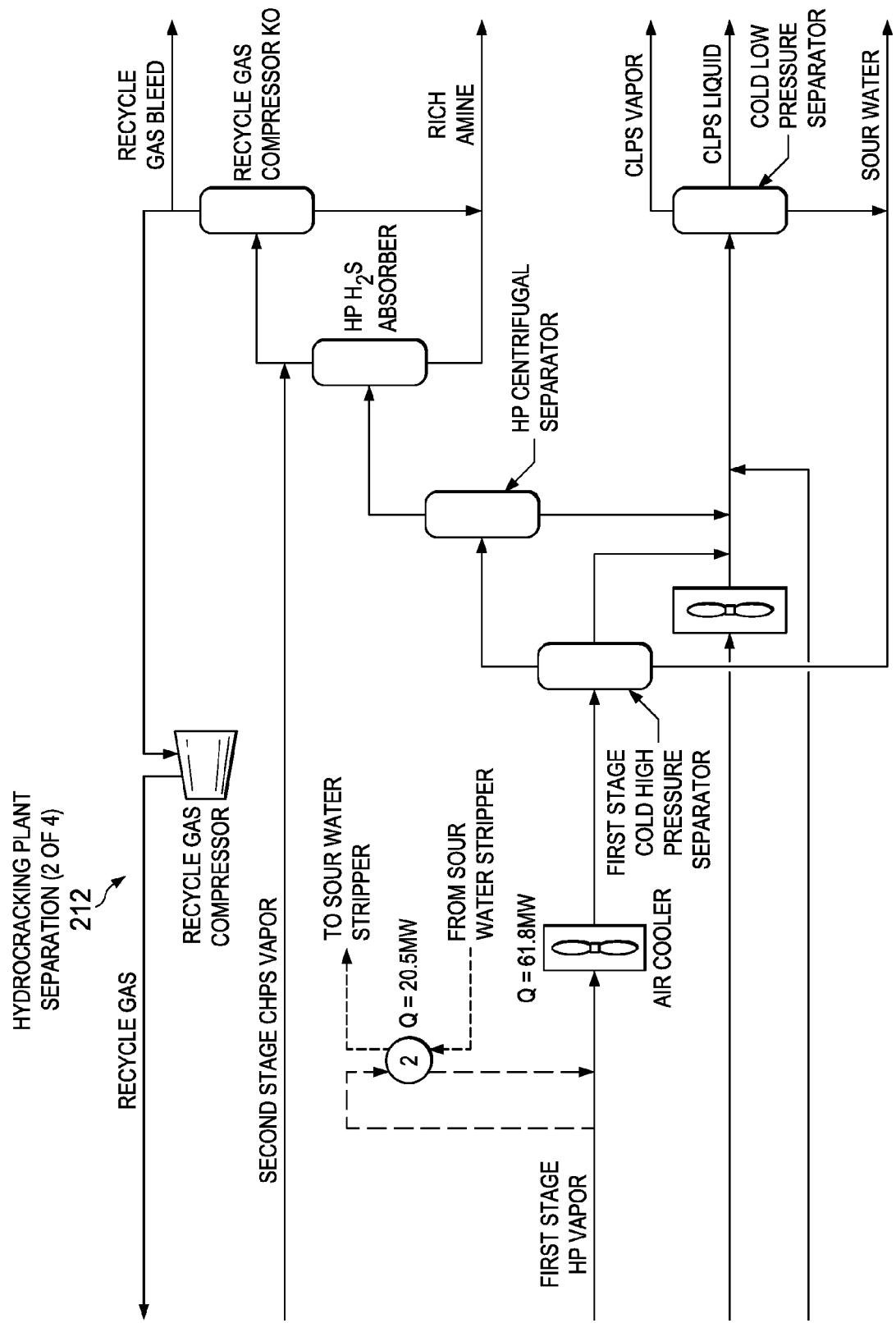
Figure 1A:
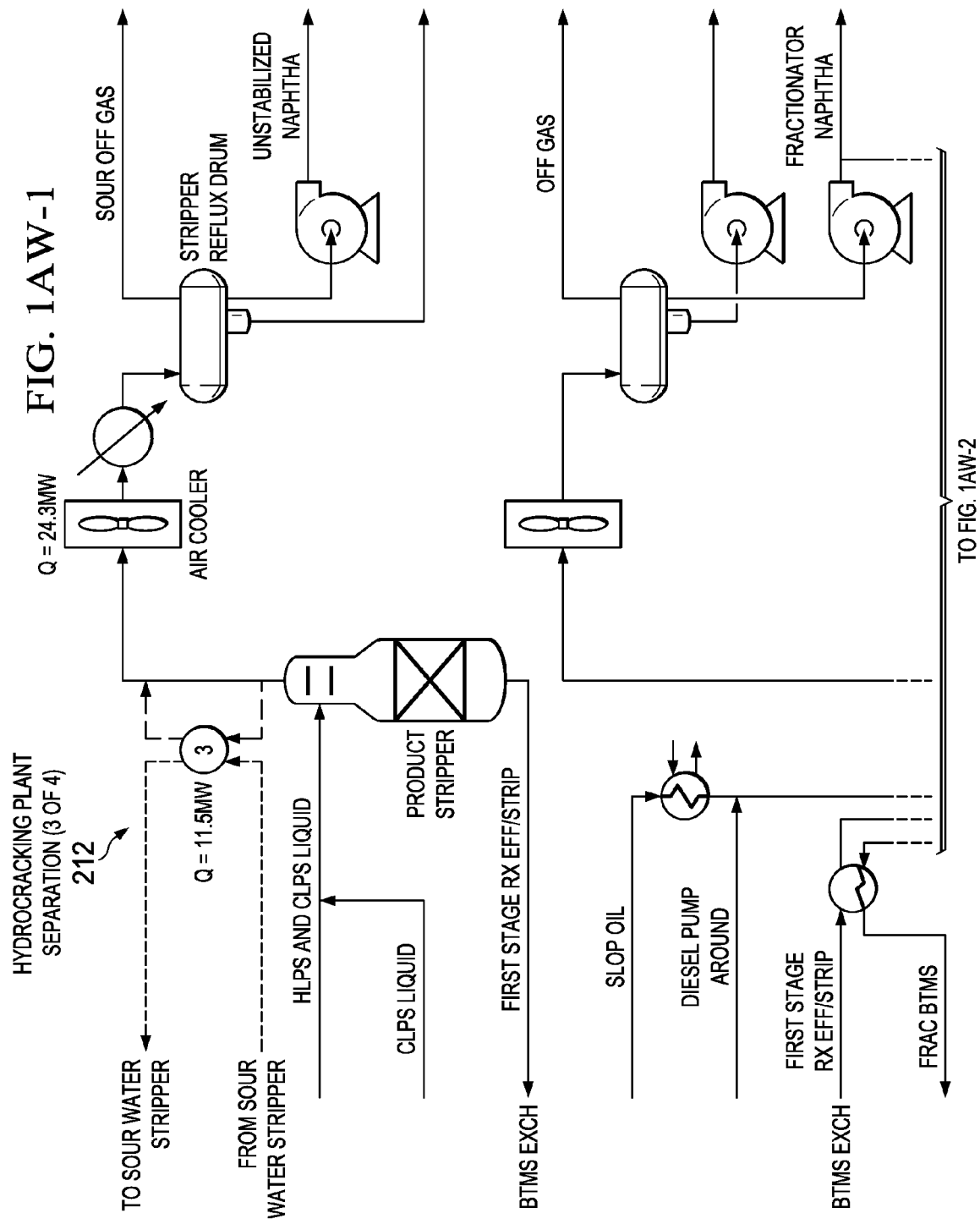
Figure 1A:
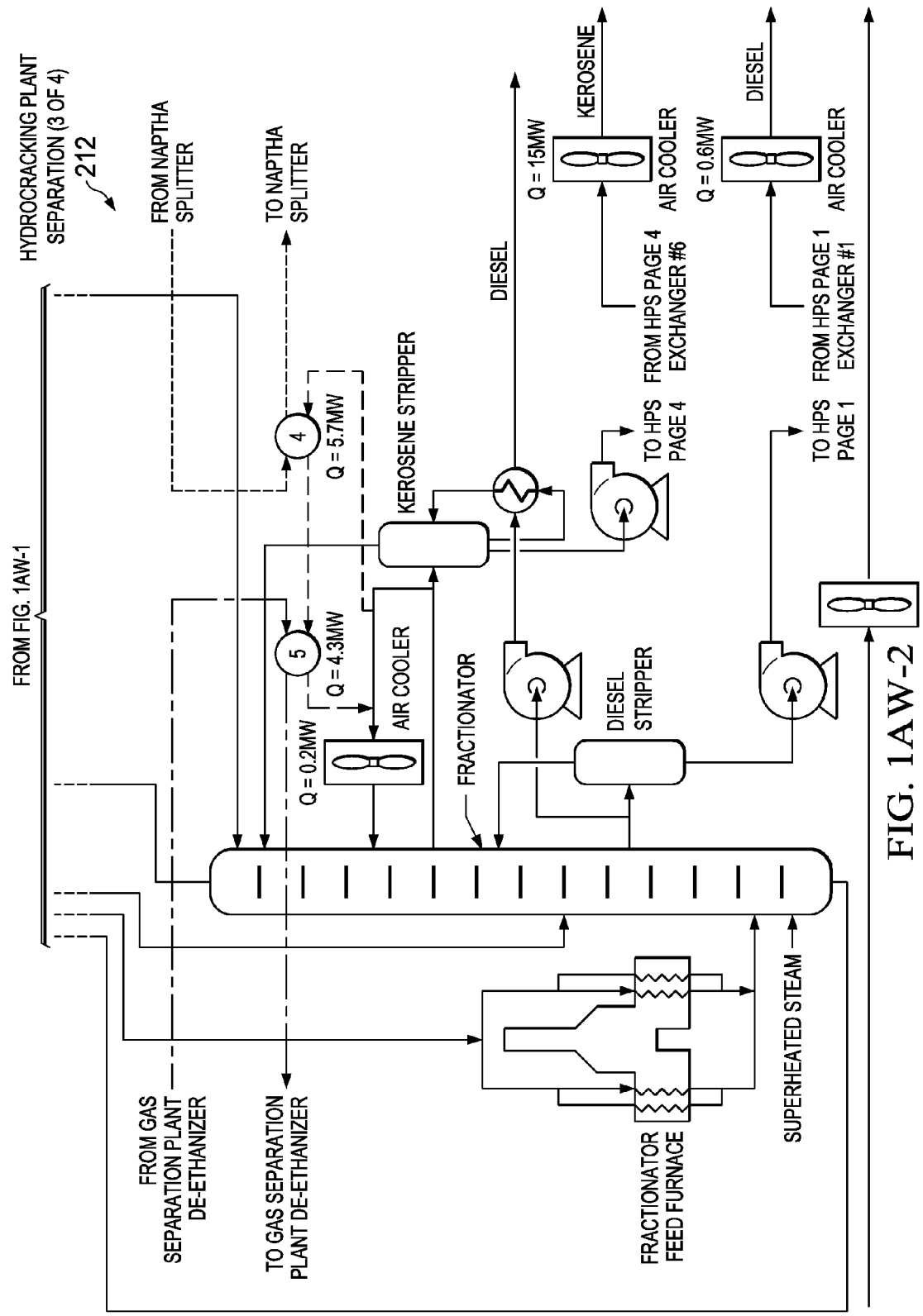
Figure 1A:
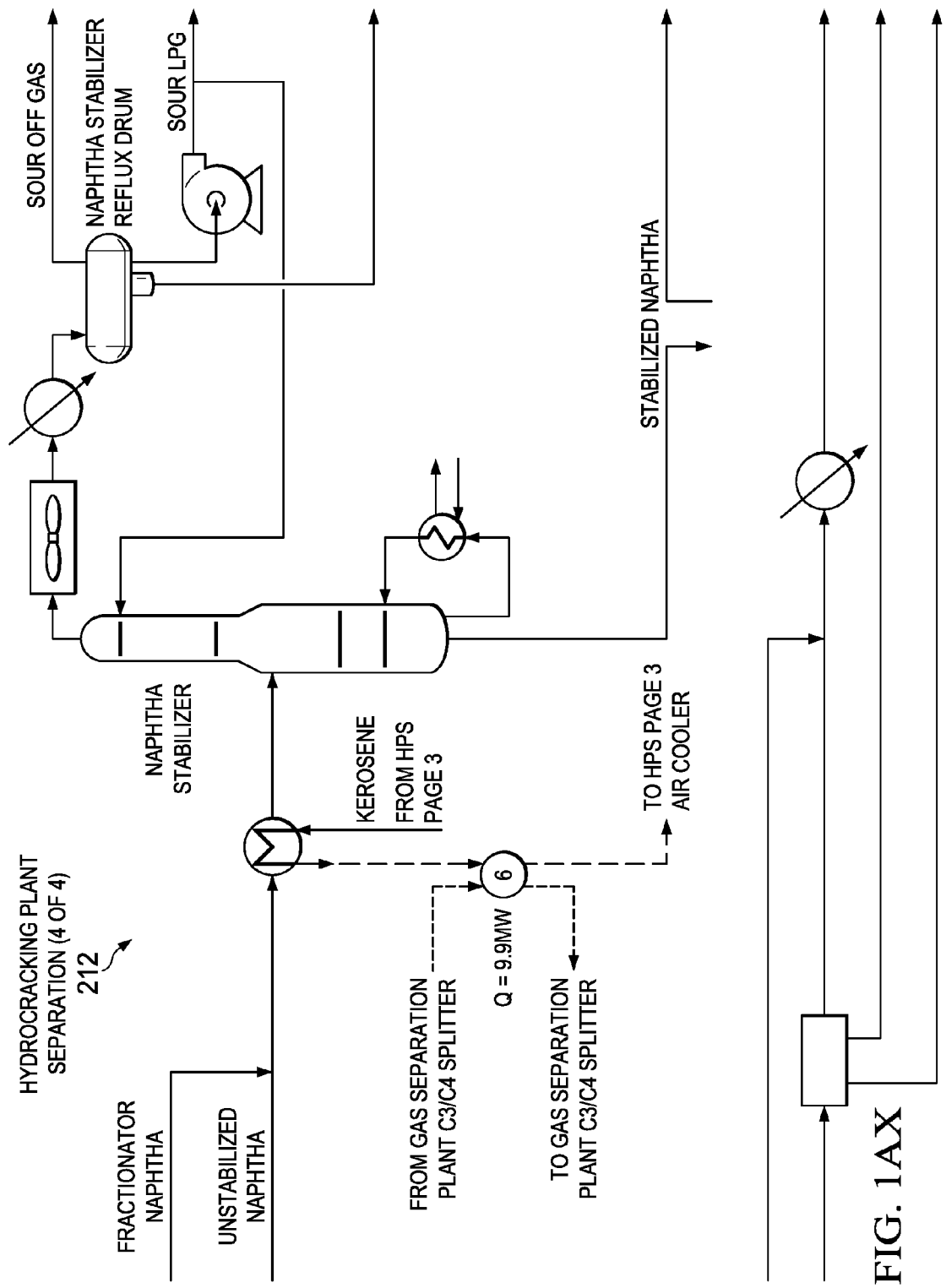
Figure 1A:
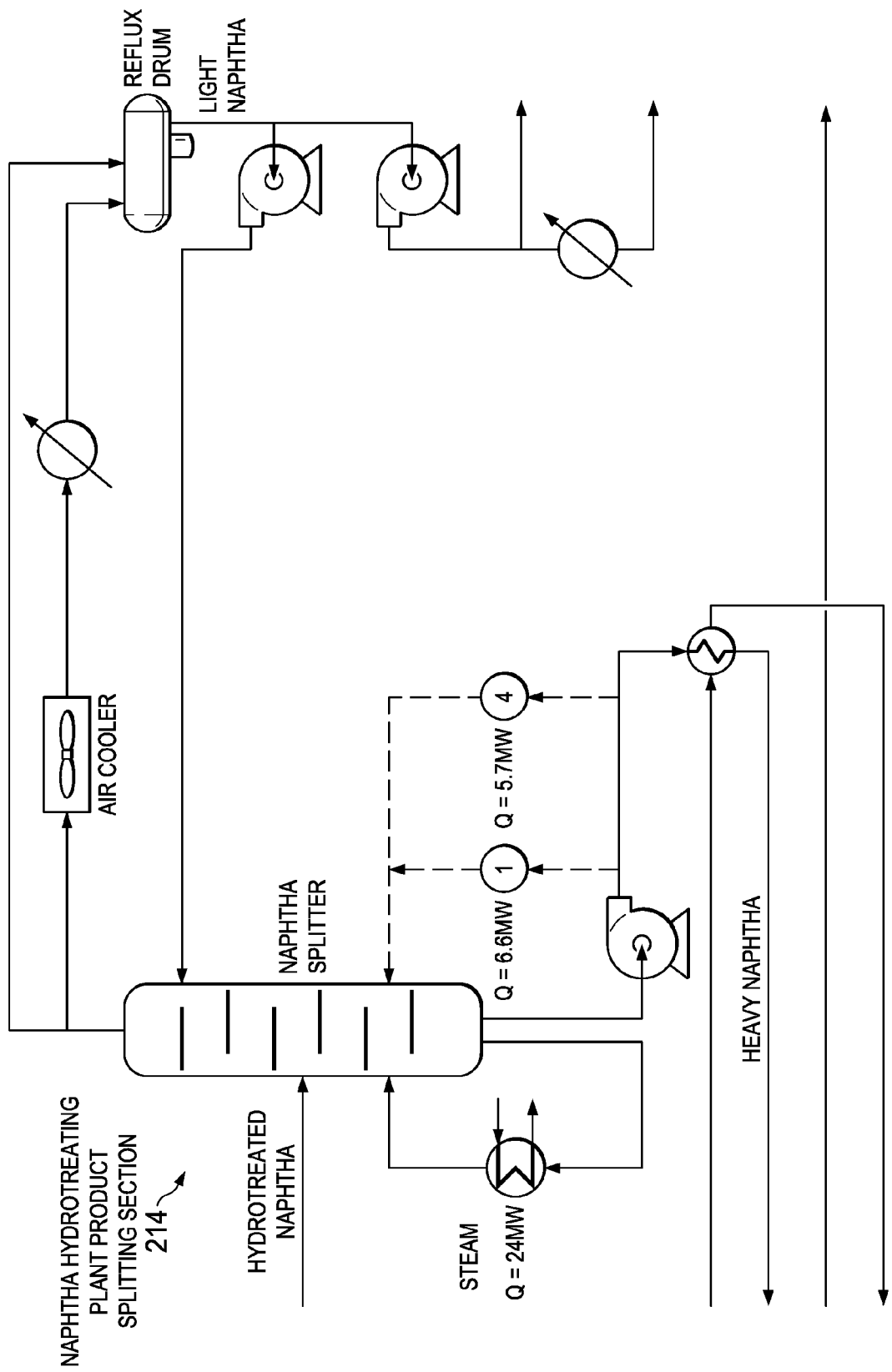
Figure 1A:
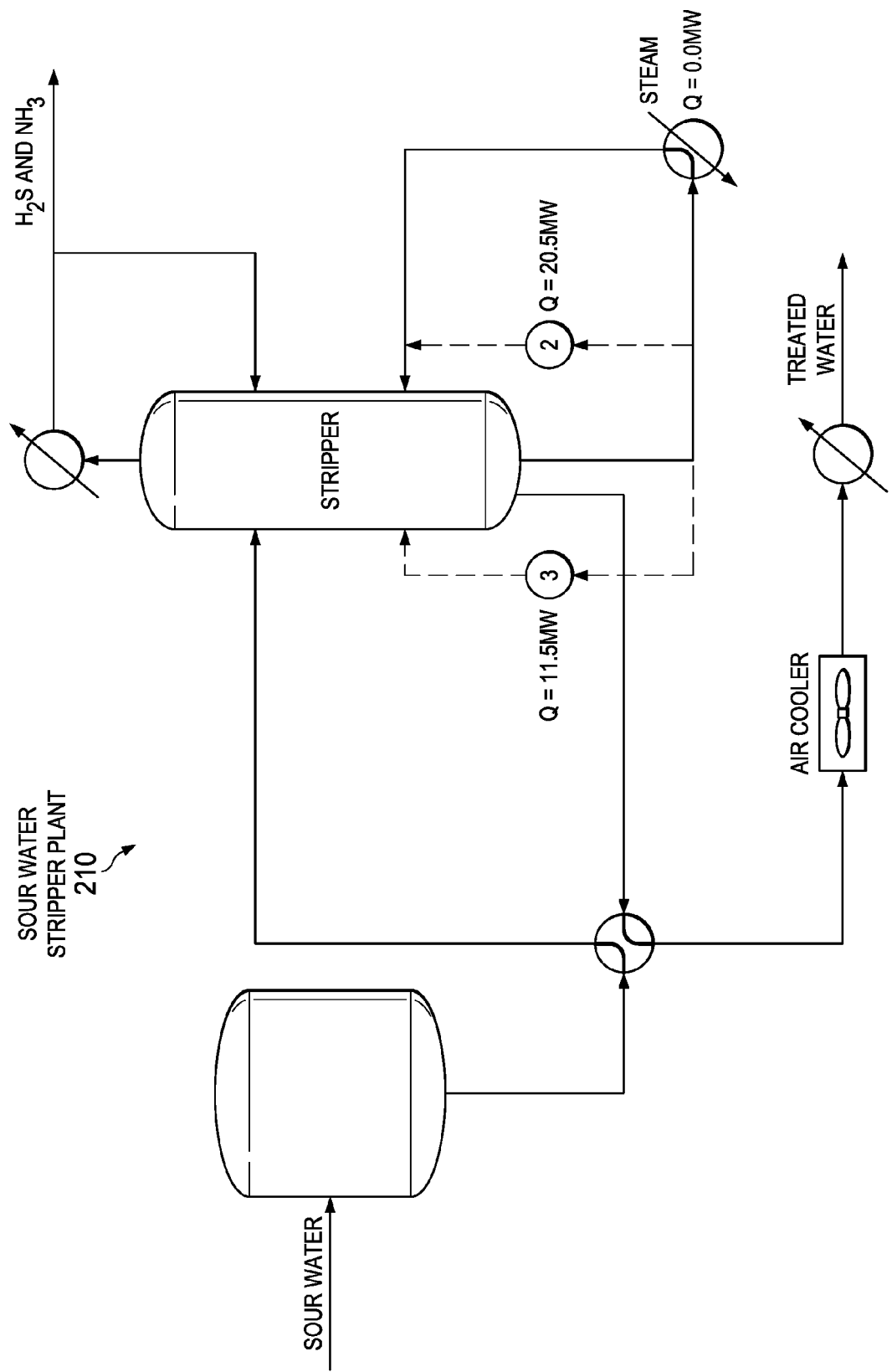
Figure 1B:
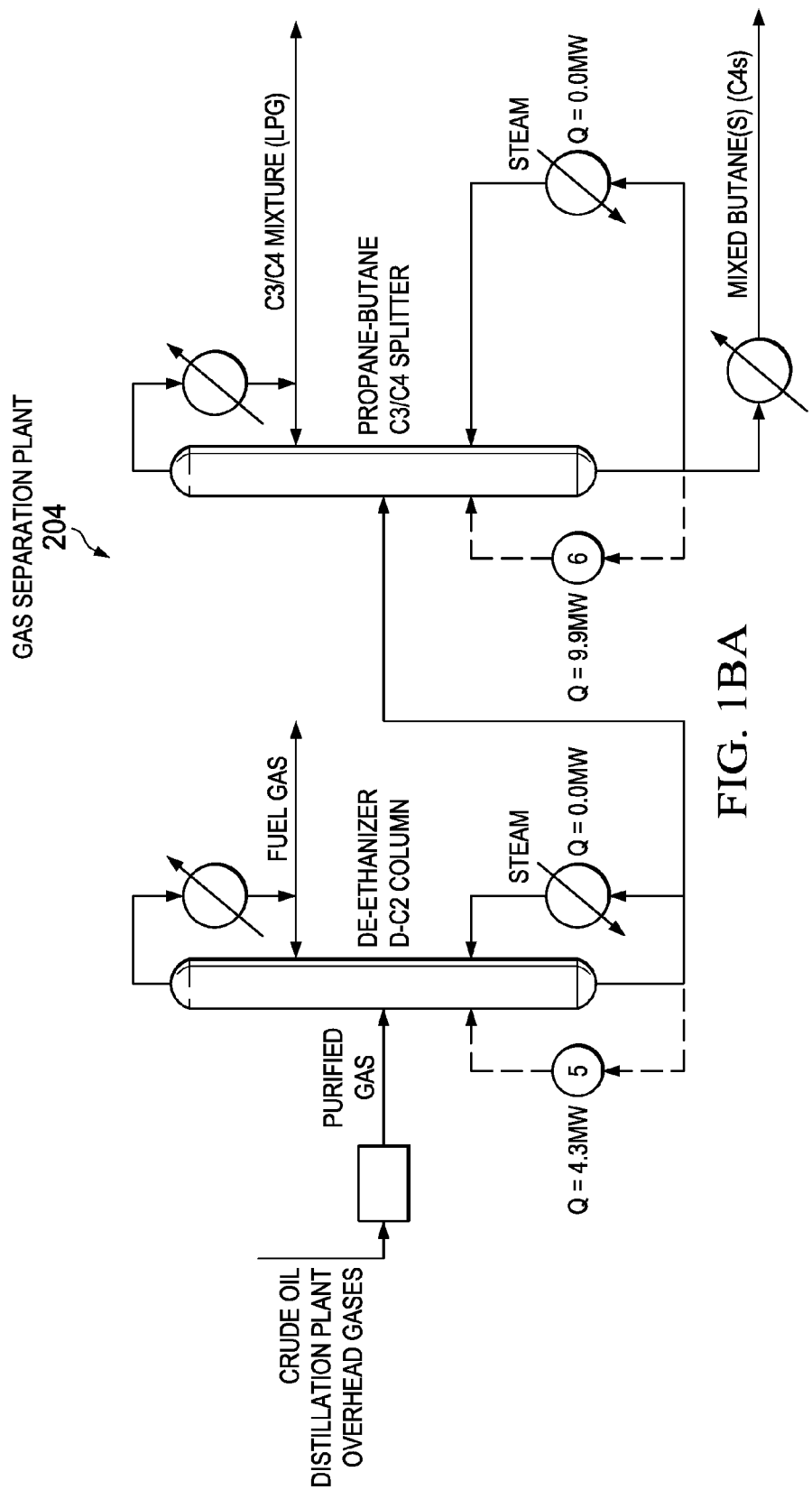
Figure 1B:
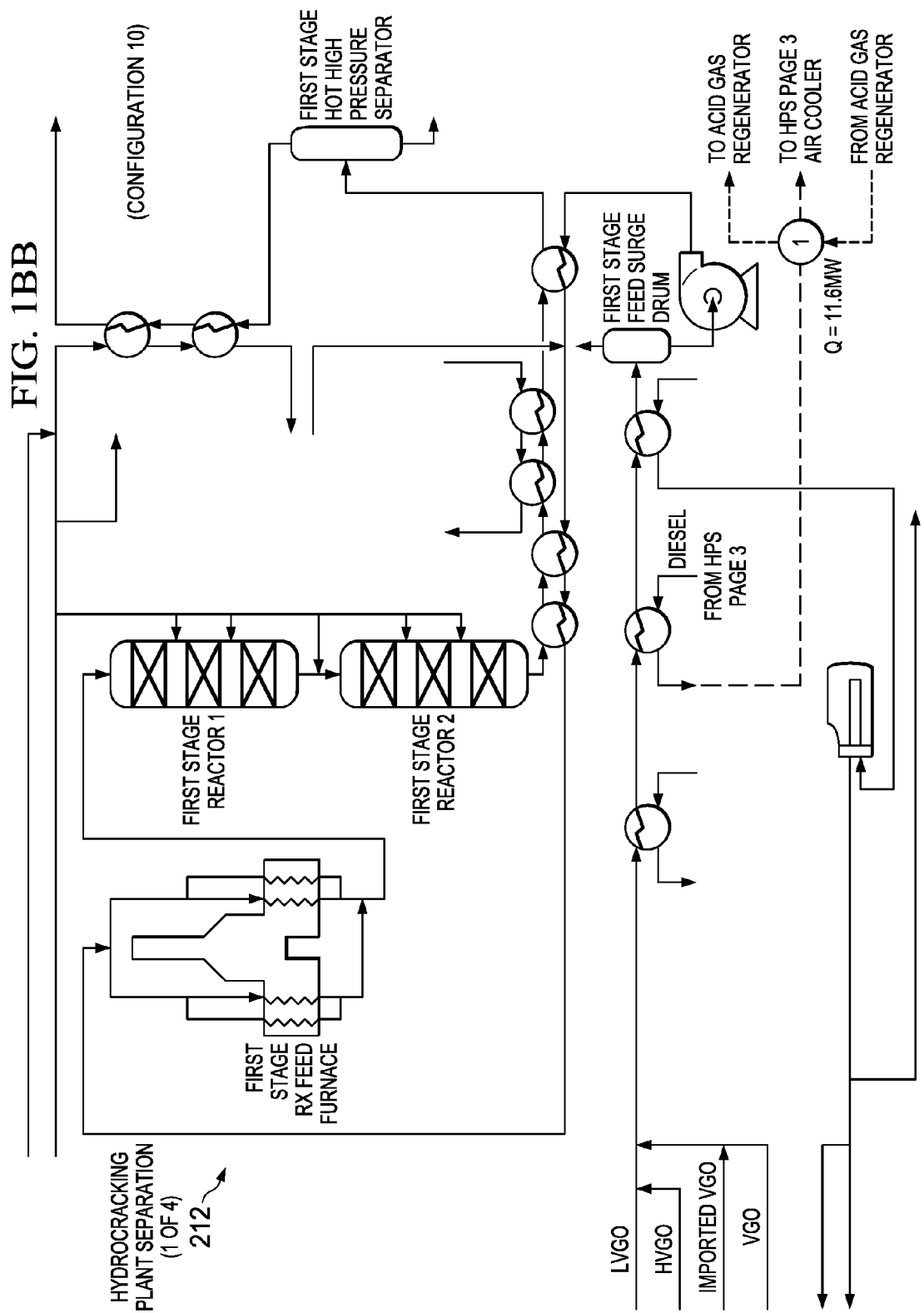
Figure 1B:
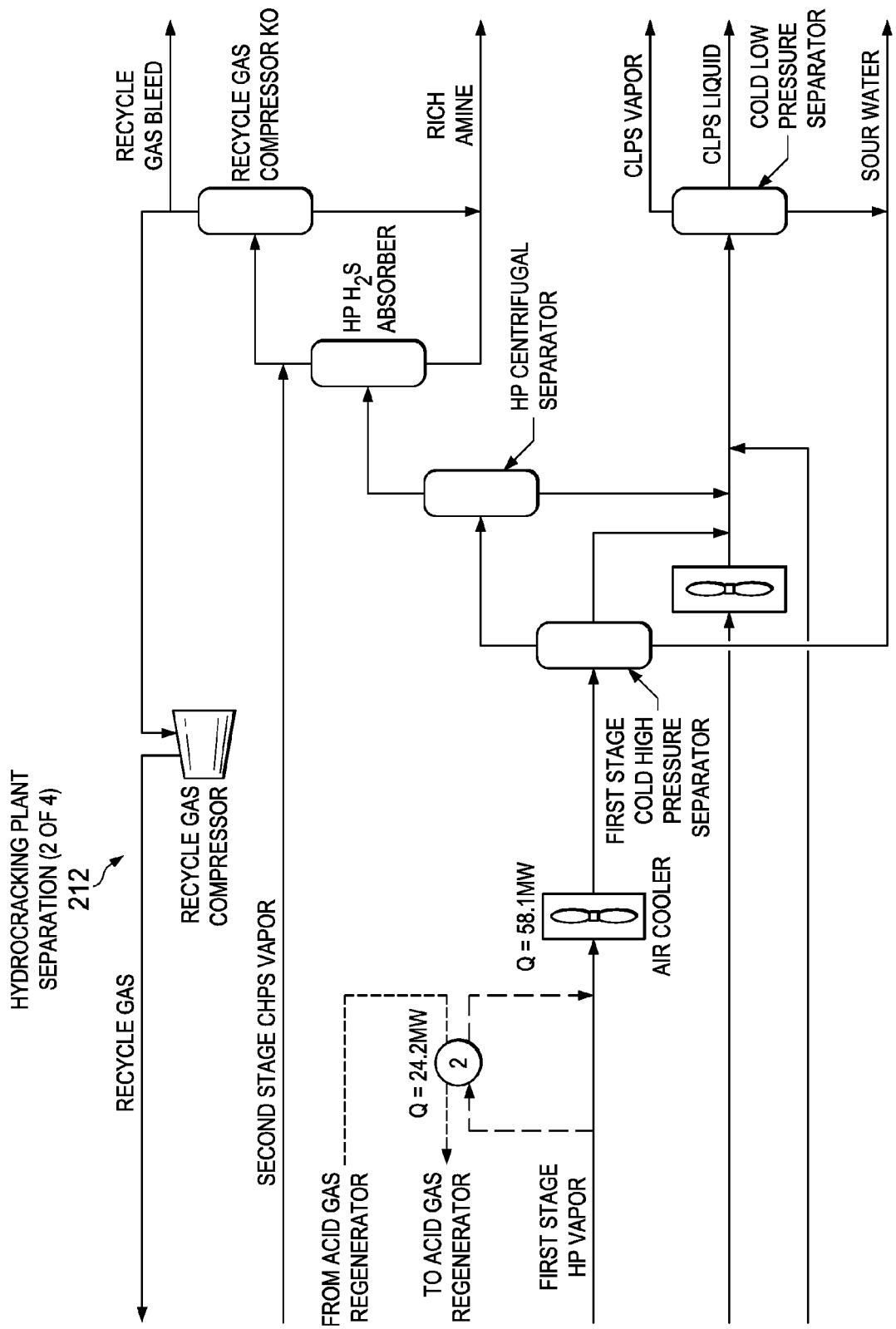
Figure 1B:
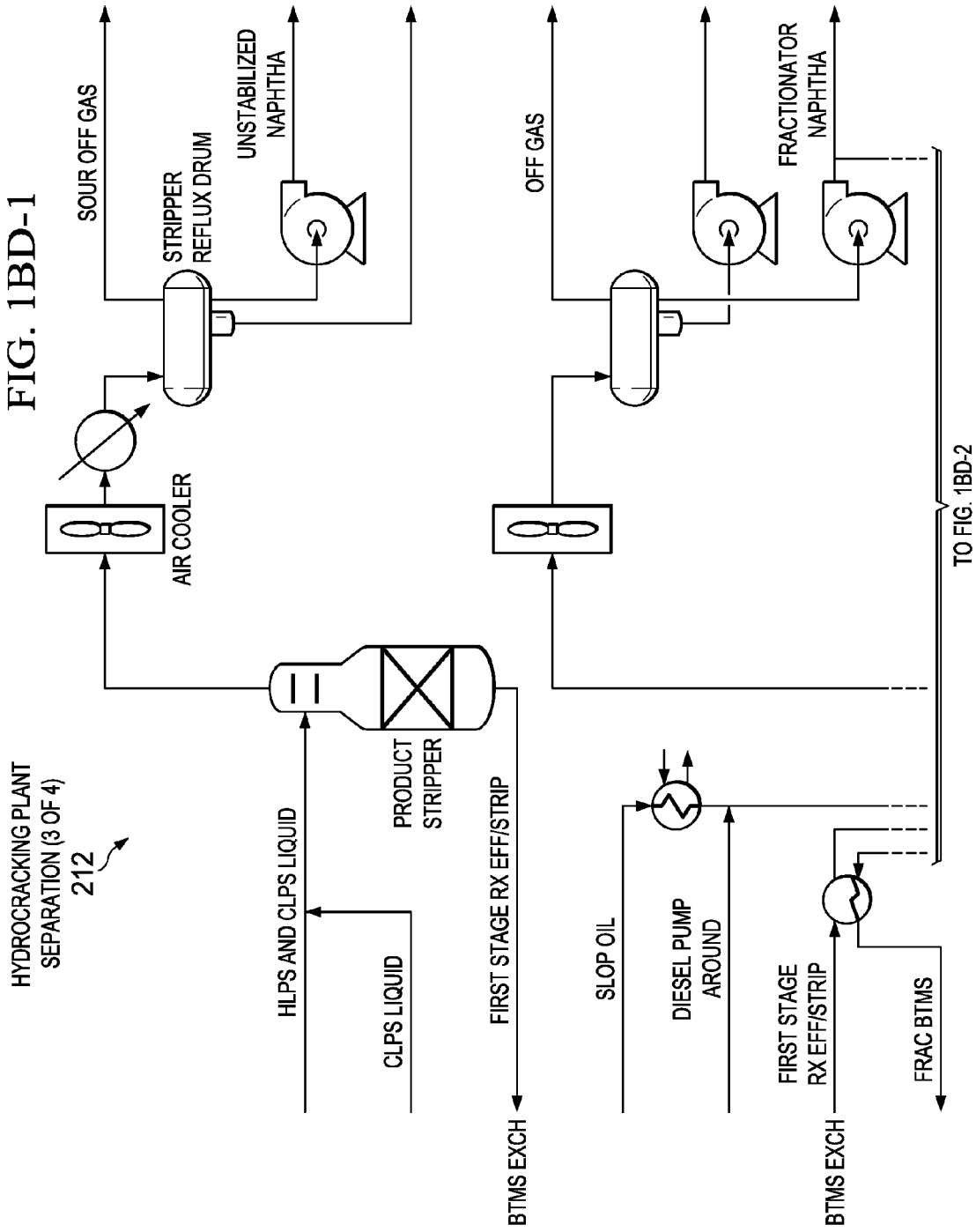
Figure 1B:
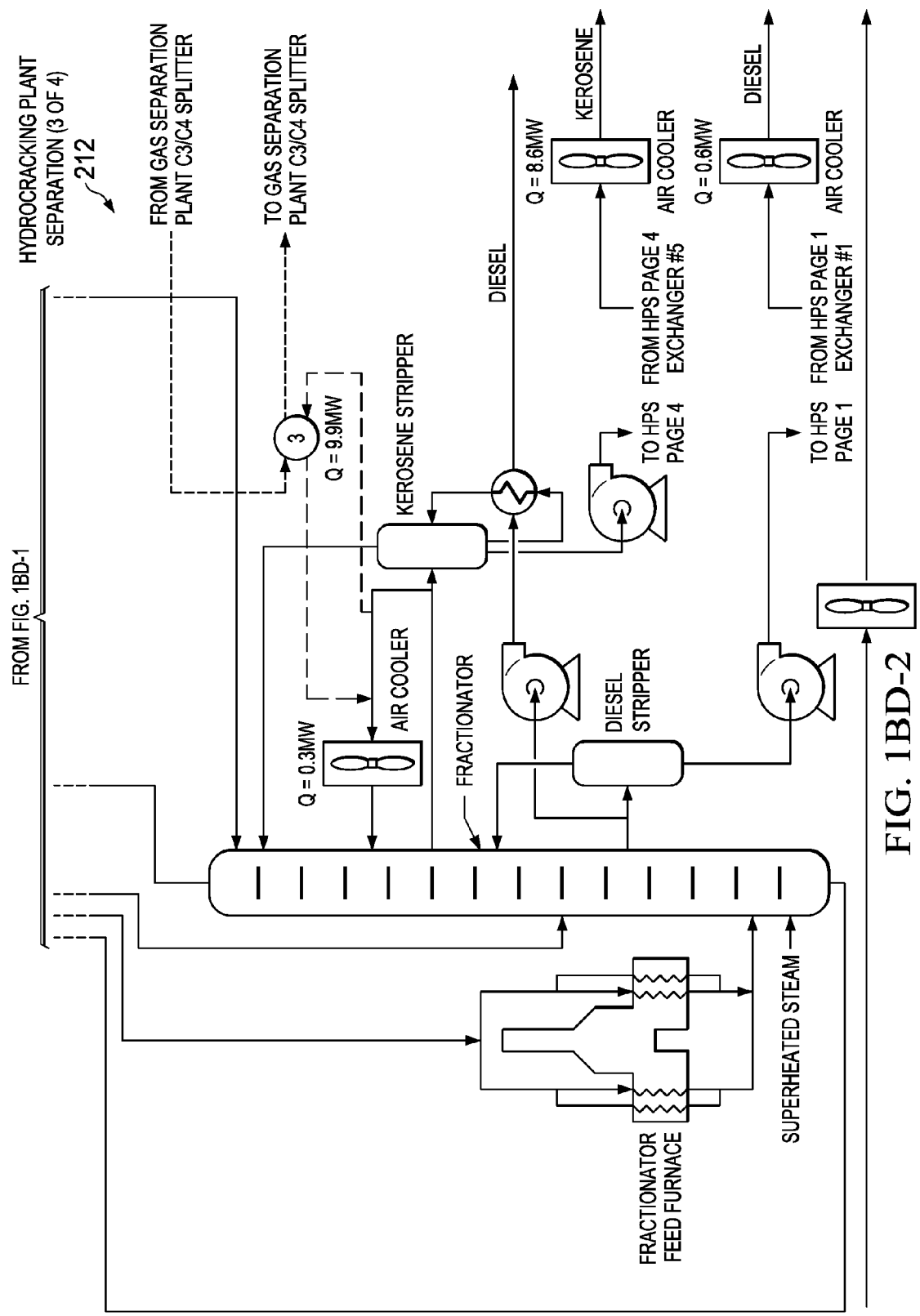
Figure 1B:
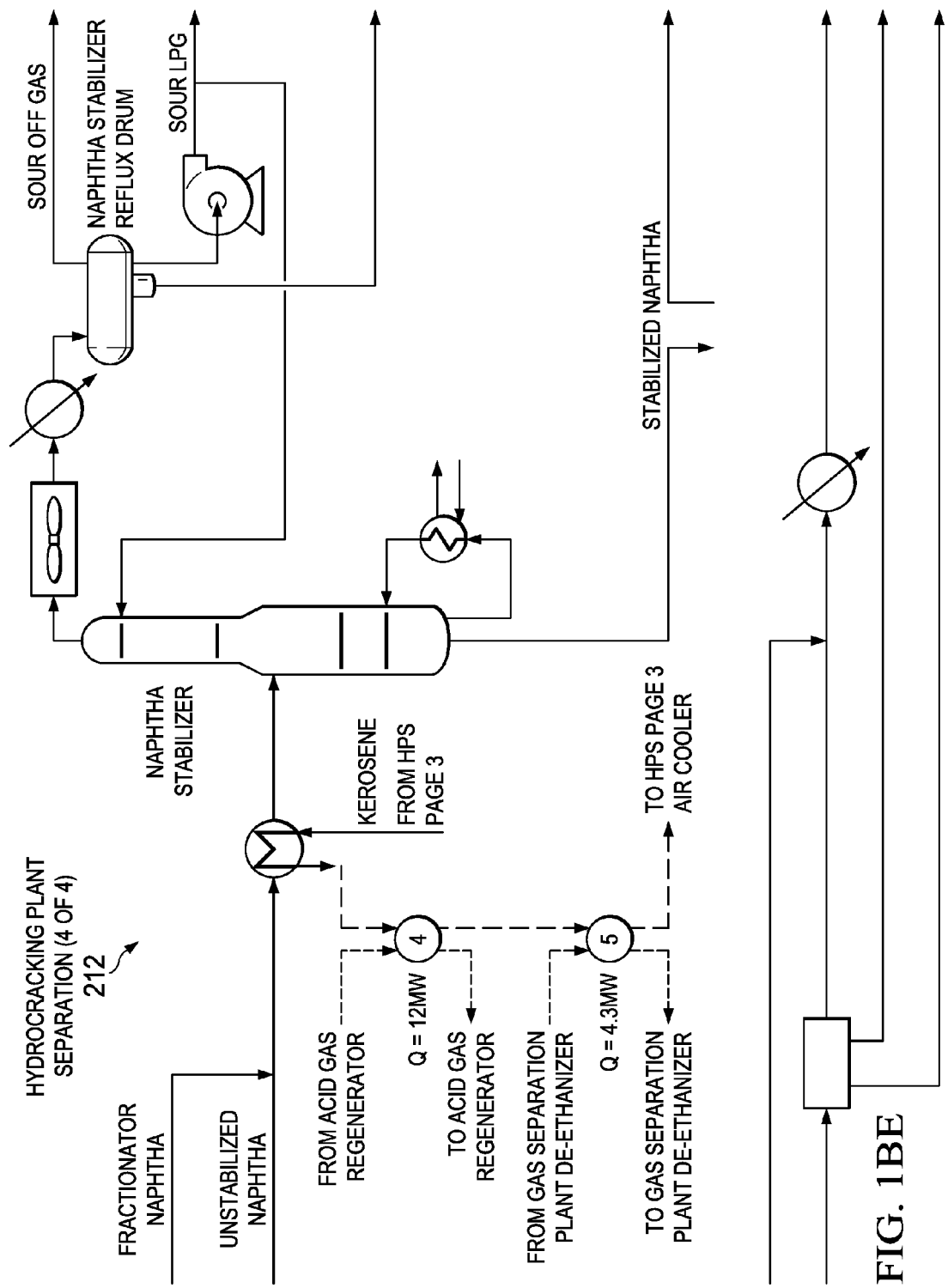
Figure 1B:
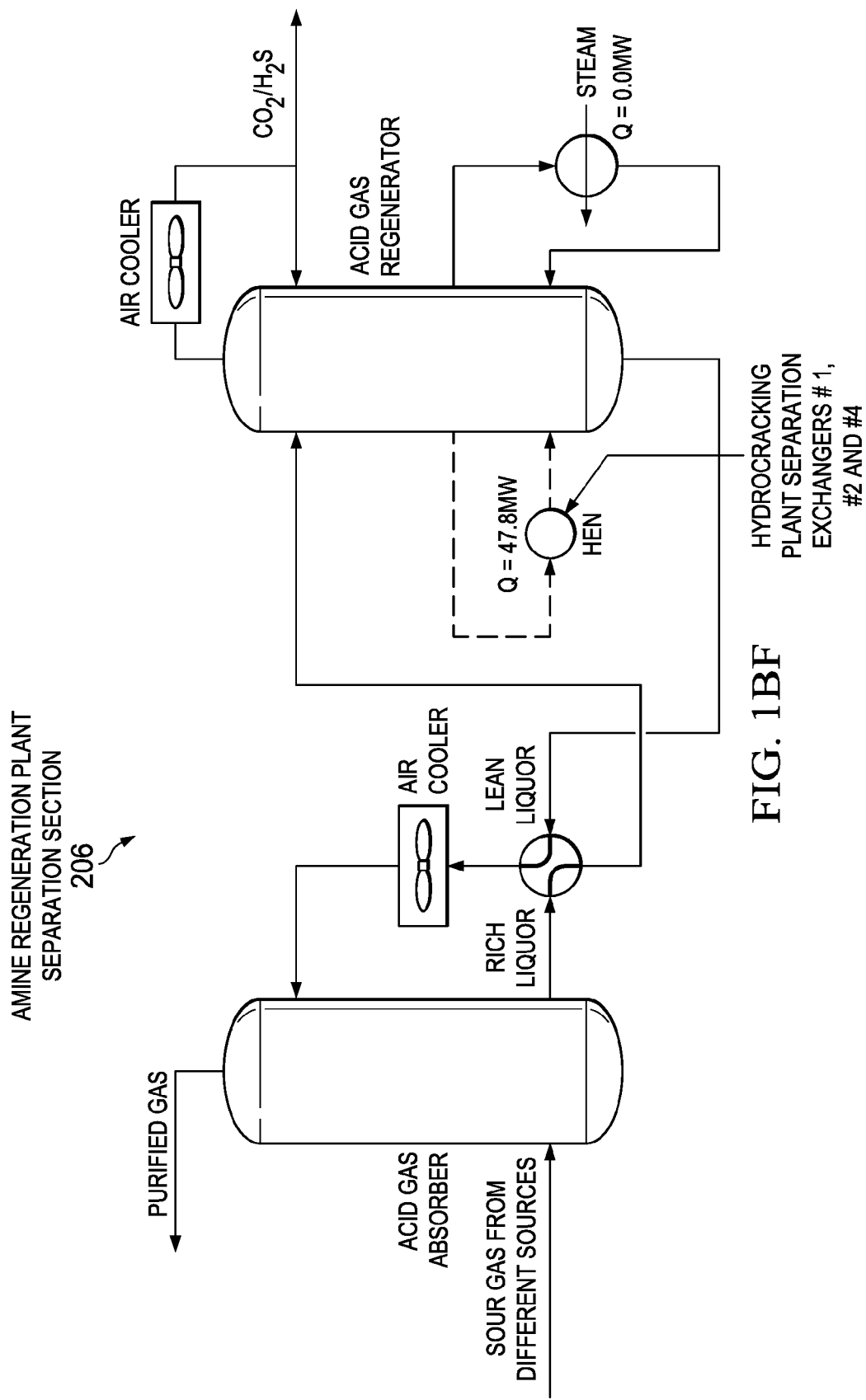
Figure 1B:
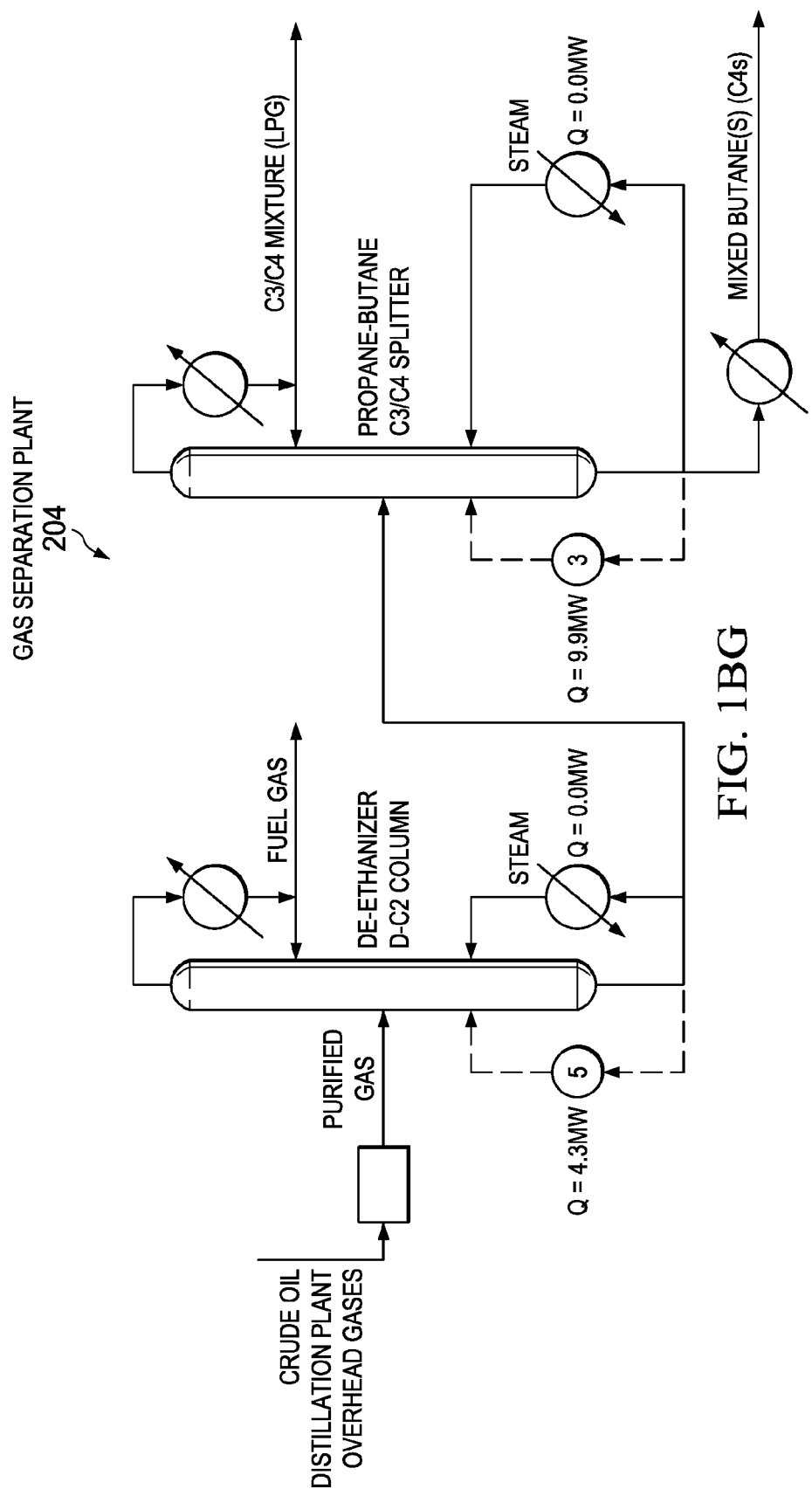
Figure 1B:
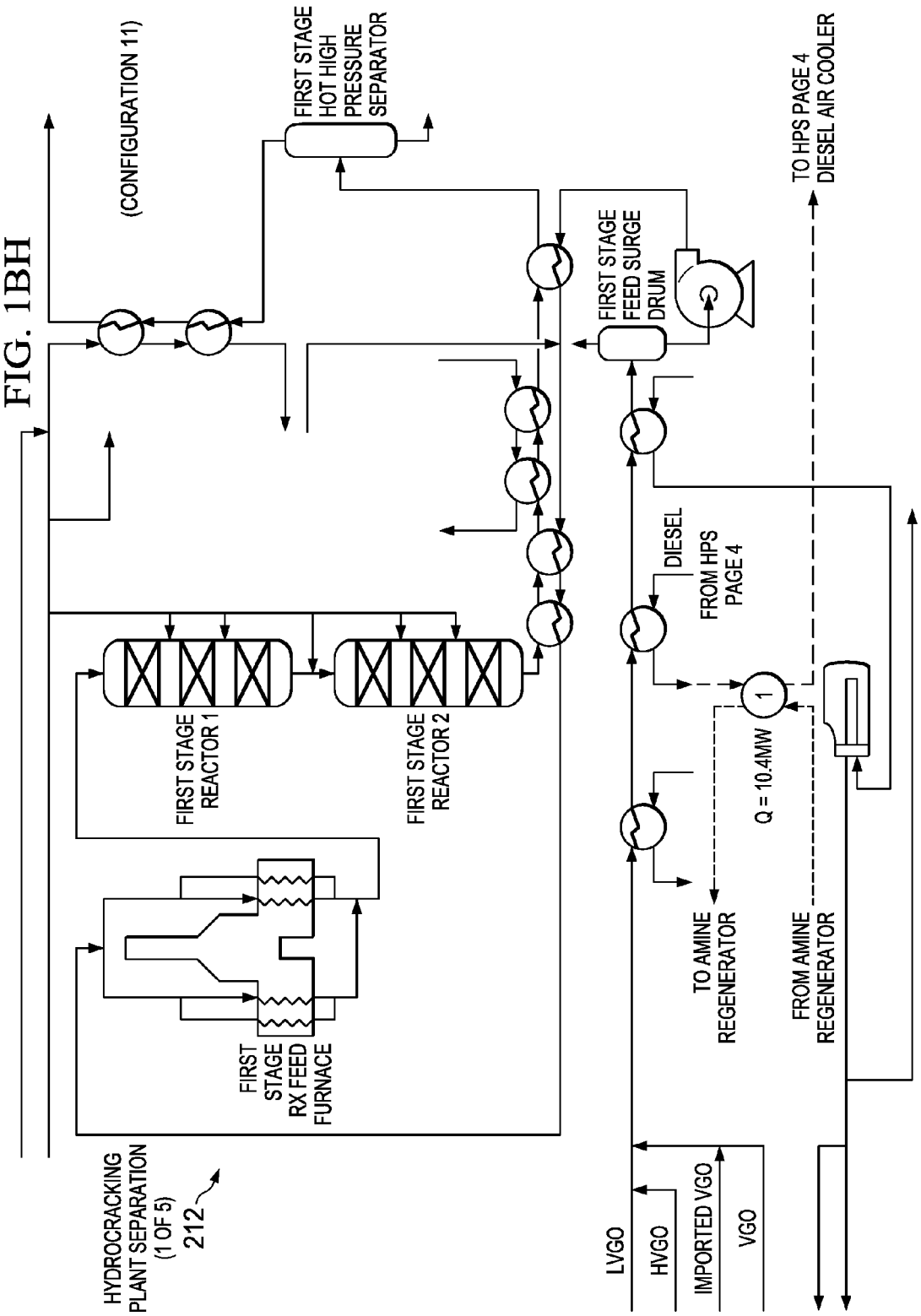
Figure 1B:
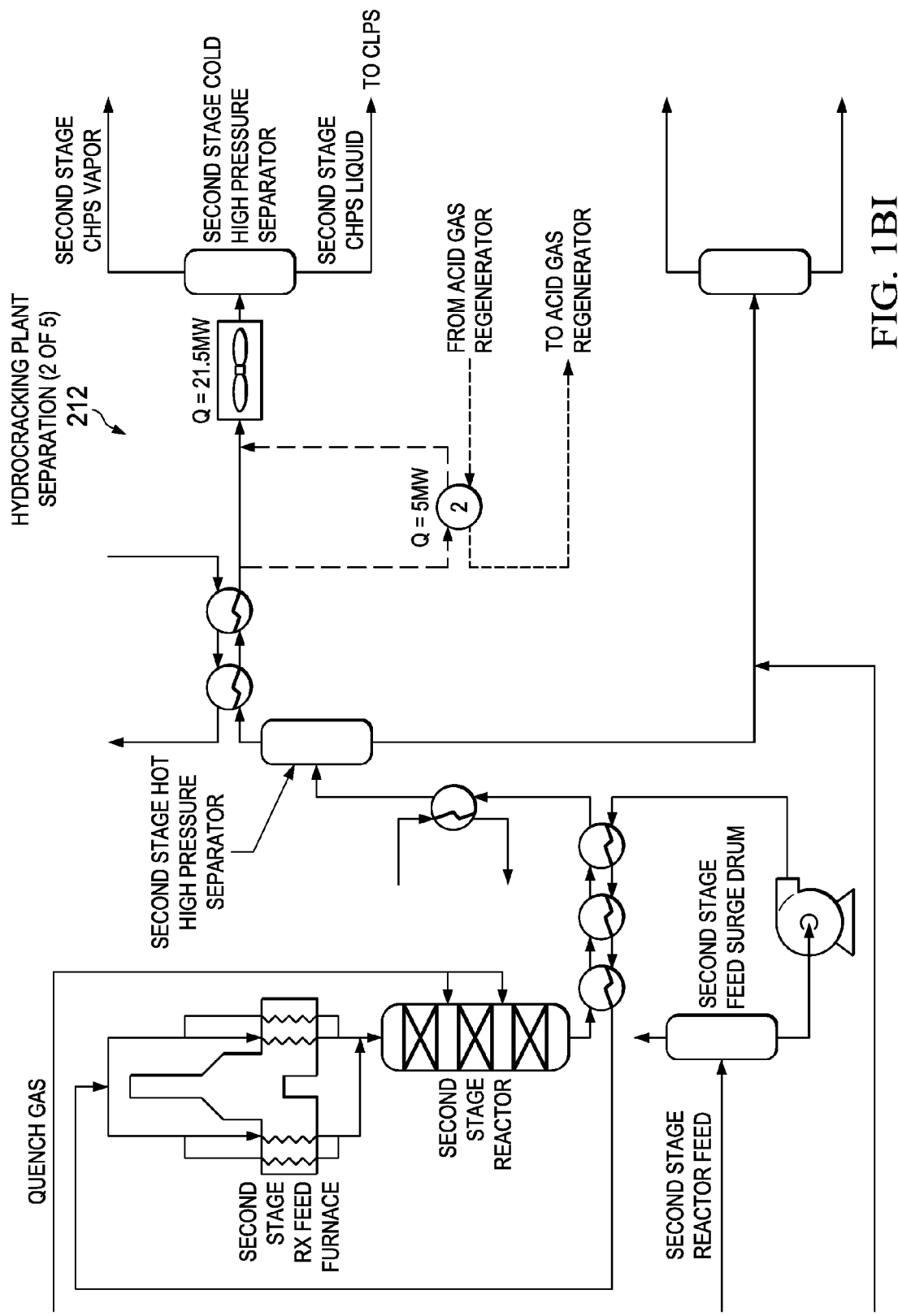
Figure 1B:
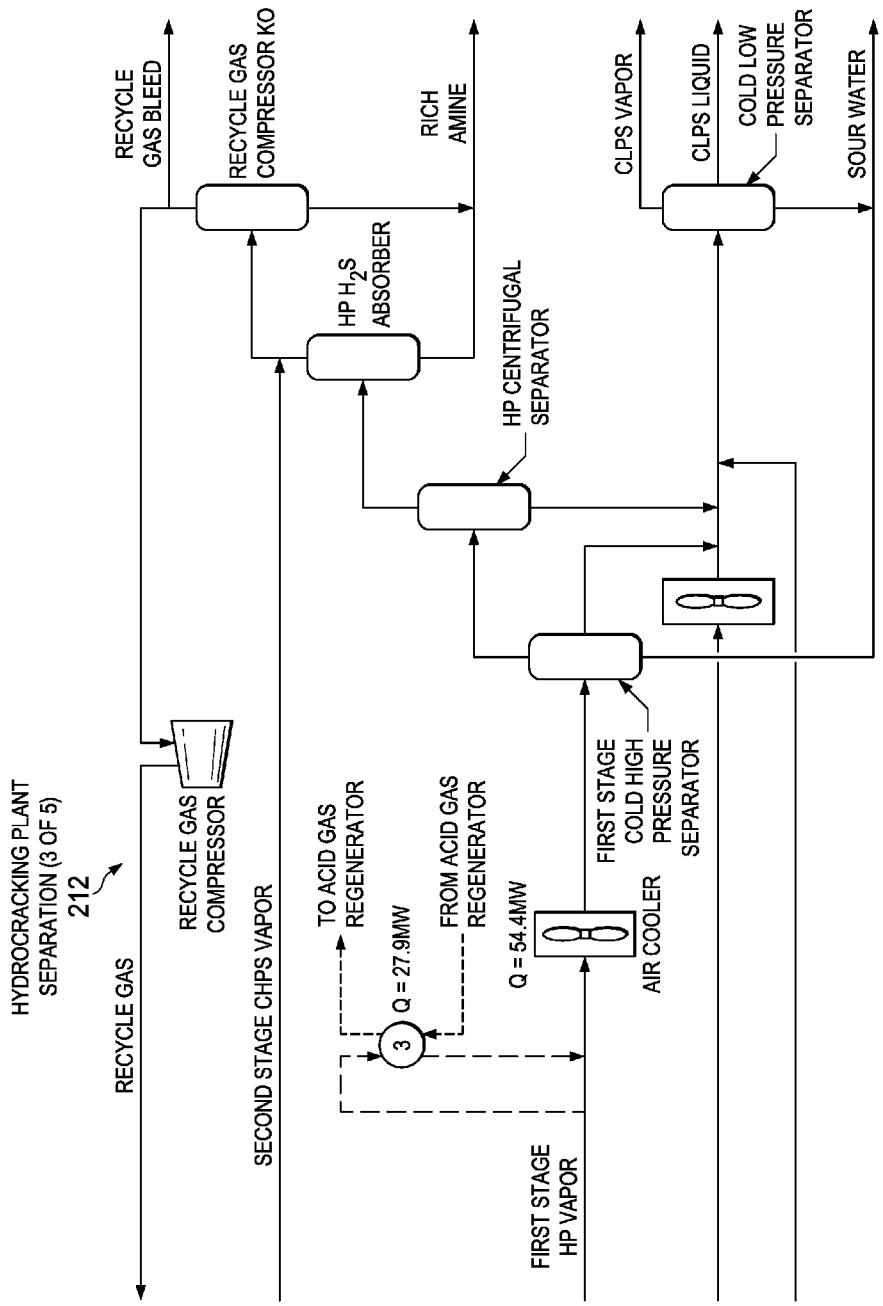
Figure 1B:
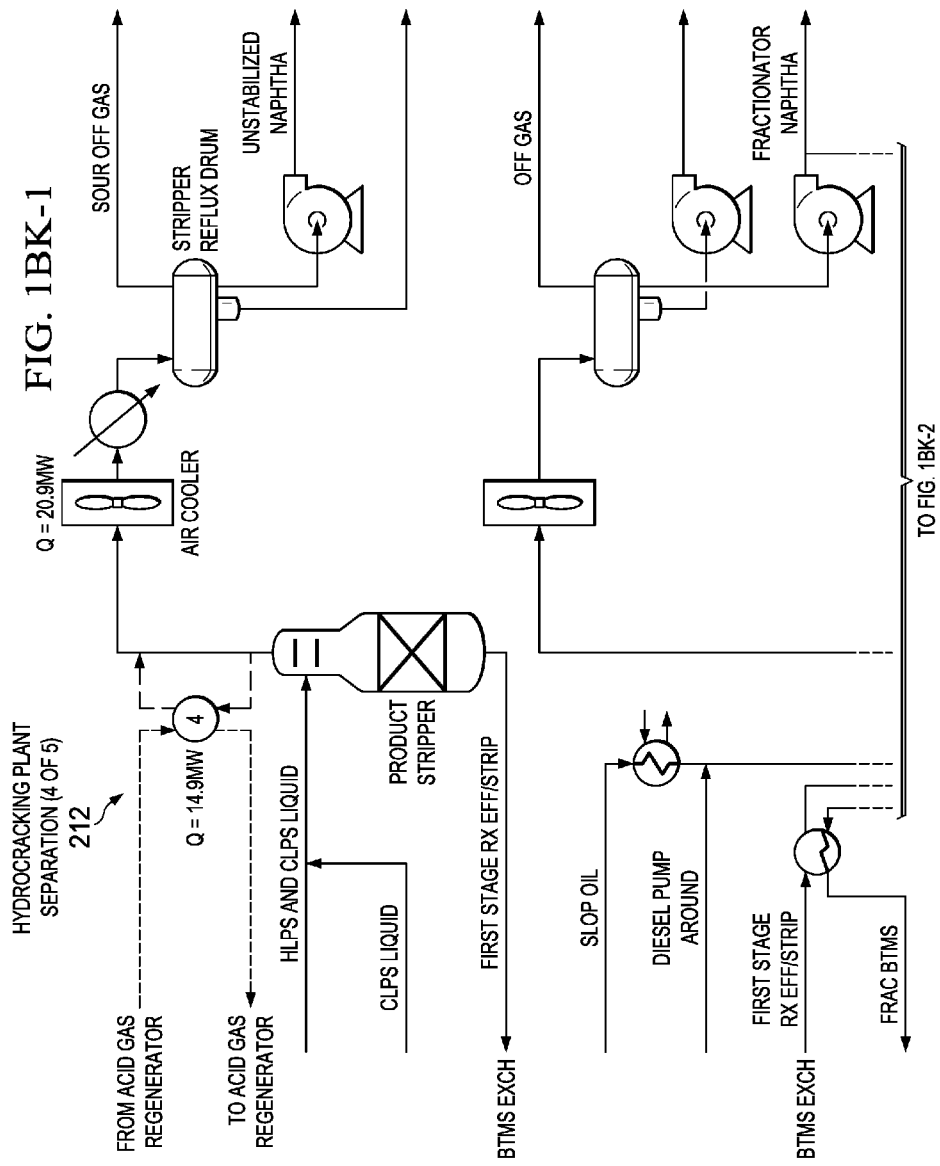
Figure 1B:
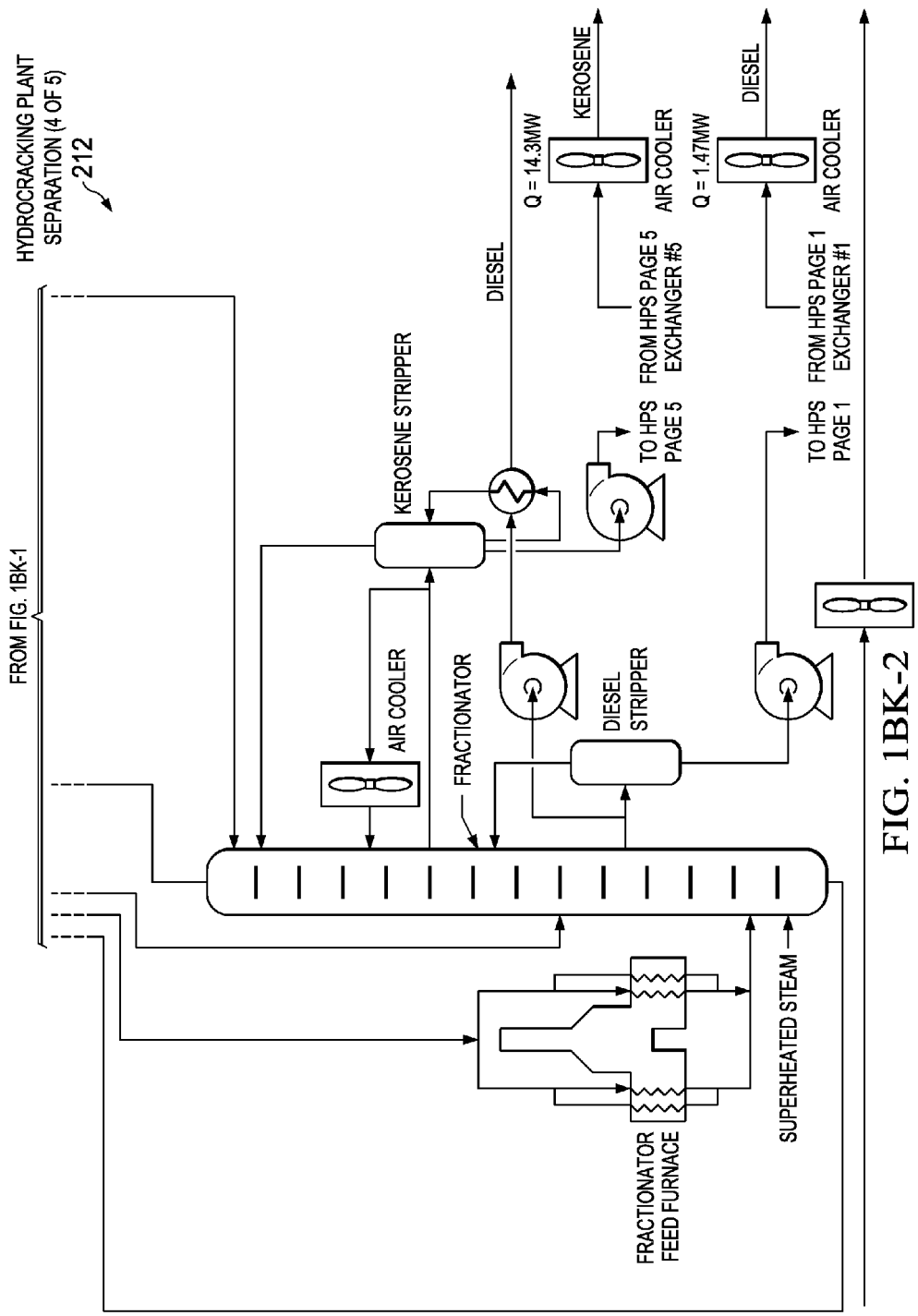
Figure 1B:
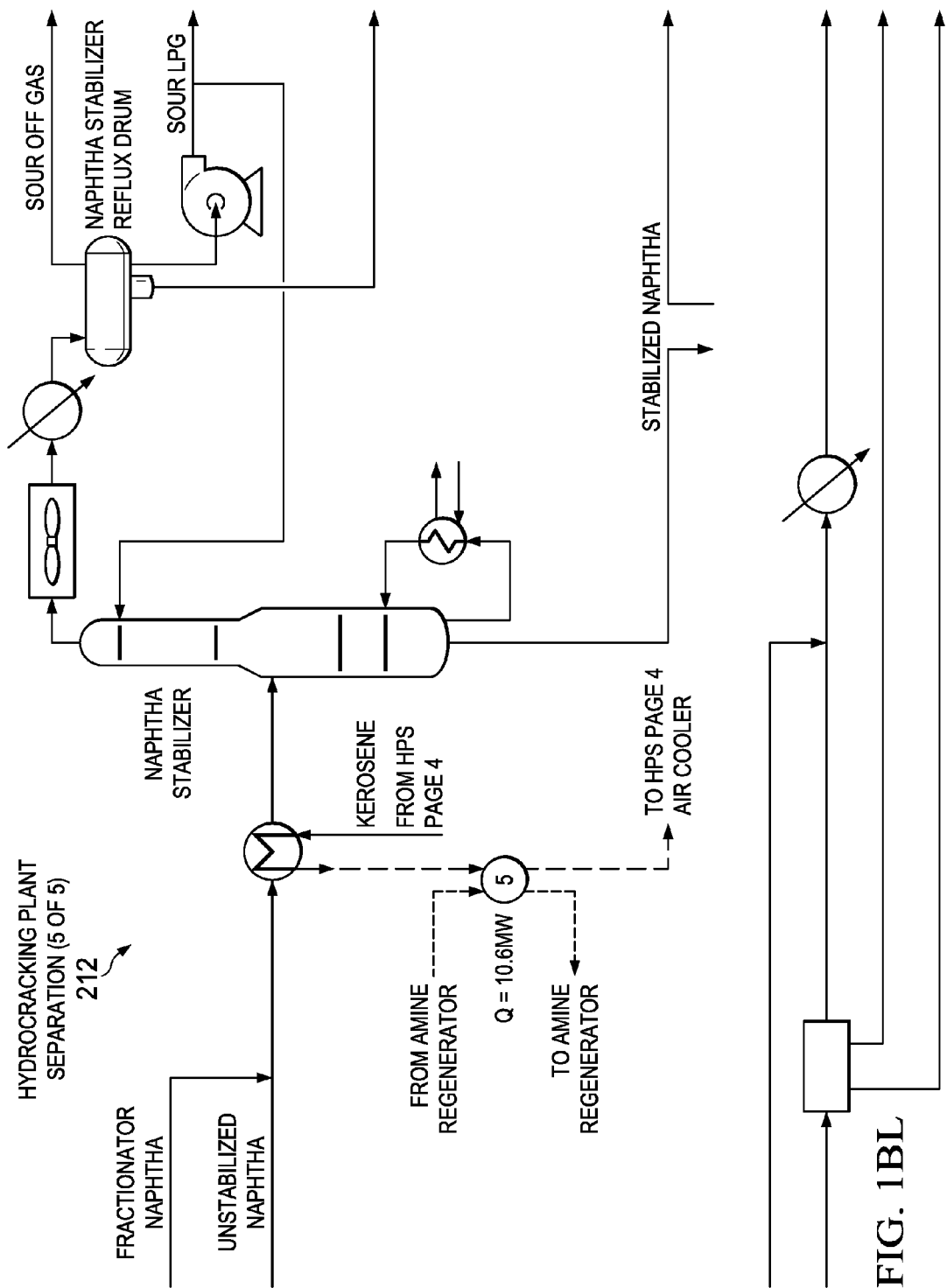
Figure 1B:
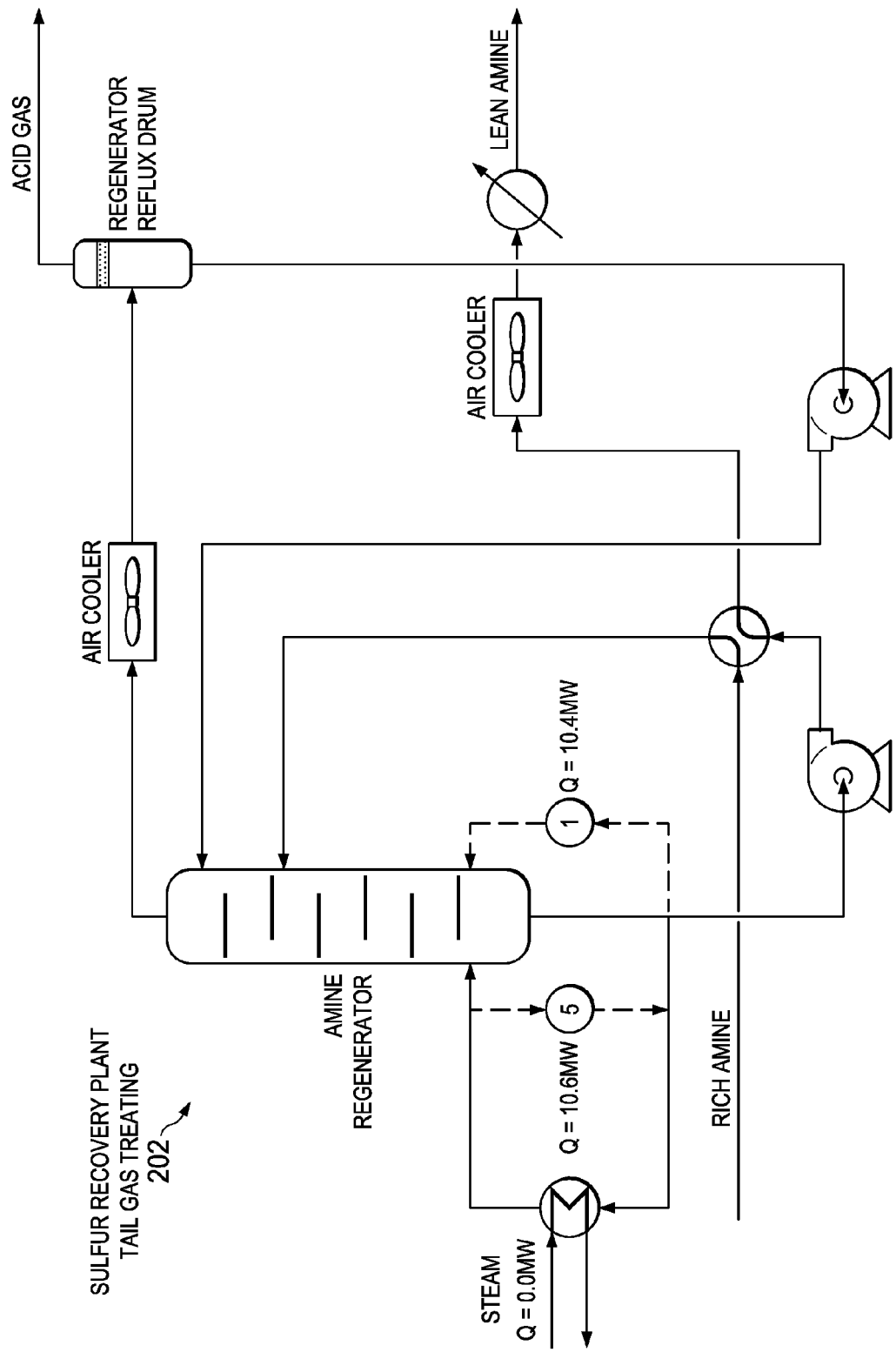
Figure 1B:
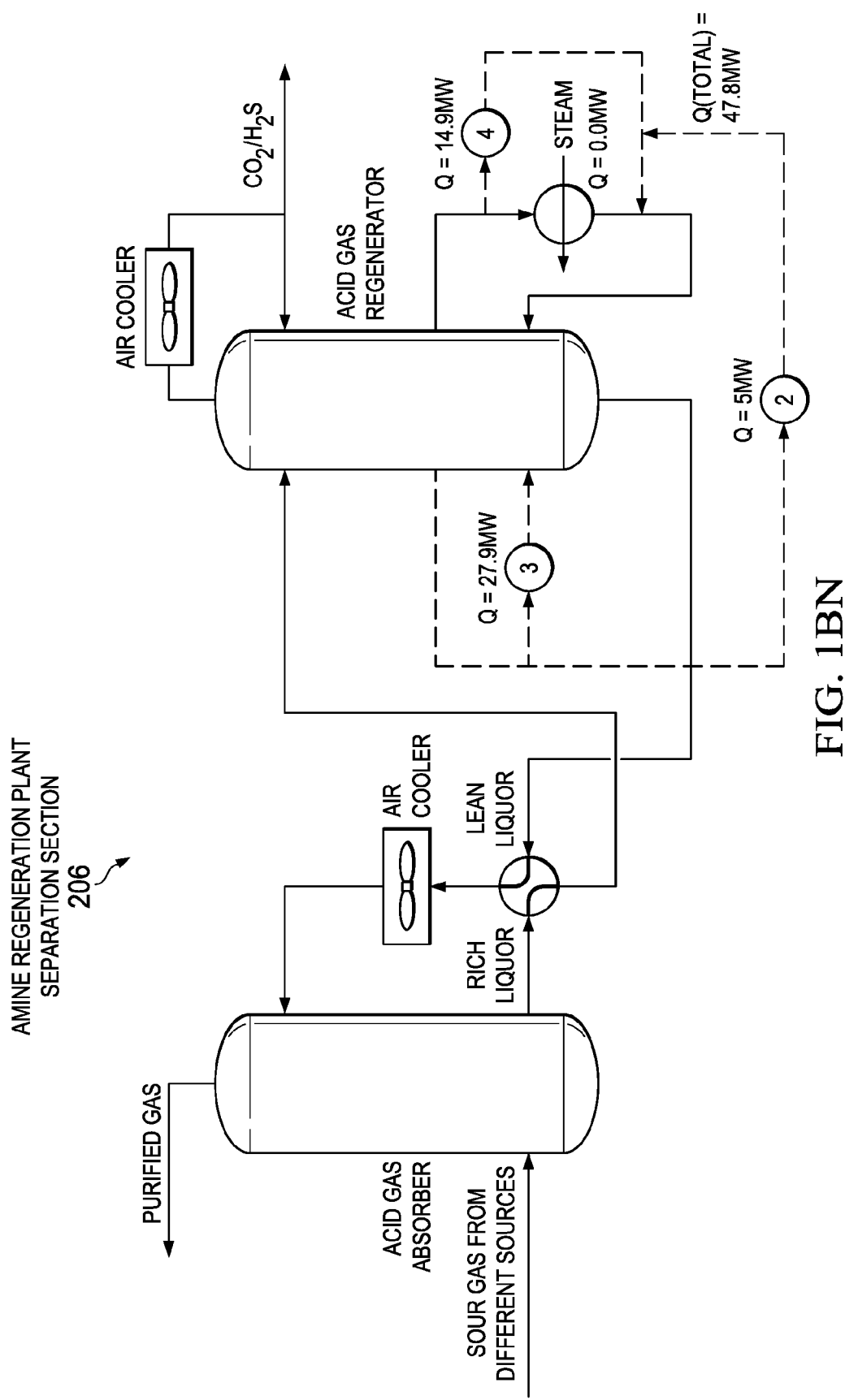
Figure 1B:
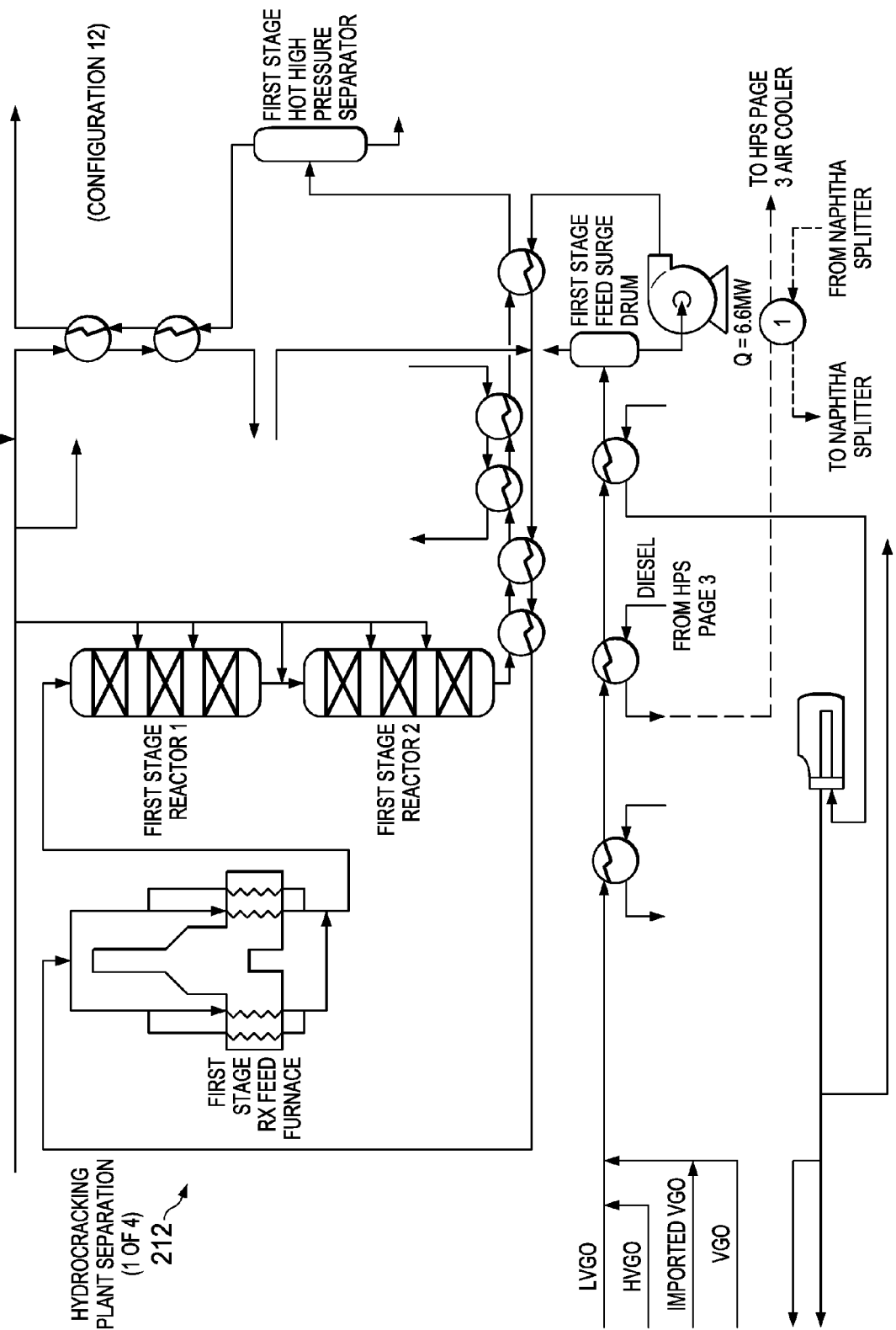
Figure 1B:
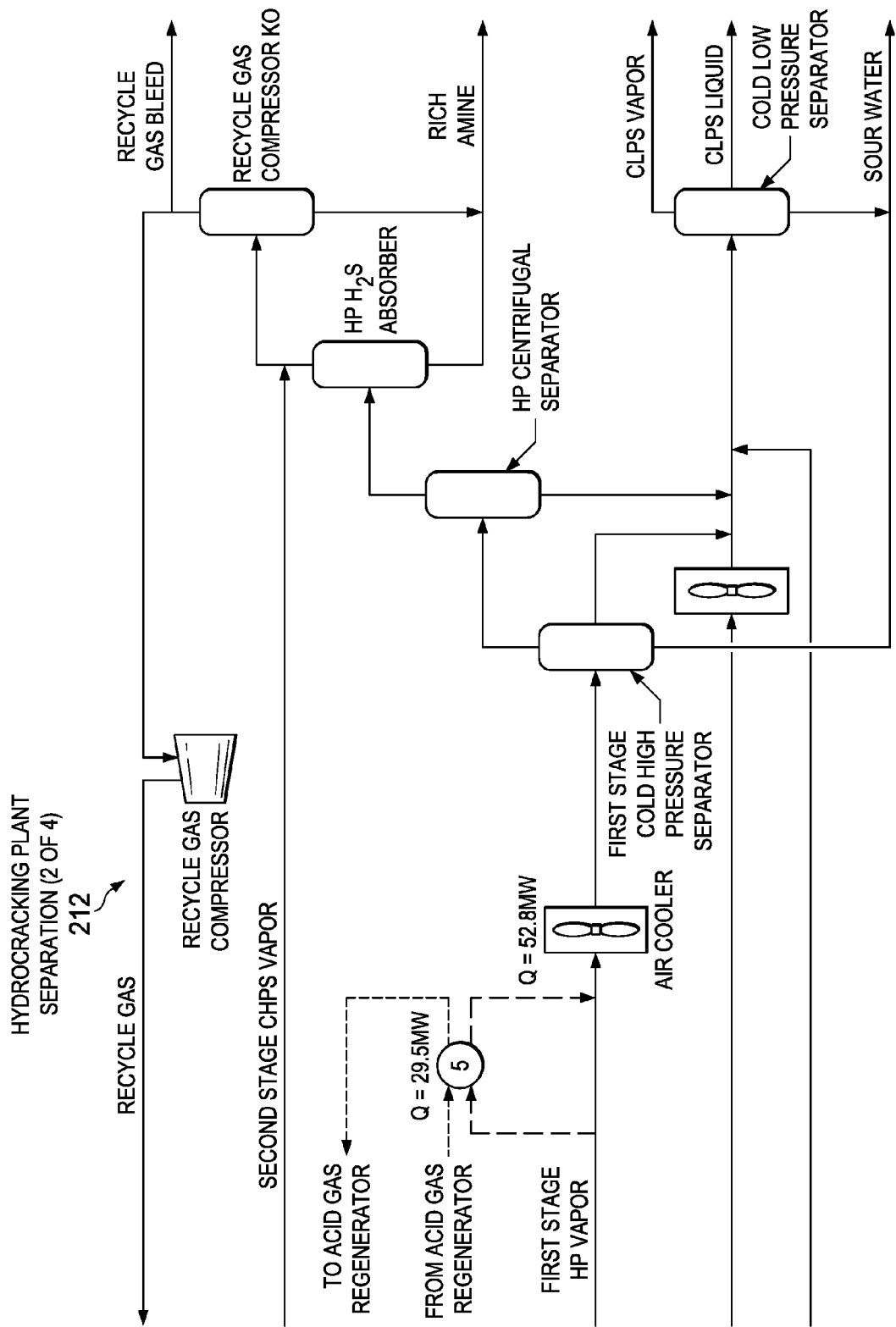
Figure 1B:
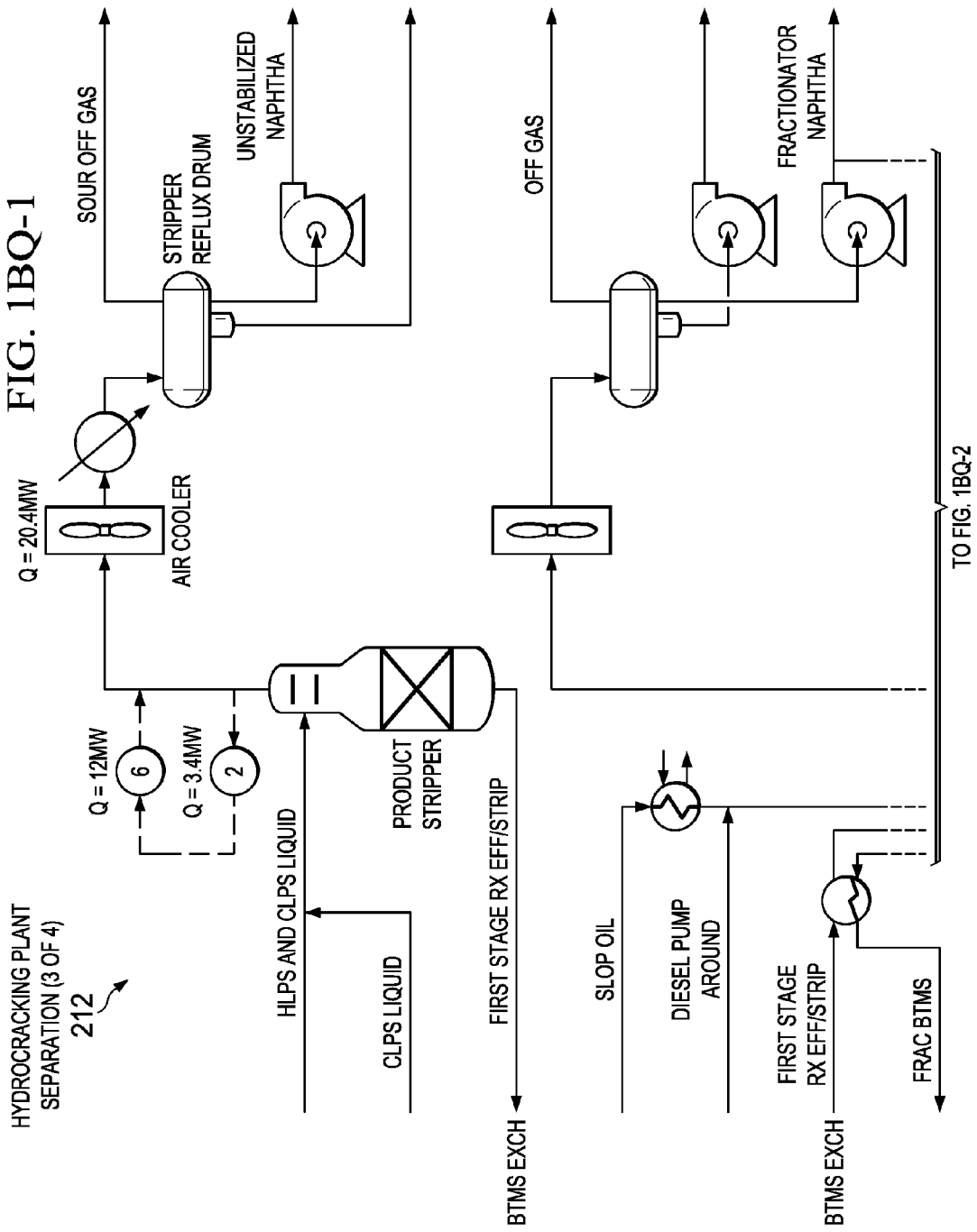
Figure 1B:
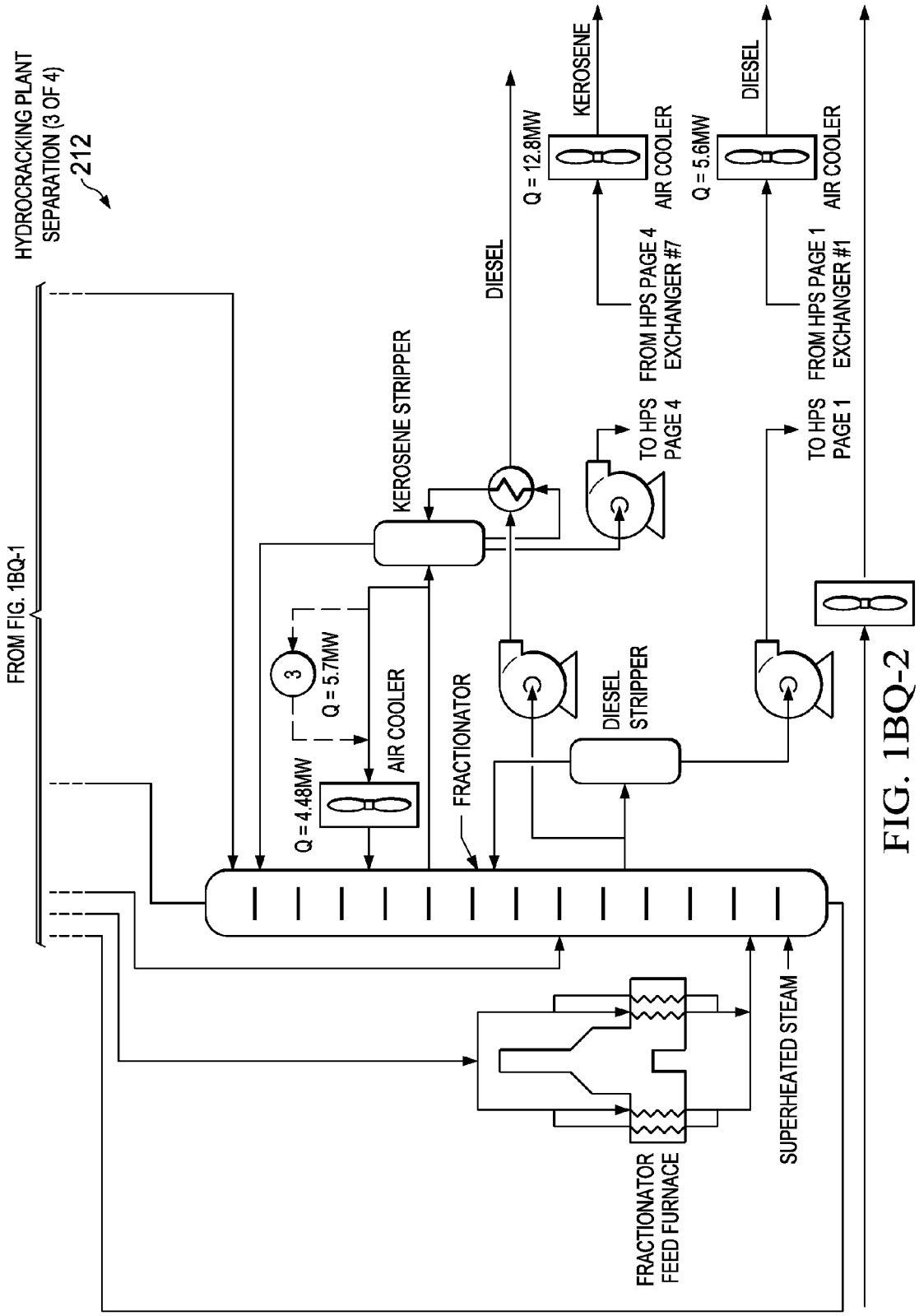
Figure 1B:
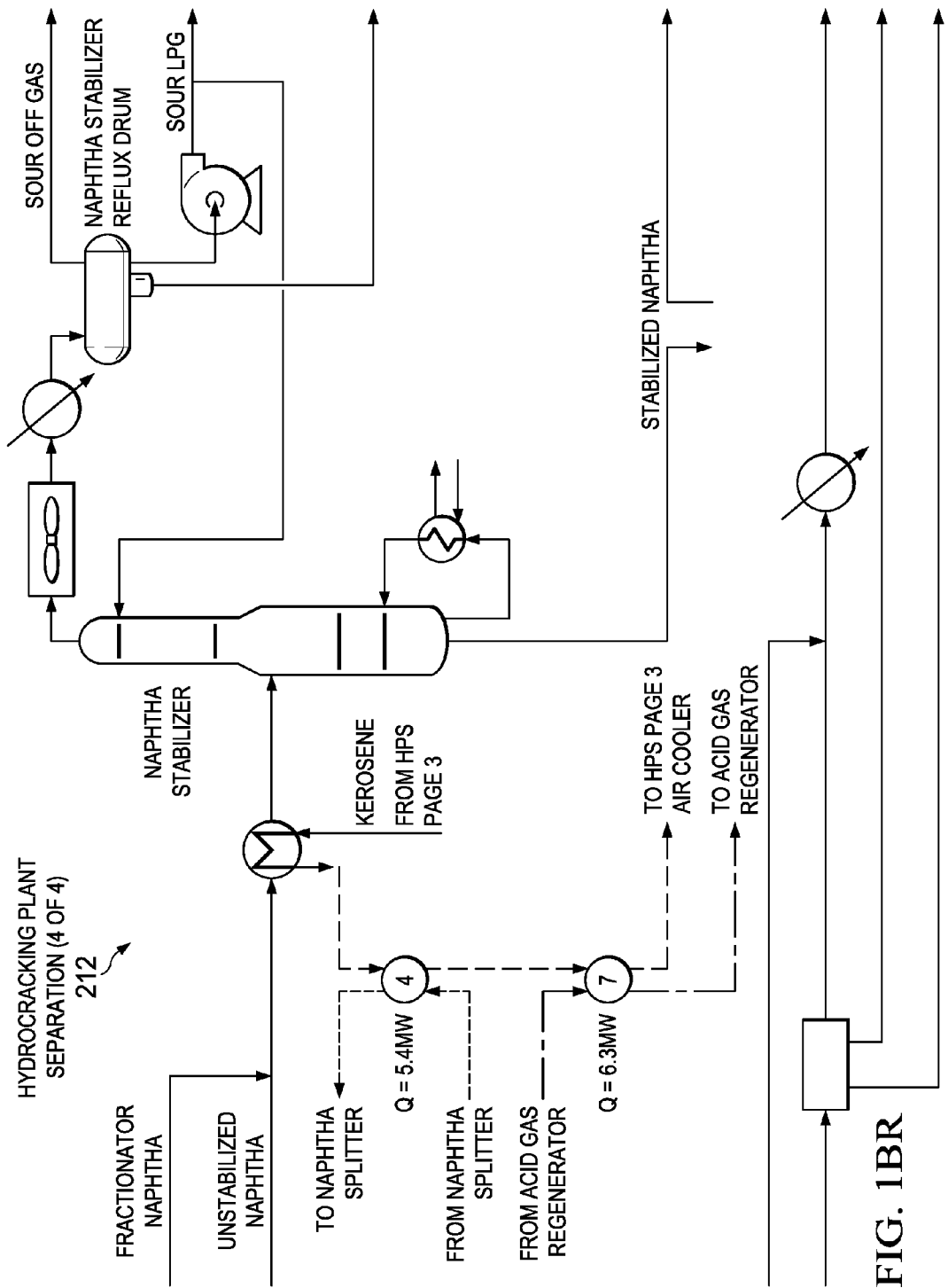
Figure 1B:
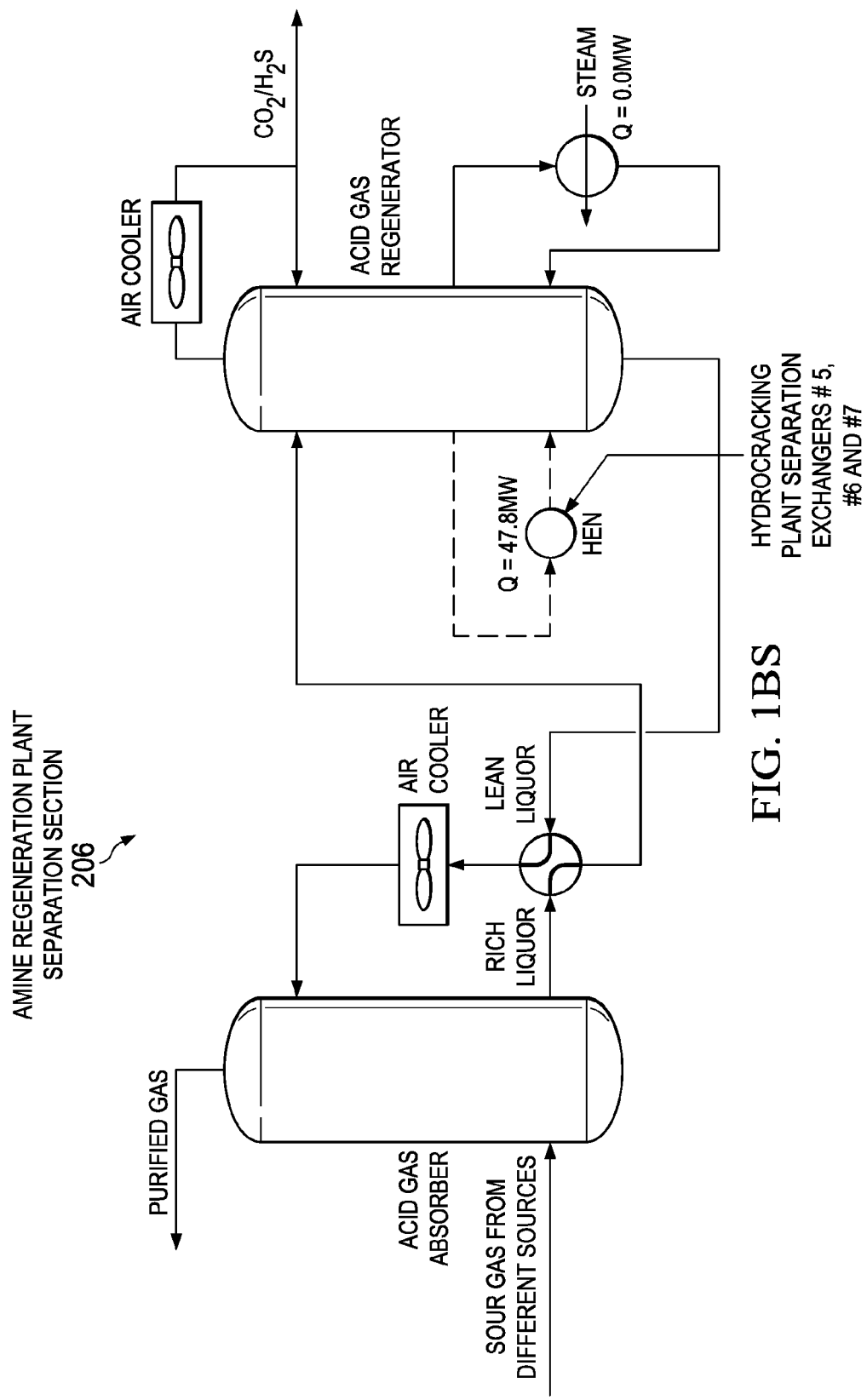
Figure 1B:
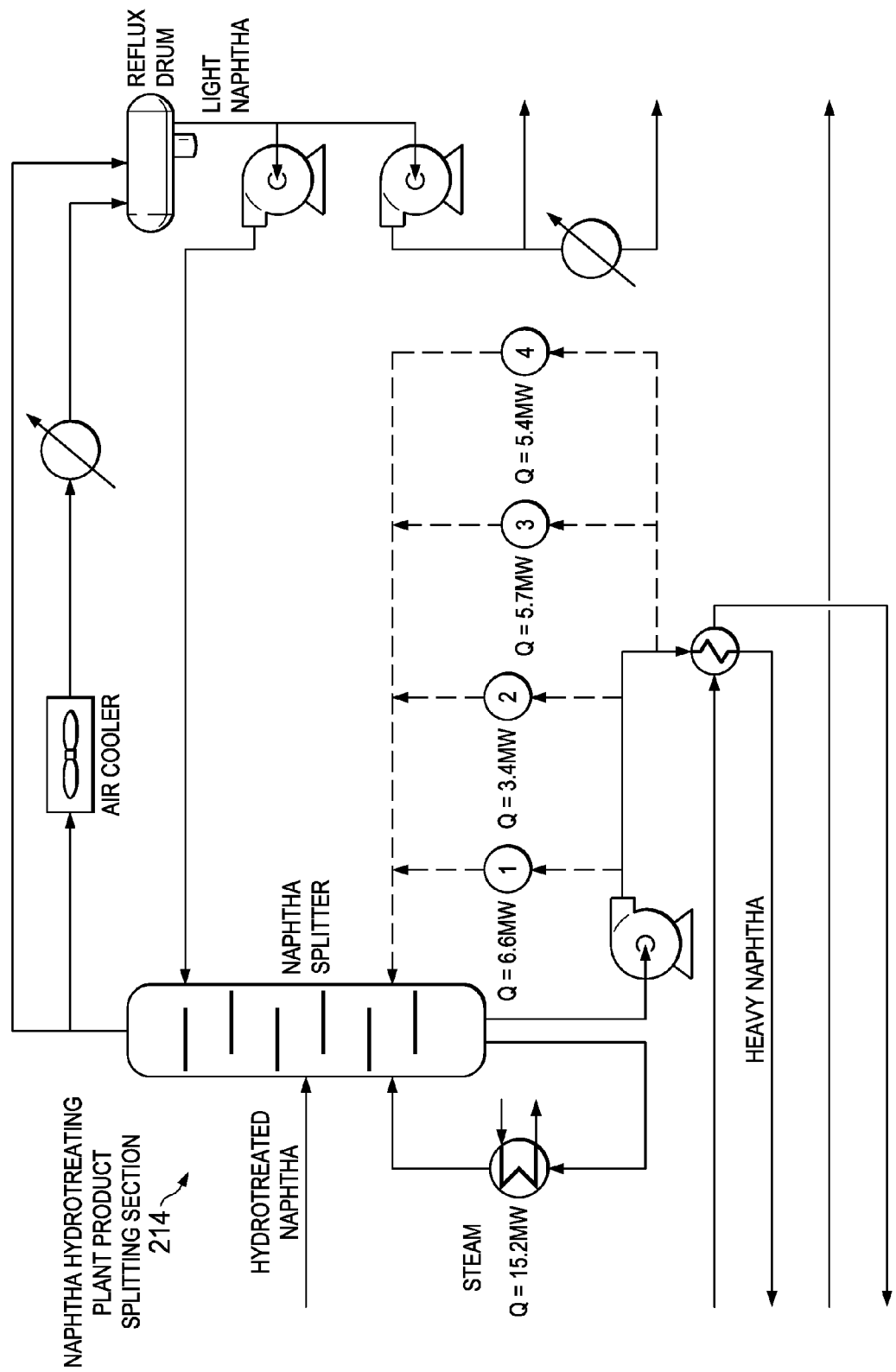
Figure 1B:
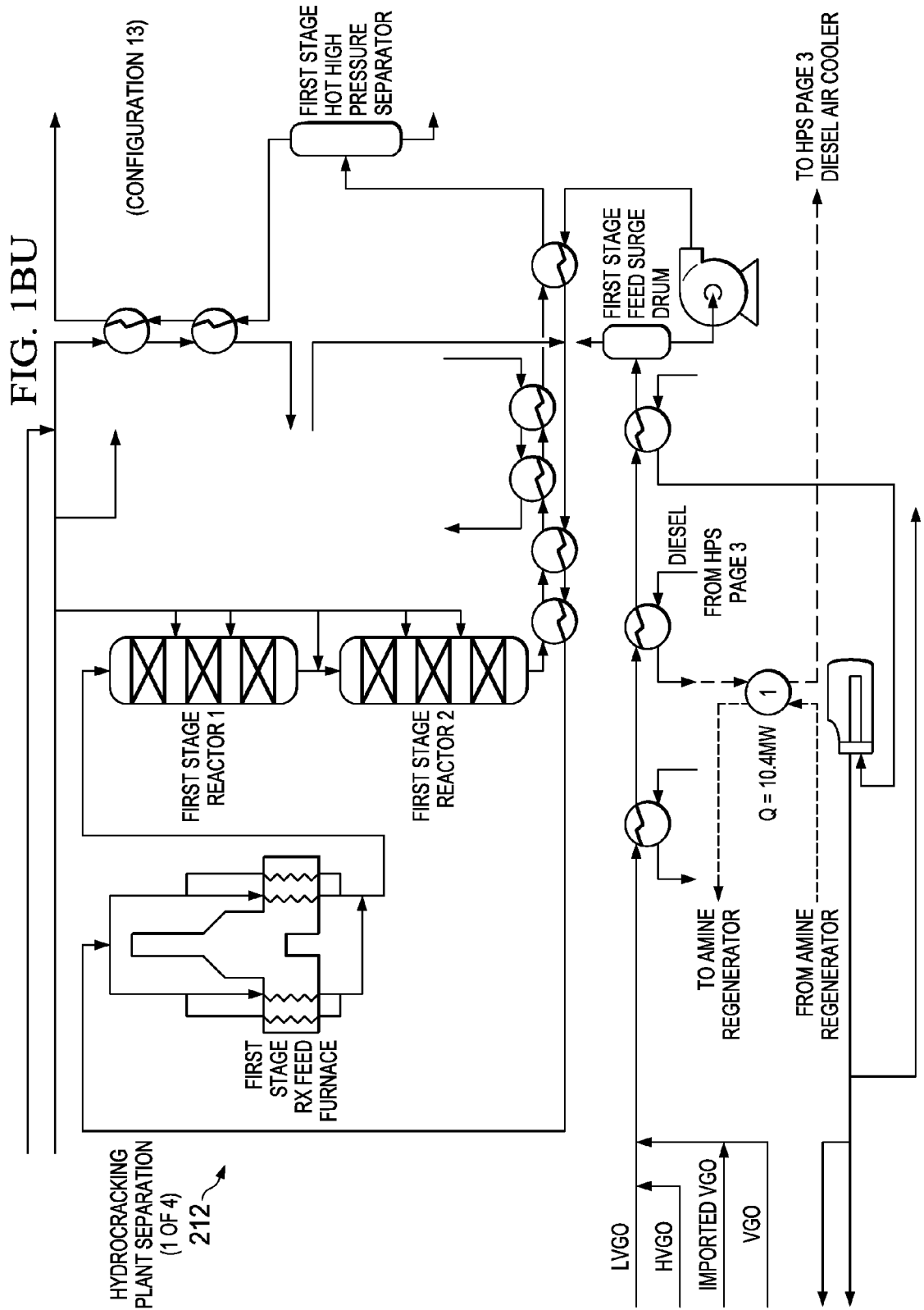
Figure 1B:
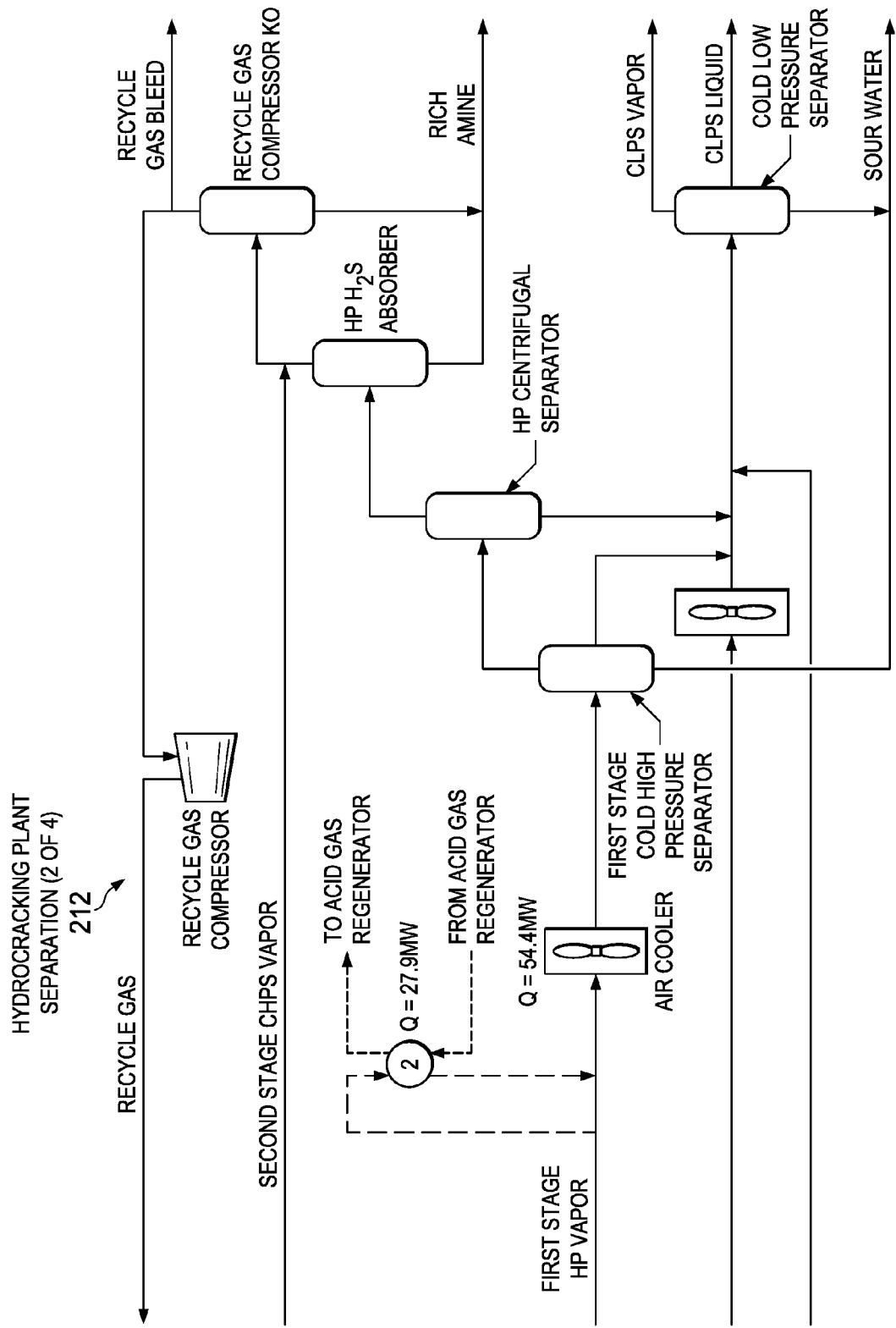
Figure 1B:
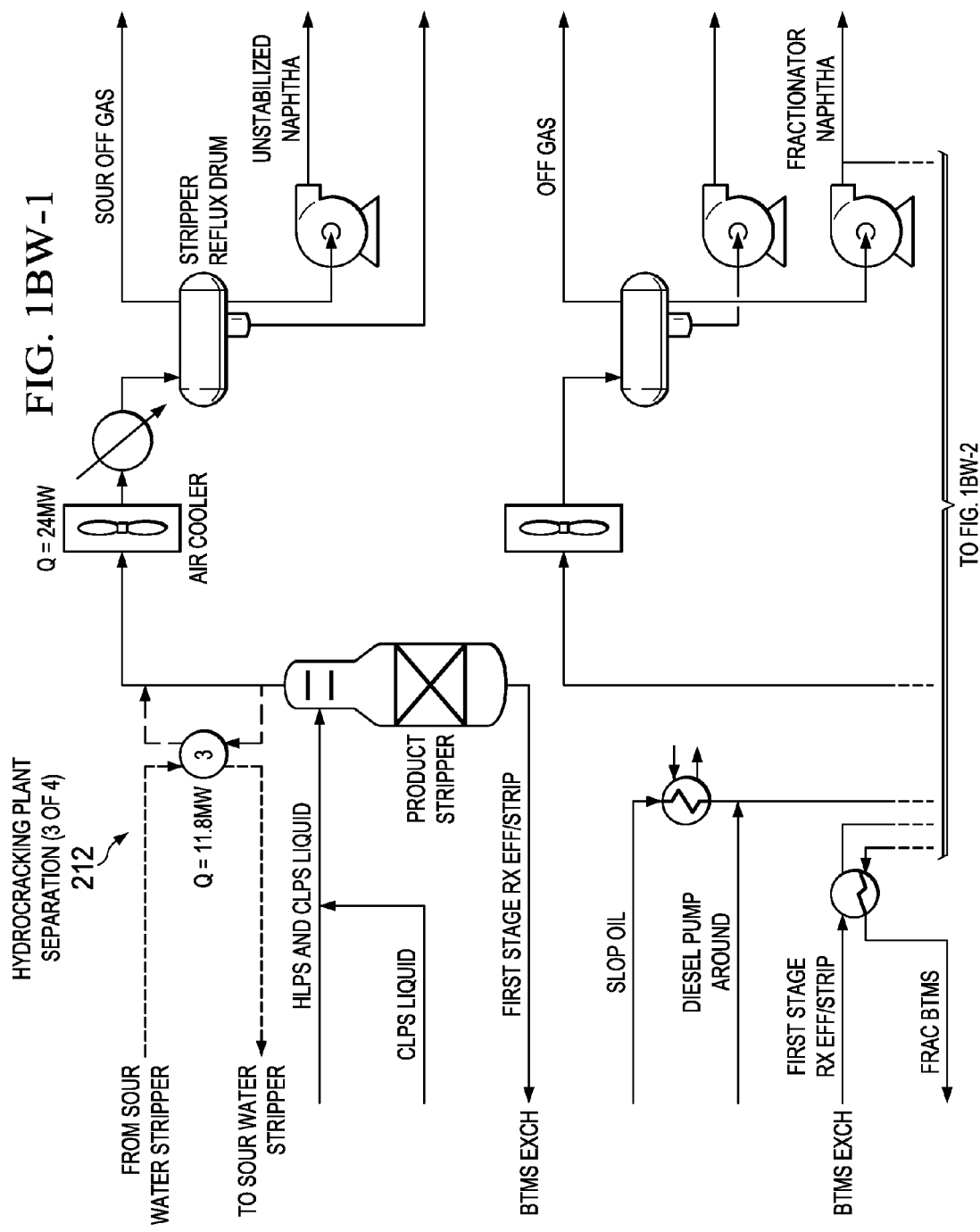
Figure 1B:
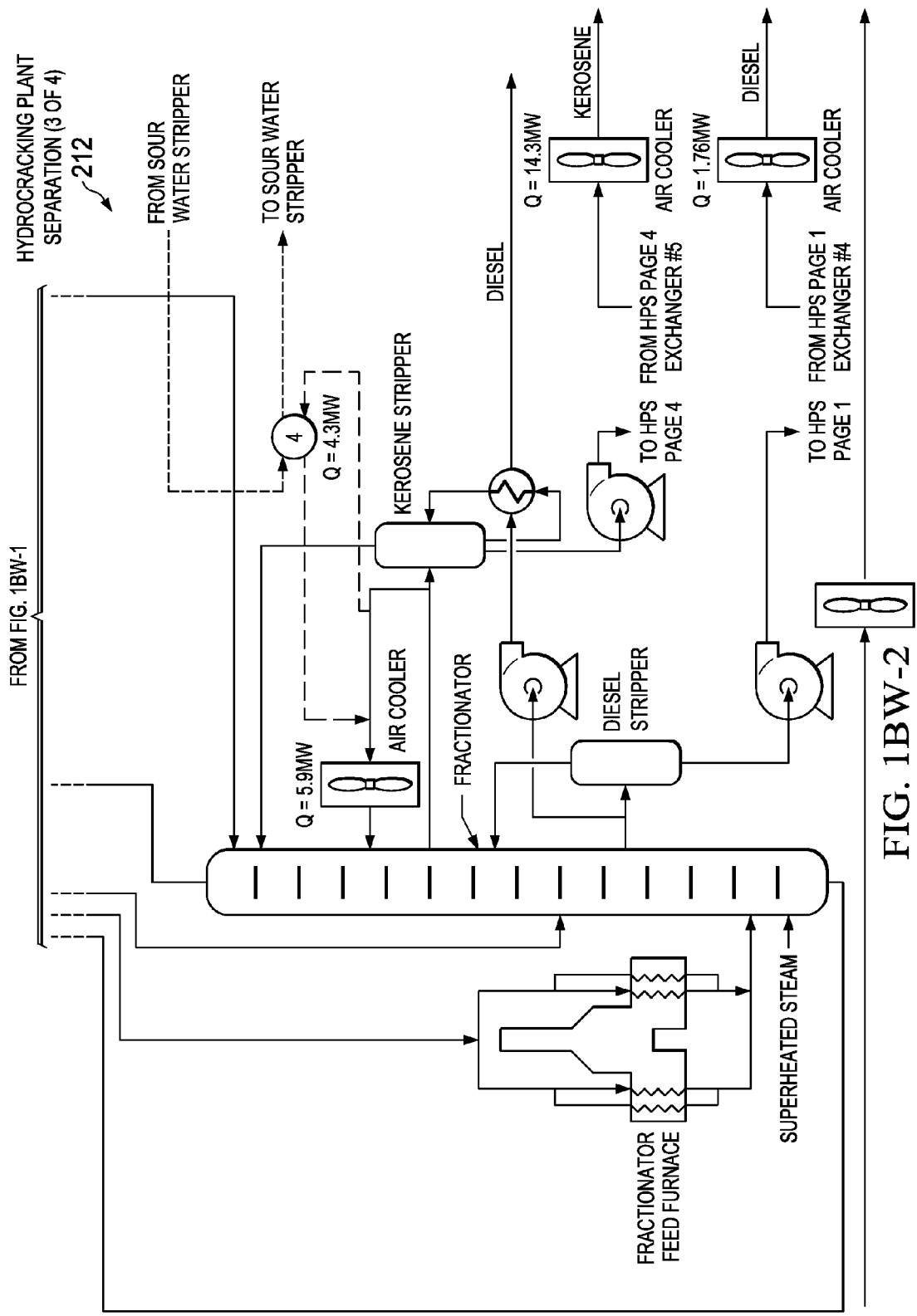
Figure 1B:
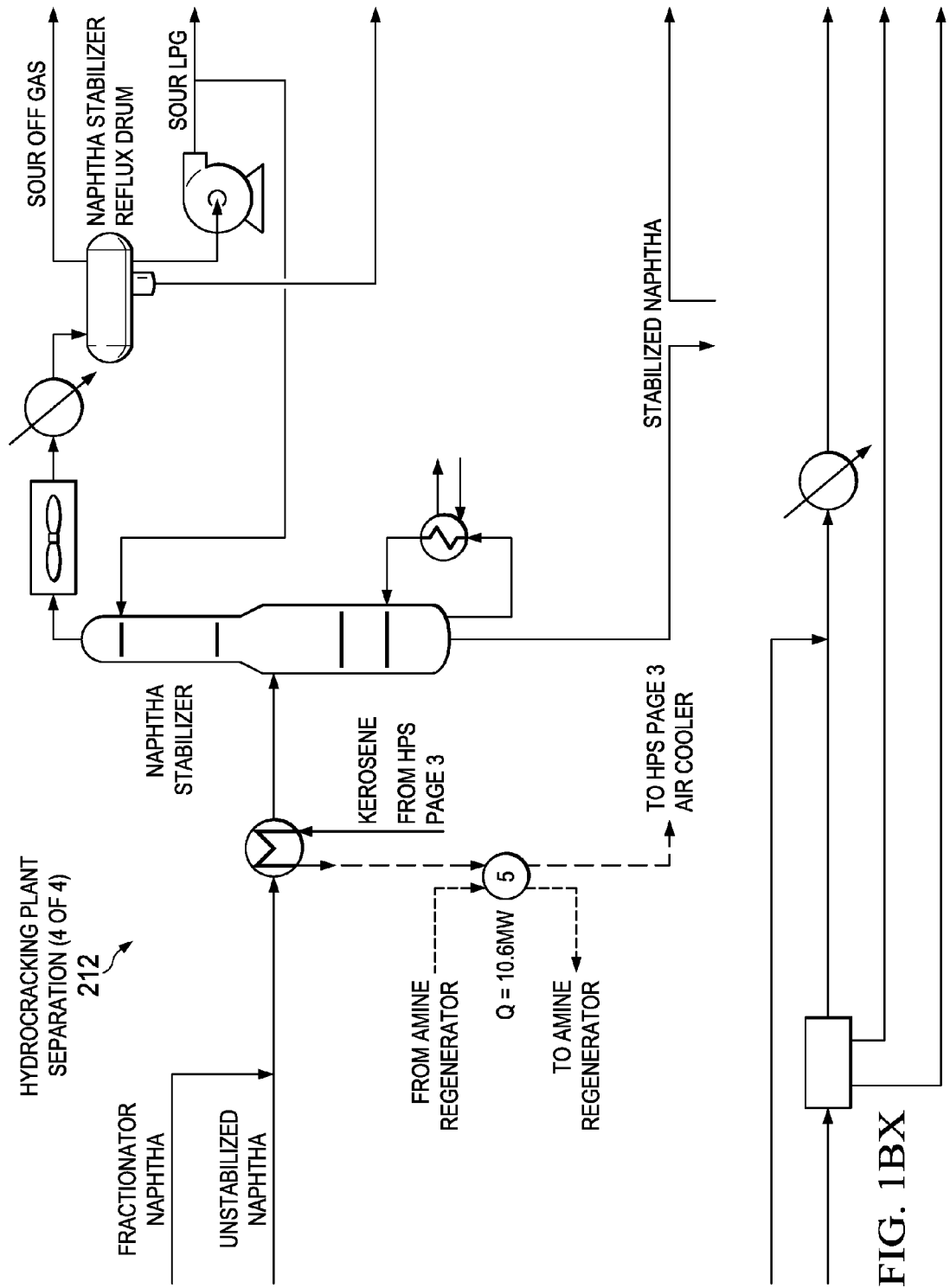
Figure 1B:
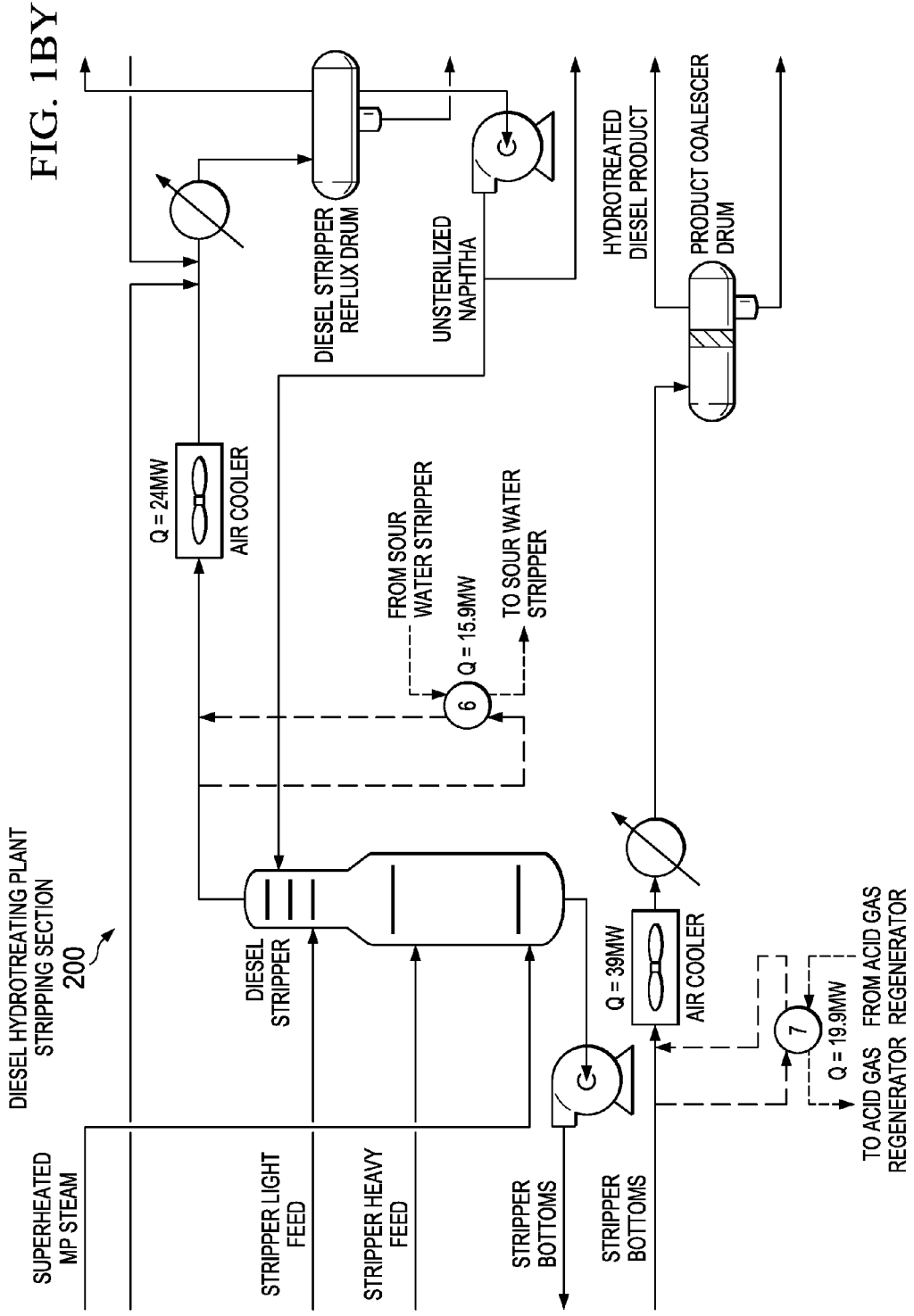
Figure 1B:
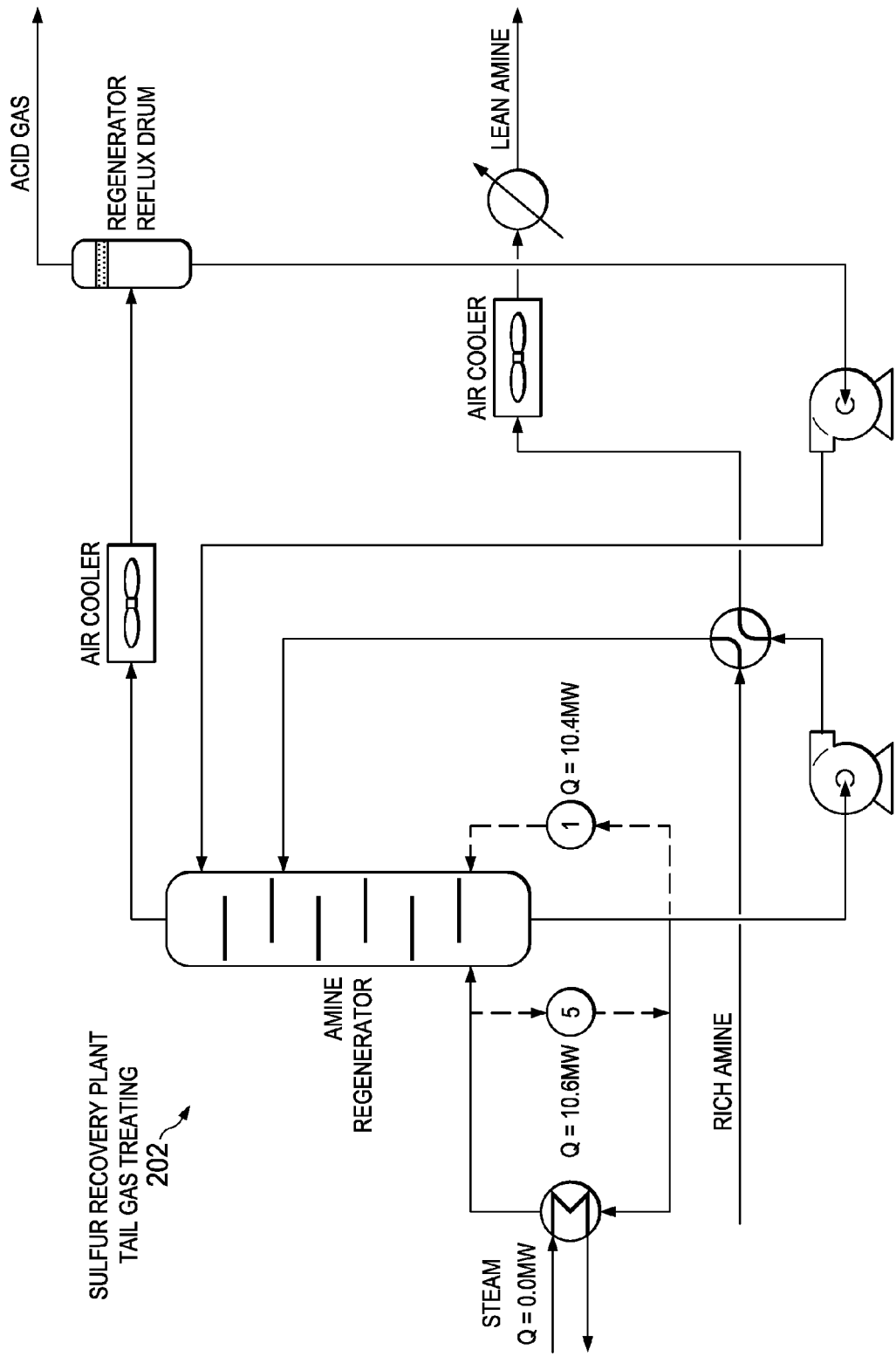
Figure 1C:
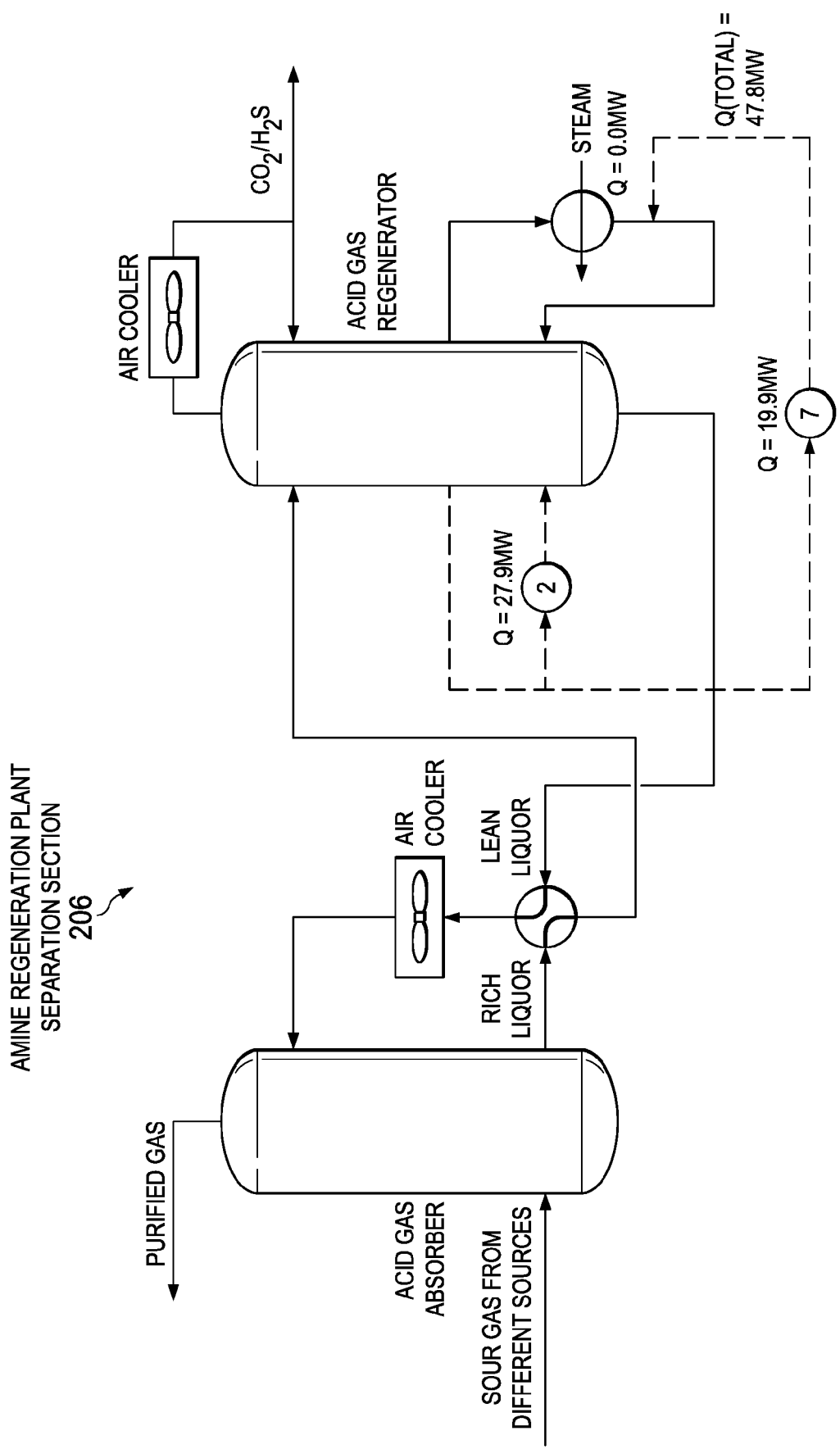
Figure 1C:
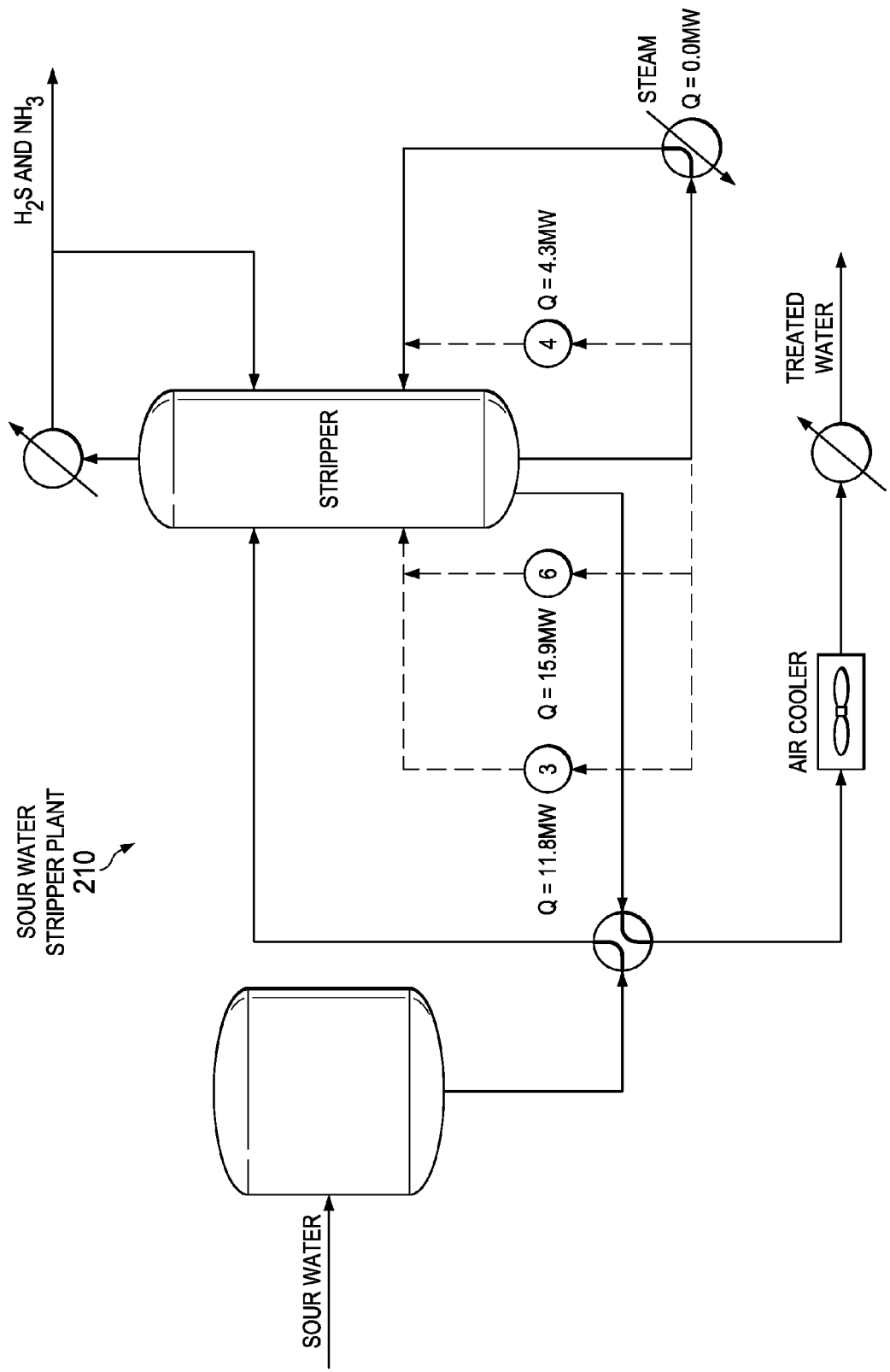
Figure 1C:
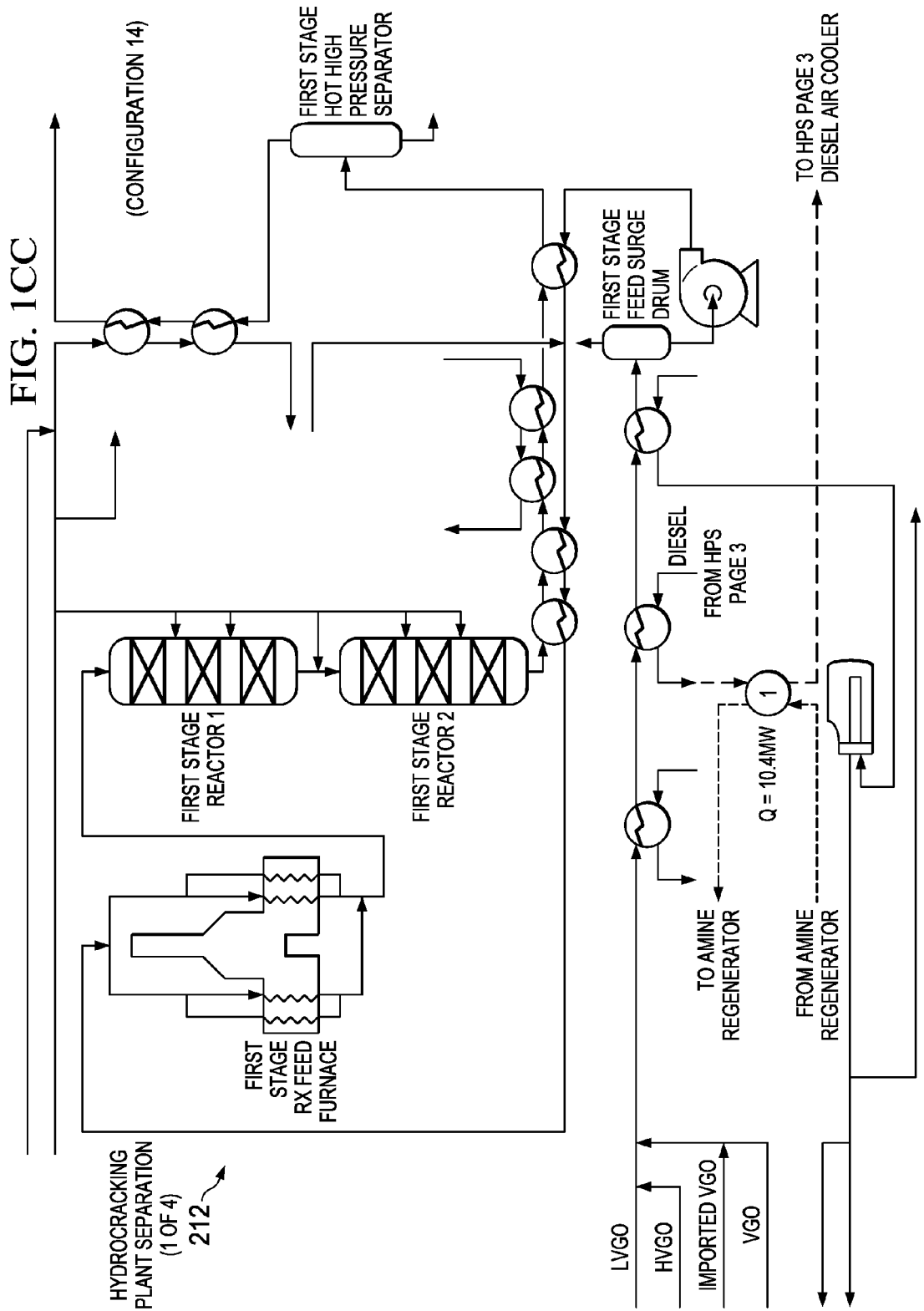
Figure 1C:
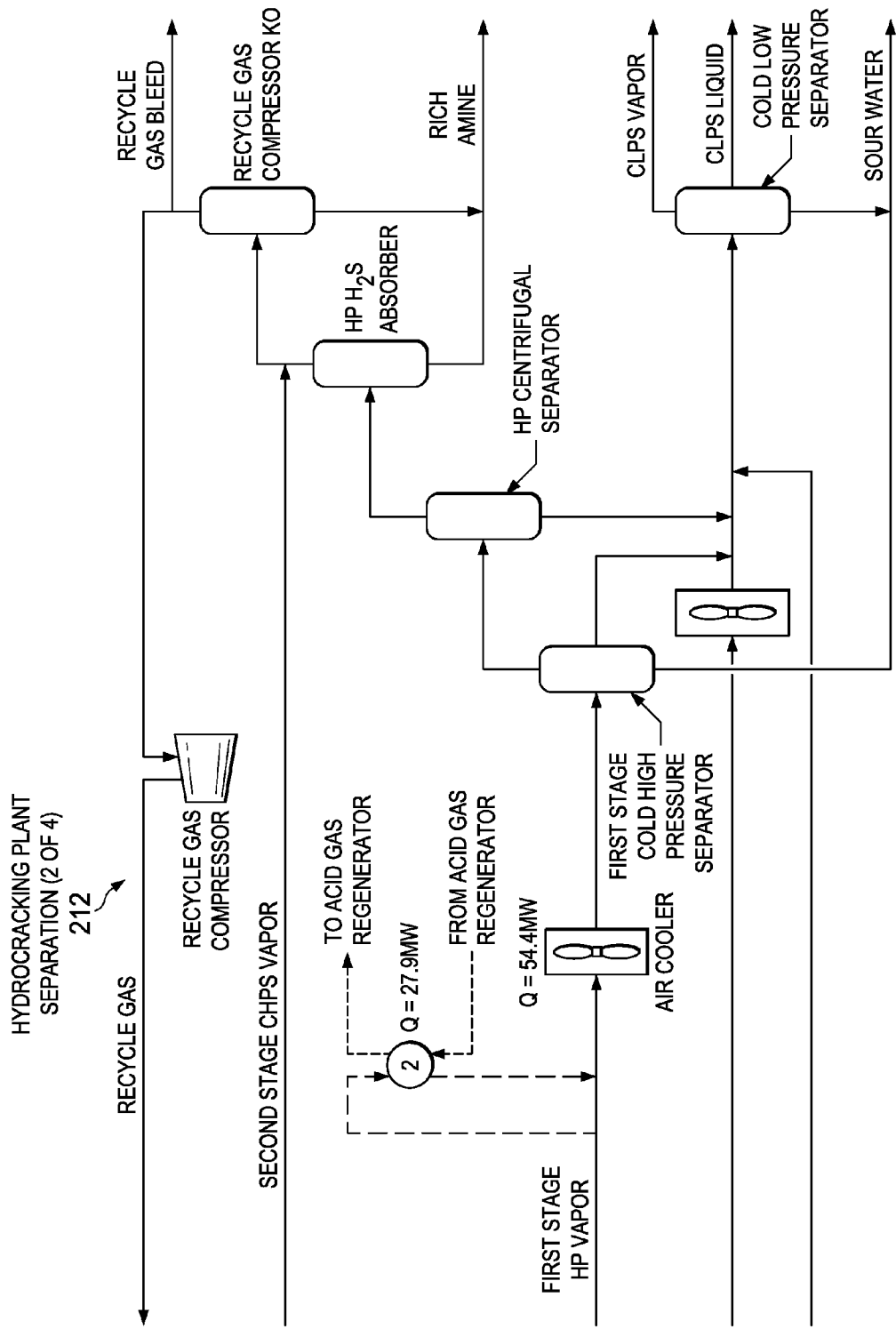
Figure 1C:
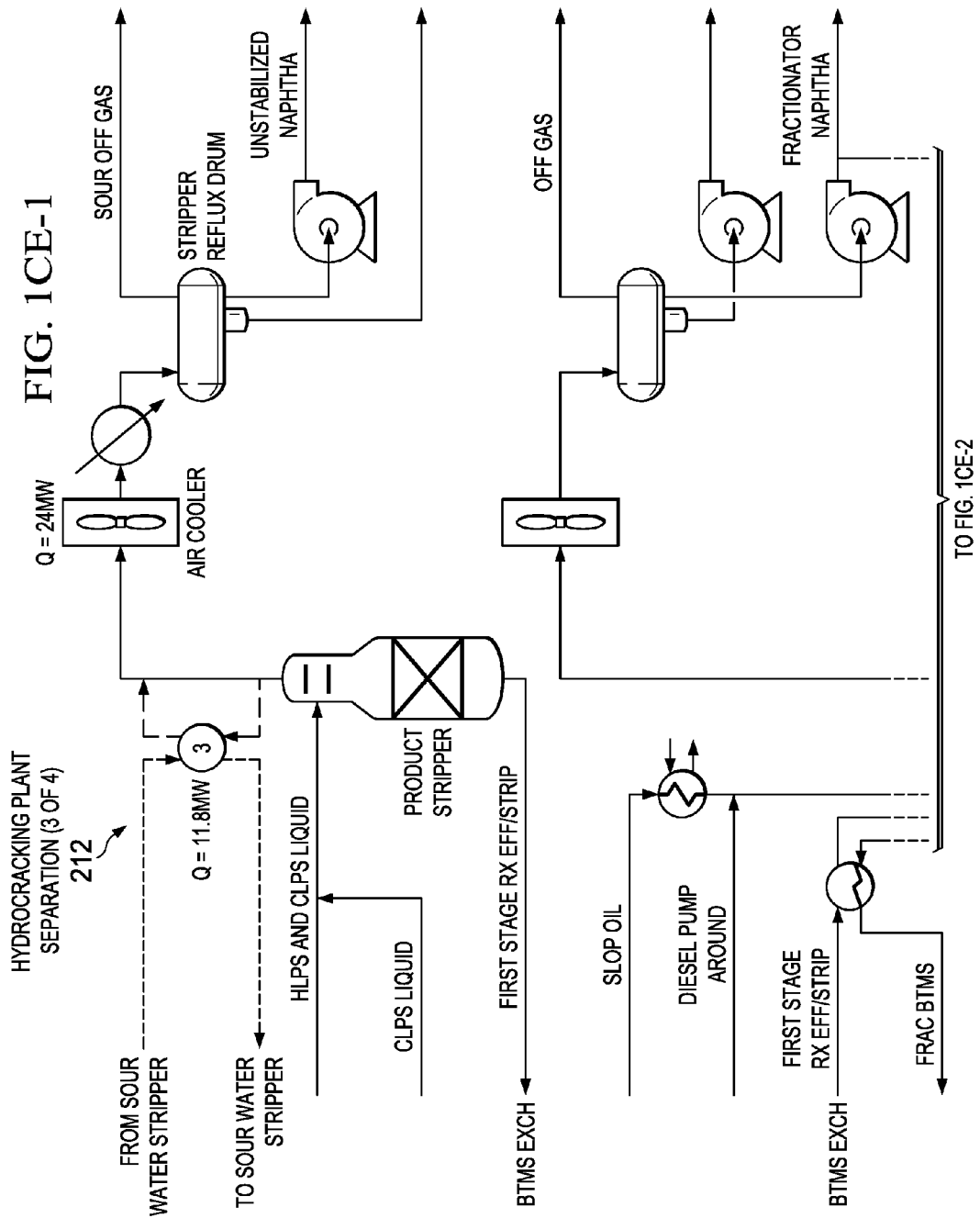
Figure 1C:
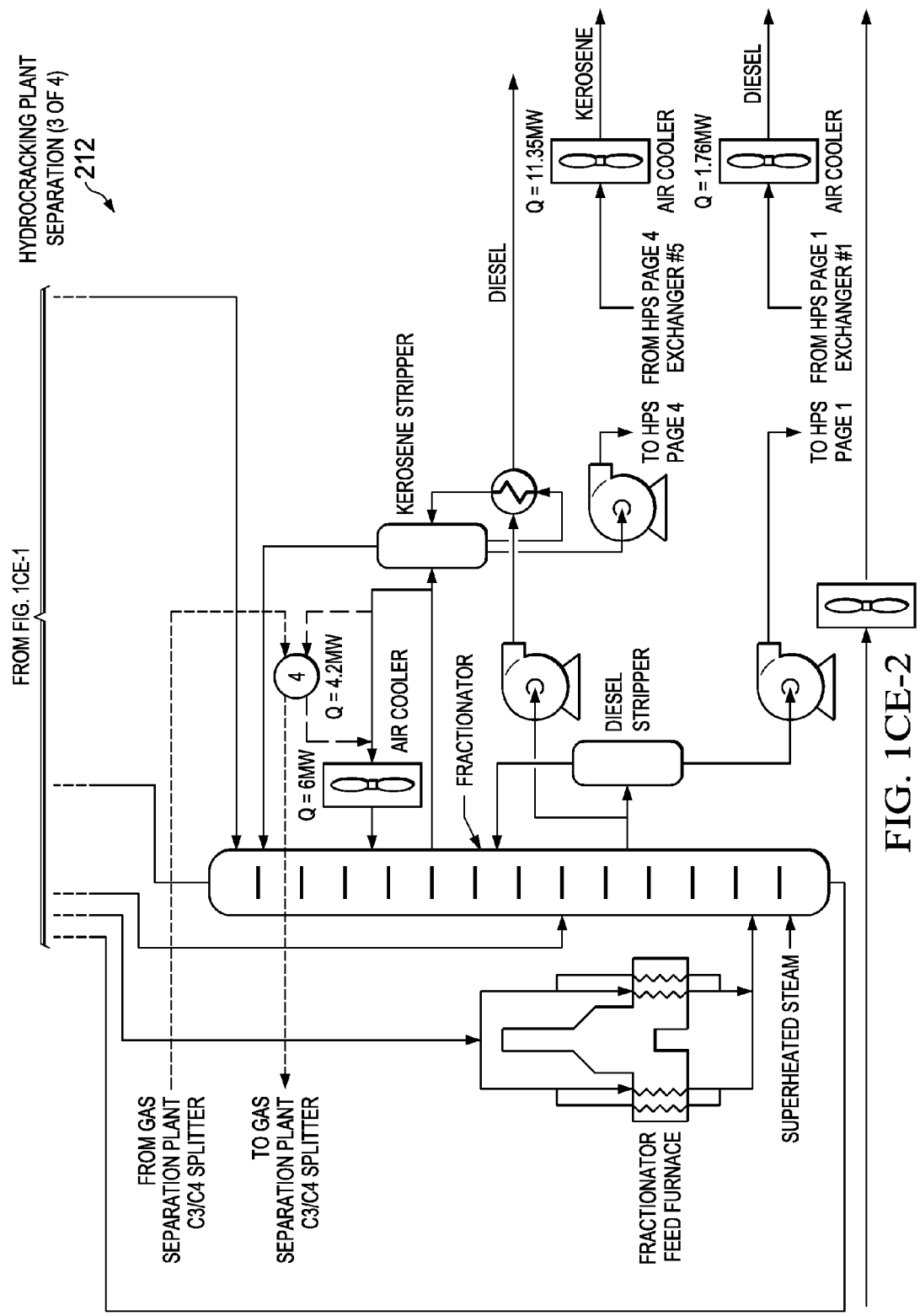
Figure 1C:
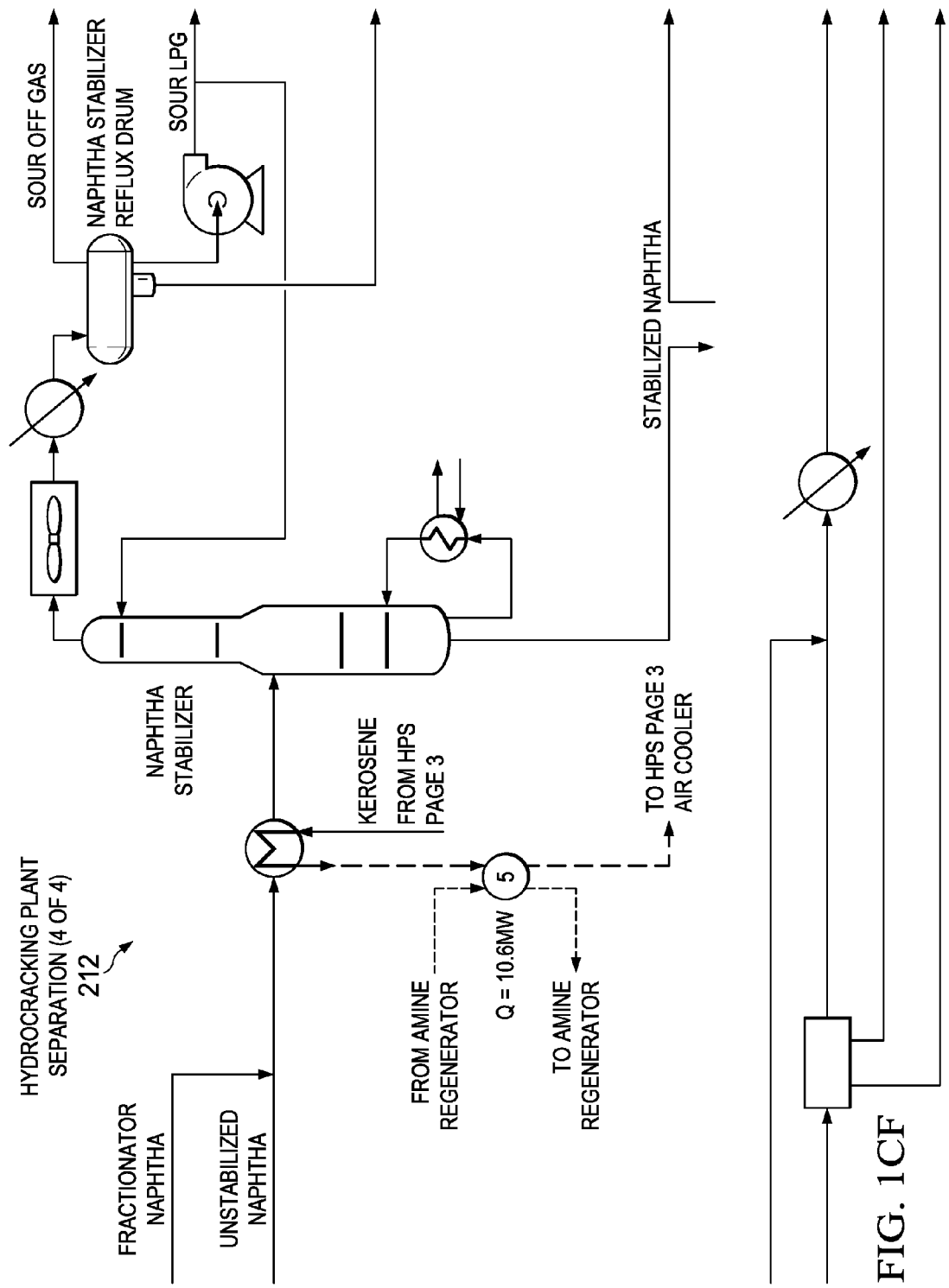
Figure 1C:
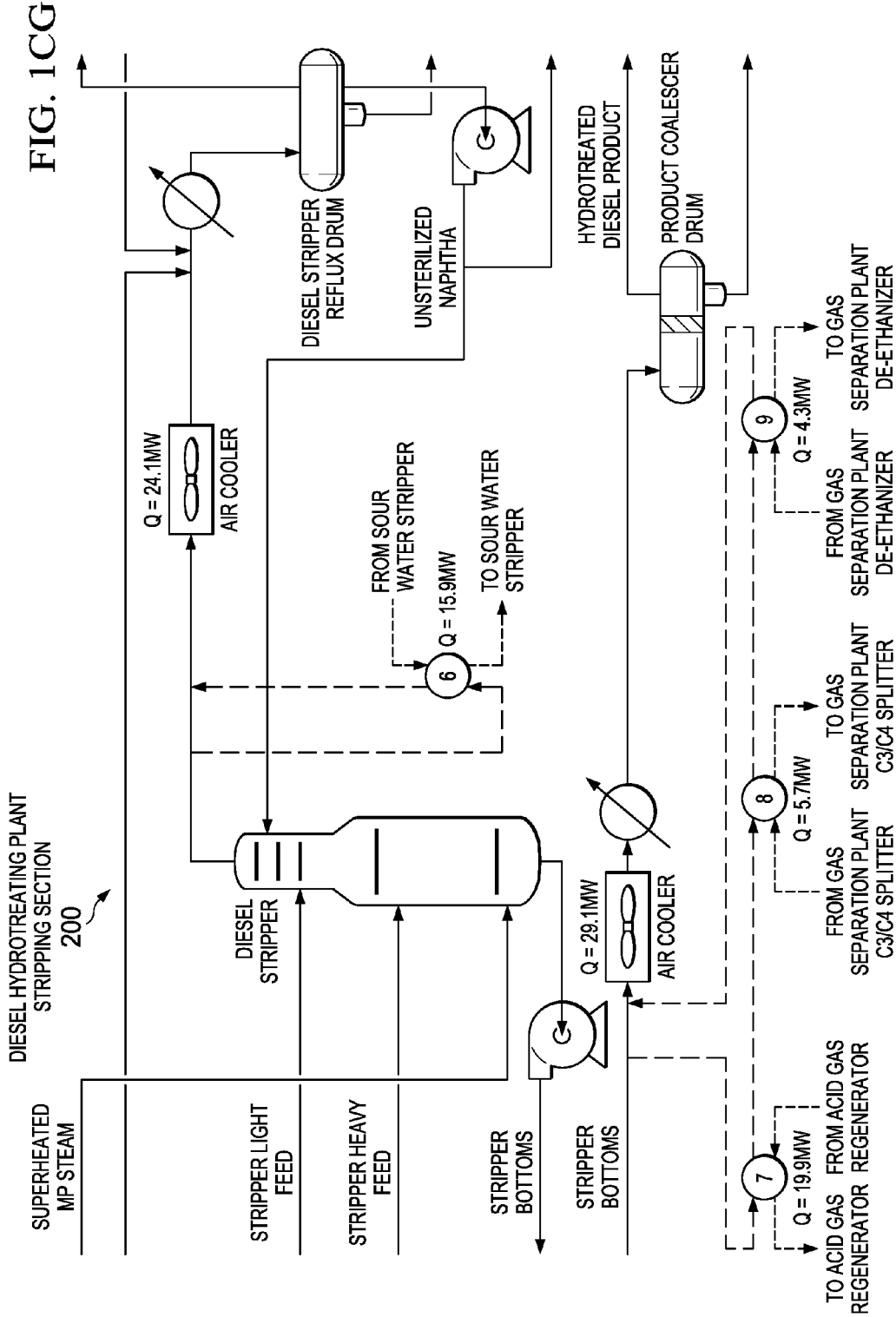
Figure 1C:
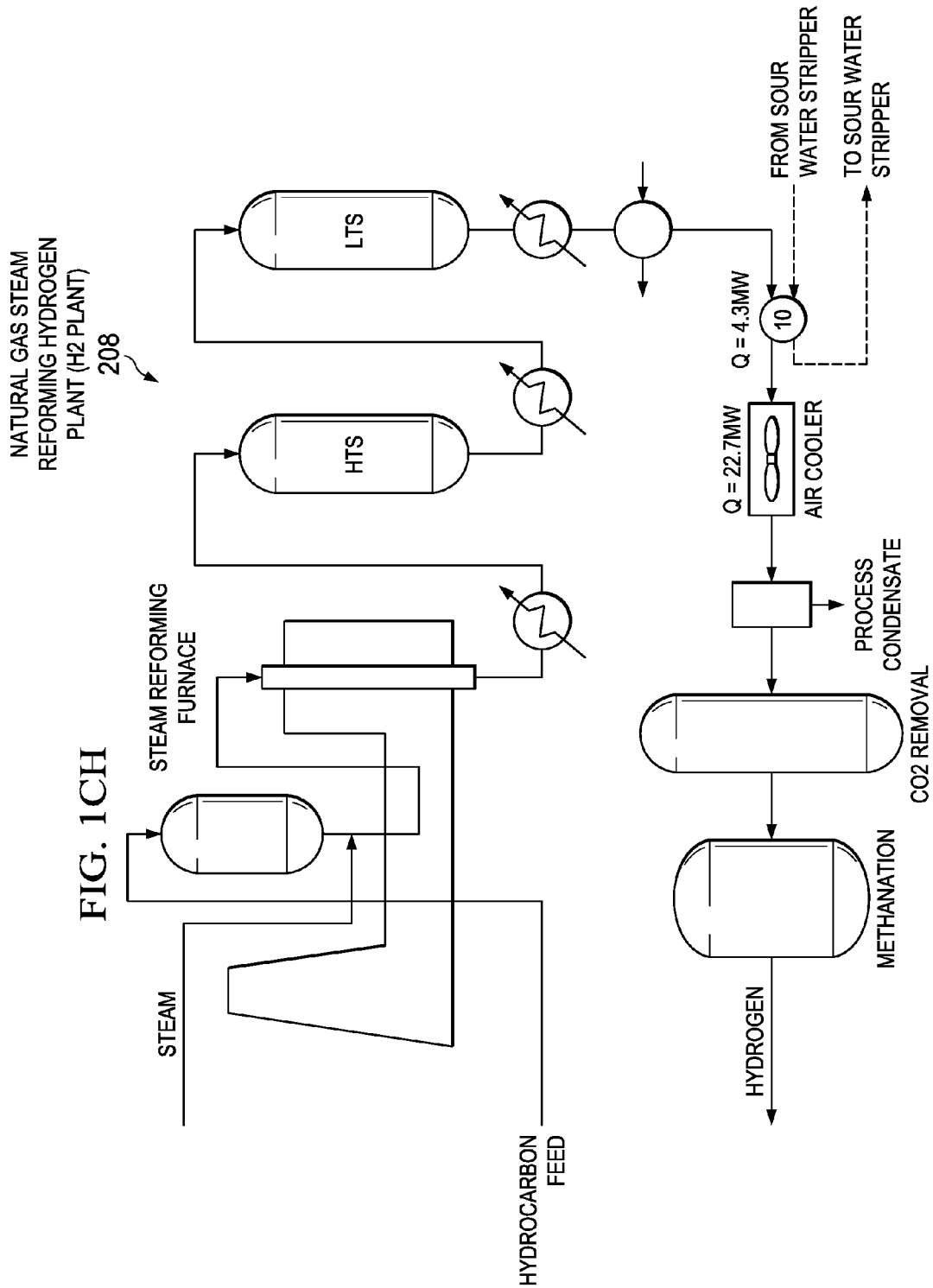
Figure 1C:
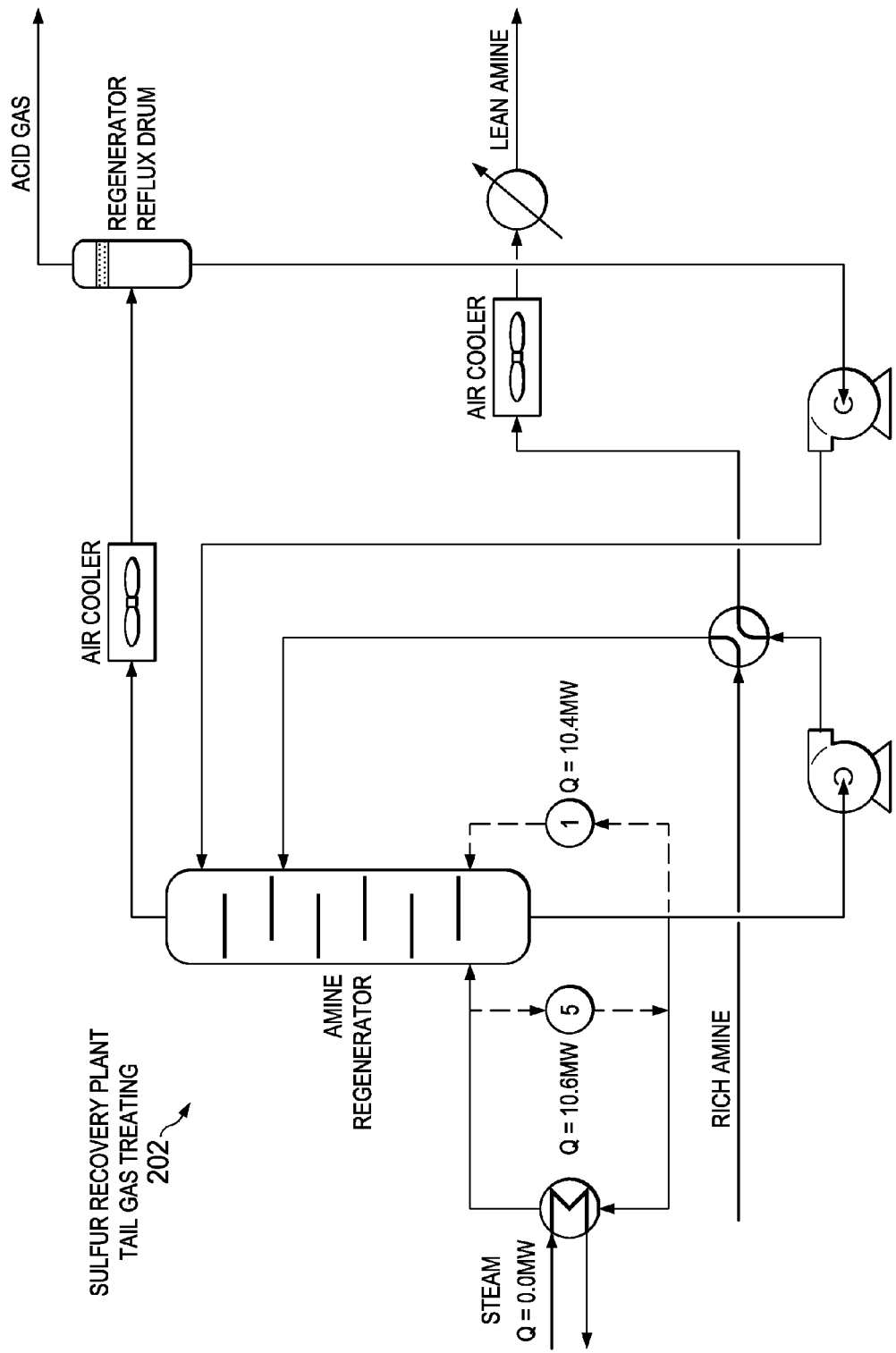
Figure 1C:
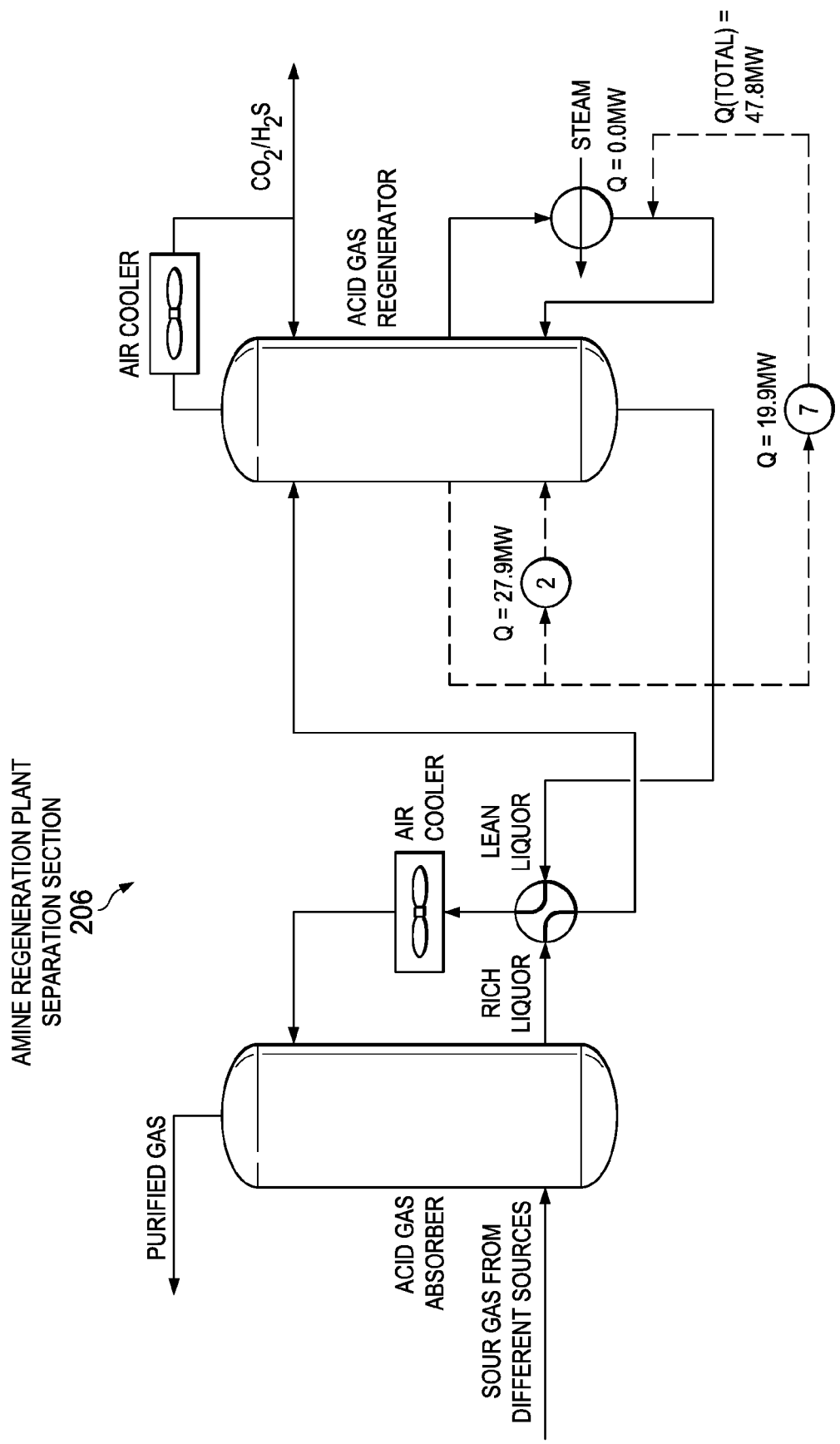
Figure 1C:
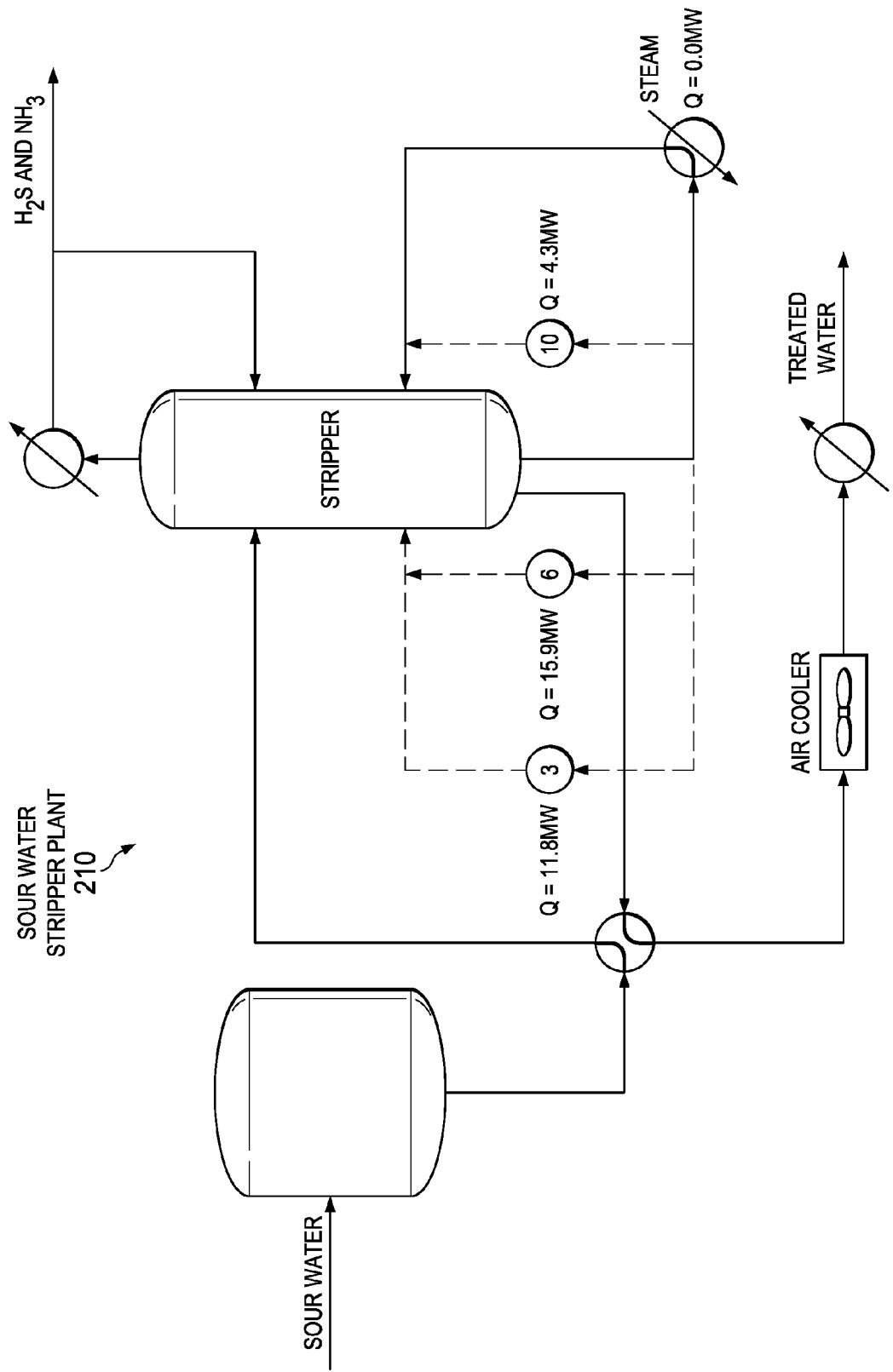
Figure 1C:
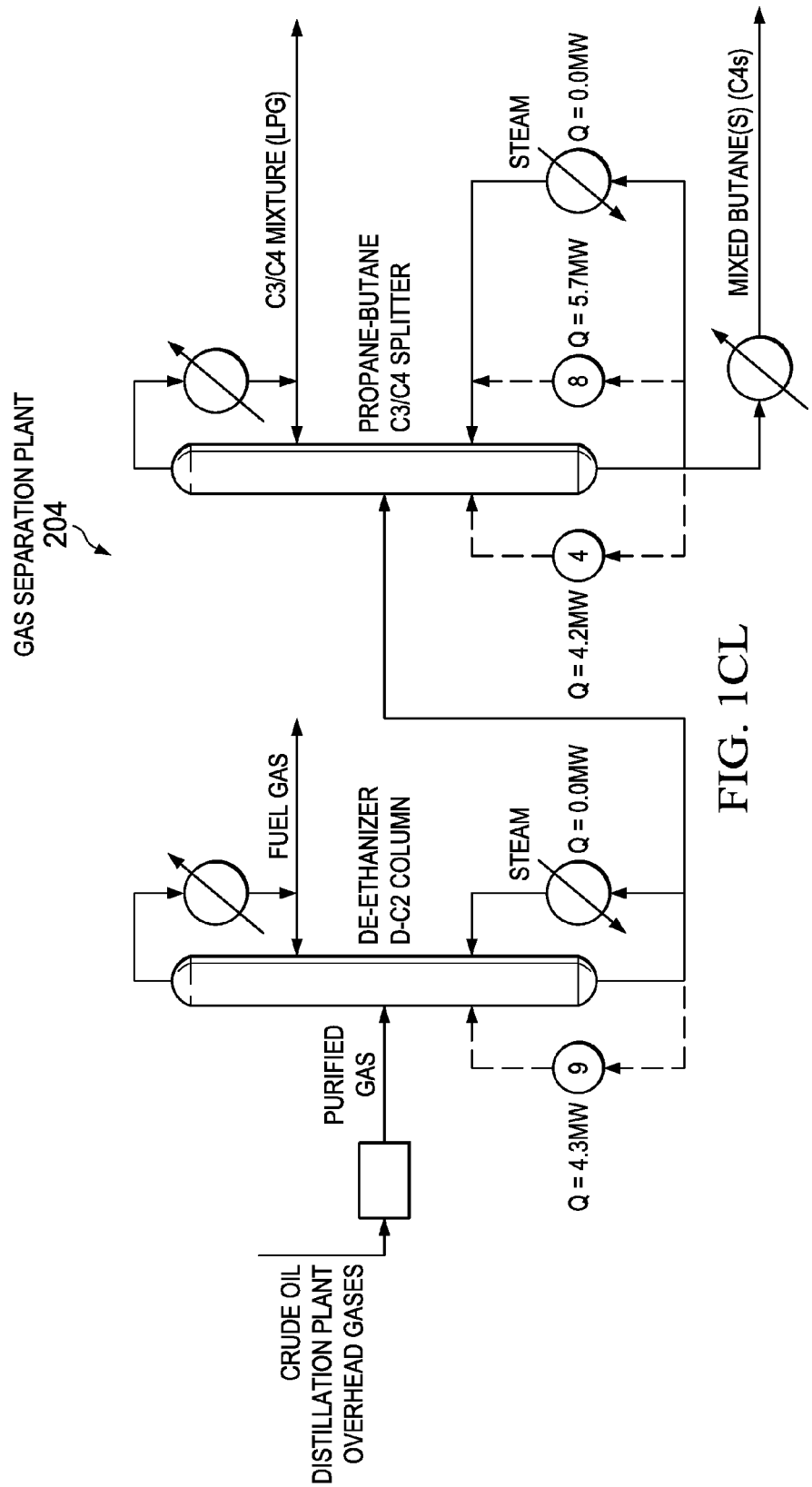
Figure 1C:
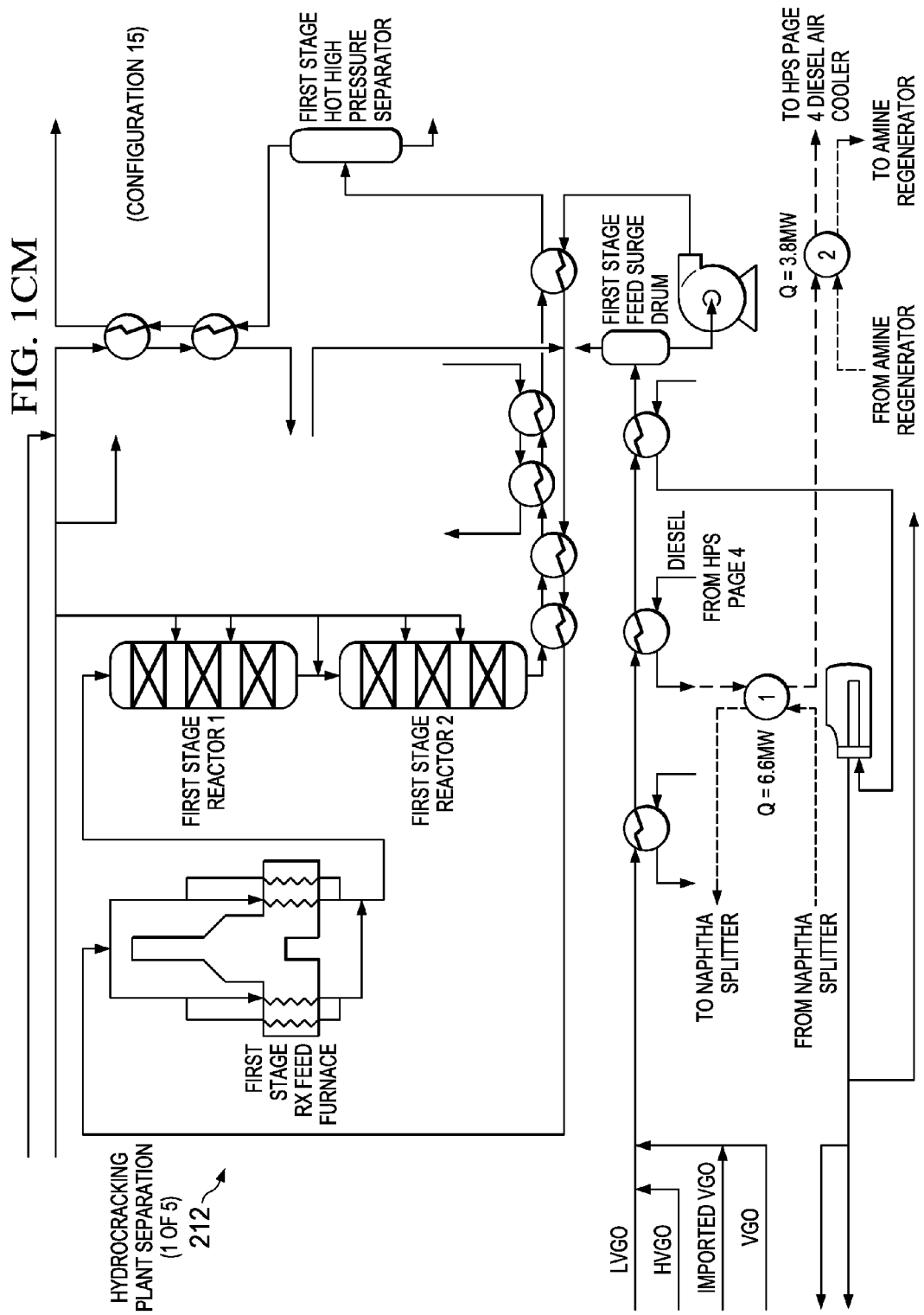
Figure 1C:
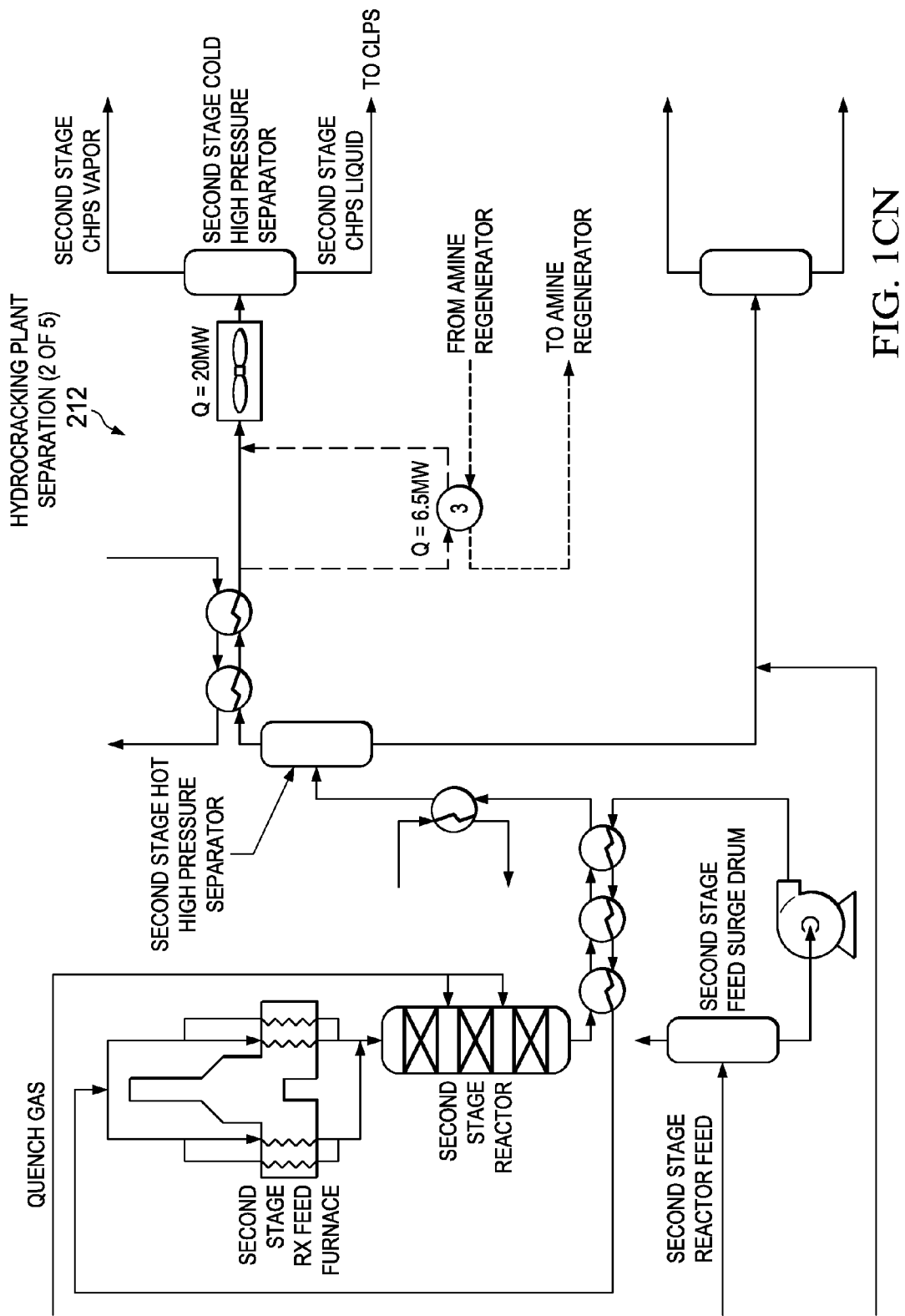
Figure 1C:
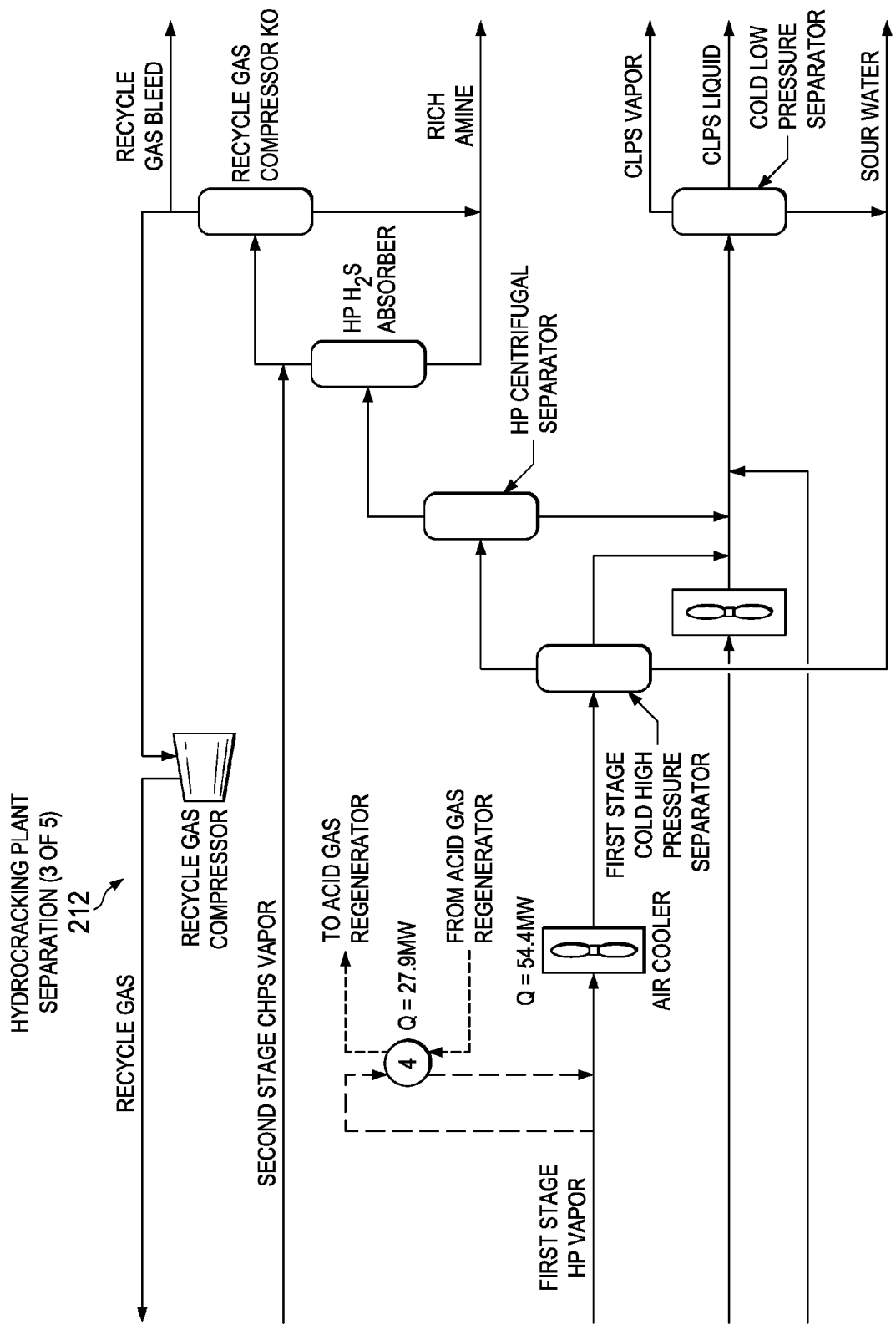
Figure 1C:
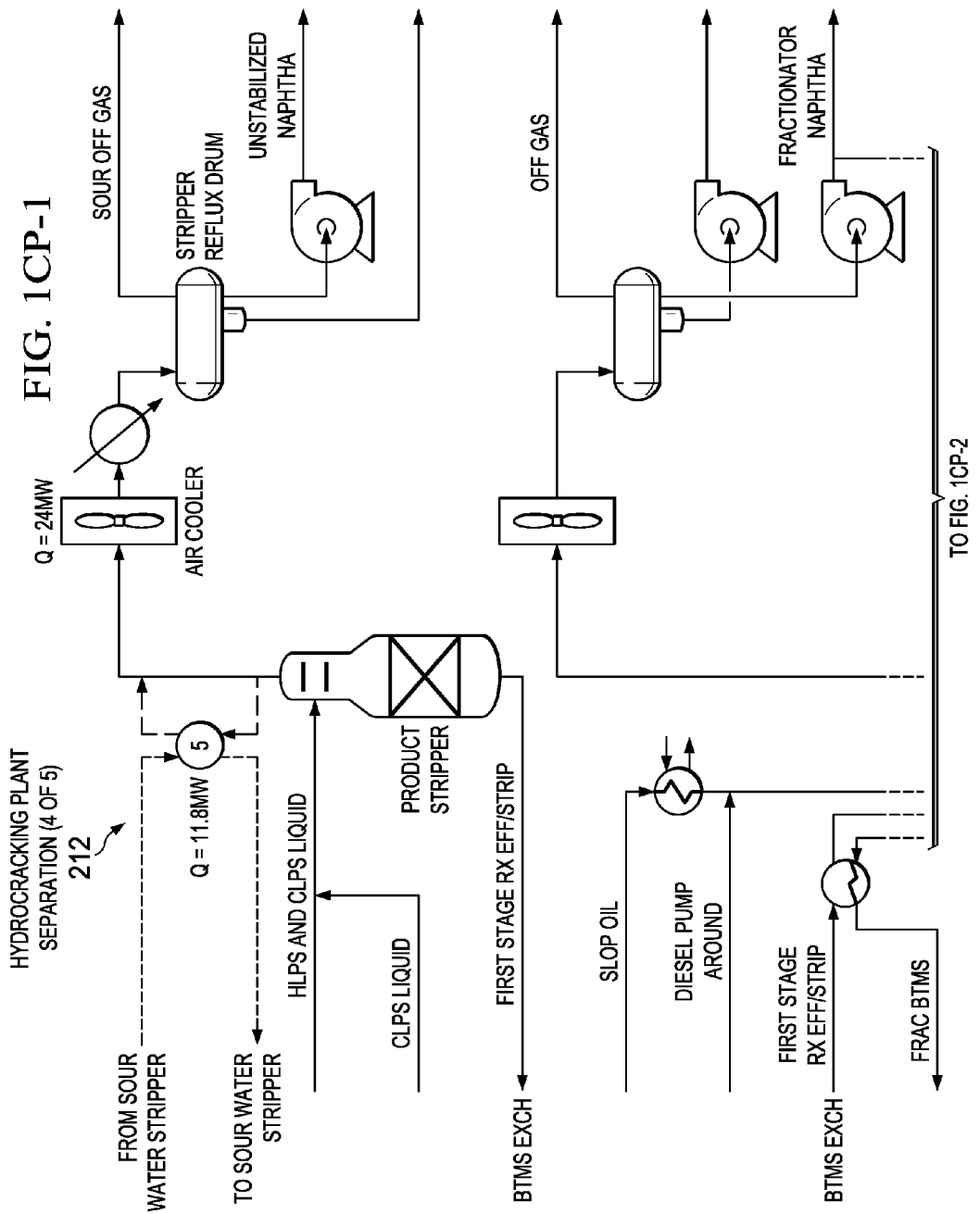
Figure 1C:
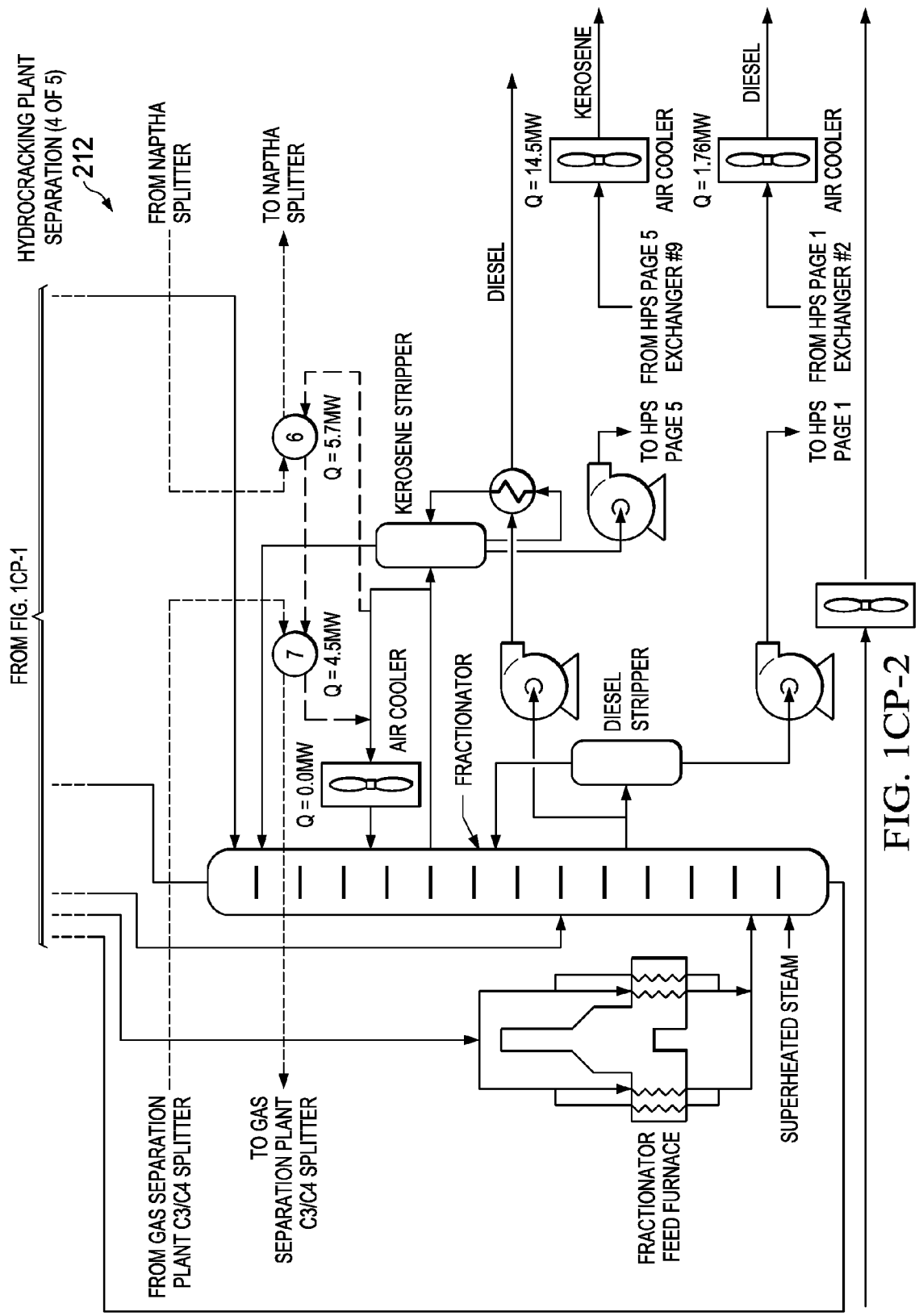
Figure 1C:
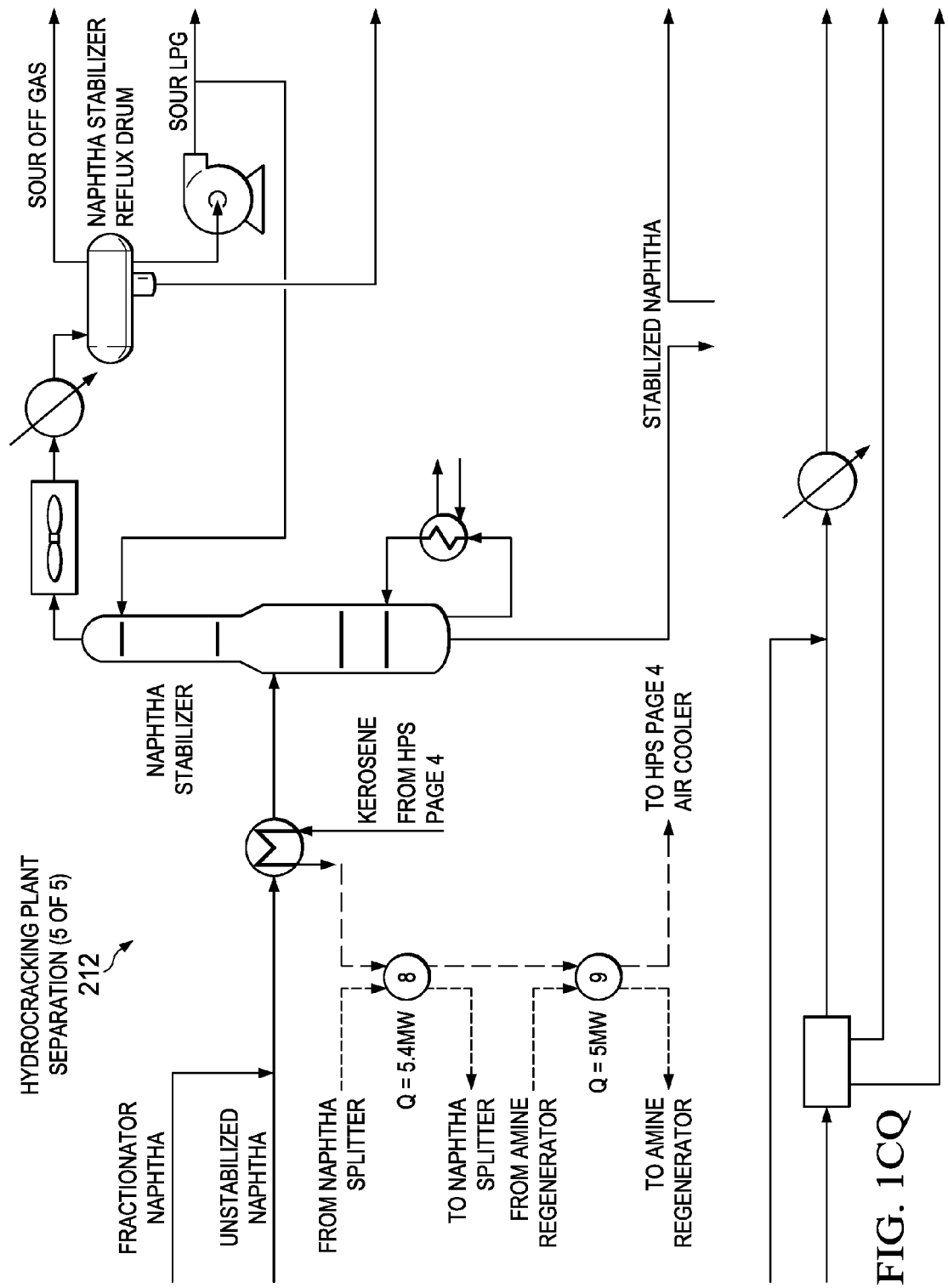
Figure 1C:
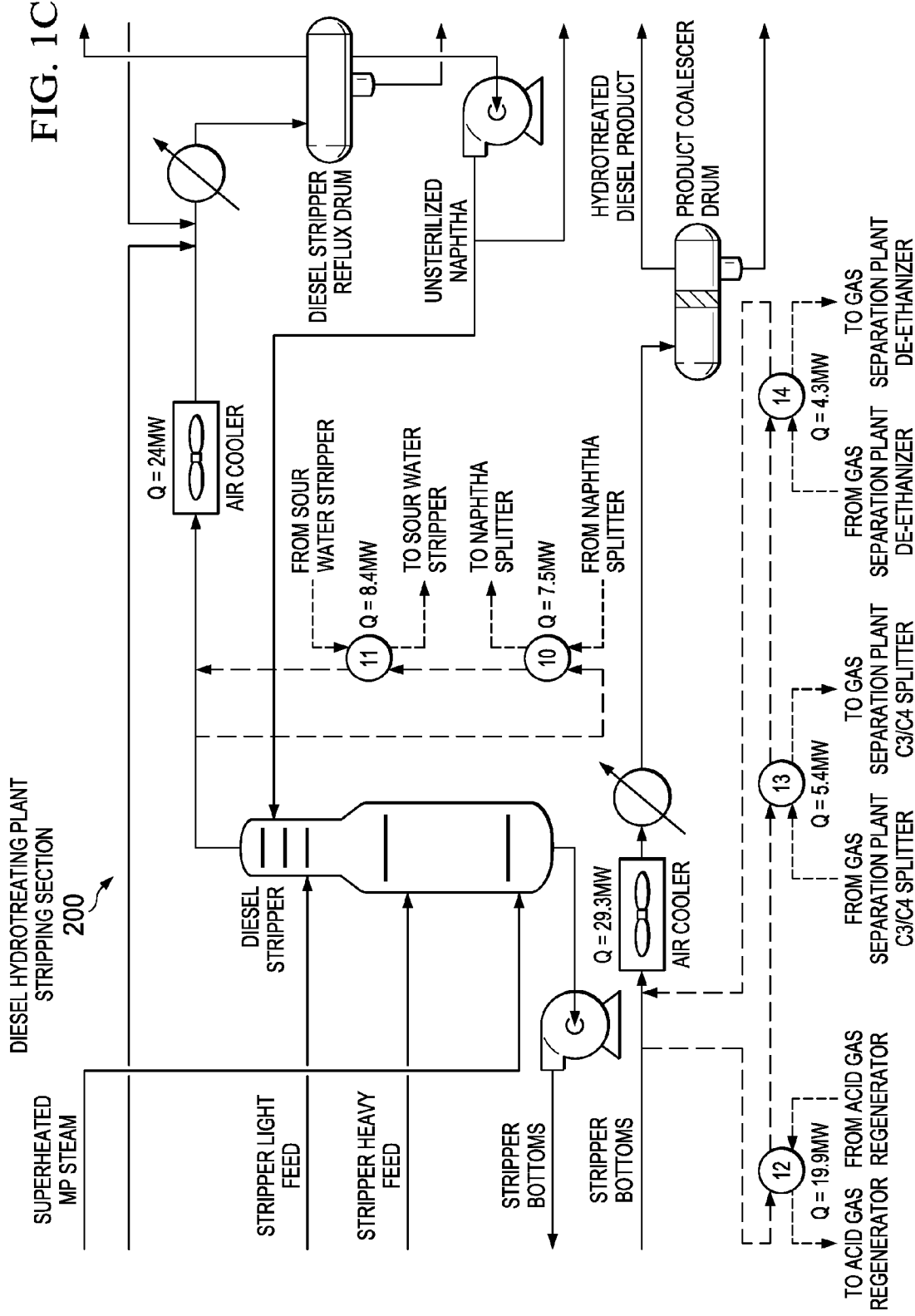
Figure 1C:
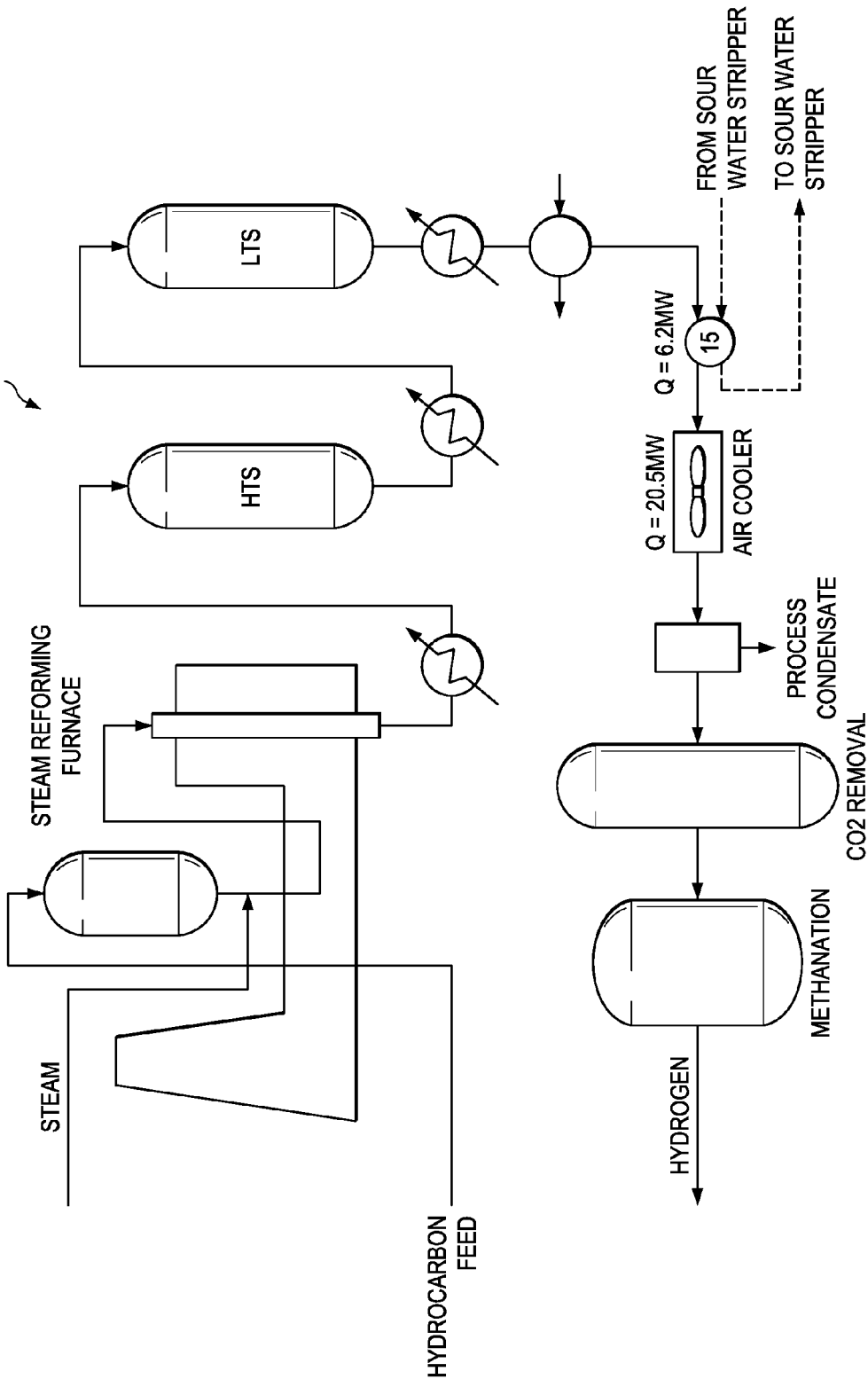
Figure 1C:
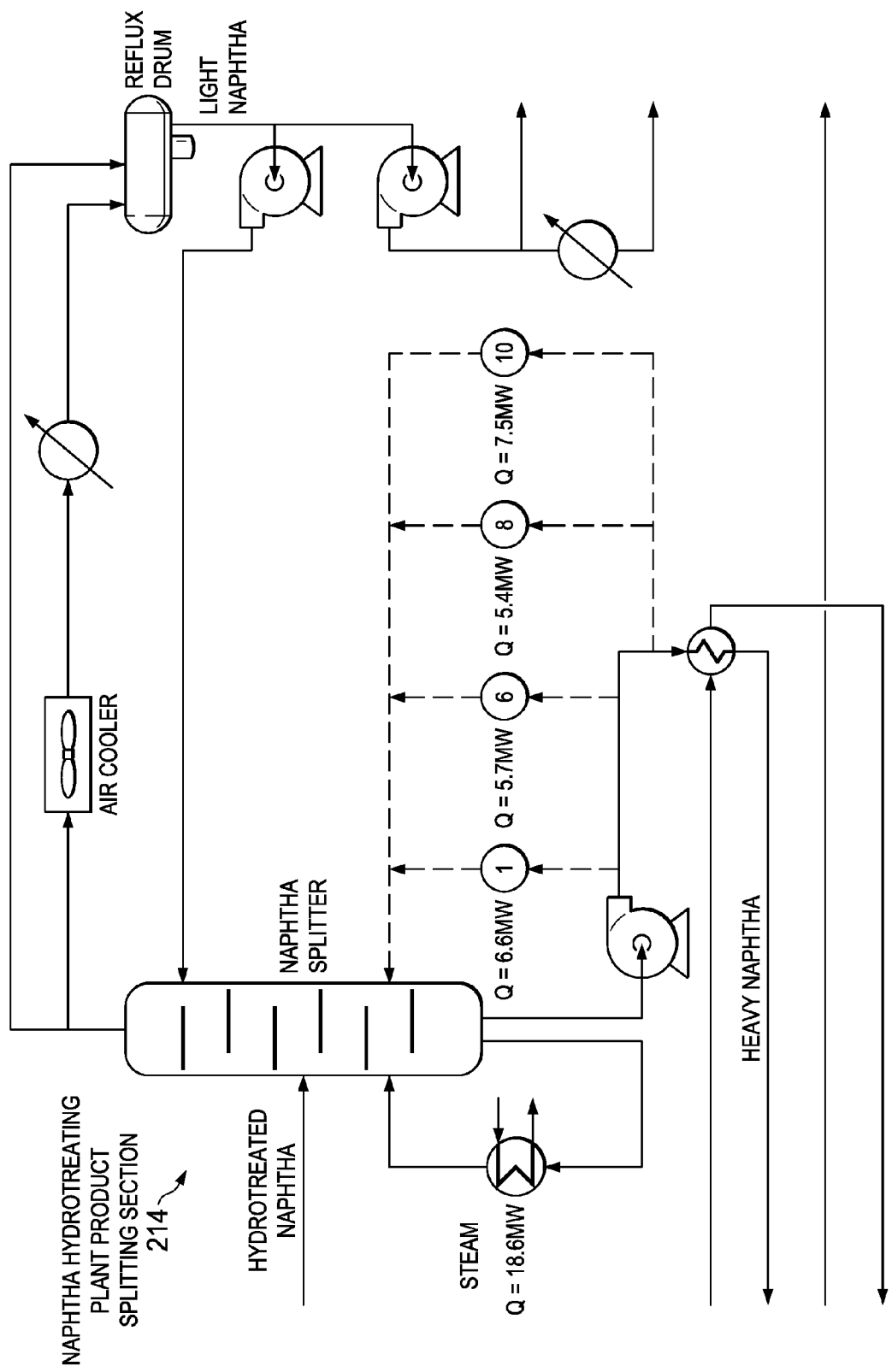
Figure 1C:
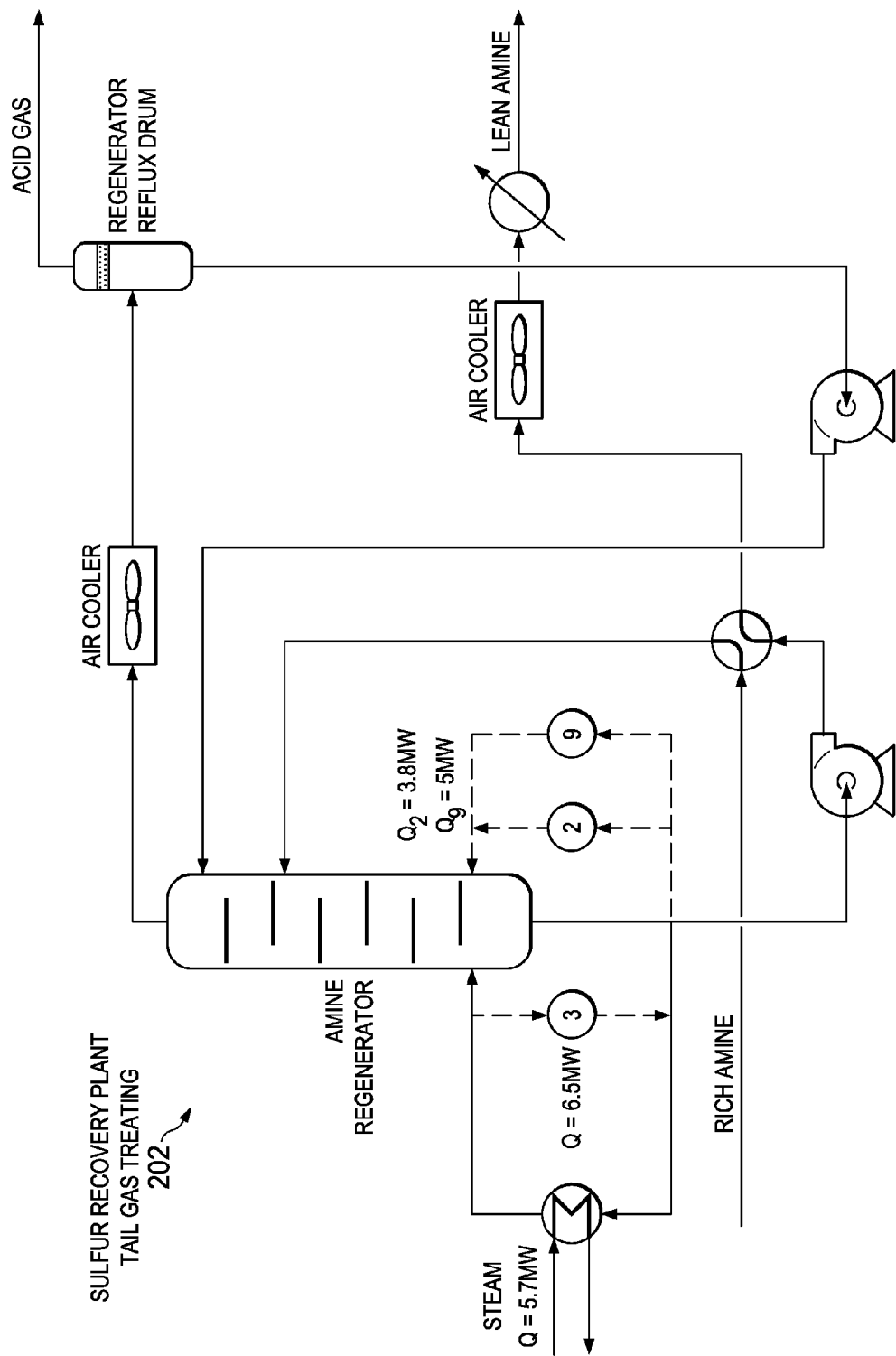
Figure 1C:
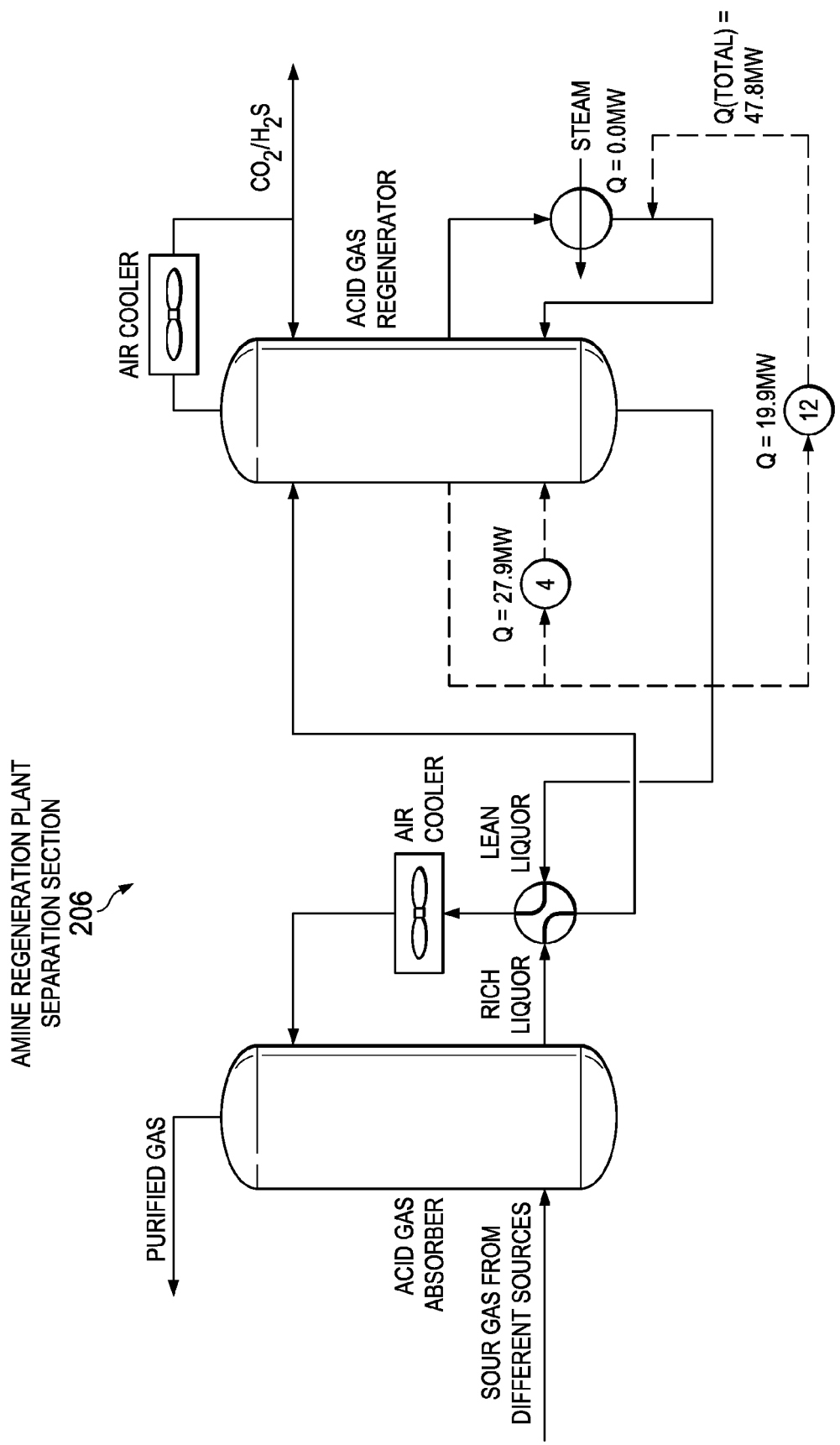
Figure 1C:
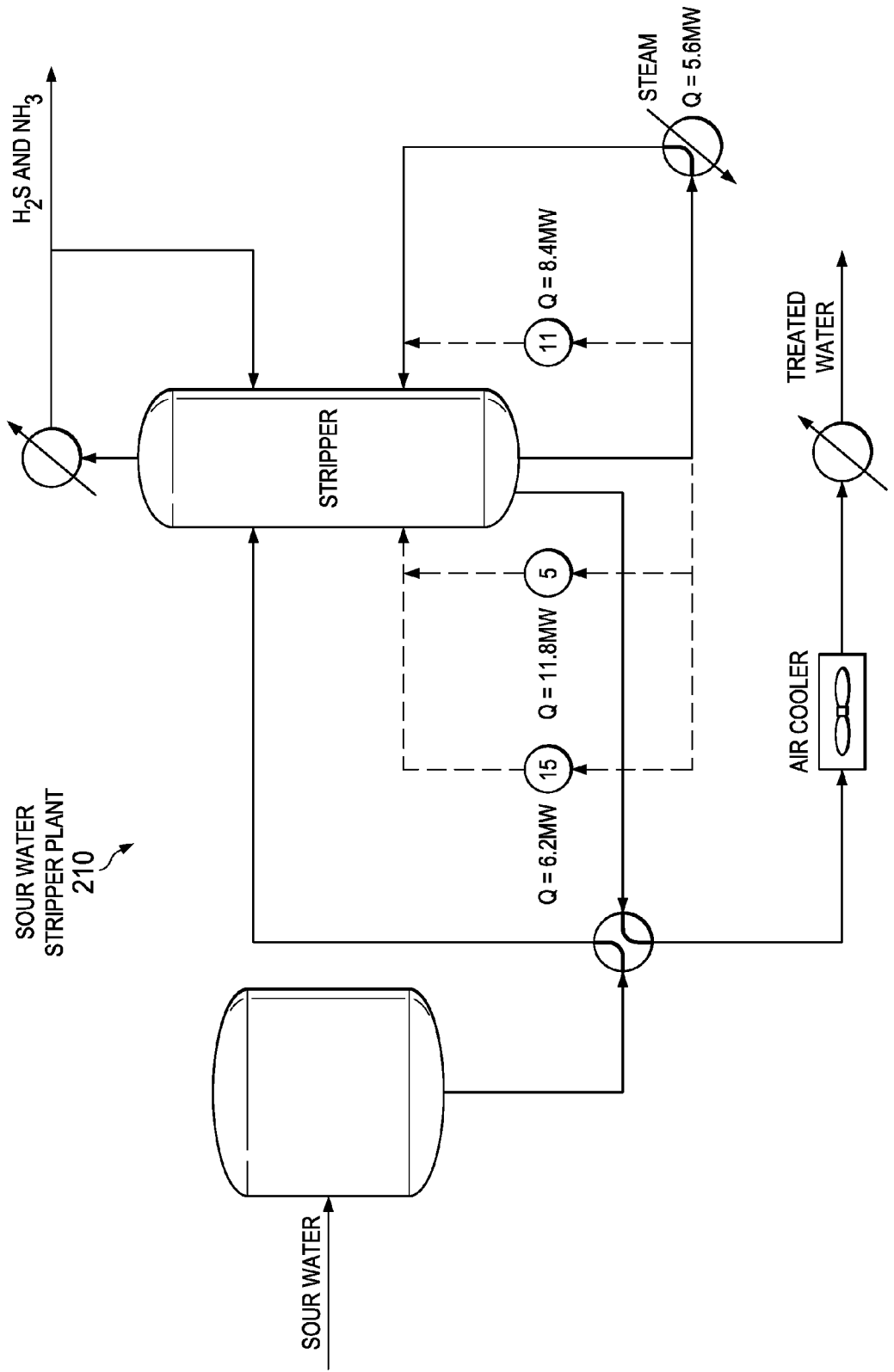
Figure 1C:
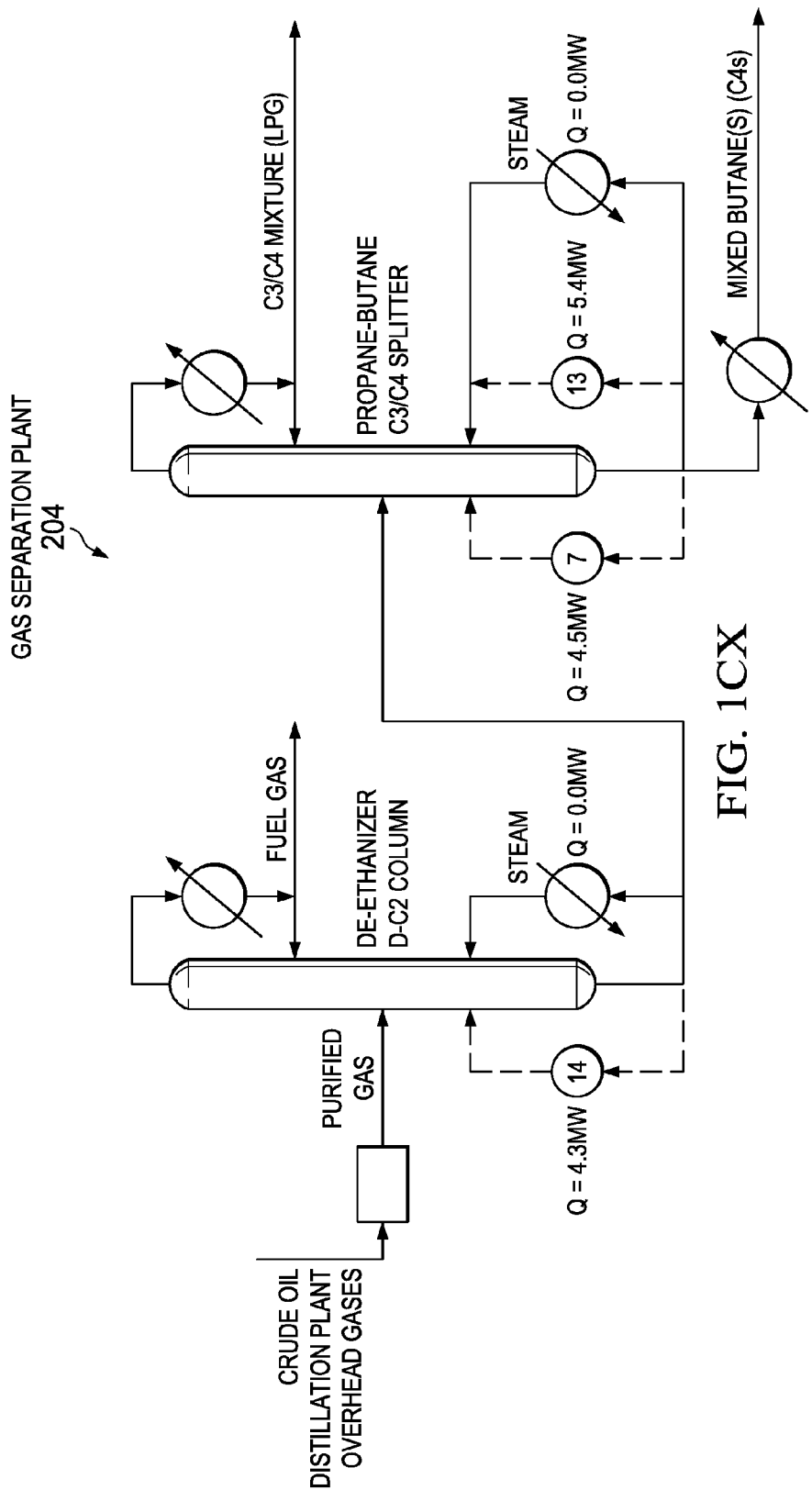

FIGS. 1C-1F show a hydrocracking plant 212 in a crude oil refining facility. FIG. 1G shows a sour water stripper plant 210 in the crude oil refining facility. The sour water stripper bottom stream can be flowed into the plant as a single stream and split into multiple streams or it can be flowed into the plant as multiple streams. As shown in FIG. 1C, a diesel product stream in the hydrocracking plant 212 directly heats a first sour water stripper bottom stream in a first heat exchanger with a thermal duty that can range between about 5 MW and 15 MW (for example, 10 MW). Also, as shown in FIG. 1D, a first stage reaction section feed to a first stage cold high pressure separator stream in the hydrocracking plant 212 directly heats the sour water stripper bottom stream in a second heat exchanger with a thermal duty that can range between about 15 MW and 25 MW, for example, 19.7 MW). As shown in FIG. 1F, a kerosene product stream in the hydrocracking plant 212 directly heats the sour water stripper bottom stream in a third heat exchanger with a thermal duty that can range between about 1 MW and 10 MW (for example, 2.3 MW). The first, second, and third heat exchangers are coupled in parallel to each other relative to the flow of sour water stripper bottoms. The transfer of heat directly to another process stream captures heat that would have otherwise been discharged to the environment. The diesel product stream, the first stage reaction section feed to a first stage cold high pressure separator stream, and the kerosene product stream are each returned to the hydrocracking plant 212 for further processing.

The heated first, second and third sour water stripper bottom stream are then flowed to the sour water stripper plant 210. As shown in FIG. 1G, the steam heat input for the sour water stripper can be 0 MW because the alternative flow paths disclosed in this configuration may satisfy the entire heat load for the operation of the column. In an alternative embodiment, the steam heat input for the sour water stripper plant can be reduced because the alternative flow paths disclosed in this configuration may partially satisfy the heat load for the operation of the column.

In this manner, the sour water stripper plant is directly heated using the waste heat recovered and reused from the hydrocracking plant, thereby saving about 32 MW of heat energy.

Configuration 3

FIGS. 1H-1M illustrate configurations and related scheme details for heating streams in a gas separation plant and a sulfur recovery plant. In some implementations, multiple first streams in multiple first plants can be directly heated using multiple second streams in a second plant. In some implementations, the multiple first plants are the sulfur recovery plant and the gas separation plant; the multiple first streams are the amine regenerator bottoms, the C3/C4 splitter bottoms and the de-ethanizer bottoms streams; the second plant is the hydrocracking plant; and the second multiple streams are the second reaction stage feed stream to a second cold high pressure separator, the first stage reaction feed stream to a first stage cold high pressure separator and the kerosene product streams.

The configurations illustrated in FIGS. 1H-1M thermally integrate the hydrocracking plant, the gas separation plant and the sulfur recovery plant in the crude oil refining facility to reduce the crude oil refining facility's energy consumption (for example, heating and cooling utilities). For example, a reduction in energy consumption by about 35 MW can translate to about 9% of the energy consumption in the crude oil refining facility. As described later, in certain schemes, a process stream (for example, a hydrocracking plant stream or other process streams) can be used to directly heat another process stream (for example, an amine regenerator stream or other process stream).

FIGS. 1H-1K show a hydrocracking plant 212 in a crude oil refining facility. FIG. 1L shows a gas separation plant 204 in the crude oil refining facility. FIG. 1M shows a sulfur recovery plant 202 in the crude oil refining facility. As shown in FIG. 1H, a second reaction stage feed stream to a second cold high pressure separator stream in the hydrocracking plant 212 directly heats a C3/C4 splitter bottom stream in a first heat exchanger with a thermal duty that can range between about 5 MW and 15 MW (for example, 9.9 MW). As shown in FIG. 1I, a first stage reaction feed stream to a first stage cold high pressure separator stream in the hydrocracking plant 212 directly heats an amine regenerator bottom stream in a second heat exchanger with a thermal duty that can range between about 15 MW and 25 MW (for example, 21 MW). As shown in FIG. 1K, a kerosene product stream in the hydrocracking plant 212 directly heats a de-ethanizer bottom stream in a third heat exchanger with a thermal duty that can range between about 1 MW and 10 MW (for example, 4.3 MW). The transfer of heat directly to another process stream captures heat that would have otherwise been discharged to the environment. The second reaction stage feed stream to a second cold high pressure separator stream, the first stage reaction feed stream to a first stage cold high pressure separator stream, and the kerosene product stream are each returned to the hydrocracking plant 212 for further processing.

The heated amine regenerator bottom stream is then flowed to the sulfur recovery plant 202. As shown in FIG. 1M, the steam heat input for the amine regenerator can be 0 MW because the alternative flow paths disclosed in this configuration may satisfy the entire heat load for the operation of the column. In an alternative embodiment, the steam heat input for the amine regenerator can be reduced because the alternative flow paths disclosed in this configuration may partially satisfy the heat load for the operation of the column.

The heated C3/C4 splitter bottom stream and the de-ethanizer bottom stream are then flowed to the gas separation plant 204. As shown in FIG. 1L, the steam heat input for the de-ethanizer column can be 0 MW because the alternative flow paths disclosed in this configuration may satisfy the entire heat load for the operation of the column. In an alternative embodiment, the steam heat input for the de-ethanizer column can be reduced because the alternative flow paths disclosed in this configuration may partially satisfy the heat load for the operation of the column. Also shown, the steam heat input for the C3/C4 splitter column can be 0 MW because the alternative flow paths disclosed in this configuration may satisfy the entire heat load for the operation of the column. In an alternative embodiment, the steam heat input for the C3/C4 splitter column can be reduced because the alternative flow paths disclosed in this configuration may partially satisfy the heat load for the operation of the column.

In this manner, the gas separation plant and the sulfur recovery plant are directly heated using the waste heat recovered and reused from the hydrocracking plant, thereby saving about 35 MW of heat energy.

Configuration 4

FIGS. 1N-1S illustrate configurations and related scheme details for heating streams in a naphtha hydro-treating plant and a sulfur recovery plant. In some implementations, multiple first streams in multiple first plants can be directly heated using multiple second streams in a second plant. In some implementations, the multiple first plants are the sulfur recovery plant and the naphtha hydrotreating plant; the multiple first streams are the amine regenerator bottoms and the naphtha splitter bottoms streams; the second plant is the hydrocracking plant; and the second multiple streams are the diesel product stream, the product stripper overheads stream, the kerosene pumparound stream, the kerosene product stream and the first reaction stage feed stream to a first stage cold high pressure separator.

The configurations illustrated in FIGS. 1N-1S thermally integrate the hydrocracking plant, the naphtha hydro-treating plant and the sulfur recovery plant in the crude oil refining facility to reduce the crude oil refining facility's energy consumption (for example, heating and cooling utilities). For example, a reduction in energy consumption by about 42 MW can translate to about 11% of the energy consumption in the crude oil refining facility. As described later, in certain schemes, a process stream (for example, a hydrocracking plant stream or other process streams) can be used to directly heat another process stream (for example, an amine regenerator stream or other process stream).

FIGS. 1N-1Q show a hydrocracking plant 212 in a crude oil refining facility. FIG. 1R shows a naphtha hydrotreating plant 214 in the crude oil refining facility. FIG. 1S shows a sulfur recovery plant 202 in the crude oil refining facility. The naphtha splitter bottoms stream can be flowed into the plant as a single stream and split into multiple streams or it can be flowed into the plant as multiple streams. The hydrocracking plant 212 includes a diesel product stream, a product stripper overhead stream, a kerosene pumparound stream and a kerosene product stream. The diesel product stream, the product stripper overheads stream, the kerosene pumparound stream and the kerosene product stream each directly heat a first, second, third and fourth naphtha splitter bottoms streams in a first heat exchanger (as shown in FIG. 1N), a second heat exchanger (as shown in FIG. 1P-1), a third heat exchanger (as shown in FIG. 1P-3), and a fourth heat exchanger (as shown in FIG. 1Q), respectively. The thermal duties of the first heat exchanger, the second heat exchanger, the third heat exchanger, and the fourth heat exchanger can range between about 1 MW and 10 MW (for example, 6.6 MW), about 1 MW and 10 MW (for example, 3.4 MW), about 1 MW and 10 MW (for example, 5.7 MW), and about 1 MW and 10 MW (for example, 5.4 MW), respectively. The first, second, third and fourth heat exchangers are coupled in parallel to each other relative to the flow of naphtha splitter bottoms. Also, as shown in FIG. 1O, a first reaction stage feed stream to a first stage cold high pressure separator directly heats an amine regenerator bottoms stream in a fifth heat exchanger with a thermal duty that can range between about 15 MW and 25 MW (for example, 21 MW). The transfer of heat directly to another process stream captures heat that would have otherwise been discharged to the environment. The diesel product stream, the product stripper overheads stream, the kerosene pump-around stream, the kerosene product stream and the first reaction stage feed stream to a first stage cold high pressure separator are each returned to the hydrocracking plant 212 for further processing.

The first, second, third and fourth heated naphtha splitter bottom streams are then flowed to the naphtha hydro-treating plant 214. As shown in FIG. 1R, the steam heat input for the naphtha splitter column can be reduced because the alternative flow paths disclosed in this configuration may partially satisfy the heat load for the operation of the column. In an alternative embodiment, the steam heat input for the naphtha splitter column can be 0 MW because the alternative flow paths disclosed in this configuration may satisfy the entire heat load for the operation of the column.

The heated amine regenerator bottom stream is then flowed to the sulfur recovery plant 202. As shown in FIG. 1S, the steam heat input for the amine regenerator can be 0 MW because the alternative flow path disclosed in this configuration may satisfy the entire heat load for the operation of the column. In an alternative embodiment, the steam heat input for the amine regenerator can be reduced because the alternative flow path disclosed in this configuration may partially satisfy the heat load for the operation of the column.

In this manner, the naphtha hydro-treating plant and the sulfur recovery plant are heated using the waste heat recovered and reused from the hydrocracking plant, thereby saving about 42 MW of heat energy.

Configuration 5

FIGS. 1T-1Y illustrate configurations and related scheme details for heating streams in a sour water stripper plant and a gas separation plant. In some implementations, multiple first streams in multiple first plants can be directly heated using multiple second streams in a second plant. In some implementations, the multiple first plants are the sour water stripper plant and the gas separation plant; the multiple first streams are the sour water stripper bottoms and the naphtha splitter bottoms streams; the second plant is the hydrocracking plant; and the second multiple streams are the second reaction section second stage cold high pressure separator feed stream, the kerosene product stream, the first reaction stage feed stream to the first stage cold high pressure separator and the product stripper overheads streams.

The configurations illustrated in FIGS. 1T-1Y thermally integrate the hydrocracking plant, the sour water stripper plant, and the gas separation plant in the crude oil refining facility to reduce the crude oil refining facility's energy consumption. A reduction in energy consumption by about 46 MW can translate to about 12% of the energy consumption in the crude oil refining facility. As described later, in certain schemes, a process stream (for example, a hydrocracking plant stream or other process streams) can be used to directly heat another process stream (for example, an amine regenerator stream or other process stream).

FIGS. 1T-1W show a hydrocracking plant 212 in a crude oil refining facility. FIG. 1X shows a sour water stripper plant 210 in the crude oil refining facility. FIG. 1Y shows a gas separation plant 204 in the crude oil refining facility. The sour water stripper bottoms stream can be flowed into the plant as a single stream and split into multiple streams or it can be flowed into the plant as multiple streams. As shown in FIG. 1T, a second reaction section second stage cold high pressure separator feed stream in the hydrocracking plant 212 directly heats a C3/C4 splitter bottoms stream in a first heat exchanger with a thermal duty that can range between about 5 MW and 15 MW (for example, 9.9 MW). As shown in FIG. 1W, a kerosene product stream in the hydrocracking plant 212 directly heats the de-ethanizer bottoms stream in a fourth heat exchanger with a thermal duty that can range between about 1 MW and 10 MW (for example, 4.3 MW). The transfer of heat directly to another process stream captures heat that would have otherwise been discharged to the environment. The second reaction section second stage cold high pressure separator feed stream and the kerosene product stream are each returned to the hydrocracking plant 212 for further processing.

The heated C3/C4 splitter bottoms stream and the heated de-ethanizer bottoms stream are each flowed to the gas separation plant 204. As shown in FIG. 1Y, the steam heat input for the C3/C4 splitter can be 0 MW because the alternative flow path disclosed in this configuration may satisfy the entire heat load for the operation of the column. In an alternative embodiment, the steam heat input for the C3/C4 splitter can be reduced because the alternative flow path disclosed in this configuration may partially satisfy the heat load for the operation of the column. As well, the steam heat input for the de-ethanizer can be 0 MW because the alternative flow path disclosed in this configuration may satisfy the entire heat load for the operation of the column. In an alternative embodiment, the steam heat input for the de-ethanizer can be reduced because the alternative flow path disclosed in this configuration may partially satisfy the heat load for the operation of the column.

Also, the hydrocracking plant 212 includes a first reaction stage feed stream to a first stage cold high pressure separator and a product stripper overheads stream. As shown in FIG. 1U, the first reaction stage feed stream to the first stage cold high pressure separator directly heats a first sour water stripper bottom stream in a second heat exchanger with a thermal duty that can range between about 15 MW and 25 MW (for example, 20.5 MW). As shown in FIG. 1V-2, the product stripper overheads stream directly heats a second sour water stripper bottom stream in a third heat exchanger with a thermal duty that can range between about 5 MW and 15 MW (for example, 11.5 MW). The second and the third heat exchangers are coupled in parallel to each other relative to the flow of sour water stripper bottoms. The transfer of heat directly to another process stream captures heat that would have otherwise been discharged to the environment. The first reaction stage feed stream to the first stage cold high pressure separator and the product stripper overheads stream are each returned to the hydrocracking plant 212 for further processing.

The heated first and second sour water stripper bottom streams are then flowed to the sour water stripper plant 210. As shown in FIG. 1X, the steam heat input for the sour water stripper can be 0 MW because the alternative flow path disclosed in this configuration may satisfy the entire heat load for the operation of the column. In an alternative embodiment, the steam heat input for the sour water stripper can be reduced because the alternative flow path disclosed in this configuration may partially satisfy the heat load for the operation of the column.

In this manner, the sour water stripper plant and the gas separation plant are heated using the waste heat recovered and reused from the hydrocracking plant. Such a recovery and reuse of waste heat can result in a savings of about 46 MW of heat energy.

Configuration 6

FIGS. 1Z-1AH illustrate configurations and related scheme details for heating an acid gas regenerator bottoms stream in an amine regeneration plant using a hydrocracking plant. For example, a reduction in energy consumption by about 48 MW can translate to about 12% of the energy consumption in the crude oil refining facility. As described later, in certain schemes, a process stream (for example, a hydrocracking plant stream or other process streams) can be used to directly heat another process stream (for example, an acid gas regenerator stream or other process stream).

Configuration 6—Scheme A

The configurations illustrated in FIGS. 1Z-1AD thermally integrate the hydrocracking plant and the amine regeneration plant in the crude oil refining facility to reduce the crude oil refining facility's energy consumption. In some implementations, a first stream in a first plant can be directly heated using multiple second streams in a second plant. In some implementations, the first plant is the amine regeneration plant; the first stream is the acid gas regenerator bottoms stream; the second plant is the hydrocracking plant; and the second multiple streams are the diesel product stream, the first reaction section feed stream to a first stage cold high pressure separator and the kerosene product streams.

FIGS. 1Z-1AC show a hydrocracking plant 212 in a crude oil refining facility. FIG. 1AD shows an amine regeneration plant in the crude oil refining facility. The acid gas regenerator bottoms stream can be flowed into the plant as a single stream and split into multiple streams or it can be flowed into the plant as multiple streams. The hydrocracking plant 212 has a diesel product stream, a first reaction section feed stream to a first stage cold high pressure separator and a kerosene product stream directly heats a first, a second, and a third acid gas regenerator bottoms stream, respectively. As shown in FIG. 1Z, the diesel product stream directly heats a first acid gas regenerator bottom stream in a first heat exchanger with a thermal duty that can range between about 5 MW and 15 MW (for example, 11.6 MW). As shown in FIG. 1AA, the first reaction section feed stream to the first stage cold high pressure separator directly heats a second acid gas regenerator bottom stream in a second heat exchanger with a thermal duty that can range between about 20 MW and 30 MW (for example, 24.2 MW). As shown in FIG. 1AC, the kerosene product stream directly heats a third acid gas regenerator bottom stream in a third heat exchanger with a thermal duty that can range between about 5 MW and 15 MW (for example, 12 MW). The first, second and the third heat exchangers are coupled in parallel to each other relative to the flow of acid gas regenerator bottoms. The transfer of heat directly to another process stream captures heat that would have otherwise been discharged to the environment. The diesel product stream, the first reaction section feed stream to a first stage cold high pressure separator and the kerosene product stream are each returned to the hydrocracking plant 212 for further processing.

The heated first, the heated second, and the heated third acid gas regenerator bottoms streams are then flowed to the amine regeneration plant 206. As shown in FIG. 1AD, the steam heat input for the acid gas regenerator can be 0 MW because the alternative flow path disclosed in this configuration may satisfy the entire heat load for the operation of the column. In an alternative embodiment, the steam heat input for the acid gas regenerator can be reduced because the alternative flow path disclosed in this configuration may partially satisfy the heat load for the operation of the column.

In this manner, the amine regeneration plant is heated using the waste heat recovered and reused from the hydrocracking plant, thereby saving about 48 MW of heat energy.

Configuration 6—Scheme B

The configurations illustrated in FIGS. 1AE-1AH thermally integrate the hydrocracking plant and the amine regeneration plant in the crude oil refining facility to reduce the crude oil refining facility's energy consumption. In some implementations, a first stream in a first plant can be directly heated using multiple second streams in a second plant. In some implementations, the first plant is the amine regeneration plant; the first stream is the acid gas regenerator bottoms stream; the second plant is the hydrocracking plant; and the second multiple streams are the first reaction section feed stream to a first stage cold high pressure separator, a product stripper overheads stream and a kerosene product stream.

FIGS. 1AE-1AG show a hydrocracking plant 212 in a crude oil refining facility. FIG. 1AH shows an amine regeneration plant in the crude oil refining facility. The acid gas regenerator bottoms stream can be flowed into the plant as a single stream and split into multiple streams or it can be flowed into the plant as multiple streams. The hydrocracking plant 212 includes a first reaction section feed stream to a first stage cold high pressure separator, a product stripper overheads stream and a kerosene product stream. As shown in FIG. 1AE, the first reaction section feed stream to the first stage cold high pressure separator directly heats a first acid gas regenerator bottom stream in a first heat exchanger with a thermal duty that can range between about 25 MW and 35 MW (for example, 27.8 MW). As shown in FIG. 1AF (represented collectively by FIGS. 1AF-1 and 1AF-2), the product stripper overheads stream directly heats a second acid gas regenerator bottom stream in a second heat exchanger with a thermal duty that can range between about 10 MW and 20 MW (for example, 14.8 MW). As shown in FIG. 1AG, the kerosene product stream directly heats a third acid gas regenerator bottom stream in a third heat exchanger with a thermal duty that can range between about 1 MW and 10 MW (for example, 5.2 MW). The first, second and the third heat exchangers are coupled in parallel to each other relative to the flow of acid gas regenerator bottoms. The transfer of heat directly to another process stream captures heat that would have otherwise been discharged to the environment. The first reaction section feed stream to a first stage cold high pressure separator, the product stripper overheads stream and the kerosene product stream are each returned to the hydrocracking plant 212 for further processing.

The heated first, the heated second, and the heated third acid gas bottoms streams are then flowed to the amine regeneration plant 206. As shown in FIG. 1AH, the steam heat input for the acid gas regenerator can be 0 MW because the alternative flow path disclosed in this configuration may satisfy the entire heat load for the operation of the column. In an alternative embodiment, the steam heat input for the acid gas regenerator can be reduced because the alternative flow path disclosed in this configuration may partially satisfy the heat load for the operation of the column.

In this manner, the amine regeneration plant is heated using the waste heat recovered and reused from the hydrocracking plant, thereby saving about 48 MW of heat energy.

Configuration 7

FIGS. 1AI-1AN illustrate configurations and related scheme details for heating streams in a naphtha hydrotreating plant and a sour water stripper plant. In some implementations, multiple first stream in multiple first plants can be directly heated using multiple second streams in a second plant. In some implementations, the multiple first plants are a naphtha hydrotreating plant and a sour water stripper plant; the multiple first streams are the naphtha splitter bottoms and the sour water stripper bottoms streams; the second plant is the hydrocracking plant; and the second multiple streams are the diesel product, the kerosene pumparound, the kerosene product, first reaction section feed stream to a first stage cold high pressure separator and the product stripper overheads streams.

The configurations illustrated in FIGS. 1AI-1AN thermally integrate a hydrocracking plant, the naphtha hydrotreating plant, and the sour water stripper plant in the crude oil refining facility to reduce the crude oil refining facility's energy consumption. A reduction in energy consumption by about 50 MW can translate to about 13% of the energy consumption in the crude oil refining facility. As described later, in certain schemes, a process stream (for example, a hydrocracking plant stream or other process streams) can be used to directly heat another process stream (for example, a sour water stripper stream or other process stream).

FIGS. 1AI-1AL show a hydrocracking plant 212 in a crude oil refining facility. FIG. 1AM shows a naphtha hydrotreating plant 214 in the crude oil refining facility. The naphtha splitter bottoms stream can be flowed into the plant as a single stream and split into multiple streams or it can be flowed into the plant as multiple streams. The hydrocracking plant 212 includes a diesel product stream, a kerosene pumparound stream and a kerosene product stream. As shown in FIG. 1AI, the diesel product stream directly heats a first naphtha splitter bottom stream in a first heat exchanger with a thermal duty that can range between about 5 MW and 10 MW (for example, 6.6 MW). As shown in FIG. 1AK (represented collectively by FIGS. 1AK-1 and 1AK-2), the kerosene pumparound stream directly heats a second naphtha splitter bottom stream in a fourth heat exchanger with a thermal duty that can range between about 1 MW and 10 MW (for example, 5.7 MW). As shown in FIG. 1AL, the kerosene product stream directly heats a third naphtha splitter bottom stream in a fifth heat exchanger with the thermal duty that can range between about 1 MW and 10 MW (for example, 5.4 MW). The first, fourth and the fifth heat exchangers are coupled in parallel to each other relative to the flow of naphtha splitter bottoms. The transfer of heat directly to another process stream captures heat that would have otherwise been discharged to the environment. The diesel product stream, the kerosene pumparound stream and the kerosene product stream are each returned to the hydrocracking plant 212 for further processing.

The heated first, the heated second, and the heated third naphtha splitter bottoms streams are then flowed to the naphtha hydro-treating plant 214. As shown in FIG. 1AM, the steam heat input for the naphtha splitter column can be reduced because the alternative flow paths disclosed in this configuration may partially satisfy the heat load for the operation of the column. In an alternative embodiment, the steam heat input for the naphtha splitter column can be 0 MW because the alternative flow paths disclosed in this configuration may satisfy the entire heat load for the operation of the column.

FIG. 1AN shows a sour water stripper plant 210 in the crude oil refining facility. The sour water stripper bottoms stream can be flowed into the plant as a single stream and split into multiple streams or it can be flowed into the plant as multiple streams. The hydrocracking plant 212 also includes a first reaction section feed stream to a first stage cold high pressure separator and a product stripper overheads stream. As shown in FIG. 1AJ, the first reaction section feed stream to the first stage cold high pressure separator directly heats a first sour water stripper bottom stream in a second heat exchanger with a thermal duty that can range between about 15 MW and 25 MW (for example, 20.5 MW). As shown in FIG. 1AK, the product stripper overheads stream directly heats a second sour water stripper bottom stream in a third heat exchanger with the thermal duty that can range between about 5 MW and 15 MW (for example, 11.5 MW). The second and third heat exchangers are coupled in parallel to each other relative to the flow of sour water stripper bottoms. The transfer of heat directly to another process stream captures heat that would have otherwise been discharged to the environment. The first reaction section feed stream to a first stage cold high pressure separator and the product stripper overheads stream are each returned to the hydrocracking plant 212 for further processing.

The heated first and the heated second sour water stripper bottoms streams are then flowed to the sour water stripper plant 210. As shown in FIG. 1AN, the steam heat input for the sour water stripper can be 0 MW because the alternative flow path disclosed in this configuration may satisfy the entire heat load for the operation of the column. In an alternative embodiment, the steam heat input for the sour water stripper can be reduced because the alternative flow path disclosed in this configuration may partially satisfy the heat load for the operation of the column.

In this manner, the naphtha hydro-treating plant and the sour water stripper plant are heated using the waste heat recovered and reused from the hydrocracking plant. Such a recovery and reuse of waste heat can result in a savings of about 50 MW of heat energy.

Configuration 8

FIGS. 1AO-1AT illustrate configurations and related schemes for heating streams in a sulfur recovery plant and a sour water stripper plant. In some implementations, multiple first stream in multiple first plants can be directly heated using multiple second streams in a second plant. In some implementations, the multiple first plants are a sulfur recovery plant and a sour water stripper plant; the multiple first streams are the amine regenerator bottoms and the sour water stripper bottoms streams; the second plant is the hydrocracking plant; and the second multiple streams are the diesel product, the kerosene product, the first reaction section feed stream to a first stage cold high pressure separator and the product stripper overheads streams.

The configurations illustrated in FIGS. 1AO-1AT thermally integrate the hydrocracking plant, the sulfur recovery plant, and the sour water stripper plant in the crude oil refining facility to reduce the crude oil refining facility's energy consumption. For example, a reduction in energy consumption by about 53 MW can translate to about 13% of the energy consumption in the crude oil refining facility. As described later, in certain schemes, a process stream (for example, a hydrocracking plant stream or other process streams) can be used to directly heat another process stream (for example, an amine regenerator stream or other process stream).

FIGS. 1AO-1AR show a hydrocracking plant 212 in a crude oil refining facility. FIG. 1AT shows a sulfur recovery plant 202 in the crude oil refining facility. The amine regenerator bottoms stream can be flowed into the plant as a single stream and split into multiple streams or it can be flowed into the plant as multiple streams. The hydrocracking plant 212 includes a diesel product stream and a kerosene product stream. As shown in FIG. 1AO, the diesel product stream directly heats a first amine regenerator bottoms stream in a first heat exchanger with a thermal duty that can range between about 5 MW and 15 MW (for example, 10.4 MW). As shown in FIG. 1AR, the kerosene product stream directly heats a second amine regenerator bottoms stream in a fourth heat exchanger with a thermal duty that can range between about 5 MW and 15 MW (for example, 10.6 MW). The first and the fourth heat exchangers are coupled in parallel to each other relative to the flow of the sulfur recovery plant amine regenerator bottoms. The transfer of heat directly to another process stream captures heat that would have otherwise been discharged to the environment. The diesel product stream and the kerosene product stream are each returned to the hydrocracking plant 212 for further processing.

The heated first and the heated second amine regenerator bottoms stream are flowed to the sulfur recovery plant 202. As shown in FIG. 1AT, the steam heat input for the amine regenerator can be 0 MW because the alternative flow path disclosed in this configuration may satisfy the entire heat load for the operation of the column. In an alternative embodiment, the steam heat input for the amine regenerator can be reduced because the alternative flow path disclosed in this configuration may partially satisfy the heat load for the operation of the column.

FIG. 1AS shows a sour water stripper plant 210 in the crude oil refining facility. The sour water stripper bottoms stream can be flowed into the plant as a single stream and split into multiple streams or it can be flowed into the plant as multiple streams. The hydrocracking plant 212 also includes a first reaction section feed stream to a first stage cold high pressure separator and a diesel product stripper overheads stream. As shown in FIG. 1AP, the first reaction feed stream to the first stage cold high pressure separator directly heats a first sour water stripper bottoms stream in a second heat exchanger with a thermal duty that can range between about 15 MW and 25 MW (for example, 20.5 MW). As shown in FIG. 1AQ (represented collectively by FIGS. 1AQ-1 and 1AQ-2), the product strippers overhead stream directly heats a second sour water stripper bottoms stream in a third heat exchanger with a thermal duty that can range between about 5 MW and 15 MW (for example, 11.5 MW). The second and the third heat exchangers are coupled in parallel to each other relative to the flow of the sour water stripper bottoms. The transfer of heat directly to another process stream captures heat that would have otherwise been discharged to the environment. The first reaction section feed stream to a first stage cold high pressure separator and the product stripper overheads stream are each returned to the hydrocracking plant 212 for further processing.

The heated first and the heated second sour water stripper bottoms streams are then flowed to the sour water stripper plant 210. As shown in FIG. 1AS, the steam heat input for the sour water stripper can be 0 MW because the alternative flow path disclosed in this configuration may satisfy the entire heat load for the operation of the column. In an alternative embodiment, the steam heat input for the sour water stripper can be reduced because the alternative flow path disclosed in this configuration may partially satisfy the heat load for the operation of the column.

In this manner, the sour water stripper plant and the sulfur recovery plant amine are heated using the waste heat recovered and reused from the hydrocracking plant. Such a recovery and reuse of waste heat can result in a savings of about 53 MW of heat energy.

Configuration 9

FIGS. 1AU-1BA illustrate configurations and the related schemes for heating streams in a naphtha hydro-treating plant, a sour water stripper plant and a gas separation plant. In some implementations, multiple first stream in multiple first plants can be directly heated using multiple second streams in a second plant. In some implementations, the multiple first plants are a naphtha hydrotreating plant, a sour water stripper plant and a gas separation plant; the multiple first streams are the naphtha splitter bottoms, the sour water stripper bottoms, the de-ethanizer bottoms and the C3/C4 splitter bottoms streams; the second plant is the hydrocracking plant; and the second multiple streams are the diesel product, the kerosene pumparound, first reaction section feed stream to a first stage cold high pressure separator, a product stripper overheads, kerosene pumparound streams.

The configurations illustrated in FIGS. 1AU-1BA thermally integrate the hydrocracking plant, the naphtha hydrotreating plant, the sour water stripper plant, and the gas separation plant in the crude oil refining facility to reduce the crude oil refining facility's energy consumption. For example, a reduction in energy consumption by about 59 MW can translate to about 15% of the energy consumption in the crude oil refining facility. As described later, in certain schemes, a process stream (for example, a hydrocracking plant stream or other process streams) can be used to directly heat another process stream (for example, a sour water stripper stream or other process stream).

FIGS. 1AU-1AX show a hydrocracking plant 212 in a crude oil refining facility. FIG. 1AY shows a naphtha hydrotreating plant 214 in the crude oil refining facility. The naphtha splitter bottoms stream can be flowed into the plant as a single stream and split into multiple streams or it can be flowed into the plant as multiple streams. The hydrocracking plant 212 includes a diesel product stream and the kerosene pumparound stream. As shown in FIG. 1AU, the diesel product stream is used to directly heat a first naphtha splitter bottoms stream in a first heat exchanger with a thermal duty that can range between about 1 MW and 10 MW (for example, 6.6 MW). As shown in FIG. 1AW (represented collectively by FIGS. 1AW-1 and 1AW-2), the kerosene pumparound stream is used to directly heat a second naphtha splitter bottoms stream in a fourth heat exchanger with a thermal duty that can range between about 1 MW and 10 MW (for example, 5.7 MW). The first and the fourth heat exchangers are coupled in parallel to each other relative to the flow of naphtha splitter bottoms. The transfer of heat directly to another process stream captures heat that would have otherwise been discharged to the environment. The diesel product stream is returned to the hydrocracking plant 212 for further processing.

The heated first and the heated second naphtha splitter bottoms streams are then flowed to the naphtha hydrotreating plant 214. As shown in FIG. 1AY, the steam heat input for the naphtha splitter column can be reduced because the alternative flow paths disclosed in this configuration may partially satisfy the heat load for the operation of the column. In an alternative embodiment, the steam heat input for the naphtha splitter column can be 0 MW because the alternative flow paths disclosed in this configuration may satisfy the entire heat load for the operation of the column.

FIG. 1AZ shows a sour water stripper plant 210 in the crude oil refining facility. The sour water stripper bottoms stream can be flowed into the plant as a single stream and split into multiple streams or it can be flowed into the plant as multiple streams. The hydrocracking plant 212 includes a first reaction section feed stream to a first stage cold high pressure separator and a product stripper overheads stream. As shown in FIG. 1AV, the first reaction section feed stream to the first stage cold high pressure separator is used to directly heat a first branch of a sour water stripper bottom stream in a second heat exchanger with a thermal duty that can range between about 15 MW and 25 MW (for example, 20.5 MW). As shown in FIG. 1AW, the product stripper overheads stream is used to directly heat a second branch of the sour water stripper bottom stream in a third heat exchanger with a thermal duty that can range between about 5 MW and 15 MW (for example, 11.5 MW). The second and third heat exchangers are coupled in parallel to each other relative to the flow of sour water stripper bottoms. The transfer of heat directly to another process stream captures heat that would have otherwise been discharged to the environment. The first reaction section feed stream to a first stage cold high pressure separator and the product stripper overheads stream are returned to the hydrocracking plant 212 for further processing.

The heated first and the heated second sour water stripper bottoms streams are then flowed to the sour water stripper plant 210. As shown in FIG. 1AZ, the steam heat input for the sour water stripper can be 0 MW because the alternative flow path disclosed in this configuration may satisfy the entire heat load for the operation of the column. In an alternative embodiment, the steam heat input for the sour water stripper can be reduced because the alternative flow path disclosed in this configuration may partially satisfy the heat load for the operation of the column.

In addition, as shown in FIG. 1AW, the kerosene pumparound stream is used to directly heat a gas separation plant de-ethanizer bottom stream in a fifth heat exchanger with a thermal duty that can range between about 1 MW and 10 MW (for example, 4.3 MW). The fifth heat exchanger is coupled in series with and is downstream of the fourth heat exchanger relative to the flow of the kerosene pumparound stream. The transfer of heat directly to another process stream captures heat that would have otherwise been discharged to the environment. In an alternative embodiment, the cooling requirement of the kerosene pumparound stream can be 0 MW because the alternative flow path disclosed in this configuration may satisfy the entire cooling requirement for the kerosene pumparound stream for the operation of the fractionator. The kerosene pumparound stream is returned to the hydrocracking plant 212 for further processing.

FIG. 1BA shows a gas separation plant 210 in the crude oil refining facility. The heated de-ethanizer bottom stream is then flowed to the gas separation plant 204. As shown in FIG. 1BA, the steam heat input for the de-ethanizer can be 0 MW because the alternative flow path disclosed in this configuration may satisfy the entire heat load for the operation of the column. In an alternative embodiment, the steam heat input for the de-ethanizer can be reduced because the alternative flow path disclosed in this configuration may partially satisfy the heat load for the operation of the column.

As shown in FIG. 1AX, the kerosene product stream is used to heat a gas separation plant C3/C4 splitter bottom stream in a sixth heat exchanger with a thermal duty that can range between about 5 MW and 15 MW (for example, 9.9 MW). The transfer of heat directly to another process stream captures heat that would have otherwise been discharged to the environment. The kerosene product stream is returned to the hydrocracking plant 212 for further processing.

The heated C3/C4 splitter bottom stream is then flowed to the gas separation plant 204. As shown in FIG. 1BA, the steam heat input for the C3/C4 splitter can be 0 MW because the alternative flow path disclosed in this configuration may satisfy the entire heat load for the operation of the column. In an alternative embodiment, the steam heat input for the C3/C4 splitter can be reduced because the alternative flow path disclosed in this configuration may partially satisfy the heat load for the operation of the column.

In this manner, the naphtha hydro-treating plant, the sour water stripper plant, the gas separation plant are heated using the waste heat recovered and reused from the hydrocracking plant. Such a recovery and reuse of waste heat can result in a savings of about 59 MW of heat energy.

Configuration 10

FIGS. 1BB-1BG illustrate configurations and the related schemes for heating streams in an amine regeneration plant and a gas separation plant. In some implementations, multiple first stream in multiple first plants can be directly heated using multiple second streams in a second plant. In some implementations, the multiple first plants are an amine regeneration plant and a gas separation plant; the multiple first streams are the acid gas regenerator bottoms, the de-ethanizer bottoms and the C3/C4 splitter bottoms streams; the second plant is the hydrocracking plant; and the second multiple streams are the diesel product, a first reaction section feed stream to a first stage cold high pressure separator a kerosene product, and the kerosene pumparound streams.

The configurations illustrated in FIGS. 1BB-1BG thermally integrate the hydrocracking plant, the amine regeneration plant and the gas separation plant in the crude oil refining facility to reduce the crude oil refining facility's energy consumption. For example, a decrease in energy consumption by about 62 MW can translate to about 16% of the energy consumption in the crude oil refining facility. As described later, in certain schemes, a process stream (for example, a hydrocracking plant stream or other process streams) can be used to directly heat another process stream (for example, a gas separation plant stream or other process stream).

FIGS. 1BB-1BE show a hydrocracking plant 212 in a crude oil refining facility. FIG. 1AY shows an amine regeneration plant 206 in the crude oil refining facility. The acid gas regenerator bottoms stream can be flowed into the plant as a single stream and split into multiple streams or it can be flowed into the plant as multiple streams. The hydrocracking plant 212 includes a diesel product stream, a first reaction section feed stream to a first stage cold high pressure separator and a kerosene product stream. As shown in FIG. 1BB, the diesel product stream directly heats a first acid gas regenerator bottoms stream in a first heat exchanger with a thermal duty that can range between about 5 MW and 15 MW (for example, 11.6 MW). As shown in FIG. 1BC, the first reaction section feed stream to the first stage cold high pressure separator directly heats a second acid gas regenerator bottoms stream in a second heat exchanger with a thermal duty that can range between about 20 MW and 30 MW (for example, 24.2 MW). As shown in FIG. 1BE, the kerosene product stream directly heats a third acid gas regenerator bottoms stream in a fourth heat exchanger with a thermal duty that can range between about 5 MW and 15 MW (for example, 12 MW). The first, second and the fourth heat exchangers are coupled in parallel to each other relative to the flow of acid gas regenerator bottoms. The transfer of heat directly to another process stream captures heat that would have otherwise been discharged to the environment. The diesel product stream and the first reaction section feed stream to a first stage cold high pressure separator are each returned to the hydrocracking plant 212 for further processing.

The heated first, the heated second and the heated third acid gas regenerator bottoms streams are then flowed to the amine regeneration plant 206. As shown in FIG. 1BF, the steam heat input for the acid gas regenerator can be 0 MW because the alternative flow path disclosed in this configuration may satisfy the entire heat load for the operation of the column. In an alternative embodiment, the steam heat input for the acid gas regenerator can be reduced because the alternative flow path disclosed in this configuration may partially satisfy the heat load for the operation of the column.

The hydrocracking plant 212 includes a kerosene pumparound stream. As shown in FIG. 1BD (represented collectively by FIGS. 1BD-1 and 1BD-2), the kerosene pumparound stream directly heats a C3/C4 splitter bottom stream in a third heat exchanger with a thermal duty that can range between about 5 MW and 15 MW (for example, 9.9 MW). The transfer of heat directly to another process stream captures heat that would have otherwise been discharged to the environment. In an alternative embodiment, the cooling requirement of the kerosene pumparound stream can be 0 MW because the alternative flow path disclosed in this configuration may satisfy the entire cooling requirement for the kerosene pumparound stream for the operation of the fractionator. The kerosene pumparound stream is returned to the hydrocracking plant 212 for further processing.

FIG. 1BG shows gas separation plant 204 in the crude oil refining facility. The heated C3/C4 splitter bottoms stream is then flowed to the gas separation plant 204. As shown in FIG. 1BG, the steam heat input for the C3/C4 splitter can be 0 MW because the alternative flow path disclosed in this configuration may satisfy the entire heat load for the operation of the column. In an alternative embodiment, the steam heat input for the C3/C4 splitter can be reduced because the alternative flow path disclosed in this configuration may partially satisfy the heat load for the operation of the column.

As shown in FIG. 1BE, the kerosene product stream directly heats a de-ethanizer bottoms stream in a fifth heat exchanger with a thermal duty that can range between about 1 MW and 10 MW (for example, 4.3 MW). The fifth heat exchanger is coupled to, is in series with and is downstream of the fourth heat exchanger relative to the flow of the kerosene product stream. The transfer of heat directly to another process stream captures heat that would have otherwise been discharged to the environment. The kerosene product stream is returned to the hydrocracking plant 212 for further processing.

The heated de-ethanizer bottoms stream is then flowed to the gas separation plant 204. As shown in FIG. 1BG, the steam heat input for the de-ethanizer can be 0 MW because the alternative flow path disclosed in this configuration may satisfy the entire heat load for the operation of the column. In an alternative embodiment, the steam heat input for the de-ethanizer can be reduced because the alternative flow path disclosed in this configuration may partially satisfy the heat load for the operation of the column.

In this manner, the amine regeneration plant and the gas separation plant are heated using the waste heat recovered and reused from the hydrocracking plant. Such a recovery and reuse of waste heat can result in a savings of about 62 MW of heat energy.

Configuration 11

FIGS. 1BH-1BN illustrate configurations and the related schemes for heating streams in an amine regeneration plant and a sulfur recovery plant. In some implementations, multiple first stream in multiple first plants can be directly heated using multiple second streams in a second plant. In some implementations, the multiple first plants are an amine regeneration plant and the sulfur recovery plant; the multiple first streams are the acid gas regenerator bottoms and the amine regenerator bottoms streams; the second plant is the hydrocracking plant; and the second multiple streams are the diesel product stream, the kerosene product stream, the second stage reaction feed stream to a second stage cold high pressure separator, the product stripper overheads stream and the first stage reaction feed stream to a first stage cold high pressure separator.

The configurations illustrated in FIGS. 1BH-1N thermally integrate the hydrocracking plant, the amine regeneration plant and the sulfur recovery plant in the crude oil refining facility to reduce the crude oil refining facility's energy consumption. For example, a reduction in energy consumption by about 69 MW can translate to about 17% of the energy consumption in the crude oil refining facility. As described later, in certain schemes, a process stream (for example, a hydrocracking plant stream or other process streams) can be used to directly heat another process stream (for example, an amine regenerator stream or other process stream).

FIGS. 1BH-1BL show a hydrocracking plant 212 in a crude oil refining facility. FIG. 1BM shows a sulfur recovery plant 202 in the crude oil refining facility. The amine regenerator bottoms stream can be flowed into the plant as a single stream and split into multiple streams or it can be flowed into the plant as multiple streams. The hydrocracking plant 212 has a diesel product stream and a kerosene product stream. As shown in FIG. 1BH, the diesel product stream directly heats a first amine regenerator bottoms stream in a first heat exchanger with a thermal duty that can range between about 5 MW and 15 MW (for example, 10.4 MW). As shown in FIG. 1BL, the kerosene product stream directly heats a second amine regenerator bottoms stream in a fifth heat exchanger with a thermal duty that can range between about 5 MW and 15 MW (for example, 11 MW). The first and the fifth heat exchangers are coupled in parallel to each other relative to the flow of the amine regenerator bottoms. The transfer of heat directly to another process stream captures heat that would have otherwise been discharged to the environment. The diesel product stream and the kerosene product stream are each returned to the hydrocracking plant 212 for further processing.

The heated first and the heated second amine regenerator bottoms stream are then flowed to the sulfur recovery plant 202. As shown in FIG. 1BM, the steam heat input for the amine regenerator can be 0 MW because the alternative flow path disclosed in this configuration may satisfy the entire heat load for the operation of the column. In an alternative embodiment, the steam heat input for the amine regenerator can be reduced because the alternative flow path disclosed in this configuration may partially satisfy the heat load for the operation of the column.

FIG. 1BN shows an amine regeneration plant 206 in the crude oil refining facility. The acid gas regenerator bottoms stream can be flowed into the plant as a single stream and split into multiple streams or it can be flowed into the plant as multiple streams. The hydrocracking plant 212 includes a second stage reaction feed stream to a second stage cold high pressure separator, a product stripper overhead stream and a first stage reaction feed stream to a first stage cold high pressure separator. As shown in FIG. 1BI, the second stage reaction feed stream to the second stage cold high pressure separator directly heats a first acid gas regenerator bottoms stream in a second heat exchanger with a thermal duty that can range between about 1 MW and 10 MW (for example, 5 MW). As shown in FIG. 1BK (represented collectively by FIGS. 1BK-1 and 1BK-2), the product stripper overhead stream directly heats a second acid gas regenerator bottoms stream in a fourth heat exchanger with a thermal duty that can range between about 10 MW and 20 MW (for example, 14.9 MW). As shown in FIG. 1BJ, the first stage reaction feed stream to the first stage cold high pressure directly heats a third acid gas regenerator bottoms stream in a third heat exchanger with a thermal duty that can range between about 25 MW and 35 MW (for example, 27.9 MW). The second, third and fourth heat exchangers are coupled in parallel to each other relative to the flow of acid gas regenerator bottoms. The transfer of heat directly to another process stream captures heat that would have otherwise been discharged to the environment. The second stage reaction feed stream to a second stage cold high pressure separator, the product stripper overhead stream and the first stage reaction feed stream to a first stage cold high pressure separator are each returned to the hydrocracking plant 212 for further processing.

The heated first, the heated second, and the heated third acid gas regenerator bottoms streams are then flowed to the amine regeneration plant 206. As shown in FIG. 1BN, the steam heat input for the acid gas regenerator can be 0 MW because the alternative flow path disclosed in this configuration may satisfy the entire heat load for the operation of the column. In an alternative embodiment, the steam heat input for the acid gas regenerator can be reduced because the alternative flow path disclosed in this configuration may partially satisfy the heat load for the operation of the column.

In this manner, the sulfur recovery plant and the amine regeneration plant are heated using the waste heat recovered and reused from the hydrocracking plant. Such a recovery and reuse of waste heat can result in savings of about 69 MW of heat energy.

Configuration 12

FIGS. 1BO-1BT illustrate configurations and related schemes for heating streams in an amine regeneration plant and a naphtha hydro-treating plant. In some implementations, multiple first stream in multiple first plants can be directly heated using multiple second streams in a second plant. In some implementations, the multiple first plants are an amine regeneration plant and a naphtha hydrotreating plant; the multiple first streams are the acid gas regenerator bottoms and the naphtha splitter bottoms streams; the second plant is the hydrocracking plant; and the second multiple streams are the diesel product stream, a product stripper overhead stream, a kerosene pumparound stream, a kerosene product stream and a first stage reaction feed stream to a first stage cold high pressure separator.

The configurations illustrated in FIGS. 1BO-1BT thermally integrate the hydrocracking plant, the amine regeneration plant and the naphtha hydro-treating plant in the crude oil refining facility to reduce the crude oil refining facility's energy consumption. For example, a reduction in energy consumption by about 69 MW can translate to about 17% of the energy consumption in the crude oil refining facility. As described later, in certain schemes, a process stream (for example, a hydrocracking plant stream or other process streams) can be used to directly heat another process stream (for example, an amine regeneration plant stream or other process stream).

FIGS. 1BO-1BR show a hydrocracking plant 212 in a crude oil refining facility. FIG. 1BT shows a naphtha hydrotreating plant 214 in the crude oil refining facility. The naphtha splitter bottoms stream can be flowed into the plant as a single stream and split into multiple streams or it can be flowed into the plant as multiple streams. The hydrocracking plant 212 includes a diesel product stream, a product stripper overhead stream, a kerosene pumparound stream and a kerosene product stream. As shown in FIG. 1BO, the diesel product stream directly heats a first naphtha splitter bottom stream in a first heat exchanger with a thermal duty that can range between about 1 MW and 10 MW (for example, 6.6 MW). As shown in FIG. 1BQ (represented collectively by FIGS. 1BQ-1 and 1BQ-2), the product stripper overhead stream directly heats a second naphtha splitter bottom stream in a second heat exchanger with a thermal duty that can range between about 1 MW and 10 MW (for example, 3.4 MW). Also, as shown in FIG. 1BQ, the kerosene pumparound stream directly heats a third e naphtha splitter bottom stream in a third heat exchanger with a thermal duty that can range between about 1 MW and 10 MW (for example, 5.7 MW). As shown in FIG. 1BR, the kerosene product stream directly heats a fourth naphtha splitter bottom stream in a fourth heat exchanger with a thermal duty that can range between about 1 MW and 10 MW (for example, 5.4 MW). The first, second, third and fourth heat exchangers are coupled in parallel to each other relative to the flow of naphtha splitter bottoms. The transfer of heat directly to another process stream captures heat that would have otherwise been discharged to the environment. The diesel product stream and the kerosene pumparound stream are returned to the hydrocracking plant 212 for further processing.

The heated first, the heated second, the heated third and the heated fourth naphtha splitter bottoms streams are then flowed to the naphtha hydro-treating plant 214. As shown in FIG. 1BT, the steam heat input for the naphtha splitter column can be reduced because the alternative flow paths disclosed in this configuration may partially satisfy the heat load for the operation of the column. In an alternative embodiment, the steam heat input for the naphtha splitter column can be 0 MW because the alternative flow paths disclosed in this configuration may satisfy the entire heat load for the operation of the column.

FIG. 1BT shows an amine regeneration plant 206 in the crude oil refining facility. The acid gas regenerator bottoms stream can be flowed into the plant as a single stream and split into multiple streams or it can be flowed into the plant as multiple streams. The hydrocracking plant 212 also includes a first stage reaction feed stream to a first stage cold high pressure separator, the product stripper overhead stream and the kerosene product stream. As shown in FIG. 1BP, the first stage reaction feed stream to the first stage cold high pressure separator directly heats a first acid gas regenerator bottoms stream in a fifth heat exchanger with a thermal duty that can range between about 25 MW and 35 MW (for example, 29.5 MW). As shown in FIG. 1BQ, the product stripper overhead stream directly heats a second acid gas regenerator bottoms stream in a sixth heat exchanger with a thermal duty that can range between about 5 MW and 15 MW (for example, 12 MW). The sixth heat exchanger is coupled to, is in series with and is downstream of the second heat exchanger relative to the flow of the product stripper overhead stream. As shown in FIG. 1BR, the kerosene product stream directly heats a third acid gas regenerator bottoms stream in a seventh heat exchanger with a thermal duty that can range between about 1 MW and 10 MW (for example, 6.3 MW). The seventh heat exchanger is coupled to, in series with and is downstream of the fourth heat exchanger relative to the flow of the kerosene product stream. The fifth, sixth and seventh heat exchangers are coupled in parallel to each other relative to the flow of acid gas regenerator bottoms. The transfer of heat directly to another process stream captures heat that would have otherwise been discharged to the environment. The first stage reaction feed stream to the first stage cold high pressure separator, the product stripper overhead stream and the kerosene product stream are returned to the hydrocracking plant 212 for further processing.

The heated first, the heated second, and the heated third acid gas regenerator bottoms streams are then flowed to the amine regeneration plant 206. As shown in FIG. 1BS, the steam heat input for the acid gas regenerator can be 0 MW because the alternative flow path disclosed in this configuration may satisfy the entire heat load for the operation of the column. In an alternative embodiment, the steam heat input for the acid gas regenerator can be reduced because the alternative flow path disclosed in this configuration may partially satisfy the heat load for the operation of the column.

In this manner, the amine regeneration plant and the naphtha hydro-treating plant are heated using the waste heat recovered and reused from the hydrocracking plant. Such a recovery and reuse of waste heat can result in savings of about 69 MW of heat energy.

Configuration 13

FIGS. 1BU-1CB illustrate configurations and related schemes for streams in an amine regeneration plant, a sulfur recovery plant and a sour water stripper plant. In some implementations, multiple first stream in multiple first plants can be directly heated using multiple second streams in multiple second plants. In some implementations, the multiple first plants are an amine regeneration plant, the sulfur recovery plant, and the sour water stripper plant; the multiple first streams are the acid gas regenerator bottoms, the amine regenerator bottoms, and the sour water stripper bottoms streams; the multiple second plants are the diesel hydrotreating plant and the hydrocracking plant; and the second multiple streams are the diesel product stream, a kerosene product stream, a first stage reaction feed stream to a first stage cold high pressure separator, a diesel stripper bottoms stream, a product stripper overheads stream, a kerosene pumparound stream and a diesel stripper overheads stream.

In some implementations, one of the multiple first plants is directly heated by only one of the multiple second plants, whereas the only one of the multiple second plants provides heat to more than one of the multiple first plants.

The configurations illustrated in FIGS. 1BU-1CB thermally integrate the hydrocracking plant, the diesel hydrotreating plant, the amine regeneration plant, the sulfur recovery plant, and the sour water stripper plant in the crude oil refining facility to reduce the crude oil refining facility's energy consumption. For example, a reduction in energy consumption by about 109 MW can translate to about 27% of the energy consumption in the crude oil refining facility. As described later, in certain schemes, a process stream (for example, a hydrocracking plant stream or other process streams) can be used to directly heat another process stream (for example, a sulfur recovery plant stream or other process stream).

FIGS. 1BU-1BX show a hydrocracking plant 212 in a crude oil refining facility. FIG. 1BZ shows a sulfur recovery plant 202 in the crude oil refining facility. The amine regenerator bottoms stream can be flowed into the plant as a single stream and split into multiple streams or it can be flowed into the plant as multiple streams. The hydrocracking plant 212 includes a diesel product stream and a kerosene product stream. As shown in FIG. 1BU, the diesel product stream directly heats a first amine regenerator bottoms stream in a first heat exchanger with a thermal duty that can range between about 5 MW and 15 MW (for example, 10.4 MW). As shown in FIG. 1BX, the kerosene product stream directly heats a second amine regenerator bottoms stream in a fifth heat exchanger with a thermal duty that can range between about 5 MW and 15 MW (for example, 11 MW). The first and the fifth heat exchangers are coupled in parallel to each other relative to the flow of the amine regenerator bottoms. The transfer of heat directly to another process stream captures heat that would have otherwise been discharged to the environment. The diesel product stream and the kerosene product stream are each returned to the hydrocracking plant 212 for further processing.

The heated first and the heated second amine regenerator bottoms stream are then flowed to the sulfur recovery plant 202. As shown in FIG. 1BZ, the steam heat input for the amine regenerator can be 0 MW because the alternative flow path disclosed in this configuration may satisfy the entire heat load for the operation of the column. In an alternative embodiment, the steam heat input for the amine regenerator can be reduced because the alternative flow path disclosed in this configuration may partially satisfy the heat load for the operation of the column.

The hydrocracking plant 212 includes a first stage reaction feed stream to a first stage cold high pressure separator. FIG. 1BY show a diesel hydrotreating plant 200 in a crude oil refining facility. FIG. 1CA shows an amine regeneration plant 206 in the crude oil refining facility. The acid gas regenerator bottoms stream can be flowed into the plant as a single stream and split into multiple streams or it can be flowed into the plant as multiple streams. The diesel hydrotreating plant 200 includes a diesel stripper bottoms stream. As shown in FIG. 1BV, the first stage reaction feed stream to the first stage cold high pressure separator directly heats a first acid gas regenerator bottoms stream in a second heat exchanger with a thermal duty that can range between about 25 MW and 35 MW (for example, 27.9 MW). As shown in FIG. 1BY, diesel stripper bottom stream directly heats a second acid gas regenerator bottoms stream in a seventh heat exchanger with a thermal duty that can range between about 15 MW and 25 MW (for example, 19.9 MW). The second and the seventh heat exchangers are coupled in parallel to each other relative to the flow of acid gas regenerator bottoms. The transfer of heat directly to another process stream captures heat that would have otherwise been discharged to the environment. The first stage reaction feed stream to a first stage cold high pressure separator is returned to the hydrocracking plant 212 for further processing. The diesel stripper bottom stream is returned to the diesel hydrotreating plant 200 for further processing.

The heated first and the heated second acid gas regenerator bottoms streams are then flowed to the amine regeneration plant 206. As shown in FIG. 1CA, the steam heat input for the acid gas regenerator can be 0 MW because the alternative flow path disclosed in this configuration may satisfy the entire heat load for the operation of the column. In an alternative embodiment, the steam heat input for the acid gas regenerator can be reduced because the alternative flow path disclosed in this configuration may partially satisfy the heat load for the operation of the column.

FIG. 1CB shows sour water stripper plant 210 in the crude oil refining facility. The sour water stripper bottoms stream can be flowed into the plant as a single stream and split into multiple streams or it can be flowed into the plant as multiple streams. The hydrocracking plant 212 also includes a product stripper overhead stream and a kerosene pumparound stream. The diesel hydrotreating plant 200 includes a diesel stripper overhead stream. As shown in FIG. 1BW (represented collectively by FIGS. 1BW-1 and 1BW-2), the product stripper overhead stream directly heats a first sour water stripper bottoms stream in the third heat exchanger with a thermal duty that can range between about 5 MW and 15 MW (for example, 11.8 MW). Also as shown in FIG. 1BW, the kerosene pumparound stream directly heats a second sour water stripper bottoms stream in a fourth heat exchanger with a thermal duty that can range between about 1 MW and 10 MW (for example, 4.3 MW). As shown in FIG. 1BY, the diesel stripper overhead stream directly heats a third sour water stripper bottoms stream in a sixth heat exchanger with a thermal duty that can range between about 10 MW and 20 MW (for example, 15.9 MW). The third, fourth and sixth heat exchangers are coupled in parallel to each other relative to the flow of sour water stripper bottoms. The transfer of heat directly to another process stream captures heat that would have otherwise been discharged to the environment. The product stripper overhead stream and a kerosene pumparound stream are each returned to the hydrocracking plant 212 for further processing. The diesel stripper overhead stream is returned to the diesel hydrotreating plant 200 for further processing.

The heated first, the heated second and the heated third sour water stripper bottoms streams are flowed to the sour water stripper plant 210. As shown in FIG. 1CB, the steam heat input for the sour water stripper can be 0 MW because the alternative flow path disclosed in this configuration may satisfy the entire heat load for the operation of the column. In an alternative embodiment, the steam heat input for the sour water stripper can be reduced because the alternative flow path disclosed in this configuration may partially satisfy the heat load for the operation of the column.

In this manner, the sulfur recovery plant is heated using the waste heat recovered and reused from the hydrocracking plant. As well, the amine regeneration plant and the sour water stripper plant are heated using the waste heat recovered and reused from both the hydrocracking plant and the diesel hydrotreating plant. Such a recovery and reuse of waste heat can result in savings of about 109 MW of heat energy.

Configuration 14

FIGS. 1CC-1CL illustrate configurations and related schemes for streams in an amine regeneration, a sulfur recovery plant, a gas separation plant and a sour water stripper plant. In some implementations, multiple first stream in multiple first plants can be directly heated using multiple second streams in multiple second plants. In some implementations, the multiple first plants are the amine regeneration plant, the sulfur recovery plant, the gas separation plant and the sour water stripper plant; the multiple first streams are the sour water stripper bottoms stream, the acid gas regenerator bottoms stream, the amine regenerator bottoms stream, and the de-ethanizer bottoms stream, and the C3/C4 splitter bottoms stream; the multiple second plants are the hydrocracking plant, a diesel hydro-treating plant and a natural gas steam reforming hydrogen plant; and the second multiple streams are the diesel product stream, a kerosene product stream, a first stage reaction feed stream to first stage cold high pressure separator, a diesel stripper bottom stream, product stripper overhead stream, diesel stripper overhead stream, low temperature shift (LTS) converter product stream and a kerosene pumparound stream.

In some implementations, one of the multiple first plants is directly heated by only one of the multiple second plants, whereas the only one of the multiple second plants provides heat to more than one of the multiple first plants. In some implementations, at least one of the multiple first plants is directly heated by only two of the multiple second plants, whereas the only two of the multiple second plants provides heat to more than one of the multiple first plants. In some implementations, at least one of the multiple first plants is directly heated by only three of the multiple second plants, whereas two of the multiple second plants provides heat to more than one of the multiple first plants and one of the multiple second plants provides heat to only the at least one of the multiple first plants.

The configurations illustrated in FIGS. 1CC-1CL thermally integrate a hydrocracking plant, a diesel hydro-treating plant, a natural gas steam reforming hydrogen plant (H2 plant), the amine regeneration plant, the sulfur recovery plant, the gas separation plant and the sour water stripper plant in the crude oil refining facility to reduce the crude oil refining facility's energy consumption. For example, a reduction in energy consumption by about 115 MW can translate to about 29% of the energy consumption in the crude oil refining facility. As described later, in certain schemes, a process stream (for example, a hydrocracking plant stream or other process streams) can be used to directly heat another process stream (for example, a gas separation plant stream or other process stream).

FIGS. 1CC-1CF show a hydrocracking plant 212 in a crude oil refining facility. FIG. 1CI shows a sulfur recovery plant 202 in the crude oil refining facility. The amine regenerator bottoms stream can be flowed into the plant as a single stream and split into multiple streams or it can be flowed into the plant as multiple streams. The hydrocracking plant 212 includes a diesel product stream and a kerosene product stream. As shown in FIG. 1CC, the diesel product stream directly heats a first amine regenerator bottom stream in a first heat exchanger with a thermal duty that can range between about 5 MW and 15 MW (for example, 10.4 MW). As shown in FIG. 1CF, the kerosene product stream directly heats a second amine regenerator bottom stream in a fifth heat exchanger with a thermal duty that can range between about 5 MW and 15 MW (for example, 10.6 MW). The first and the fifth heat exchangers are coupled in parallel to each other relative to the flow of the amine regenerator bottoms. The transfer of heat directly to another process stream captures heat that would have otherwise been discharged to the environment. The diesel product stream and a kerosene product stream are each returned to the hydrocracking plant 212 for further processing.

The heated first and the heated second amine regenerator bottoms streams are then flowed to the sulfur recovery plant 202. As shown in FIG. 1CI, the steam heat input for the sulfur recovery plant amine regenerator can be 0 MW because the alternative flow path disclosed in this configuration may satisfy the entire heat load for the operation of the column. In an alternative embodiment, the steam heat input for the sulfur recovery plant amine regenerator can be reduced because the alternative flow path disclosed in this configuration may partially satisfy the heat load for the operation of the column.

The hydrocracking plant 212 includes a first stage reaction feed stream to first stage cold high pressure separator. In FIG. 1CG shows a diesel hydrotreating plant 212 in a crude oil refining facility. The diesel hydrotreating plant 200 includes a diesel stripper bottom stream. FIG. 1CJ shows an amine regeneration plant 206 in the crude oil refining facility. The acid gas regenerator bottoms stream can be flowed into the plant as a single stream and split into multiple streams or it can be flowed into the plant as multiple streams. As shown in FIG. 1CD, the first stage reaction feed stream to first stage cold high pressure separator directly heats a first acid gas regenerator bottom stream in a second heat exchanger with a thermal duty that can range between about 25 MW and 35 MW (for example, 27.9 MW). As shown in FIG. 1CG, the diesel stripper bottom directly heats a second acid gas regenerator bottom stream in a seventh heat exchanger with a thermal duty that can range between about 15 MW and 25 MW (for example, 19.9 MW). The second and the seventh heat exchangers are coupled in parallel to each other relative to the flow of acid gas regenerator bottoms. The transfer of heat directly to another process stream captures heat that would have otherwise been discharged to the environment. The first stage reaction feed stream to first stage cold high pressure separator is returned to the hydrocracking plant 212 for further processing.

The heated first and the heated second acid gas regenerator bottoms streams are then flowed to the amine regeneration plant 206. As shown in FIG. 1CJ, the steam heat input for the acid gas regenerator can be 0 MW because the alternative flow path disclosed in this configuration may satisfy the entire heat load for the operation of the column. In an alternative embodiment, the steam heat input for the acid gas regenerator can be reduced because the alternative flow path disclosed in this configuration may partially satisfy the heat load for the operation of the column.

The hydrocracking plant 212 includes a product stripper overhead stream. The diesel hydro-treating plant 200 includes a diesel stripper overhead stream. FIG. 1CH shows a natural gas steam reforming hydrogen plant 208 in the crude oil refining facility. The natural gas steam reforming hydrogen plant 208 includes a low temperature shift (LTS) converter product stream. FIG. 1CK shows a sour water stripper plant 210 in the crude oil refining facility. The sour water stripper bottoms stream can be flowed into the plant as a single stream and split into multiple streams or it can be flowed into the plant as multiple streams. As shown in FIG. 1CE (represented collectively by FIGS. 1CE-1 and 1CE-2), the product stripper overhead stream directly heats a first sour water stripper bottoms stream in a third heat exchanger with a thermal duty that can range between about 5 MW and 15 MW (for example, 11.8 MW). Also, as shown in FIG. 1CG, the diesel stripper overhead stream directly heats a second sour water stripper bottoms stream in a sixth heat exchanger with a thermal duty that can range between about 10 MW and 20 MW (for example, 15.9 MW). As shown in FIG. 1CH, the LTS converter product stream directly heats a third sour water stripper bottom stream in a tenth heat exchanger with a thermal duty that can range between about 1 MW and 10 MW (for example, 4.3 MW). The third, sixth and tenth heat exchangers are coupled in parallel to each other relative to the flow of sour water stripper bottoms. The transfer of heat directly to another process stream captures heat that would have otherwise been discharged to the environment. The product stripper overhead stream is returned to the hydrocracking plant 212 for further processing. The diesel stripper overhead stream is returned to the diesel hydro-treating plant 200 for further processing. The LTS converter product stream is returned to the natural gas steam reforming hydrogen plant 208 for further processing.

The heated first, the heated second, and the heated third sour water stripper bottoms streams are flowed to the sour water stripper plant 210. As shown in FIG. 1CK, the steam heat input for the sour water stripper can be 0 MW because the alternative flow path disclosed in this configuration may satisfy the entire heat load for the operation of the column. In an alternative embodiment, the steam heat input for the sour water stripper can be reduced because the alternative flow path disclosed in this configuration may partially satisfy the heat load for the operation of the column.

The hydrocracking plant 212 includes a kerosene pump-around stream. The diesel hydro-treating plant 200 includes the diesel stripper bottom stream. FIG. 1CL shows a gas separation plant 204 in the crude oil refining facility. The C3/C4 splitter bottoms stream can be flowed into the plant as a single stream and split into multiple streams or it can be flowed into the plant as multiple streams. As shown in FIG. 10E, the kerosene pumparound stream directly heats a first C3/C4 splitter bottoms stream in a fourth heat exchanger with a thermal duty that can range between about 1 MW and 10 MW (for example, 4.2 MW). As shown in FIG. 1CG, the diesel stripper bottom stream directly heats a second C3/C4 splitter bottoms stream in an eighth heat exchanger with a thermal duty that can range between about 1 MW and 10 MW (for example, 5.7 MW). The eighth heat exchanger is coupled in series with and is downstream of the seventh heat exchanger relative to the flow of the diesel stripper bottom stream. The fourth and the eighth heat exchangers are coupled in parallel to each other relative to the flow of the C3/C4 splitter bottoms stream. The transfer of heat directly to another process stream captures heat that would have otherwise been discharged to the environment. The kerosene pumparound stream is returned to the hydrocracking plant 212 for further processing.

The heated first and the second C3/C4 splitter bottoms streams are then flowed to the gas separation plant 204. As shown in FIG. 1CL, the steam heat input for the C3/C4 splitter can be 0 MW because the alternative flow path disclosed in this configuration may satisfy the entire heat load for the operation of the column. In an alternative embodiment, the steam heat input for the C3/C4 splitter can be reduced because the alternative flow path disclosed in this configuration may partially satisfy the heat load for the operation of the column.

The diesel hydro-treating plant 200 includes the diesel stripper bottom stream. Also, as shown in FIG. 1CG, the diesel stripper bottoms stream 200 directly heats a de-ethanizer bottom stream in a ninth heat exchanger with a thermal duty that can range between about 1 MW and 10 MW (for example, 4.3 MW). The ninth heat exchanger is coupled in series with and is downstream of the eighth heat exchanger and the seventh heat exchanger relative to the flow of the diesel stripper bottom stream. The transfer of heat directly to another process stream captures heat that would have otherwise been discharged to the environment. The diesel stripper bottom stream is returned to the hydrocracking plant 212 for further processing.

The heated de-ethanizer bottom stream is flowed to the gas separation plant 204. As shown in FIG. 1CL, the steam heat input for the de-ethanizer can be 0 MW because the alternative flow path disclosed in this configuration may satisfy the entire heat load for the operation of the column.

In an alternative embodiment, the steam heat input for the de-ethanizer can be reduced because the alternative flow path disclosed in this configuration may partially satisfy the heat load for the operation of the column.

In this manner, the sulfur recovery plant is heated using the waste heat recovered and reused from the hydrocracking plant. The amine regeneration plant and the gas separation plant are both heated using the waste heat recovered and reused from both the hydrocracking plant and the diesel hydrotreating plant. The sour water stripper plant is heated using the waste heat recovered and reused from the hydrocracking plant, the diesel hydrotreating plant and the natural gas steam reforming hydrogen plant. Such a recovery and reuse of waste heat can result in savings of about 115 MW of heat energy.

Configuration 15

FIGS. 1CM-1CX illustrate configurations and related schemes for streams in, amine regeneration plant, a sulfur recovery plant, a gas separation plant, a naphtha hydrotreating plant and a sour water stripper plant. In some implementations, multiple first stream in multiple first plants can be directly heated using multiple second streams in multiple second plants. In some implementations, the multiple first plants are the amine regeneration plant, the sulfur recovery plant, the gas separation plant, the naphtha hydrotreating plant and the sour water stripper plant; the multiple first streams are the naphtha splitter bottoms stream, sour water stripper bottoms stream, the acid gas regenerator bottoms stream, the amine regenerator bottoms stream, and the de-ethanizer bottoms stream, and the C3/C4 splitter bottoms stream; the multiple second plants are the hydrocracking plant, a diesel hydro-treating plant and a natural gas steam reforming hydrogen plant; and the second multiple streams are the diesel product stream, a kerosene product stream, a first stage reaction feed stream to first stage cold high pressure separator, the second stage reaction feed stream to a second stage cold high pressure separator, a diesel stripper bottom stream, product stripper overhead stream, diesel stripper overhead stream, the low temperature shift (LTS) converter product stream and a kerosene pumparound stream.

In some implementations, one of the multiple first plants is directly heated by only one of the multiple second plants, whereas the only one of the multiple second plants provides heat to more than one of the multiple first plants. In some implementations, at least one of the multiple first plants is directly heated by only two of the multiple second plants, whereas the only two of the multiple second plants provides heat to more than one of the multiple first plants. In some implementations, at least one of the multiple first plants is directly heated by only three of the multiple second plants, whereas two of the multiple second plants provides heat to more than one of the multiple first plants and one of the multiple second plants provides heat to only the at least one of the multiple first plants.

The configurations illustrated in FIGS. 1CM-1CX thermally integrate the hydrocracking plant, a diesel hydrotreating plant, the natural gas steam reforming hydrogen plant (H2 plant), amine regeneration plant, the sulfur recovery plant, the gas separation plant, the naphtha hydrotreating plant and the sour water stripper plant in the crude oil refining facility to reduce the crude oil refining facility's energy consumption. For example, a reduction in energy consumption by about 129 MW can translate to about 32% of the energy consumption in the crude oil refining facility. As described later, in certain schemes, a process stream (for example, a hydrocracking plant stream or other process streams) can be used to directly heat another process stream (for example, a gas separation plant stream or other process stream).

FIGS. 1CM-1CQ shows a hydrocracking plant 212 in the crude oil refining facility. The hydrocracking plant 212 includes a diesel product stream, a kerosene pumparound stream and a kerosene product stream. FIG. 1CR shows a diesel hydrotreating plant 200 in the crude oil refining facility. The diesel hydrotreating plant 200 includes a diesel stripper overheat stream. FIG. 1CT shows a naphtha hydrotreating plant 214 in the crude oil refining facility. The naphtha splitter bottoms stream can be flowed into the plant as a single stream and split into multiple streams or it can be flowed into the plant as multiple streams. As shown in FIG. 1CM, the diesel product stream directly heats a first naphtha splitter bottoms stream in a first heat exchanger with a thermal duty that can range between about 1 MW and 10 MW (for example, 6.6 MW). As shown in FIG. 1CP (represented collectively by FIGS. 1CP-1 and 1CP-2), the kerosene pumparound stream directly heats a second naphtha splitter bottoms stream in a sixth heat exchanger with a thermal duty that can range between about 1 MW and 10 MW (for example, 5.7 MW). As shown in FIG. 1CQ, the kerosene product stream directly heats a third naphtha splitter bottoms stream in an eighth heat exchanger with a thermal duty that can range between about 1 MW and 10 MW (for example, 5.4 MW). As shown in FIG. 1CR, the diesel stripper overhead stream in the diesel hydro-treating plant 200 directly heats a fourth naphtha splitter bottoms stream in a tenth heat exchanger with a thermal duty that can range between about 5 MW and 15 MW (for example, 7.5 MW). The first, sixth, eighth and tenth heat exchangers are coupled in parallel to each other relative to the flow of the naphtha splitter bottoms. The transfer of heat directly to another process stream captures heat that would have otherwise been discharged to the environment.

The heated first, the heated second, the heated third and the heated fourth naphtha splitter bottoms streams are flowed to the naphtha hydro-treating plant 214. As shown in FIG. 1CT, the steam heat input for the naphtha splitter column can be reduced because the alternative flow paths disclosed in this configuration may partially satisfy the heat load for the operation of the column. In an alternative embodiment, the steam heat input for the naphtha splitter column can be 0 MW because the alternative flow paths disclosed in this configuration may satisfy the entire heat load for the operation of the column.

FIG. 1CT shows a sulfur recovery plant 202 in the crude oil refining facility. The amine regenerator bottoms stream can be flowed into the plant as a single stream and split into multiple streams or it can be flowed into the plant as multiple streams. The hydrocracking plant 212 includes the diesel product stream, a second stage reaction feed stream to a second stage cold high pressure separator and the kerosene product stream. As shown in FIG. 1CM, the diesel product stream directly heats a first amine regenerator bottoms stream in a second heat exchanger with a thermal duty that can range between about 1 MW and 10 MW (for example, 3.8 MW). The second heat exchanger is coupled in series with and is downstream of the first heat exchanger relative to the flow of the diesel product stream. As shown in FIG. 1CN, the second stage reaction feed stream to the second stage cold high pressure separator directly heats a second amine regenerator bottoms stream in a third heat exchanger with a thermal duty that can range between about 5 MW and 15 MW (for example, 6.5 MW). As shown in FIG. 1CQ, the kerosene product stream directly heats a third amine regenerator bottoms stream in a ninth heat exchanger with a thermal duty that can range between about 1 MW and 10 MW (for example, 5 MW). The ninth heat exchanger is coupled in series with and is downstream of the eighth heat exchanger relative to the flow of the kerosene product stream. The transfer of heat directly to another process stream captures heat that would have otherwise been discharged to the environment. The diesel product stream, the second stage reaction feed stream to a second stage cold high pressure separator and the kerosene product stream are each returned to the hydrocracking plant 212 for further processing.

The heated first, the heated second and the heated third amine regenerator bottoms streams are flowed to the sulfur recovery plant 202. As shown in FIG. 1CU, the steam heat input for the amine regenerator can be reduced because the alternative flow path disclosed in this configuration may partially satisfy the heat load for the operation of the column. In an alternative embodiment, the steam heat input for the amine regenerator can be 0 MW because the alternative flow path disclosed in this configuration may satisfy the entire heat load for the operation of the column.

FIG. 1CV shows an amine regeneration plant 206 in the crude oil refining facility. The acid gas regenerator bottoms stream can be flowed into the plant as a single stream and split into multiple streams or it can be flowed into the plant as multiple streams. The hydrocracking plant 212 includes a first stage reaction feed stream to a first stage cold high pressure separator. The diesel hydrotreating plant 200 includes a diesel stripper bottom stream. As shown in FIG. 1CO, the first stage reaction feed stream to first stage cold high pressure separator directly heats a first acid gas regenerator bottoms stream in a fourth heat exchanger with a thermal duty that can range between about 25 MW and 35 MW (for example, 27.9 MW). As shown in FIG. 1CR, the stripper bottom stream in the diesel hydro-treating plant 200 directly heats a second acid gas regenerator bottoms stream in a twelfth heat exchanger with a thermal duty that can range between about 15 MW and 25 MW (for example, 19.9 MW). The fourth and the twelfth heat exchangers are coupled in parallel to each other relative to the flow of acid gas regenerator bottoms. The transfer of heat directly to another process stream captures heat that would have otherwise been discharged to the environment. The first stage reaction feed stream to first stage cold high pressure separator is returned to the hydrocracking plant 212 for further processing.

The heated first and the heated acid gas regenerator bottoms streams are flowed to the amine regeneration plant 206. As shown in FIG. 1CV, the steam heat input for the acid gas regenerator can be 0 MW because the alternative flow path disclosed in this configuration may satisfy the entire heat load for the operation of the column. In an alternative embodiment, the steam heat input for the acid gas regenerator can be reduced because the alternative flow path disclosed in this configuration may partially satisfy the heat load for the operation of the column.

The hydrocracking plant 212 includes a product stripper overhead stream. The diesel hydrotreating plant 200 includes a diesel stripper overhead stream. FIG. 1CS shows a natural gas steam reforming hydrogen plant 208 in the crude oil refining facility. The natural gas steam reforming hydrogen plant 208 includes a low temperature shift (LTS) converter product stream. FIG. 1CW shows a sour water stripper plant 210 in the crude oil refining facility. The sour water stripper bottoms stream can be flowed into the plant as a single stream and split into multiple streams or it can be flowed into the plant as multiple streams. As shown in FIG. 1CP, the product stripper overhead stream directly heats a first sour water stripper bottoms stream in a fifth heat exchanger with a thermal load that can range between about 10 MW and 20 MW (for example, 11.8 MW). As shown in FIG. 1CR, the diesel stripper overhead stream directly heats a second sour water stripper bottoms stream in an eleventh heat exchanger with a thermal load that can range between about 10 MW and 20 MW (for example, 8.4 MW). The eleventh heat exchanger is coupled in series with and is downstream of the tenth heat exchanger relative to the flow of the diesel stripper overhead stream. As shown in FIG. 1CS, the LTS converter product stream directly heats a third sour water stripper bottoms stream in a fifteenth heat exchanger with a thermal load that can range between about 1 MW and 10 MW (for example, 6.2 MW). The fifth, the eleventh and the fifteenth heat exchangers are coupled in parallel to each other relative to the flow of sour water stripper bottoms. The transfer of heat directly to another process stream captures heat that would have otherwise been discharged to the environment. The product stripper overhead stream is returned to the hydrocracking plant 212 for further processing. The diesel stripper overhead stream is returned to the diesel hydro-treating plant 200 for further processing. The LTS converter product stream is returned to the natural gas steam reforming hydrogen plant 208 for further processing.

The heated first, the heated second and the heated third sour water stripper bottoms stream are then flowed to the sour water stripper plant 210. As shown in FIG. 1CW, the steam heat input for the sour water stripper can be reduced because the alternative flow path disclosed in this configuration may partially satisfy the heat load for the operation of the column. In an alternative embodiment, the steam heat input for the sour water stripper can be 0 MW because the alternative flow path disclosed in this configuration may satisfy the entire heat load for the operation of the column.

The hydrocracking plant 212 includes a kerosene pump-around stream. The diesel hydrotreating plant 200 includes the diesel stripper bottoms stream. FIG. 1CX shows a gas separation plant 204 in the crude oil refining facility. The C3/C4 splitter bottoms stream can be flowed into the plant as a single stream and split into multiple streams or it can be flowed into the plant as multiple streams. As shown in FIG. 1CP, the kerosene pumparound stream directly heats a first C3/C4 splitter bottom stream in a seventh heat exchanger with a thermal load that can range between about 1 MW and 10 MW (for example, 5 MW). The seventh heat exchanger is coupled in series with and is downstream of the sixth heat exchanger relative to the flow of the kerosene pumparound stream. As shown in FIG. 1CP, the cooling requirement of the kerosene pumparound stream can be 0 MW because the alternative flow path disclosed in this configuration may satisfy the entire cooling requirement for the kerosene pumparound stream for the operation of the fractionator column. As shown in FIG. 1CR, the diesel stripper bottom stream directly heats a second C3/C4 splitter bottoms stream in a thirteenth heat exchanger with a thermal load that can range between about 1 MW and 10 MW (for example, 4.5 MW). The seventh and the thirteenth heat exchangers are coupled in parallel to each other relative to the flow of C3/C4 splitter bottoms. The thirteenth heat exchanger is coupled in series with and is downstream of the twelfth heat exchanger relative to the flow of the diesel stripper bottom stream. The transfer of heat directly to another process stream captures heat that would have otherwise been discharged to the environment. The kerosene pumparound stream is returned to the hydrocracking plant 212 for further processing.

The heated first and the heated second C3/C4 splitter bottoms stream are flowed to the gas separation plant 204. As shown in FIG. 1CX, the steam heat input for the C3/C4 splitter can be 0 MW because the alternative flow path disclosed in this configuration may satisfy the entire heat load for the operation of the column. In an alternative embodiment, the steam heat input for the C3/C4 splitter can be reduced because the alternative flow path disclosed in this configuration may partially satisfy the heat load for the operation of the column.

The diesel hydrotreating plant 200 includes the diesel stripper bottoms stream. As shown, the diesel stripper bottom stream directly heats a de-ethanizer bottom stream in a fourteenth heat exchanger with a thermal load that can range between about 1 MW and 10 MW (for example, 4.3 MW). The fourteenth heat exchanger is coupled in series with and is downstream of the thirteenth heat exchanger and from the twelfth heat exchanger relative to the flow of the diesel stripper bottom stream. The transfer of heat directly to another process stream captures heat that would have otherwise been discharged to the environment. The diesel stripper bottoms stream is returned to the diesel hydrotreating plant 200 for further processing.

The heated de-ethanizer bottom stream is flowed to the gas separation plant 204. As shown in FIG. 1CX, the steam heat input for the de-ethanizer can be 0 MW because the alternative flow path disclosed in this configuration may satisfy the entire heat load for the operation of the column. In an alternative embodiment, the steam heat input for the de-ethanizer can be reduced because the alternative flow path disclosed in this configuration may partially satisfy the heat load for the operation of the column.

In this manner, the naphtha hydrotreating plant, the amine regeneration plant, and the gas separation plant are heated using the waste heat recovered and reused from the hydrocracking plant and diesel hydrotreating plant. The sulfur recovery plant is heated using the waste heat recovered and reused from the hydrocracking plant. The sour water stripper plant is heated using the waste heat recovered and reused from the hydrocracking plant, the diesel hydrotreating plant and the natural gas steam reforming hydrogen plant. Such a recovery and reuse of waste heat can result in savings of about 129 MW of heat energy.

In summary, this disclosure describes configurations and related processing schemes of direct or indirect inter-plants (or both) heating systems synthesized for grassroots medium grade crude oil semi-conversion refineries to increase energy efficiency from specific portions of low grade waste heat sources. The disclosure also describes configurations and related processing schemes of direct or indirect inter-plants (or both) heating systems synthesized for integrated medium grade crude oil semi-conversion refineries and aromatics complex for increasing energy efficiency from specific portions of low grade waste sources.

The economics of industrial production, the limitations of global energy supply, and the realities of environmental conservation are concerns for all industries. It is believed that the world's environment has been negatively affected by global warming caused, in part, by the release of GHG into the atmosphere. Implementations of the subject matter described here can alleviate some of these concerns, and, in some cases, prevent certain refineries, which are having difficulty in reducing their GHG emissions, from having to shut down. By implementing the techniques described here, specific plants in a refinery or a refinery, as a whole, can be made more efficient and less polluting by recovery and reusing from specific portions of low grade waste heat sources.

Thus, particular implementations of the subject matter have been described. Other implementations are within the scope of the following claims.

The invention claimed is:

1. A method implemented in a crude oil refining facility, the method comprising:
   in a crude oil refining facility comprising a plurality of oil refining plants, each oil refining plant configured to perform at least one oil refining process, each oil refining plant comprising a plurality of interconnected oil refining sub-systems, wherein a plurality of streams at respective temperatures flow between the plurality of oil refining sub-systems:
      flowing a hydrocracking plant stream from a hydrocracking plant of the plurality of oil refining plants to a first heat exchanger, the hydrocracking plant stream comprising at least one of a first stage reaction section feed to a first stage cold high pressure separator stream, a diesel product stream, a kerosene product stream, a second reaction stage feed stream to a second cold high pressure separator stream, a product stripper overheads stream, a kerosene pumparound stream;
      flowing a stream from a first oil refining plant of the plurality of oil refining plants to the first heat exchanger, the first oil refining plant being different from the hydrocracking plant and comprising at least one of a sulfur recovery plant, a sour water stripper plant, a gas separation plant through which a gas separation plant stream comprising at least one of C2 to C4 flows, a naphtha hydro-treating plant, an amine regeneration plant separation section, wherein an acid gas regenerator bottoms stream comprising a weak amine salt flows through the amine regeneration plant, wherein the first heat exchanger transfers heat from the hydrocracking plant stream to the stream from the first oil refining plant; and
      utilizing the stream from the first oil refining plant heated by the hydrocracking plant stream in an oil refining process at the first oil refining plant.

2. The method of claim 1, wherein the first oil refining plant is the sulfur recovery plant, the stream is an amine regenerator bottoms stream, the hydrocracking plant stream is the first stage reaction section feed to the first stage cold high pressure separator stream, and wherein utilizing the stream from the first oil refining plant heated by the hydrocracking plant stream in an oil refining process at the first oil refining plant further comprises:
   heating the amine regenerator bottoms stream using the first stage reaction section feed to a first stage cold high pressure separator stream; and
   flowing the heated amine regenerator bottoms stream through a sulfur recovery plant amine regenerator bottoms of the sulfur recovery plant.

3. The method of claim 1, wherein the first oil refining plant is the sour water stripper plant, the stream is a sour water stripper bottoms stream, wherein the hydrocracking plant stream comprises the diesel product stream, the first stage reaction section feed to the first stage cold high pressure separator stream and the kerosene product stream, and wherein utilizing the stream from the first oil refining plant heated by the hydrocracking plant stream in an oil refining process at the first oil refining plant comprises:

heating the sour water stripper bottoms stream using the diesel product stream in the first heat exchanger;
heating the sour water stripper bottoms stream using the first stage reaction section feed to the first stage cold high pressure separator stream in a second heat exchanger;
heating the sour water stripper bottoms using the kerosene product stream in a third heat exchanger; and
flowing the heated sour water stripper bottoms stream through the sour water stripper plant.

4. The method of claim 3, wherein the first heat exchanger, the second heat exchanger and the third heat exchanger are fluidically coupled to each other in parallel.

5. The method of claim 1, wherein the first oil refining plant comprises the gas separation plant and the sulfur recovery plant, wherein the stream comprises a C3/C4 splitter bottoms stream in the gas separation plant, a sulfur recovery plant bottom cold stream in the sulfur recovery plant and a de-ethanizer bottoms stream in the gas separation plant, wherein the hydrocracking plant stream is the second reaction stage feed stream to the second cold high pressure separator stream, the first stage reaction feed stream to the first stage cold high pressure separator stream and the kerosene product stream, and wherein utilizing the stream from the first oil refining plant heated by the hydrocracking plant stream in an oil refining process at the first oil refining plant comprises:
heating the C3/C4 splitter bottoms stream in the gas separation plant using the second reaction stage feed stream to the second cold high pressure separator stream in the first heat exchanger;
heating the sulfur recovery plant bottom cold stream in the sulfur recovery plant using the first stage reaction feed stream to the first stage cold high pressure separator stream in a second heat exchanger;
heating the de-ethanizer bottoms stream in the gas separation plant using the kerosene product stream in a third heat exchanger;
flowing the heated sulfur recovery plant bottom cold stream to the sulfur recovery plant;
flowing the heated de-ethanizer bottoms stream to the gas separation plant; and
flowing the heated C3/C4 splitter bottoms stream to the gas separation plant.

6. The method of claim 1, wherein the first oil refining plant comprises the naphtha hydro-treating plant and the sulfur recovery plant, wherein the stream comprises a naphtha splitter bottoms stream in the naphtha hydro-treating plant and an amine regenerator bottoms stream in the sulfur recovery plant, wherein the hydrocracking plant stream the diesel product stream, the product stripper overheads stream, the kerosene pumparound stream, the kerosene product stream, and the first reaction stage feed stream to a first stage cold high pressure separator, and wherein utilizing the stream from the first oil refining plant heated by the hydrocracking plant stream in an oil refining process at the first oil refining plant comprises:
heating a naphtha splitter bottoms stream in the naphtha hydro-treating plant using the diesel product stream, the product stripper overheads stream, the kerosene pumparound stream and the kerosene product stream in a first heat exchanger, a second heat exchanger, a third heat exchanger and a fourth heat exchanger, respectively;
heating the amine regenerator bottoms stream in the sulfur recovery plant using the first reaction stage feed stream to the first stage cold high pressure separator in a fifth heat exchanger;
flowing the heated naphtha splitter bottoms stream to the naphtha hydro-treating plant; and
flowing the heated amine regenerator bottoms stream to the sulfur recovery plant.

7. The method of claim 6, wherein the first heat exchanger, the second heat exchanger, the third heat exchanger and the fourth heat exchanger are fluidically coupled to each other in parallel.

8. The method of claim 1, wherein the first oil refining plant comprises the sour water stripper plant and the gas separation plant, wherein the stream comprises a sour water stripper bottom cold stream, a C3/C4 splitter bottoms stream and a de-ethanizer bottoms stream in the gas separation plant, wherein the hydrocracking plant stream comprises the second reaction section second stage cold high pressure separator feed stream, the first reaction stage feed stream to the first stage cold high pressure separator, the product stripper overhead stream and the kerosene product stream, and wherein utilizing the stream from the first oil refining plant heated by the hydrocracking plant stream in an oil refining process at the first oil refining plant comprises:
heating the C3/C4 splitter bottoms stream in the gas separation plant using the second reaction section second stage cold high pressure separator feed stream in the first heat exchanger; and
heating a first branch of the sour water stripper bottoms stream in the sour water stripper plant using the first reaction stage feed stream to the first stage cold high pressure separator in a second heat exchanger;
heating a second branch of the sour water stripper bottoms stream using the product stripper overhead stream in a third heat exchanger;
heating the de-ethanizer bottoms stream in the gas separation plant using the kerosene product stream in a fourth heat exchanger;
flowing the heated first branch and the heated second branch to the sour water stripper plant; and
flowing the heated de-ethanizer bottoms stream and the heated C3/C4 splitter bottoms stream to the gas separation plant.

9. The method of claim 8, wherein the second heat exchanger and the third heat exchanger are fluidically coupled to each other in parallel.

10. The method of claim 1, wherein the first oil refining plant comprises the amine regeneration plant separation section, wherein the stream comprises the acid gas regenerator bottoms stream in the amine regeneration plant separation section, wherein the hydrocracking plant stream comprises the diesel product stream, the first reaction section feed stream to the first stage cold high pressure separator and the kerosene product stream, and wherein utilizing the stream from the first oil refining plant heated by the hydrocracking plant stream in an oil refining process at the first oil refining plant comprises:
heating a first branch of the acid gas regenerator bottoms stream in the amine regeneration plant separation section using the diesel product stream in a first heat exchanger;
heating a second branch of the acid gas regenerator bottoms stream using the first reaction section feed stream to the first stage cold high pressure separator in a second heat exchanger;

heating a third branch of the acid gas regenerator bottoms stream using the kerosene product stream in a third heat exchanger;

flowing the first branch, the second branch and the third branch to the amine regeneration plant separation section acid gas regenerator bottom.

11. The method of claim 10, wherein the first heat exchanger, the second heat exchanger and the third heat exchanger are coupled to each other in parallel.

12. The method of claim 1, wherein the first oil refining plant comprises the amine regeneration plant separation section, wherein the stream comprises the acid gas regenerator bottoms stream in the amine regeneration plant separation section, wherein the hydrocracking plant stream comprises the first reaction section feed stream to the first stage cold high pressure separator, the product stripper overhead stream and the kerosene product stream, and wherein utilizing the stream from the first oil refining plant heated by the hydrocracking plant stream in an oil refining process at the first oil refining plant comprises:

heating a first branch of the acid gas regenerator bottoms stream in the amine regeneration plant separation section using the first reaction section feed stream to the first stage cold high pressure separator in the first heat exchanger;

heating a second branch of the acid gas regenerator bottoms stream using the product stripper overhead stream in a second heat exchanger;

heating a third branch of the acid gas regenerator bottoms stream using the kerosene product stream in a third heat exchanger;

flowing the first branch, the second branch and the third branch to the amine regeneration plant separation section acid gas regenerator bottom.

13. The method of claim 12, wherein the first heat exchanger, the second heat exchanger and the third heat exchanger are coupled to each other in parallel.

14. The method of claim 1, wherein the first oil refining plant comprises the naphtha hydro-treating plant and the sour water stripper plant, wherein the stream comprises a naphtha splitter bottoms stream in the naphtha hydro-treating plant and a sour water stripper bottoms stream in the sour water stripper plant, wherein the hydrocracking plant stream comprises the diesel product stream, the kerosene pumparound stream, the kerosene product stream, the first reaction section feed stream to the first stage cold high pressure separator and the product stripper overheads stream, and wherein utilizing the stream from the first oil refining plant heated by the hydrocracking plant stream in an oil refining process at the first oil refining plant comprises:

heating a first branch of the naphtha splitter bottoms stream in the naphtha hydro-treating plant using the diesel product stream in a first heat exchanger;

heating a first branch of the sour water stripper bottoms stream in the sour water stripper plant using the first reaction section feed stream to the first stage cold high pressure separator in a second heat exchanger;

heating a second branch of the sour water stripper bottoms stream using the product stripper overheads stream in a third heat exchanger;

heating a second branch of the naphtha splitter bottoms stream using the kerosene pumparound stream in a fourth heat exchanger;

heating a third branch of the naphtha splitter bottoms stream using the kerosene product stream in a fifth heat exchanger;

flowing the heated first branch and the heated second branch of the sour water stripper bottoms stream to the sour water stripper plant; and flowing the heated first branch, the heated second branch and the heated third branch of the naphtha splitter bottoms stream to the naphtha hydro-treating plant.

15. The method of claim 14, wherein the first heat exchanger, the fourth heat exchanger and the fifth heat exchanger are fluidically coupled to each other in parallel.

16. The method of claim 14, wherein the second heat exchanger and the third heat exchanger are fluidically coupled to each other in parallel.

17. The method of claim 1, wherein the first oil refining plant comprises the sulfur recovery plant and the sour water stripper plant, wherein the stream comprises an amine regenerator bottoms stream in the sulfur recovery plant and a sour water stripper bottoms stream, wherein the hydrocracking plant stream comprises the kerosene product stream, the diesel product stream, the first reaction section feed stream to the first stage cold high pressure separator and the product stripper overheads stream, and wherein utilizing the stream from the first oil refining plant heated by the hydrocracking plant stream in an oil refining process at the first oil refining plant comprises:

heating a first branch of the amine regenerator bottoms stream in the sulfur recovery plant using the diesel product stream in the first heat exchanger;

heating a second branch of the amine regenerator bottoms stream using the kerosene product overhead stream in a fourth heat exchanger;

heating a first branch of the sour water stripper bottoms stream in the sour water stripper plant using the first reaction feed stream to the first stage cold high pressure separator in a second heat exchanger;

heating a second branch of the sour water stripper bottoms stream using the product stripper overheads stream in a third heat exchanger;

flowing the heated first branch and the heated second branch of the amine regenerator bottoms stream to the sour water stripper plant; and flowing the heated first branch and the heated second branch of the sour water stripper bottoms stream to the sulfur recovery plant.

18. The method of claim 17, wherein the first heat exchanger and the fourth heat exchanger are fluidically coupled to each other in parallel.

19. The method of claim 17, wherein the second heat exchanger and the third heat exchanger are fluidically coupled to each other in parallel.

20. The method of claim 1, wherein the first oil refining plant comprises the naphtha hydro-treating plant, the sour water stripper plant, and the gas separation plant, wherein the stream comprises a naphtha splitter bottoms stream in the naphtha hydro-treating plant, a sour water stripper bottoms stream in the sour water stripper plant, a de-ethanizer bottoms stream in the gas separation plant and a C3/C4 splitter bottoms stream in the gas separation plant, wherein the hydrocracking plant stream comprises the diesel product stream, the kerosene pumparound stream, the first reaction section feed stream to the first stage cold high pressure separator, the product stripper overheads stream and the kerosene product stream, and wherein utilizing the stream from the first oil refining plant heated by the hydrocracking plant stream in an oil refining process at the first oil refining plant comprises:

heating a first branch of the naphtha splitter bottoms stream in the naphtha hydro-treating plant using the diesel product stream in the first heat exchanger;

heating a first branch of the sour water stripper bottoms stream in the sour water stripper plant using the first reaction section feed stream to the first stage cold high pressure separator in a second heat exchanger;

heating a second branch of the sour water stripper bottoms stream using the product stripper overheads stream in a third heat exchanger;

heating a second branch of the naphtha splitter bottoms plant stream using the kerosene pumparound stream in a fourth heat exchanger;

heating the de-ethanizer bottoms stream in the gas separation plant using the kerosene product stream in a fifth heat exchanger;

heating the C3/C4 splitter bottom stream in the gas separation plant using the kerosene product stream in a sixth heat exchanger;

flowing the heated first branch and the heated second branch of the sour water stripper bottoms stream to the sour water stripper plant;

flowing the heated first branch and the heated second branch of the naphtha splitter bottoms stream to the naphtha hydro-treating plant; and flowing the heated de-ethanizer bottoms stream and the heated C3/C4 splitter bottom streams to the gas separation plant.

21. The method of claim 20, wherein the first heat exchanger and the fourth heat exchanger are fluidically coupled to each other in parallel.

22. The method of claim 20, wherein the second heat exchanger and the third heat exchanger are fluidically coupled to each other in parallel.

23. The method of claim 1, wherein the first oil refining plant comprises the amine regeneration plant separation section and the gas separation plant, wherein the stream comprises the acid gas regenerator bottoms stream in the amine regeneration plant separation section, a de-ethanizer bottoms stream and a C3/C4 splitter bottoms stream in the gas separation plant, wherein the hydrocracking plant stream comprises the diesel product stream, the first reaction section feed stream to the first stage cold high pressure separator, and the kerosene product stream, and wherein utilizing the stream from the first oil refining plant heated by the hydrocracking plant stream in an oil refining process at the first oil refining plant comprises:

heating a first branch of the acid gas regenerator bottoms stream in the amine regeneration plant separation section using the diesel product stream in the first heat exchanger;

heating a second branch of the acid gas regenerator bottoms stream using the first reaction section feed stream to the first stage cold high pressure separator in a second heat exchanger;

heating the C3/C4 splitter bottoms stream in the gas separation plant using the kerosene pumparound stream in a third heat exchanger;

heating a third branch of the amine regeneration unit bottom stream using the kerosene product stream in a fourth heat exchanger;

heating the de-ethanizer bottoms stream in the gas separation plant using the kerosene product stream in a fifth heat exchanger; and flowing the heated first branch, the heated second branch and the heated third branch to the acid gas removal plant; and flowing the heated C3/C4 splitter bottoms stream and the heated de-ethanizer bottoms stream to the gas separation plant.

24. The method of claim 23, wherein the first heat exchanger, the second heat exchanger and the fourth heat exchanger are fluidically coupled to each other in parallel.

25. The method of claim 1, wherein the first oil refining plant comprises the amine regeneration plant separation section and the sulfur recovery plant, wherein the stream comprises an amine regenerator bottoms stream in the sulfur recovery plant and an acid gas regenerator bottoms stream in the amine regeneration plant separation section, wherein the hydrocracking plant stream comprises the diesel product stream, the kerosene product stream, the second stage reaction feed stream to the second stage cold high pressure separator, the stripper overhead stream, and the first stage reaction feed stream to the first stage cold high pressure separator, and wherein utilizing the stream from the first oil refining plant heated by the hydrocracking plant stream in an oil refining process at the first oil refining plant comprises:

heating a first branch of the amine regenerator bottoms stream in the sulfur recovery plant using the diesel product stream in the first heat exchanger;

heating a second branch of a sulfur recovery plant tail gas treating stream in the sulfur recovery plant using the kerosene product stream in a fifth heat exchanger; and heating a first branch of the acid gas regenerator bottoms stream in the amine regeneration plant separation section using the second stage reaction feed stream to the second stage cold high pressure separator in a second heat exchanger;

heating a second branch of the acid gas regenerator bottoms stream using the stripper overhead stream in a fourth heat exchanger;

heating a third branch of the acid gas regenerator bottoms stream using the first stage reaction feed stream to the first stage cold high pressure in a third heat exchanger;

flowing the heated first branch and the heated second branch of the sulfur recovery plant streams to the sulfur recovery plant; and flowing the heated first branch, the heated second branch and the heated third branch of the acid gas regenerator bottoms stream to the amine regeneration plant separation section.

26. The method of claim 25, wherein the first heat exchanger and the fifth heat exchanger are fluidically coupled to each other in parallel.

27. The method of claim 25, wherein the second heat exchanger, the third heat exchanger and the fourth heat exchanger are fluidically coupled to each other in parallel.

28. The method claim 1, wherein the first oil refining plant comprises the amine regeneration plant separation section and the naphtha hydro-treating plant, wherein the stream comprises a naphtha splitter bottoms stream in the naphtha hydro-treating plant and an acid gas regenerator bottoms stream in the amine regeneration plant separation section and an acid gas removal stream in the amine regeneration plant separation section, wherein the hydrocracking plant stream comprises the diesel product stream, the product stripper overhead stream, the kerosene pumparound stream, the kerosene product stream, the first stage reaction feed stream to the first stage cold high pressure separator, the product stripper overhead stream, and the kerosene product stream, and wherein utilizing the stream from the first oil refining plant heated by the hydrocracking plant stream in an oil refining process at the first oil refining plant comprises:

heating a first branch of the naphtha splitter bottoms stream in the naphtha hydro-treating plant using the diesel product stream in the first heat exchanger;

heating a second branch of the naphtha splitter bottom streams in the naphtha hydro-treating plant using the product stripper overhead stream in a second heat exchanger;

heating a third branch of the naphtha splitter bottoms stream in the naphtha hydro-treating plant using the kerosene pumparound stream in a third heat exchanger;

heating a fourth branch of the naphtha splitter bottoms stream in the naphtha hydro-treating plant using the kerosene product stream in a fourth heat exchanger;

heating a first branch of the acid gas regenerator bottoms stream in the amine regeneration plant separation section using the first stage reaction feed stream to the first stage cold high pressure separator in a fifth heat exchanger;

heating a second branch of the acid gas regenerator bottoms stream using the product stripper overhead stream in a sixth heat exchanger;

heating an acid gas removal branch stream in the amine regeneration plant separation section using the kerosene product stream in a seventh heat exchanger;

flowing the heated first branch, the heated second branch, the heated third branch and the heated fourth branch of the naphtha splitter bottoms stream to the naphtha hydro-treating plant; and flowing the heated first branch and the heated second branch of the acid gas regenerator bottoms stream, and the heated acid gas removal branch stream to the amine regeneration plant separation section.

29. The method of claim 28, wherein the fifth heat exchanger, the sixth heat exchanger and the seventh heat exchanger are fluidically coupled to each other in parallel.

30. The method of claim 28, wherein the first heat exchanger, the second heat exchanger, the third heat exchanger and the fourth heat exchanger are fluidically coupled to each other in parallel.

31. The method of claim 28, wherein the second heat exchanger and the sixth heat exchanger are fluidically coupled to each other in series.

32. The method of claim 1, further comprising utilizing the stream from the first oil refining plant heated by the hydrocracking plant stream and by a diesel hydro-treating plant stream in a diesel hydro-treating plant in the oil refining process at the first oil refining plant, wherein the first oil refining plant comprises the amine regeneration plant separation section, the sulfur recovery plant and the sour water stripper plant, wherein the stream comprises an amine regenerator bottoms stream in the sulfur recovery plant, an acid gas regenerator bottoms stream in the amine regeneration plant separation section and a bottom stream in the sour water stripper plant, wherein the hydrocracking plant stream comprises the diesel product stream, the kerosene product stream, the first stage reaction feed stream to the first stage cold high pressure separator, the diesel product stream, the stripper overhead stream, the kerosene pumparound stream and the diesel stripper overhead stream, wherein the diesel hydro-treating plant stream comprises the diesel product stream and a stripper overhead stream, and wherein utilizing the stream from the first oil refining plant heated by the hydrocracking plant stream and the diesel hydro-treating plant stream in the oil refining process at the first oil refining plant comprises:

heating a first branch of the amine regenerator bottoms stream in the sulfur recovery plant using the hydrocracking plant diesel product stream in the first heat exchanger;

heating a first branch of the acid gas regenerator bottoms stream in the amine regeneration plant separation section using the first stage reaction feed stream to first stage cold high pressure separator in a second heat exchanger;

heating a first branch of the bottom stream in the sour water stripper plant using the hydrocracking plant stripper overhead stream in a third heat exchanger;

heating a second branch of the bottom stream in the sour water stripper plant using the kerosene pumparound stream in a fourth heat exchanger;

heating a second branch of the amine regenerator bottoms stream using the kerosene product stream in a fifth heat exchanger;

heating a third branch of the bottom stream in the sour water stripper plant using the diesel hydro-treating plant diesel stripper overhead stream in a sixth heat exchanger;

heating a second branch of the acid gas regenerator bottoms stream using the diesel hydro-treating plant diesel product stream in a seventh heat exchanger; and flowing the heated first branch of the acid gas regenerator bottoms stream and the heated second branch of the acid gas regenerator bottoms stream to the amine regeneration plant separation section;

flowing the heated first branch of the amine regenerator bottoms stream and the heated second branch of the amine regenerator bottoms stream to the sulfur recovery plant; and flowing the heated first branch of the bottom stream, the heated second branch of the bottom stream and the heated third branch of the bottom stream to the sour water stripper plant.

33. The method of claim 32, wherein the first heat exchanger and the fifth heat exchanger are fluidically coupled to each other in parallel.

34. The method of claim 32, wherein the second heat exchanger and the seventh heat exchanger are fluidically coupled to each other in parallel.

35. The method of claim 32, wherein the third heat exchanger, the fourth heat exchanger and the sixth heat exchanger are fluidically coupled to each other in parallel.

36. The method of claim 1, wherein the first oil refining plant comprises the amine regeneration plant separation section, the sulfur recovery plant, the gas separation plant and the sour water stripper plant, wherein the stream comprises an amine regenerator bottoms stream in the sulfur recovery plant, an acid gas regenerator stream in the amine regeneration plant separation section, a bottom stream in the sour water stripper plant, a C3/C4 splitter bottoms stream in the gas separation plant and a de-ethanizer bottoms stream in the gas separation plant, wherein the hydrocracking plant stream comprises the diesel product stream, the kerosene product stream, the first stage reaction feed stream to the first stage cold high pressure separator, the stripper overhead stream, the kerosene pumparound stream, and the diesel Hydro-treating plant comprises a diesel stripper bottom stream, and a stripper overhead stream and a hot stream to be cooled in a hydrogen plant in the crude oil refining facility, and wherein utilizing the stream from the first oil refining plant heated by the hydrocracking plant stream, the Hydro-treating stream and hydrogen plant stream in an oil refining process at the first oil refining plant comprises:

heating a first branch of the amine regenerator bottoms stream in the sulfur recovery plant using the hydrocracking plant diesel product stream in a first heat exchanger;

heating a first branch of the acid gas regenerator bottoms stream in the amine regeneration plant separation section using the first stage reaction feed stream to first stage cold high pressure separator in a second heat exchanger;

heating a first branch of the bottom stream in the sour water stripper plant using the hydrocracking plant stripper overhead stream in a third heat exchanger;

heating a first branch of the C3/C4 splitter bottoms stream in the gas separation plant using the kerosene pump-around stream in a fourth heat exchanger;

heating a second branch of the amine regenerator bottoms stream using the kerosene product stream in a fifth heat exchanger;

heating a third branch of the bottom stream in the sour water stripper plant using the diesel hydro-treating plant stripper overhead stream in a sixth heat exchanger;

heating a second branch of the acid gas regenerator bottoms stream using the diesel hydro-treating plant stripper bottom product in a seventh heat exchanger;

heating a second branch of the C3/C4 splitter bottoms stream using the diesel hydro-treating plant stripper bottom stream in an eighth heat exchanger;

heating the de-ethanizer bottoms stream in the gas separation plant using the diesel hydro-treating plant stripper bottom in a ninth heat exchanger;

flowing the heated first branch of the amine regenerator bottoms stream and the heated second branch of the amine regenerator bottoms stream to the sulfur recovery plant; heating a fourth branch of the bottom stream in the sour water stripper plant using the hot stream to be cooled in the hydrogen plant in a tenth heat exchanger;

flowing the heated first branch of the acid gas regenerator bottoms stream and the heated second branch of the acid gas regenerator bottoms stream to the amine regeneration plant separation section;

flowing the heated first branch of the bottom stream, the heated third branch of the bottom stream and the heated fourth branch of the bottom stream to the sour water stripper plant; and flowing the heated first branch of the C3/C4 splitter bottoms stream, the heated second branch of the C3/C4 splitter bottoms stream and the heated de-ethanizer bottoms stream to the gas separation plant.

37. The method of claim 36, wherein the first heat exchanger and the fifth heat exchanger are fluidically coupled to each other in parallel.

38. The method of claim 37, wherein the second heat exchanger and the seventh heat exchanger are fluidically coupled to each other in parallel.

39. The method of claim 37, wherein the third heat exchanger, the sixth heat exchanger and the tenth heat exchanger are fluidically coupled to each other in parallel.

40. The method of claim 37, wherein the seventh heat exchanger and the eighth heat exchanger are fluidically coupled to each other in series.

41. The method of claim 37, wherein the fourth heat exchanger and the eighth heat exchanger are fluidically coupled to each other in parallel.

42. The method of claim 37, wherein the eighth heat exchanger and the ninth heat exchanger are fluidically coupled to each other in series.

43. The method of claim 1, wherein the first oil refining plant comprises the acid gas removal plant, the sulfur recovery plant, the gas separation plant, the naphtha hydro-treating plant and the sour water stripper plant, wherein the stream comprises a naphtha splitter bottoms stream in the naphtha hydro-treating plant, a bottom stream in the acid gas removal plant, a sulfur plant amine regenerator bottoms stream in the acid gas removal plant, a sour water stripper bottoms stream in the sour water stripper plant, a C3/C4 splitter bottoms stream in the gas separation plant, a de-ethanizer bottoms stream in the gas separation plant, wherein the hydrocracking plant stream comprises the diesel product stream, the kerosene pumparound stream, the kerosene product stream, the diesel stripper overhead stream, the second stage reaction feed stream to the second stage cold high pressure separator, the first stage reaction feed stream to the first stage cold high pressure separator, and a diesel Hydro-treating plant stripper bottom product stream, a stripper overhead stream and a hot stream to be cooled in a hydrogen plant in the crude oil facility, and wherein utilizing the stream from the first oil refining plant heated by the hydrocracking plant stream, the diesel Hydro-treating plant stream and the hydrogen plant stream in an oil refining process at the first oil refining plant comprises:

heating a first branch of the naphtha splitter bottoms stream in the naphtha hydro-treating plant using the hydrocracking plant diesel product stream in the first heat exchanger;

heating a first branch of the amine regenerator bottoms stream in the sulfur recovery plant using the hydrocracking plant diesel product stream in a second heat exchanger;

heating a second branch of the amine regenerator bottoms stream using the second stage reaction feed stream to the second stage cold high pressure separator in a third heat exchanger;

heating the bottom stream in the amine regeneration plant separation section using the first stage reaction feed stream to first stage cold high pressure separator in a fourth heat exchanger;

heating a first branch of the sour water stripper bottoms stream in the sour water stripper plant using the hydrocracking plant stripper overhead stream in a fifth heat exchanger;

heating a second branch of the naphtha splitter bottoms stream using the kerosene pumparound stream in a sixth heat exchanger;

heating a first branch of the C3/C4 splitter bottoms stream in the gas separation plant using the kerosene pump-around stream in a seventh heat exchanger;

heating a third branch of the naphtha splitter bottoms stream using the kerosene product stream in an eighth heat exchanger;

heating a first branch of the amine regenerator bottoms stream in the sulfur plant using the kerosene product stream in a ninth heat exchanger;

heating a fourth branch of the naphtha splitter bottoms stream using the diesel plant stripper bottom product stream in a tenth heat exchanger;

heating a second branch of the sour water stripper bottoms stream using the diesel stripper overhead stream in an eleventh heat exchanger;

heating a second branch of the amine regenerator bottoms stream using the stripper bottom product stream in a twelfth heat exchanger;

heating a second branch of the C3/C4 splitter bottoms stream using the diesel stripper bottom stream in a thirteenth heat exchanger;

heating the de-ethanizer bottoms stream in the gas separation plant using the diesel plant stripper bottom product stream in a fourteenth heat exchanger;

heating a third branch of the sour water stripper bottoms stream using the hot stream to be cooled in the hydrogen plant in a fifteenth heat exchanger;

flowing the heated first branch of the naphtha splitter bottoms stream, the heated second branch of the naphtha splitter bottoms stream, the heated third branch of the naphtha splitter bottoms stream and the heated fourth branch of the naphtha splitter bottoms stream to the naphtha hydro-treating plant;

flowing the heated first branch of the amine regenerator bottoms stream, the heated second branch of the amine regenerator bottoms stream and the heated third branch of the amine regenerator bottoms stream to the sulfur recovery plant;

flowing the heated first branch of the acid gas removal plant amine regenerator bottom stream and the heated second branch of the acid gas removal plant amine regenerator bottom stream to the acid gas removal plant;

flowing the heated first branch of the sour water stripper bottoms stream, the heated second branch of the sour water stripper bottoms stream and the heated third branch of the sour water stripper bottoms stream to the sour water stripper plant; and flowing the heated first branch of the C3/C4 splitter bottoms stream, the heated second branch of the C3/C4 splitter bottoms stream and the heated de-ethanizer bottoms stream to the gas separation plant.

44. The method of claim 43, wherein the first heat exchanger, the sixth heat exchanger, the eighth heat exchanger and the tenth heat exchanger are fluidically coupled to each other in parallel.

45. The method of claim 43, wherein the first heat exchanger and the second heat exchanger are fluidically coupled to each other in series.

46. The method of claim 43, wherein the eighth heat exchanger and the ninth heat exchanger are coupled to each other in series.

47. The method of claim 43, wherein the fourth heat exchanger and the twelfth heat exchanger are fluidically coupled to each other in parallel.

48. The method of claim 43, wherein the tenth heat exchanger and the eleventh heat exchanger are fluidically coupled to each other in series.

49. The method of claim 43, wherein the fifth heat exchanger, the eleventh heat exchanger and the fifteenth heat exchanger are fluidically coupled to each other in parallel.

50. The method of claim 43, wherein the sixth heat exchanger and the seventh heat exchanger are fluidically coupled to each other in series.

51. The method of claim 43, wherein the seventh heat exchanger and the thirteenth heat exchanger are fluidically coupled to each other in parallel.

52. The method of claim 43, wherein the twelfth heat exchanger and the thirteenth heat exchanger are fluidically coupled to each other in series.

* * * * *